US011603543B2

(12) United States Patent
Scholz et al.

(10) Patent No.: US 11,603,543 B2
(45) Date of Patent: Mar. 14, 2023

(54) FUSOGENIC LIPID NANOPARTICLES FOR TARGET CELL-SPECIFIC PRODUCTION OF A THERAPEUTIC PROTEIN

(71) Applicant: Oisin Biotechnologies, Inc., Seattle, WA (US)

(72) Inventors: Matthew Rein Scholz, Seattle, WA (US); John David Lewis, Encinitas, CA (US); Gary Charles Hudson, Redwood City, CA (US)

(73) Assignee: OISIN BIOTECHNOLOGIES, INC., Seattle, WA (US)

(*) Notice: Subject to any disclaimer, the term of this patent is extended or adjusted under 35 U.S.C. 154(b) by 885 days.

(21) Appl. No.: 16/388,775

(22) Filed: Apr. 18, 2019

(65) Prior Publication Data
US 2020/0109419 A1 Apr. 9, 2020

Related U.S. Application Data

(60) Provisional application No. 62/659,676, filed on Apr. 18, 2018, provisional application No. 62/821,084, filed on Mar. 20, 2019.

(51) Int. Cl.
C12N 15/88 (2006.01)
A61K 9/127 (2006.01)
A61K 31/7105 (2006.01)
C12N 9/16 (2006.01)
A61K 31/711 (2006.01)
A61K 9/00 (2006.01)

(52) U.S. Cl.
CPC ............ C12N 15/88 (2013.01); A61K 9/1271 (2013.01); A61K 31/711 (2013.01); A61K 31/7105 (2013.01); C12N 9/16 (2013.01); A61K 9/0019 (2013.01); C12N 2310/20 (2017.05); C12N 2320/32 (2013.01); C12N 2830/002 (2013.01)

(58) Field of Classification Search
None
See application file for complete search history.

(56) References Cited

U.S. PATENT DOCUMENTS

| 5,869,337 | A | 2/1999 | Crabtree et al. |
| 9,968,076 | B2 | 5/2018 | Kirkland |
| 10,098,911 | B2 | 10/2018 | Pule et al. |
| 2003/0129221 | A1 | 7/2003 | Semple et al. |
| 2004/0044185 | A1 | 3/2004 | Duncan |
| 2006/0002895 | A1 | 1/2006 | McDonnell et al. |
| 2011/0244026 | A1 | 10/2011 | Guild et al. |
| 2011/0286980 | A1 | 11/2011 | Brenner |
| 2012/0183534 | A1 | 7/2012 | Gruber |
| 2013/0150430 | A1 | 6/2013 | Croce et al. |
| 2014/0314831 | A1 | 10/2014 | Duncan et al. |
| 2015/0064137 | A1 | 3/2015 | Lichtsteiner |
| 2015/0306039 | A1* | 10/2015 | Akinc .................. C12N 15/88 514/786 |
| 2015/0374842 | A1 | 12/2015 | Brown et al. |
| 2016/0010110 | A1 | 1/2016 | Scholz |
| 2016/0166613 | A1 | 6/2016 | Spencer et al. |
| 2018/0117173 | A1 | 5/2018 | Krizhanovsky |
| 2019/0330657 | A1 | 10/2019 | Scholz |
| 2020/0009268 | A1 | 1/2020 | Scholz |

FOREIGN PATENT DOCUMENTS

| EP | 1767642 | A1 | 3/2007 |
| JP | 2002530436 | A | 9/2002 |
| WO | WO-9209298 | A1 | 6/1992 |
| WO | WO-9909191 | A1 | 2/1999 |
| WO | WO-9924582 | A1 | 5/1999 |
| WO | WO-0031238 | A2 | 6/2000 |
| WO | WO-0244206 | A2 | 6/2002 |
| WO | WO-02101076 | A2 | 12/2002 |

(Continued)

OTHER PUBLICATIONS

Alemany, R.: Chapter four—Design of improved oncolytic adenoviruses. Adv Cancer Res. 115:93-114(2012).

(Continued)

Primary Examiner — Anand U Desai
(74) Attorney, Agent, or Firm — Wilson Sonsini Goodrich & Rosati

(57) ABSTRACT

Provided nucleic acid-based expression construct for the target cell-specific production of a therapeutic protein, such as a pro-apoptotic protein, within a target cell, including a target cell that is associated with aging, disease, or other condition, in particular a target cell that is a senescent cell or a cancer cell. Also provided are formulations and systems, including fusogenic lipid nanoparticle (LNP) formulations and systems, for the delivery of nucleic acid-based expression constructs as well as methods for making and using such nucleic acid-based expression constructs, formulations, and systems for reducing, preventing, and/or eliminating the growth and/or survival of a cell, such as a senescent cell and/or a cancer cell, which is associated with aging, disease, or other condition as well as methods for the treatment of aging, disease, or other conditions by the in vivo administration of a formulation, such as a fusogenic LPN formulation, comprising an expression construct for the target cell-specific production of a therapeutic protein, such as a pro-apoptotic protein, in a target cell that is associated with aging, disease, or other condition, in particular a target cell that is a senescent cell or a cancer cell.

28 Claims, 66 Drawing Sheets

Specification includes a Sequence Listing.

(56) References Cited

FOREIGN PATENT DOCUMENTS

| WO | WO-2006043354 A1 | 4/2006 |
| WO | WO-2008154644 A1 | 12/2008 |
| WO | WO-2012040825 A1 | 4/2012 |
| WO | WO-2012177927 A1 | 12/2012 |
| WO | WO-2014160661 A2 | 10/2014 |
| WO | 2016185481 A2 | 11/2016 |
| WO | WO-2018129563 A1 | 7/2018 |
| WO | WO-2019204666 A1 | 10/2019 |
| WO | WO-2020163408 A2 | 8/2020 |
| WO | WO-2020163408 A3 | 11/2020 |

OTHER PUBLICATIONS

Alharbi et al.: The role of HOX genes in normal hematopoiesis and acute leukemia. Leukemia 27(5): 1000-1008 (2013).
Anesti et al.: Delivery of RNA interference triggers to sensory neurons in vivo using herpes simplex virus. Expert Opin Biol Ther. 10(1): 89-103 (2010).
Baker, et al. Clearance of p16Ink4a-positive senescent cells delays ageing-associated disorders. Nature. Nov. 2, 2011;479(7372):232-6.
Boussif et al.: Enhanced in vitro and in vivo cationic lipid-mediated gene delivery with a fluorinated glycerophosphoethanolamine helper lipid. J Gene Med. 3(2): 109-114 (2001).
Bungener et al.: Delivery of protein antigens to the immune system by fusion-active virosomes: a comparison with liposomes and ISCOMs. Biosci Rep. 22(2): 323-338 (2002).
Buschmann et al. Chitosans for delivery of nucleic acids. Advanced drug delivery reviews 65.9(2013): 1234-1270.
Campbell et al.: Increased expression of the interleukin-11 receptor and evidence of STAT3 activation in prostate carcinoma. Am J Pathol. 158(1): 25-32 (2001).
Cantile et al.: cAMP induced modifications of HOX D gene expression in prostate cells allow the identification of a chromosomal area involved in vivo with neuroendocrine differentiation of human advanced prostate cancers. J Cell Physiol. 205(2): 202-210 (2005).
Cantile et al.: HOX D13 expression across 79 tumor tissue types. Int J Cancer. 125(7): 1532-1541 (2009).
Cantile et al.: Hyperexpression of locus C genes in the HOX network is strongly associated in vivo with human bladder transitional cell carcinomas. Oncogene. 22(41): 6462-6468 (2003).
Cantile et al.: The HOX genes network in uro-genital cancers: mechanisms and potential therapeutic implications. Curr Med Chem. 18(32): 4872-4884 (2011).
Cardone et al.: Regulation of Cell Death Protease Caspase-9 by Phosphorylation. Science 282(5392): 1318-1321 (1998).
Carlotti et al.: Development of an inducible suicide gene system based on human caspase 8. Cancer Gene Ther. 12(7): 627-639 (2005).
Carrithers et al.: Enhanced susceptibility to endotoxic shock and impaired STAT3 signaling in CD31-deficient mice. Am J Pathol. 166(1): 185-196 (2005).
Chikh et al.: Liposomal delivery of CTL epitopes to dendritic cells. Biosci Rep. 22(2): 339-353 (2002).
Chung et al.: Age-related alterations in expression of apoptosis regulatory proteins and heat shock proteins in rat skeletal muscle. Biochim Biophys Acta. 1762(1):103-109 (2006).
Cillo et al.: The HOX gene network in hepatocellular carcinoma. Int J Cancer. 129(11): 2577-2587 (2011).
Clackson et al.: Redesigning an FKBP-ligand interface to generate chemical dimerizers with novel specificity. Proc Natl Acad Sci U S A. 95(18): 10437-10442 (1998).
Clancy et al.: Reovirus FAST protein transmembrane domains function in a modular, primary sequence-independent manner to mediate cell-cell membrane fusion. J Virol. 83(7): 2941-2950 (2009).
Clevenger, C.V.: Roles and regulation of stat family transcription factors in human breast cancer. Am J Pathol. 165(5): 1449-1460 (2004).

Corcoran et al.: The p14 fusion-associated small transmembrane (FAST) protein effects membrane fusion from a subset of membrane microdomains. J Biol Chem. 281(42): 31778-31789 (2006).
Di Stasi et al., "Inducible apoptosis as a safety switch for adoptive cell therapy," New England Journal of Medicine, 365(18): 1673-1683 (2011).
Ding et al.: Gold nanoparticles for nucleic acid delivery. Mol Ther. 22(6): 1075-1083 (2014).
Dreyer, J.: Lentiviral vector-mediated gene transfer and RNA silencing technology in neuronal dysfunctions. Mol Biotechnol. 47(2): 169-187 (2011).
Elsabahy et al.: Non-viral nucleic acid delivery: key challenges and future directions, Curr. Drug Deliv 8(3): 235-244 (2011).
Enlow et al.: Potent engineered PLGA nanoparticles by virtue of exceptionally high chemotherapeutic loadings. Nano Lett. 11(2): 808-813 (2011).
Farhood et al.: The role of dioleoyl phosphatidylethanolamine in cationic liposome mediated gene transfer. Biochim Biophys Acta. 1235(2): 289-295 (1995).
Fletcher et al.: A dialkynoyl analogue of DOPE improves gene transfer of lower-charged, cationic lipoplexes. Org Biomol Chem. 4(2): 196-199 (2006).
Fournier et al.: Comparative study of 64Cu/NOTA-[D-Tyr6,βAla11,Thi1,Nle14]BBN(6-14) monomer and dimers for prostate cancer PET imaging. EJNMMI Res. 2: 8, 15 pages total (2012).
Gagniuc et al.: Eukaryotic genomes may exhibit up to 10 generic classes of gene promoters. BMC Genomics. 13: 512, 17 pages total (2012).
Gaucheron et al.: Improved in vitro gene transfer mediated by fluorinated lipoplexes in the presence of a bile salt surfactant. J Gene Med. 3(4): 338-344 (2001).
Gaucheron et al.: In vitro cationic lipid-mediated gene delivery with fluorinated glycerophosphoethanolamine helper lipids. Bioconjug Chem. 12(6): 949-963 (2001).
Gee et al.: Overexpression of TFAP2C in invasive breast cancer correlates with a poorer response to anti-hormone therapy and reduced patient survival. J Pathol. 217(1): 32-41 (2009).
Gomes et al.: Role and regulation of the forkhead transcription factors FOXO3a and FOXM1 in carcinogenesis and drug resistance. Chin J Cancer. 32(7): 365-370 (2013).
Goodson, "Chapter 6: Dental Applications." Medical Applications of Controlled Release. 1984, vol. 2, p. 115-138.
Gratton et al.: The effect of particle design on cellular internalization pathways. Proc Natl Acad Sci U S A. 105(33): 11613-11618 (2008).
Grimm et al.: Adeno-associated virus vectors for short hairpin RNA expression. Methods Enzymol. 392: 381-405 (2005).
Gruner et al.: X-ray diffraction study of the polymorphic behavior of N-methylated dioleoylphosphatidylethanolamine. Biochemistry. 27(8): 2853-2866 (1988).
Hajitou, A.: Targeted systemic gene therapy and molecular imaging of cancer contribution of the vascular-targeted AAVP vector. Adv Genet. 69: 65-82 (2010).
Herreros-Villanueva et al.: Embryonic stem cell factors and pancreatic cancer. World J Gastroenterol . 20(9): 2247-2254 (2014).
Huang et al.: Development of hybrid viral vectors for gene therapy. Biotechnol Adv. 31(2): 208-223 (2013).
Iuliucci et al.: Intravenous safety and pharmacokinetics of a novel dimerizer drug, AP1903, in healthy volunteers. J Clin Pharmacol. 41(8): 870-879 (2001).
Jafari et al.: Nonviral approach for targeted nucleic acid delivery. Curr Med Chem. 19(2): 197-208 (2012).
Jensen et al.: Design of an inhalable dry powder formulation of DOTAP-modified PLGA nanoparticles loaded with siRNA. J Control Release. 157(1): 141-148 (2012).
Kasai et al.: DNA-based methods to prepare helper virus-free herpes amplicon vectors and versatile design of amplicon vector plasmids. Curr Gene Ther. 6(3): 303-314 (2006).
Kaufmann et al.: Virus chimeras for gene therapy, vaccination, and oncolysis: adenoviruses and beyond. Trends Mol Med. 18(7): 365-376 (2012).
Kelley et al.: YPEL3, a p53-regulated gene that induces cellular senescence. Cancer Res. 70(9): 3566-3575 (2010).

(56) References Cited

OTHER PUBLICATIONS

Kelly et al.: Shape-specific, monodisperse nano-molding of protein particles. J Am Chem Soc. 130(16): 5438-5439 (2008).
Kichler et al.: Influence of membrane-active peptides on lipospermine/DNA complex mediated gene transfer. Bioconjug Chem. 8(2): 213-221 (1997).
Krabbe et al.: Fusogenic Viruses in Oncolytic Immunotherapy. Cancers (Basel). 10(7): 216, 19 pages total (2018).
Krishnamurthy et al.: p16INK4a induces an age-dependent decline in islet regenerative potential. Nature. 443(7110): 453-457 (2006).
Lau et al.: Oligomerization of fusogenic peptides promotes membrane fusion by enhancing membrane destabilization. Biophys J. 86(1 Pt 1): 272-284 (2004).
Li, et al., (2004). GALA: a designed synthetic pH-responsive amphipathic peptide with applications in drug and gene delivery. Adv Drug Deliv Rev, 56(7): 967-985.
Li et al.: Recent advances in delivery of drug-nucleic acid combinations for cancer treatment. J Control Release 172(2): 589-600 (2013).
Liu et al.: Activation of the apoptotic endonuclease DFF40 (caspase-activated DNase or nuclease). Oligomerization and direct interaction with histone H1. J Biol Chem. 274(20): 13836-13840 (1999) [Accessed on Oct. 1, 2020].
Liu et al.: Expression of p16(INK4a) in peripheral blood T-cells is a biomarker of human aging. Aging Cell. 8(4): 439-448 (2009).
Livak et al.: Analysis of relative gene expression data using real-time quantitative PCR and the 2(-Delta Delta C(T)) Method . Methods 25(4): 402-408 (2001).
Lofthouse, S.: Immunological aspects of controlled antigen delivery. Adv Drug Deliv Rev. 54(6): 863-870 (2002).
Lowe et al.: Prostate-specific expression of Bax delivered by an adenoviral vector induces apoptosis in LNCaP prostate cancer cells. Gene Ther. 8(18): 1363-1371 (2001).
Marconi et al.: HSV as a vector in vaccine development and gene therapy. Adv Exp Med Biol. 655: 118-144 (2009).
Marconi et al.: HSV as a vector in vaccine development and gene therapy. Human Vaccines 4(2): 91-105 (2008).
McCarty, D.M.: Self-complementary AAV vectors; advances and applications. Mol Ther. 16(10): 1648-1656 (2008).
Merkel et al.: Using mechanobiological mimicry of red blood cells to extend circulation times of hydrogel microparticles. Proc Natl Acad Sci U S A. 108(2): 586-591 (2011).
Metselaar et al.: Liposomes for intravenous drug targeting: design and applications. Mini Rev Med Chem. 2(4): 319-329 (2002).
Midoux et al.: Chemical vectors for gene delivery: a current review on polymers, peptides and lipids containing histidine or imidazole as nucleic acids carriers. Br J Pharmacol. 157(2): 166-178 (2009).
Midoux et al.: Specific gene transfer mediated by lactosylated poly-L-lysine into hepatoma cells. Nucleic Acids Res. 21(4): 871-878 (1993).
Mineev et al.: Structural investigation of influenza virus hemagglutinin membrane-anchoring peptide. Protein Eng Des Sel. 26(9): 547-552 (2013).
Morgan et al.: Targeting HOX transcription factors in prostate cancer. BMC Urology 14: 17, 9 pages total (2014).
Mowa et al.: Therapeutic potential of adenoviral vectors for delivery of expressed RNAi activators. Expert Opin Drug Deliv. 7(12): 1373-1385 (2010).
Mriouah et al.: Abstract 5143: Fusogenic targeted liposomes: novel nanotherapy for specific treatment of prostate cancer. AACR; Cancer Res 77(13 Suppl): Abstract nr 5143 (2017).
Nesbitt, R.L.: Targeted Intracellular Therapeutic Delivery Using Liposomes Formulated with Multifunctional FAST proteins. Electronic Thesis and Dissertation Repository. 388. https://ir.lib.uwo.ca/etd/388 126 pages total (2012).
Noureddine et al.: Probing the functional impact of sequence variation on p53-DNA interactions using a novel microsphere assay for protein-DNA binding with human cell extracts. PLoS Genet. 5(5):e1000462, 13 pages (2009).

O'Hagan, D.T.: Recent developments in vaccine delivery systems. Curr Drug Targets Infect Disord. 1(3): 273-286 (2001).
O'Hagan et al.: Microparticles as vaccine adjuvants and delivery systems. Expert Rev Vaccines. 2(2): 269-283 (2003).
Olsson et al.: Role of E2F3 expression in modulating cellular proliferation rate in human bladder and prostate cancer cells. Oncogene. 26(7): 1028-1037 (2007).
Parhamifar et al.: Live-cell fluorescent microscopy platforms for real-time monitoring of polyplex-cell interaction: Basic guidelines. Methods. 68(2): 300-307 (2014).
Park, Y.S.: Tumor-Directed Targeting of Liposomes. Bioscience Reports 22(2):267-281 (2002).
PCT/US2019/028207 International Preliminary Reporton Patentability with Written Opinion dated Oct. 20, 2020.
PCT/US2019/028207 International Search Report and Written Opinion dated Jul. 29, 2019.
Prata et al.: A new helper phospholipid for gene delivery. Chem Commun (Camb). (13): 1566, 6 pages total (2008).
Primo et al.: Lentiviral vectors for cutaneous RNA managing. Exp Dermatol . 21(3): 162-170 (2012).
Reeves et al.: Prostate cancer cells home to bone using a novel in vivo model: modulation by the integrin antagonist GLPG0187. Cancer Therapy. Int J Cancer. 136(7): 1731-1740 (2015).
Rychak et al.: Nucleic acid delivery with microbubbles and ultrasound. Adv Drug Deliv Rev. 72: 82-93 (2014).
Sakurai et al.: Effects of erythrocytes and serum proteins on lung accumulation of lipoplexes containing cholesterol or DOPE as a helper lipid in the single-pass rat lung perfusion system. Eur J Pharm Biopharm. 52(2): 165-172 (2001).
Sanchez-Garcia et al.: The fusogenic peptide HA2 impairs selectivity of CXCR4-targeted protein nanoparticles. Chem Commun (Camb). 53(33): 4565-4568 (2017).
Sasaki et al.: An artificial virus-like nano carrier system: enhanced endosomal escape of nanoparticles via synergistic action of pH-sensitive fusogenic peptide derivatives. Anal Bioanal Chem. 391(8): 2717-2727 (2008).
Seo et al.: A novel method to label preformed liposomes with 64Cu for positron emission tomography (PET) imaging. Bioconjug Chem. 19(12): 2577-2584 (2008).
Shah et al.: Double-inducible gene activation system for caspase 3 and 9 in epidermis. Genesis. 45(4): 194-199 (2007).
Shariat et al.: Adenovirus-mediated transfer of inducible caspases: a novel "death switch" gene therapeutic approach to prostate cancer. Cancer Res. 61(6): 2562-2571 (2001).
Singh et al.: Recent advances in vaccine adjuvants. Pharm Res. 19(6): 715-728 (2002).
Sioud et al.: Cationic liposome-mediated delivery of siRNAs in adult mice. Biochem Biophys Res Commun. 312(4): 1220-1225 (2003).
Sizovs et al.: Precisely tunable engineering of sub-30 nm monodisperse oligonucleotide nanoparticles. J Am Chem Soc. 136(1): 234-240 (2014).
Smale, S.T.: Core promoters: active contributorsto combinatorial gene regulation. Genes Dev. 15(19): 2503-2508 (2001) [Accessed on Sep. 29, 2020].
Staunstrup et al.: Integrase-defective lentiviral vectors—a stage for nonviral integration machineries. Curr Gene Ther. 11(5): 350-362 (2011).
Straathof et al.: An inducible caspase 9 safety switch for T-cell therapy. Blood. 105(11): 4247-4254 (2005) [Accessed on Oct. 1, 2020].
Sudo, et al. Human-derived fusogenic peptides for the intracellular delivery of proteins. J. Control. Release 255, 1-11 (2017).
Szebeni, J.: Complement activation-related pseudoallergy: a stress reaction in blood triggered by nanomedicines and biologicals. Mol Immunol. 61(2): 163-173 (2014).
Talbot et al.: Acyl chain unsaturation and vesicle curvature alter outer leaflet packing and promote poly(ethylene glycol)-mediated membrane fusion. Biochemistry. 36(19): 5827-5836 (1997).
Thompson, C.B.: Apoptosis in the pathogenesis and treatment of disease. Science. 267(5203): 1456-1462 (1995).

(56) References Cited

OTHER PUBLICATIONS

Tu et al.: A fusogenic segment of glycoprotein H from herpes simplex virus enhances transfection efficiency of cationic liposomes. J Gene Med. 10(6): 646-654 (2008).
Ulrich, A.S.: Biophysical Aspects of using Liposomes as Delivery vehicles. Bioscience Reports 22(2):129-150 (2002).
Van Deursen, Jan M. The role of senescent cells in ageing. Nature. May 22, 2014;509(7501):439-46.
Vasir et al.: Biodegradable nanoparticles for cytosolic delivery of therapeutics. Adv Drug Deliv Rev. 59(8): 718-728 (2007).
Wagner, E.: Application of membrane-active peptides for nonviral gene delivery. Adv Drug Deliv Rev. 38(3): 279-289 (1999).
Wagner et al.: Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. 89(17): 7934-7938 (1992).
Wagner et al.: Progress and outlook of inorganic nanoparticles for delivery of nucleic acid sequences related to orthopedic pathologies: a review. Tissue Eng Part B Rev. 18(1): 1-14 (2012).
Wang, et al. Characterization of regulatory elements on the promoter region of p16(INK4a) that contribute to overexpression of p16 in senescent fibroblasts. J Biol Chem. Dec. 28, 2001;276(52):48655-61. Epub Oct. 11, 2001.
Wang et al.: The complex role of multivalency in nanoparticles targeting the transferrin receptor for cancer therapies. J Am Chem Soc. 132(32): 11306-11313 (2010).
Williams et al.: AP-2gamma promotes proliferation in breast tumour cells by direct repression of the CDKNIA gene. EMBO J. 28(22): 3591-3601 (2009).
Wong et al.: Expression of the fusogenic p14 FAST protein from a replication-defective adenovirus vector does not provide a therapeutic benefit in an immunocompetent mouse model of cancer. Cancer Gene Ther. 23(10): 355-364 (2016).
Wong et al.: Lipid, sugar and liposaccharide based delivery systems. Curr Med Chem. 8(9): 1123-1136 (2001).
Wu et al.: Sp1 is Essential for p16INK4a Expression in Human Diploid Fibroblasts during Senescence. PLoS ONE 2(1):e164, 1-8 (2007).
Xie et al.: A mini review of biodegradable calcium phosphate nanoparticles for gene delivery. Curr Pharm Biotechnol. 14(10): 918-925 (2013).
Xie et al.: Adenovirus-mediated tissue-targeted expression of a caspase-9-based artificial death switch for the treatment of prostate cancer. Cancer Res. 61(18): 6795-6804 (2001).
Yi et al.: SIRT1 and p53, effect on cancer, senescence and beyond. Biochim Biophys Acta. 1804(8): 1684-1689 (2010).
Zhang et al.: A powerful cooperative interaction between a fusogenic peptide and lipofectamine for the enhancement of receptor-targeted, non-viral gene delivery via integrin receptors. J Gene Med. 3(6): 560-568 (2001).
Zhang et al.: Adsorption of DNA oligonucleotides by titanium dioxide nanoparticles. Langmuir. 30(3): 839-845 (2014).
Zhao et al., An EBF3-Mediated Transcriptional Program That Induces Cell Cycle Arrest and Apoptosis. Cancer Research 66(19): 9445-9452 (2006).
Zhou et al.: Antigen Delivery to Mucosa-associated Lymphoid Tissues Using Liposomes as a Carrier. Bioscience Reports. 22(2):355-369. Apr. 2002.
Zhou et al.: Current methods for loading dendritic cells with tumor antigen for the induction of antitumor immunity. J Immunother. 25(4): 289-303 (2002).
Zhou et al.: Liposome-mediated cytoplasmic delivery of proteins: an effective means of accessing the MHC class I-restricted antigen presentation pathway. Immunomethods. 4(3): 229-235 (1994).
BAAR, Targeted Apoptosis of Senescent Cells Restores Tissue Homeostasis in Response to Chemotoxicity and Aging, Cell, 2017, p. 132, v. 169 [NPL_BAAR].
Nov. 15, 2018 Non-Final Office Action U.S. Appl. No. 14/862,161.
Jan. 19, 2017 Restriction Requirement U.S. Appl. No. 14/862,161.
Mar. 15, 2018 Final Office Action U.S. Appl. No. 14/862,161.
Apr. 11, 2022 Notice of Allowance U.S. Appl. No. 16/476,865.
Jun. 17, 2019 Final Office Action U.S. Appl. No. 14/862,161.
Jul. 14, 2017 Non-Final Office Action U.S. Appl. No. 14/862,161.
Aug. 8, 2022 Notice of Allowance U.S. Appl. No. 16/476,865.
Bayle, J.H., et al., "Rapamycin Analogs with Differential Binding Specificity Permit Orthogonal Control of Protein Activity", Chem. Bio, 2006, 13:99-107.
Glinka, E., "Eukaryotic expression vectors bearing genes encoding cytotoxic proteins for cancer gene therapy", Plasmid, 68(2), pp. 69-85, May 18, 2012 (May 18, 2012).
Li, S. et al., "In vivo gene transfer via intravenous administration of cationic lipid-protamine-DNA (LPD) complexes", Gene Therapy, 4, pp. 891-900, Sep. 1, 1997 (Jan. 9, 1997).
PCT/US2020/016679 International Preliminary Report on Patentability dated Aug. 10, 2021.
PCT/US2020/016679 International Search Report and Written Opinion dated Oct. 5, 2020.
Stavrou, M., et al., "A Rapamycin-Activated Caspase 9-Based Suicide Gene", Molecular Therapy, 2018, vol. 26, No. 5, pp. 1266-1276.
Donehower, L. et al., "The tumor suppressor p53", Biochimica et Biophysica Acta, 1993, vol. 1155, No. 2, pp. 181-205.
Wang, S. et al., "p73 or p53 Directly Regulates Human p53 Transcription to Maintain Cell Cycle Checkpoints", Cancer Res, 2006 vol. 66, No. 14, pp. 6982-6989.

* cited by examiner

FIG. 3

| Company | Technology | Type | MTD | Clinical Studies |
|---|---|---|---|---|
| Merck | Liposomal DOTAP siRNA | CL | 0.45 mg/kg | Phase I (various, alternative dosing, 3x/day) |
| Calando/Arrowhead | RONDEL lipopolymer | CL | 0.81 mg/kg | Phase I (CALAA-01) |
| BIND | PEG-PEI Cholesterol Lipopolymer | CL | Max mg/kg | Phase I (BIND-014) (blockade by bladder) |
| Marina Biotech ProNAi | Smarticles (amphoteric liposomes) | CCL | 3.3 mg/kg | Phase I (PNT2258) |
| Marina Biotech | DiLA² | CCL | 1 mg/kg | Phase I |
| Arbutus (Tekmira) Alnylam | SNALP | CCL | 0.9 mg/kg | 7 programs in Phase I and II |
| MD Anderson (Anil Sood) | DOPC liposomes | NL | >10 mg/kg | Phase I (siRNA-DOPC-EphA2) |
| innovaSCREEN | Fusogenix LNPs | NL | >15 mg/kg | Estimated from rat toxicity study |

Homodimerizer
AP1903

Homodimerizer
AP20187

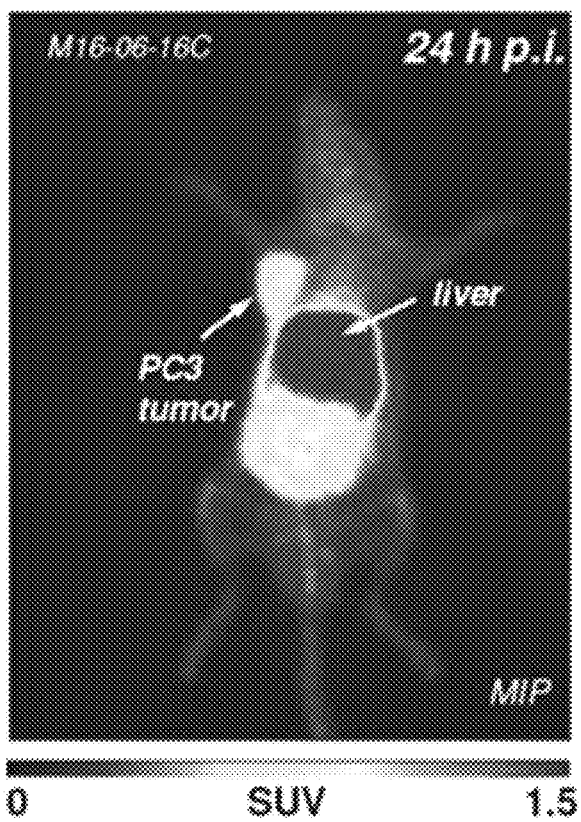 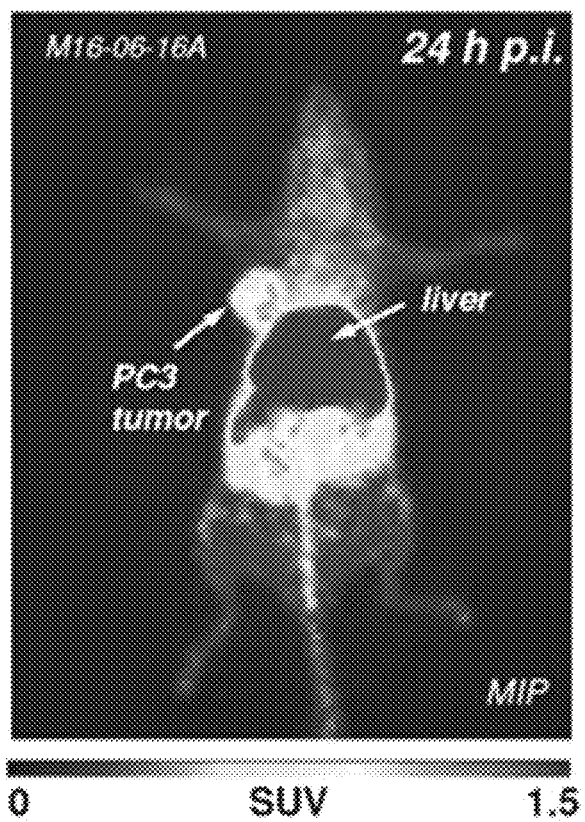
FIG. 7A  FIG. 7B p16-targeting construct
(aging/senescence)

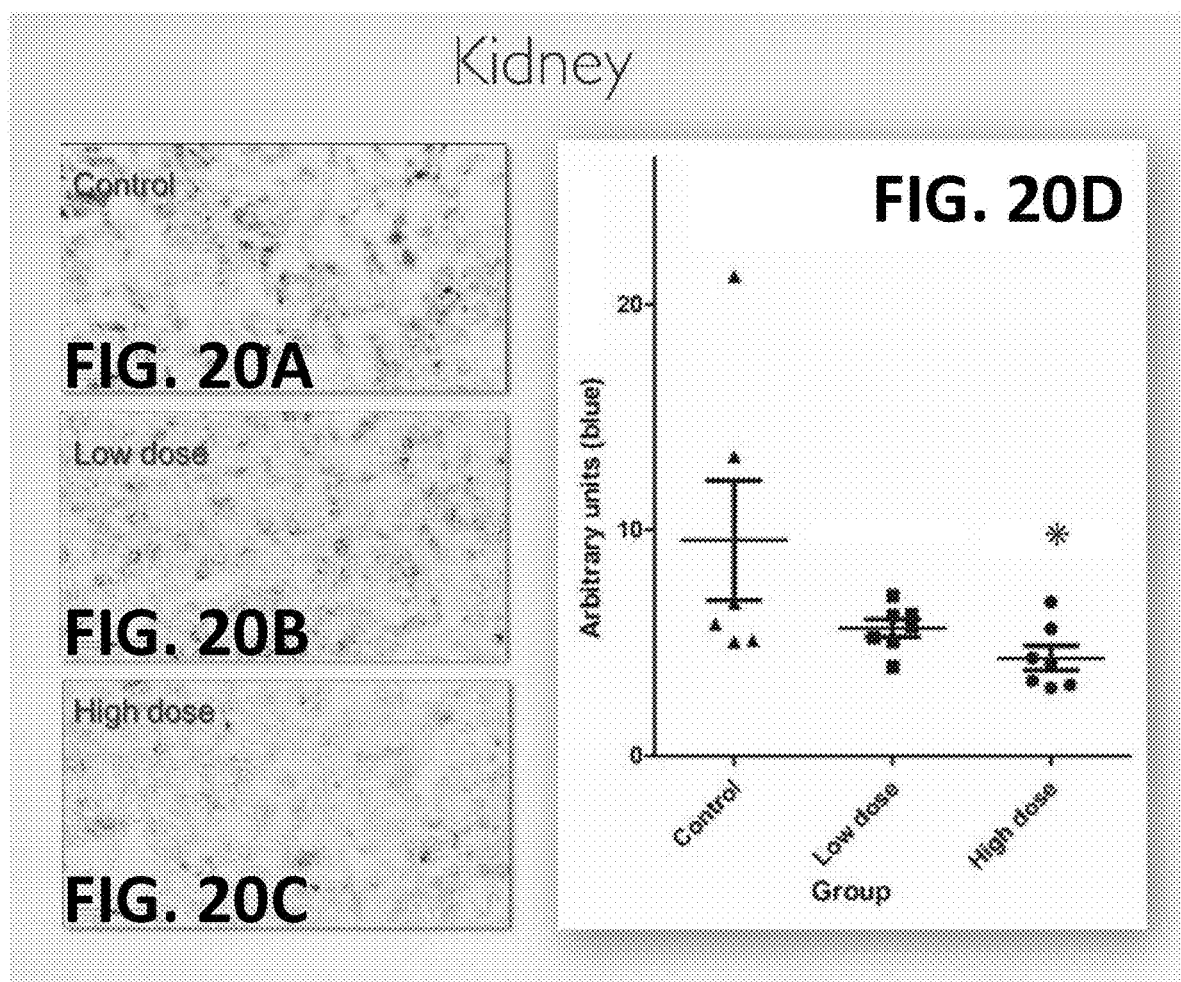

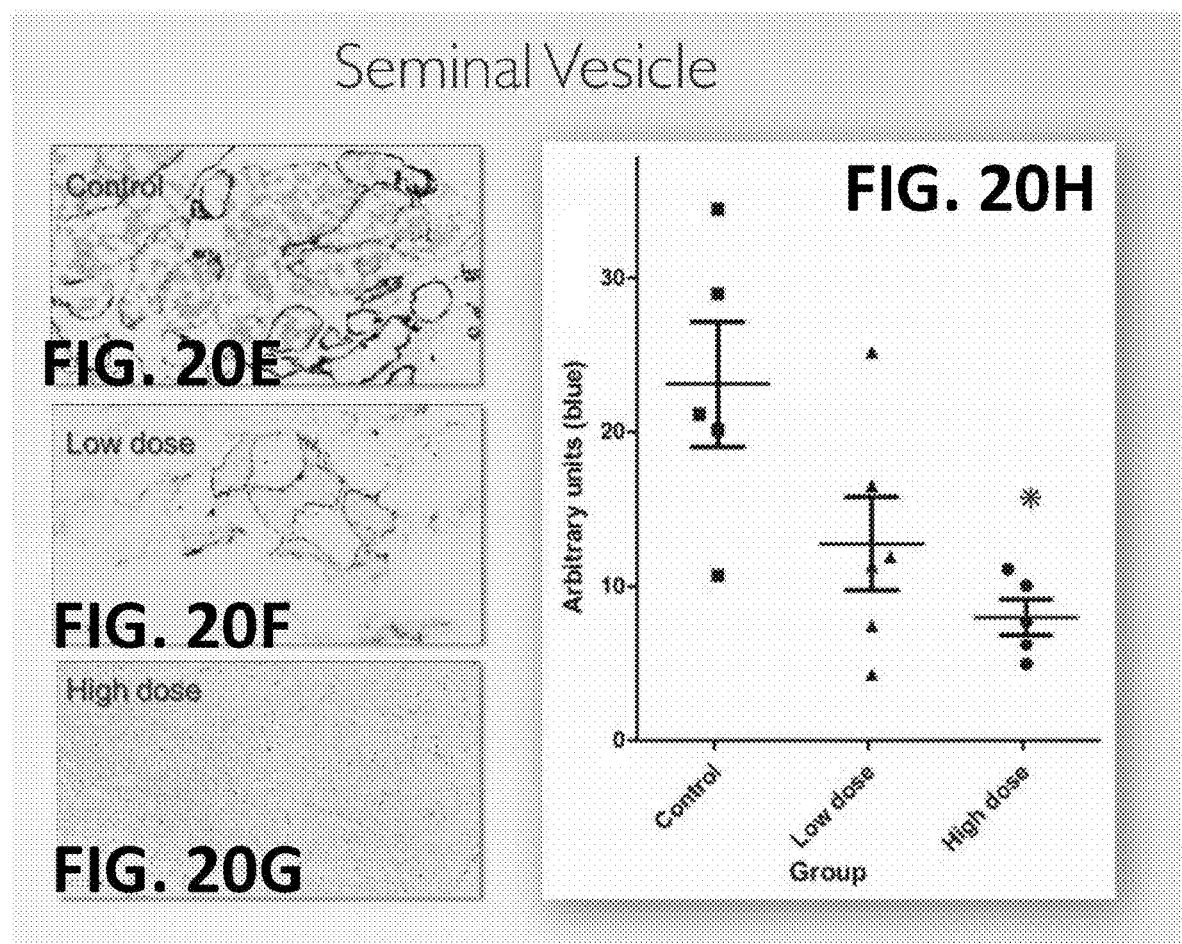

p53-targeting construct
(oncology)

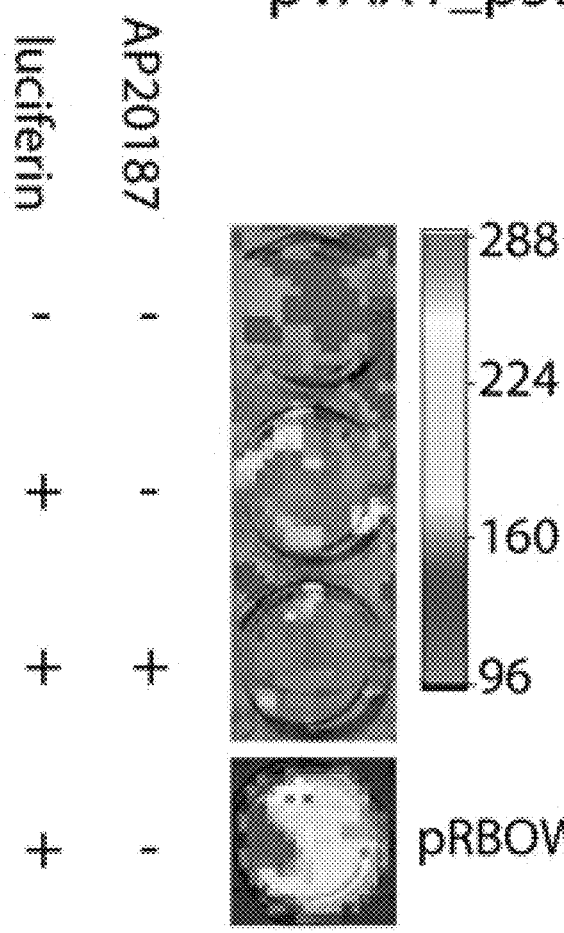
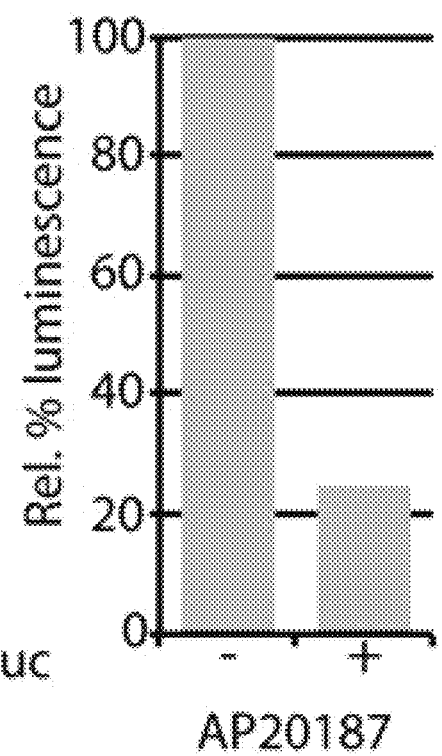
FIG. 43A  FIG. 43B

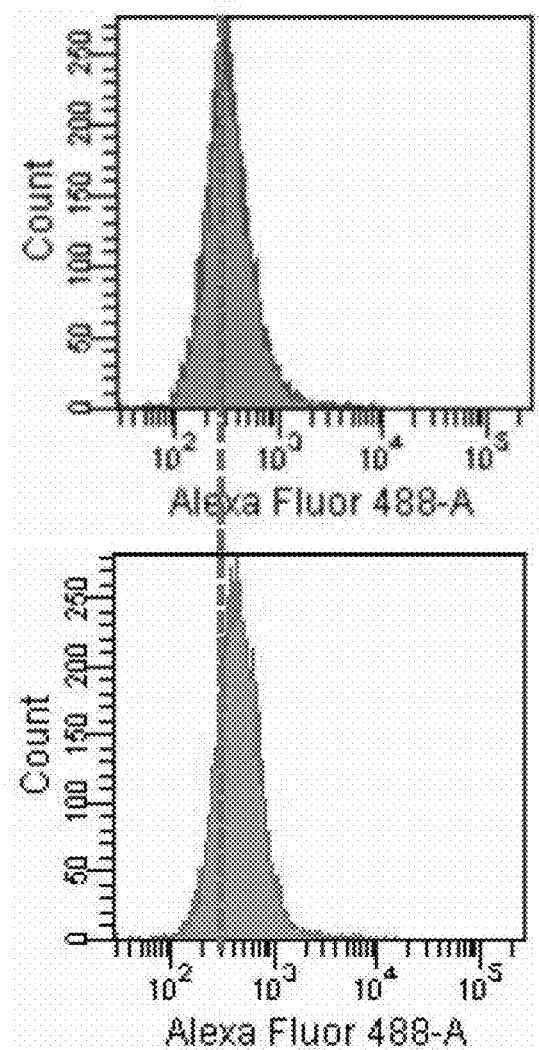
FIG. 44A pVax-p53 alone
FIG. 44B pVax-p53 + AP20187

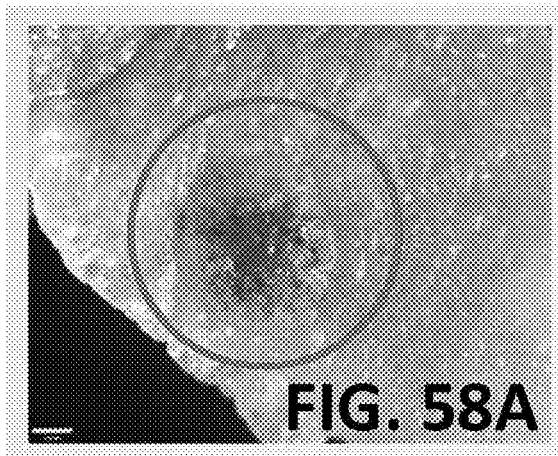
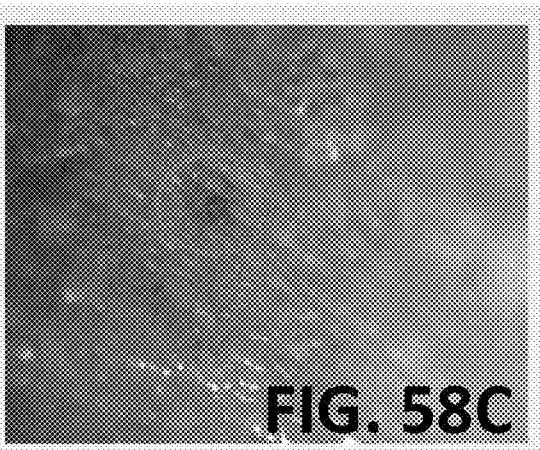
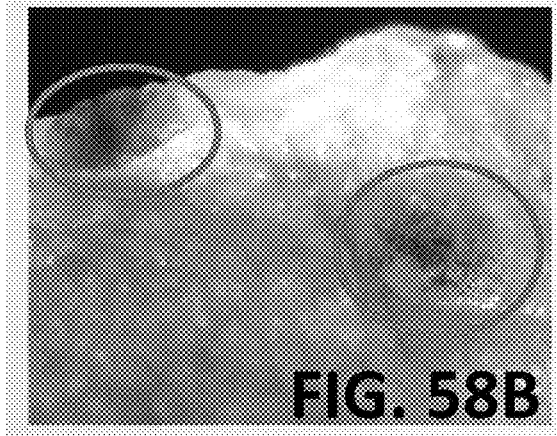
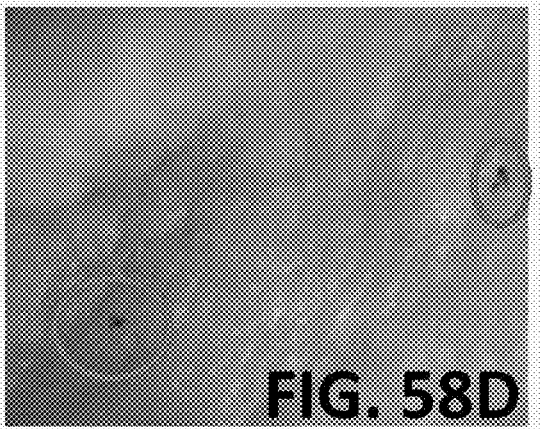
Control LNP      P53-iCasp9 LNP

FUSOGENIC LIPID NANOPARTICLES FOR TARGET CELL-SPECIFIC PRODUCTION OF A THERAPEUTIC PROTEIN

CROSS-REFERENCE TO RELATED APPLICATIONS

This U.S. non-provisional patent application claims the benefit of U.S. Provisional Patent Application 62/659,676, filed Apr. 18, 2018, and U.S. Provisional Patent Application 62/821,084, filed Mar. 20, 2019. The entirety of the 62/659,676 and 62/821,084 Provisional Patent Applications are incorporated by reference herein.

SEQUENCE LISTING

The present application includes a Sequence Listing in electronic format as a txt file entitled "OSIN-01-0303USU1_2019-04-18_SEQLIST_ST25," which was created on Apr. 18, 2019 and which has a size of 68,831 bytes. The present application includes a Sequence Listing as a PDF file also entitled "OSIN-01-0303USU1_2019-04-18_SEQLIST_ST25" and created on Apr. 18, 2019. The contents of the txt and PDF files entitled "OSIN-01-0303USU1_2019-04-18_SEQLIST_ST25" are identical and are incorporated by reference herein.

BACKGROUND OF THE DISCLOSURE

Technical Field

The present disclosure relates, generally, to the field of medicine, including the treatment of disease, promotion of longevity, anti-aging, and health extension. More specifically, this disclosure concerns compositions and methods for reducing the growth and/or survival of cells that are associated with aging, disease, and other conditions. Provided are expression constructs for target cell specific expression of therapeutic proteins, which constructs exploit unique intracellular functionality, including transcription regulatory functionality, that is present within a target cell but is either absent from or substantially reduced in a normal, non-target cell. Such expression constructs are used in systems that include a vector for the delivery of a nucleic acid to a target cell, which vectors may comprise, but do not necessarily require, a fusogenic lipid nanoparticle and, optionally, a targeting moiety for enhancing the delivery of an expression construct to a target cell.

Description of the Related Art

Cancer cells, senescent cells, and other cells having an undesirable phenotype can accumulate over the course of a person's life and, without appropriate treatment, such cells can contribute to or even cause a person's morbidity and, ultimately, mortality.

The role of senescent cells in disease and the potential benefits of eliminating senescent cells has been discussed in scientific publications such as Baker et al. Nature 479:232-6 (2011). Systems and methods have been described that purport to address the problem of accumulating senescent cells. For example, Grigg, PCT Patent Publication No. WO 1992/009298, describes a system for preventing or reversing cell senescence with chemical compounds similar to carnosine and Gruber, U.S. Patent Publication No. 2012/0183534, describes systems for killing senescent cells with radiation, ultrasound, toxins, antibodies, and antibody-toxin conjugates, which systems include senescent cell-surface proteins for use in targeting of therapeutic molecules.

The selective killing of senescent cells has proven impractical in mammals other than genetically-modified laboratory research animals. Currently-available systems and methods exhibit substantial systemic toxicity, inadequate targeting of cells of interest, and a lack of adequate safety features. These shortcomings in the art have hampered the development of safe and effective therapies for the treatment of certain cancers and for slowing the effects of aging.

SUMMARY OF THE DISCLOSURE

The present disclosure is based upon the discovery that a cell, such as a cell that is associated with aging, a disease, and/or another condition (collectively, "a target cell"), can be selectively killed, in a target cell-specific manner, without the need for the targeted delivery of a therapeutic agent to the target cell. The expression constructs, systems, and methods described herein overcome safety and efficacy concerns that are associated with existing technologies that employ targeted delivery of therapeutic agents, which technologies have yielded limited therapeutic benefit to patients in need thereof.

As described herein, the present disclosure provides expression cassettes, systems, and methods for inducing, in a target cell-specific manner, the expression of a nucleic acid that encodes a protein that, when produced in a cell, reduces or eliminates the growth and/or survival of a cell, such as a cell that is associated with aging, disease, and/or other condition.

The expression cassettes, systems, and methods described herein exploit the unique transcription regulatory machinery that is intrinsic to certain cells that are associated with age (such as senescent cells), disease (such as cancers, infectious diseases, and bacterial diseases), as well as other conditions, which transcription regulatory machinery is not operative, or exhibits substantially reduced activity, in a normal cell (i.e., "a non-target cell") that is not associated with aging, disease, or other condition.

The presently-disclosed expression cassettes, systems, and methods achieve a high degree of target cell specificity as a consequence of intracellular functionality that is provided by, and unique to, the target cell, which intracellular functionality is not provided by, or is substantially reduced in, a normal, non-target cell. Thus, the presently disclosed systems and methods employ nucleic acid delivery vectors that are non-specific with respect to the cell type to which the nucleic acid is delivered and, indeed, the vectors described herein need not be configured for target cell-specific delivery of a nucleic acid (e.g., an expression cassette) to achieve target cell specificity and, consequently, the therapeutically effective reduction, prevention, and/or elimination in the growth and/or survival of a target cell.

Within certain embodiments, the present disclosure provides expression constructs for the targeted production of therapeutic proteins within a target cell, such as a cell that is associated with aging, disease, and/or another condition. The expression constructs disclosed herein comprise: (1) a transcriptional promoter that is activated in response to one or more factors each of which is produced within a target cell and (2) a nucleic acid that is operably linked to and under regulatory control of the transcriptional promoter, wherein the nucleic acid encodes a therapeutic protein that can reduce, prevent, and/or eliminate the growth and/or survival of a cell, including the target cell.

Within certain aspects of these embodiments, the transcriptional promoter is activated in a target cell that is associated with a disease, condition, or age but is not activated in a normal mammalian cell that is not associated with the disease, condition, or aging. Target cell-specific transcriptional activation is achieved by the action of one or more factors that are produced in the target cell but not produced in a normal mammalian cell, including a normal human cell, such as normal skeletal myoblasts, normal adipose cells, normal cells of the eye, normal brain cells, normal liver cells, normal colon cells, normal lung cells, normal pancreas cells, and/or normal heart cells, which normal cells are not associated with the disease, condition, or aging.

Within other aspects of these embodiments, the target cell can be a mammalian cell or a bacterial cell. Target mammalian cells can include human cells such as senescent cells, cancer cells, precancerous cells, dysplastic cells, and cells that are infected with an infectious agent.

In certain aspects of these embodiments wherein the human target cell is a senescent cell, the transcriptional promoter can include a transcriptional promoter, such as the p16INK4a/CDKN2A transcriptional promoter, which is responsive to activation by transcription factors such as SP1, ETS1, and/or ETS2. In other aspects of these embodiments wherein the human target cell is a senescent cell, the transcriptional promoter can include a transcriptional promoter, such as the p21/CDKN1A transcriptional promoter, which is responsive to p53/TP53.

In a target cell, such as a senescent cell, transcriptional promoters induce the expression of a nucleic acid that encodes a therapeutic protein such as, for example, Casp3, Casp8, Casp9, BAX, DFF40, HSV-TK, and cytosine deaminase as well as inducible and self-activating variants of Casp3, Casp8, Casp9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include the p21$^{cip1/waf1}$ promoter, the p27$^{kip1}$ promoter, the p57$^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein such as, for example, Casp3, Casp8, Casp9, BAX, DFF40, HSV-TK, and cytosine deaminase as well as inducible and self-activating variants of Casp3, Casp8, Casp9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

In still further aspects of these embodiments wherein the target cell is a human cell that is infected with an infectious agent, such as a virus, including, for example, a herpes virus, a polio virus, a hepatitis virus, a retrovirus virus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein such as, for example, Casp3, Casp8, Casp9, BAX, DFF40, HSV-TK, and cytosine deaminase as well as inducible and self-activating variants of Casp3, Casp8, Casp9, BAX, DFF40, HSV-TK, and cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

Within other embodiments, the present disclosure provides systems for the targeted production of a therapeutic protein within a target cell. These systems comprise a vector that is capable of delivering a nucleic acid to a cell, including a target cell as well as a non-target cell, wherein the vector comprises an expression construct for the targeted production of a therapeutic protein within a target cell (e.g., a cell that is associated with age, disease, or other condition) but not within a non-target cell, wherein the expression construct comprises a transcriptional promoter that is activated in response to one or more factors each of which is produced within said target cell; and a nucleic acid that is operably linked to and under regulatory control of the transcriptional promoter, wherein the nucleic acid encodes a therapeutic protein that can reduce, prevent, and/or eliminate the growth and/or survival of a cell in which it is produced, including a target cell.

Within certain aspects of these embodiments, formulations and systems include lipid nanoparticle (LNP) formulations and systems wherein an LPN encapsulates a polynucleotide construct (e.g., a plasmid DNA) comprising a coding region for a pro-apoptotic protein, such as a caspase protein, and wherein the coding region is under the regulatory control of a target cell-specific transcriptional promoter, such as a senescent cell-specific transcriptional promoter or a cancer cell-specific transcriptional promoter. Exemplary cell-specific transcriptional promoters include p16, p22, p53. Exemplary coding regions for pro-apoptotic proteins include coding regions for Casp3, Casp8, Casp9, BAX, DFF40, HSV-TK, and cytosine deaminase proteins. Pro-apoptotic proteins include inducible Casp3, Casp8, Casp9, BAX, DFF40, HSV-TK, and cytosine deaminase proteins and self-activating Casp3, Casp8, Casp9, BAX, DFF40, HSV-TK, and cytosine deaminase proteins, which are exemplified herein by an inducible Caspase 9 (iCasp9) or a self-activating Caspase 9 (saCasp9).

Inducible pro-apoptotic proteins, including iCasp9 proteins, can include a dimerization domain, such as an FKBP or FK506 binding protein domain, that binds to a chemical inducer of dimerization (CID), such as AP1903 or AP20187. Clackson, *Proc Natl Acad Sci USA*. 95:10437-10442 (1998). Inducible Caspase 9 (iCasp9; Ariad, Erie, Pa.) may be activated in the presence of AP1903. U.S. Pat. No. 5,869,337 and Straathof, *Blood* 105:4247-4254 (2005). Exemplary human genes encoding FKBP domains include AIP, AIPL1, FKBP1A, FKBP1B, FKBP2, FKBP3, FHBP5, FKBP6, FKBP7, FKBP8, FKBP8, FKBP9L, FKBP10, FKBP11, FKBP14, FKBP15, FKBP52, and L00541473.

Within other aspects of these embodiments, lipid nanoparticles (LNP) are fusogenic lipid nanoparticles, such as fusogenic lipid nanoparticles comprising a fusogenic protein, such as a fusogenic p14 FAST fusion protein from reptilian reovirus to catalyze lipid mixing between the LNP and target cell plasma membrane. Suitable fusogenic proteins are described in PCT Patent Publication Nos. WO2012/040825A1 and WO2002/044206A2, Lau, *Biophys. J.* 86:272 (2004), Nesbitt, Master of Science Thesis (2012), Zijlstra, *AACR* (2017), Mrlouah, *PAACRAM* 77(13Suppl): Abst 5143 (2017), Krabbe, *Cancers* 10:216 (2018), Sanchez-Garcia, *ChemComm* 53:4565 (2017), Clancy, *J Virology* 83(7):2941 (2009), Sudo, *J Control Release* 255:1 (2017), Wong, *Cancer Gene Therapy* 23:355 (2016), and Corcoran, *JBC* 281(42):31778 (2006) and are exemplified by the P14 and P14e15 proteins having the amino acid sequences presented in Table 1.

TABLE 1

| Fusogenic Protein Sequences | | |
|---|---|---|
| P14 | MGSGPSNFVNHAPGEAIVTGLEKGADKVAGTISHTIWEVIAG LVALLTFLAFGFWLFKYLQKRRERRQLTEFQKRYLRNSYR LSEIQRPISQHEYEDPYEPPSRRKPPPPPYSTYVNIDNVSAI* | SEQ ID NO: 16 |
| P14e15 | MGSGPSNFVNHAPGEAIVTGLEKGADKVAGTISHTIWEVIAG LVALLTFLAFGFWLFKYLQWYNRKSKNKKRKEQIREQIELG LLSYGAGVASLPLLNVIAHNPGSVISATPIYKGPCTGVPNSRL LQITSGTAEENTRILNHDGRNPDGSINV* | SEQ ID NO: 17 |

Contacting a cell expressing an iCasp9 protein with a CID facilitates the dimerization of the iCasp9 protein, which triggers apoptosis in a target cell. AP1903 has been used in humans multiple times, its intravenous safety has been confirmed, and its pharmacokinetics determined. Iuliucci, *J Clin Pharmacol* 41(8):870-9 (2001) and Di Stasi, *N Engl J Med* 365:1673-83 (2011). iCasp9+AP1903 were used successfully in humans to treat GvHD after allogeneic T cell transplant. Di Stasi, *N Engl J Med* 365:1673-83 (2011).

Within certain embodiments, a polynucleotide encoding a self-activating caspase, such as a self-activating Caspase 9 (saCasp9), may be employed wherein expression of the caspase polynucleotide is under the regulatory control of a factor that is active in a target cell population, such as a senescent cell population or a cancer cell population. Self-activating caspases activate in the absence of a chemical inducer of dimerization (CID). Cells expressing self-activating caspases, such as saCasp9, apoptose almost immediately. It will be appreciated by those of skill in the art that such self-activating caspases may be advantageously employed for the induction of apoptosis in a rapidly dividing cell, such as a rapidly dividing tumor cell, where an inducible caspase protein would be diluted out before administration of a CID. Moreover, because cell death with a self-activating caspase occurs over a longer period of time as compared to an inducible caspase, the risk of tumor lysis syndrome is reduced with a self-activating caspase.

Formulations comprising a plasmid DNA encapsulated with a LNP formulation are non-toxic and non-immunogenic in animals at doses of >15 mg/kg and exhibit an efficiency in excess of 80× greater than that achievable with neutral lipid formulations and 2-5× greater than that achievable with cationic lipid formulations. LNP cargo is deposited directly into the cytoplasm thereby bypassing the endocytic pathway.

Within further aspect of these embodiments, the system further comprises one or more safety features that permit additional control over the expression of the nucleic acid within the expression construct or the functionality of a therapeutic protein encoded by the nucleic acid such as, for example, by requiring the contacting of a target cell with a chemical or biological compound that, in addition to the intracellular factor that promotes transcriptional activation of the promoter within the expression construct or promotes the functionality of the therapeutic protein, such as by promoting the dimerization of as well as inducible variants of Casp3, Casp8, Casp9, BAX, DFF40, HSV-TK, and cytosine deaminase.

A further safety element that may be employed in the expression constructs and systems of the present disclosure includes a tamoxifen-inducible Cre construct using Life Technologies Gateway Cloning Vector System employing a pDEST26 plasmid for mammalian expression. For example, a fusion protein of Cre and estrogen receptor can be constitutively expressed and induced upon the addition of tamoxifen, which permits activated Cre to re-orient the transcriptional promoter, thereby expressing the therapeutic protein.

Within yet other aspects of these embodiments, the system may further comprise a nucleic acid that encodes a detectable marker, such as a bioluminescent marker, thereby allowing the identification of cells that express the therapeutic protein and, in the case of an inducible therapeutic protein such as an inducible Casp3, Casp8, Casp9, will be killed by the administration of a compound that promotes activity of the therapeutic protein, such as by inducing the dimerization of an inducible Casp3, Casp8, Casp9.

Within further embodiments, the present disclosure provides methods for reducing, preventing, and/or eliminating the growth of a target cell, which methods comprise contacting a target cell with a system for the targeted production of a therapeutic protein within a target cell, wherein the system comprises a vector that is capable of delivering a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises: (a) a transcriptional promoter that is activated in response to one or more factors each of which factors is produced within a target cell and (b) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell.

Within still further embodiments, the present disclosure provides methods for the treatment of an aging human or a human that is afflicted with a disease or another condition, wherein the aging, disease, or other condition is associated with a target cell within the human, the methods comprising administering to the human a system for the targeted production of a therapeutic protein within a target cell, wherein the system comprises a vector that is capable of delivering a nucleic acid to a cell, wherein the vector comprises an expression construct for the targeted production of a therapeutic protein within a target cell (e.g., a cell that is associated with age, disease, or other condition) but not within a non-target cell, wherein the expression construct comprises: (a) a transcriptional promoter that is activated in response to one or more factors each of which factors is produced within a target cell and (b) a nucleic acid that is operably linked to and under regulatory control of the transcriptional promoter, wherein the nucleic acid encodes a therapeutic protein that is produced upon expression of the nucleic acid and wherein production of the therapeutic protein in the target cell (i.e., the cell that is associated with age, disease, or other condition) reduces, prevents, and/or eliminates growth and/or survival of the target cell thereby slowing aging in the human and/or slowing, reversing, and/or eliminating the disease or condition in the human.

Within further embodiments, the present disclosure provides lipid nanoparticle (LNP) formulation for the targeted production of a therapeutic protein within a target cell, which LNP formulation comprise: (a) a lipid nanoparticle vector for the non-specific delivery of a nucleic acid to mammalian cells, which mammalian cells include both target cells or non-target cells, wherein said lipid nanoparticle includes one or more lipid(s) and one or more fusogenic protein(s), and (b) an expression construct for the preferential production of a therapeutic protein within a target cell.

LNP formulations according to certain aspects of these embodiments include one or more lipid(s) at a concentration ranging from 1 mM to 100 mM, or from 5 mM to 50 mM, or from 10 mM to 30 mM, or from 15 mM to 25 mM. LNP formulations exemplified herein include one or more lipid(s) at a concentration of about 20 mM.

Within certain illustrative LNP formulations, one or more lipid(s) is selected from 1,2-dioleoyl-3-dimethyl ammonium-propane (DODAP), 1,2-dioleoyl-3-trimethylammonium-propane (DOTAP), 1,2-dioleoyl-sn-glycero-3-phosphoethanolamine (DOPE), Cholesterol, and 1,2-dimyristoyl-rac-glycero-3-methoxypolyethylene glycol (DMG-PEG). LNP formulations may two or more lipids selected from the group consisting of DODAP, DOTAP, DOPE, Cholesterol, and DMG-PEG.

Exemplified herein are LNP formulations including DODAP, DOTAP, DOPE, Cholesterol, and DMG-PEG at a molar ratio of 35-55 mole % DODAP:10-20 mole % DOTAP:22.5-37.5 mole % DOPE:4-8 mole % Cholesterol:3-5 mole % DMG-PEG; or at a molar ratio of about 45 mole % DODAP:about 15 mole % DOTAP:about 30 mole % DOPE:about 6 mole % Cholesterol:about 4 mole % DMG-PEG. Within certain aspects, the LNP formulations include DODAP, DOTAP, DOPE, Cholesterol, and DMG-PEG at a molar ratio of 45 mole % DODAP:15 mole % DOTAP:30 mole % DOPE:6 mole % Cholesterol:4 mole % DMG-PEG.

LNP formulations according to other aspects of these embodiments include one or more fusogenic protein(s) at a concentration ranging from 0.5 µM to 20 or from 1 µM to 10 µM, or from 3 µM to 4 µM. Exemplified herein are LNP formulations wherein fusogenic protein(s) are present at a concentration of 3.5 µM. Exemplary, suitable fusogenic protein(s) include the p14 fusogenic protein (SEQ ID NO: 16) and a the p14e15 fusogenic protein (SEQ ID NO: 17).

Within additional aspects of these embodiments, LNP formulations include expression constructs comprising (i) a transcriptional promoter that is activated in response to one or more factors that are preferentially produced within said target cells as compared to said non-target cells and (ii) a nucleic acid that is operably linked to and under regulatory control of said transcriptional promoter, wherein said nucleic acid encodes a therapeutic protein that can reduce, prevent, and/or eliminate the growth and/or survival of mammalian cells, including both target cells and non-target cells and wherein said therapeutic protein is produced within said target cells but is not produced in said non-target cells.

Exemplified herein are LNP formulations including expression constructs at a concentration ranging from 20 µg/mL to 1.5 mg/mL, of from 100 µg/mL to 500 µg/mL, or at a concentration of 250 µg/mL.

A suitable exemplary LNP formulation includes the following: for each 1 mL of LNP, the lipid concentration is 20 mM, the DNA content is 250 µg, and the fusogenic protein (e.g., p14 or p14e15) is at 3.5 µM wherein the lipid formulation comprises DODAP:DOTAP:DOPE:Cholesterol:DMG-PEG at a mole % ratio of 45:15:30:6:4, respectively.

Within still further aspects of these embodiments, LNP formulations include expression constructs having a transcriptional promoter selected from a p16 transcriptional promoter, a p21 transcriptional promoter, and a p53 transcriptional promoter, and include transcriptional promoters that are responsive to a factor selected from SP1, ETS1, ETS2, and p53/TP53. Exemplified herein are LNP formulations wherein said transcriptional promoter is a p16INK4a/CDKN2A transcriptional promoter or a p21/CDKN1A transcriptional promoter.

Within related aspects of these embodiments, LNP formulations include expression constructs having a transcriptional promoter that is responsive to a factor selected from EBF3, O/E-1, Pax-5, E2A, p53, VP16, MLL, HSF1, NF-IL6, NFAT1, AP-1, AP-2, HOX, E2F3, and/or NF-κB. Exemplified herein are LNP formulations wherein said transcriptional promoter is a $p21^{cip1/waf1}$ promoter, the $p27^{kip1}$ promoter, the $p57^{kip2}$ promoter, the TdT promoter, the Rag-1 promoter, the B29 promoter, the Blk promoter, the CD19 promoter, the BLNK promoter, and the λ5 promoter.

Within other related aspects of these embodiments, LNP formulations include expression constructs that include a nucleic acid that encodes a therapeutic protein, such as a therapeutic protein selected from a caspase (Casp), an inducible caspase (iCasp), a self-activating caspase (saCasp), BAX, DFF40, HSV-TK, and cytosine deaminase. Exemplified herein are LNP formulations that include expression constructs having a nucleic acid that encodes a Casp9, including, for example, an inducible Casp9 (iCasp9) or a self-activating Casp9 (saCasp9).

Other embodiments of the present disclosure provide methods for reducing, preventing, and/or eliminating the growth of a target cell, which comprise contacting a target cell with an LNP formulation having (a) a lipid nanoparticle vector for the non-specific delivery of a nucleic acid to mammalian cells, which mammalian cells include both target cells or non-target cells, wherein said lipid nanoparticle includes one or more lipid(s) and one or more fusogenic protein(s), and (b) an expression construct for the preferential production of a therapeutic protein within a target cell.

Within certain aspects of these embodiments the methods employ LNP formulations comprising (i) a transcriptional promoter that is activated in response to one or more factors that are preferentially produced within target cells as compared to non-target cells and (ii) a nucleic acid that is operably linked to and under regulatory control of the transcriptional promoter, wherein the nucleic acid encodes a therapeutic protein that can reduce, prevent, and/or eliminate the growth and/or survival of mammalian cells, including both target cells and non-target cells and wherein said therapeutic protein is produced within the target cells but is not produced in the non-target cells.

Other embodiments of the present disclosure provide methods for the treatment of a disease or condition in a patient, including a human patient, having a target cell, wherein the method comprises administering to the patient an LNP formulation having (a) a lipid nanoparticle vector for the non-specific delivery of a nucleic acid to mammalian cells, wherein the mammalian cells include both target cells or non-target cells, and wherein the lipid nanoparticle includes one or more lipid(s) and one or more fusogenic protein(s) and (b) an expression construct for the preferential production of a therapeutic protein within a target cell.

Within certain aspects of these embodiments the methods employ LNP formulations comprising (i) a transcriptional promoter that is activated in response to one or more factors that are preferentially produced within target cells as compared to non-target cells and (ii) a nucleic acid that is operably linked to and under regulatory control of the transcriptional promoter, wherein the nucleic acid encodes a therapeutic protein that can reduce, prevent, and/or eliminate the growth and/or survival of mammalian cells, including both target cells and non-target cells and wherein said therapeutic protein is produced within the target cells but is not produced in the non-target cells.

These and other related aspects of the present disclosure will be better understood in light of the following drawings and detailed description, which exemplify certain aspects of the various embodiments.

BRIEF DESCRIPTION OF THE DRAWINGS

FIG. 3 is a table comparing the reported maximum tolerated dose (MTD) for clinical stage lipid-based in vivo delivery technologies. The MTD of >15 mg/kg for fusogenic lipid nanoparticles of the present disclosure was estimated from rat toxicity data.

FIGS. 7A-7B present data obtained in mice that were administered intravenously Fusogenix lipid nanoparticles labeled with $^{64}$Cu-NOTA [1,4,7-triazacyclononane-1,4,7-triacetic acid]. See, Fournier, *EJNMMI Research* 2:8 (2012). $^{64}$Cu was detected via positron emission tomography (PET). FIG. 7A presents PET data obtained from a mouse to which $^{64}$Cu-NOTA-liposomes without protein were administered. FIG. 7B presents PET data obtained from a mouse to which $^{64}$Cu-NOTA-liposome-p14 were administered.

FIG. 10) and of anti-p14 and anti-LNP antibody responses (FIG. 11), which demonstrate the safety and tolerability of exemplary fusogenic lipid nanoparticles utilizing a reptilian reovirus p14

FAST fusion protein (Fusogenix™). As shown, virtually no antibody response was observed in immune competent mice (with and without adjuvant).

Figure 12:
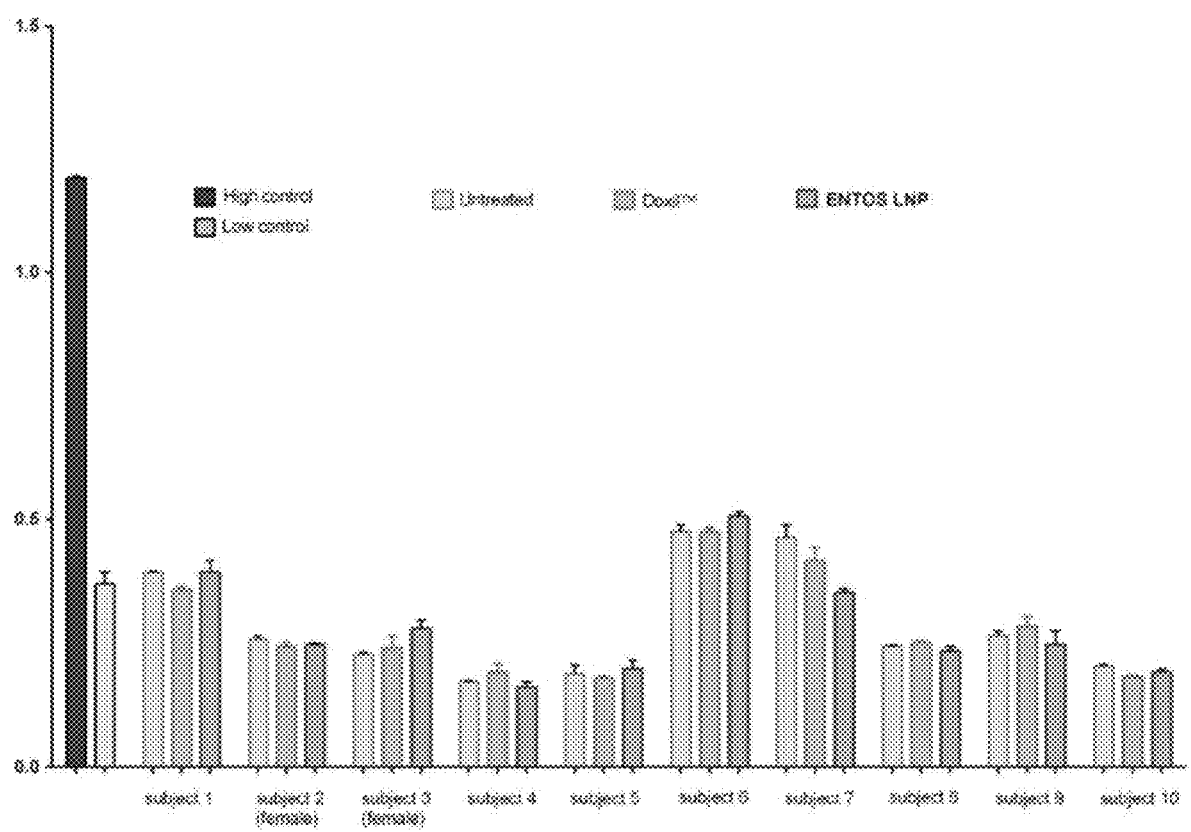
Figure 13:
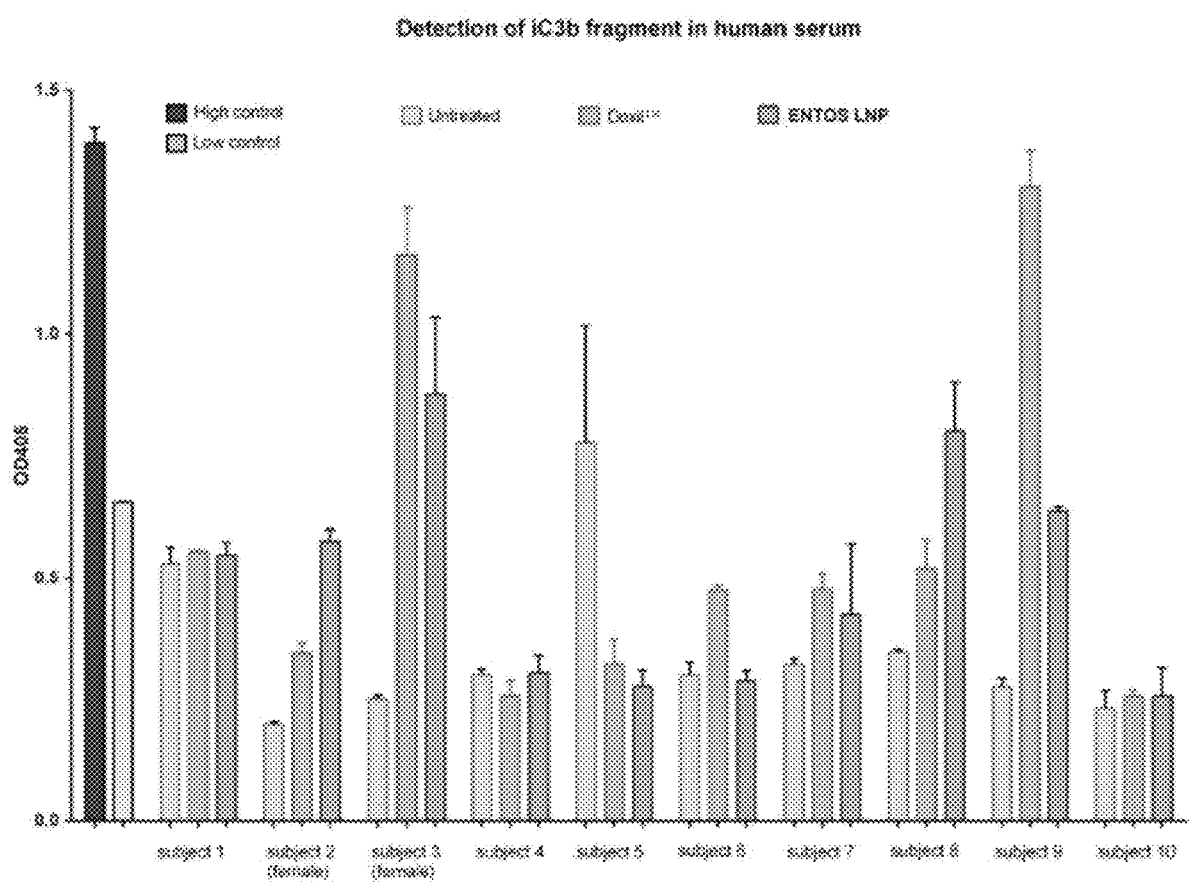

FIGS. 12 and 13 are bar graphs of data from in vitro anti-p14 and anti-LNP antibody neutralization assays showing that lipid nanoparticle formulations according to the present disclosure are non-reactive with C4d (FIG. 12) and less reactive with iC3b (FIG. 13) as compared to Doxil in 8 out of 10 human samples tested for Complement activation-related psuedoallergy (CARPA) using C4d and iC3b complement ELISA assays as described in Szebeni, *Mol Immunol* 61(2):163-73 (2014).

Figure 14:
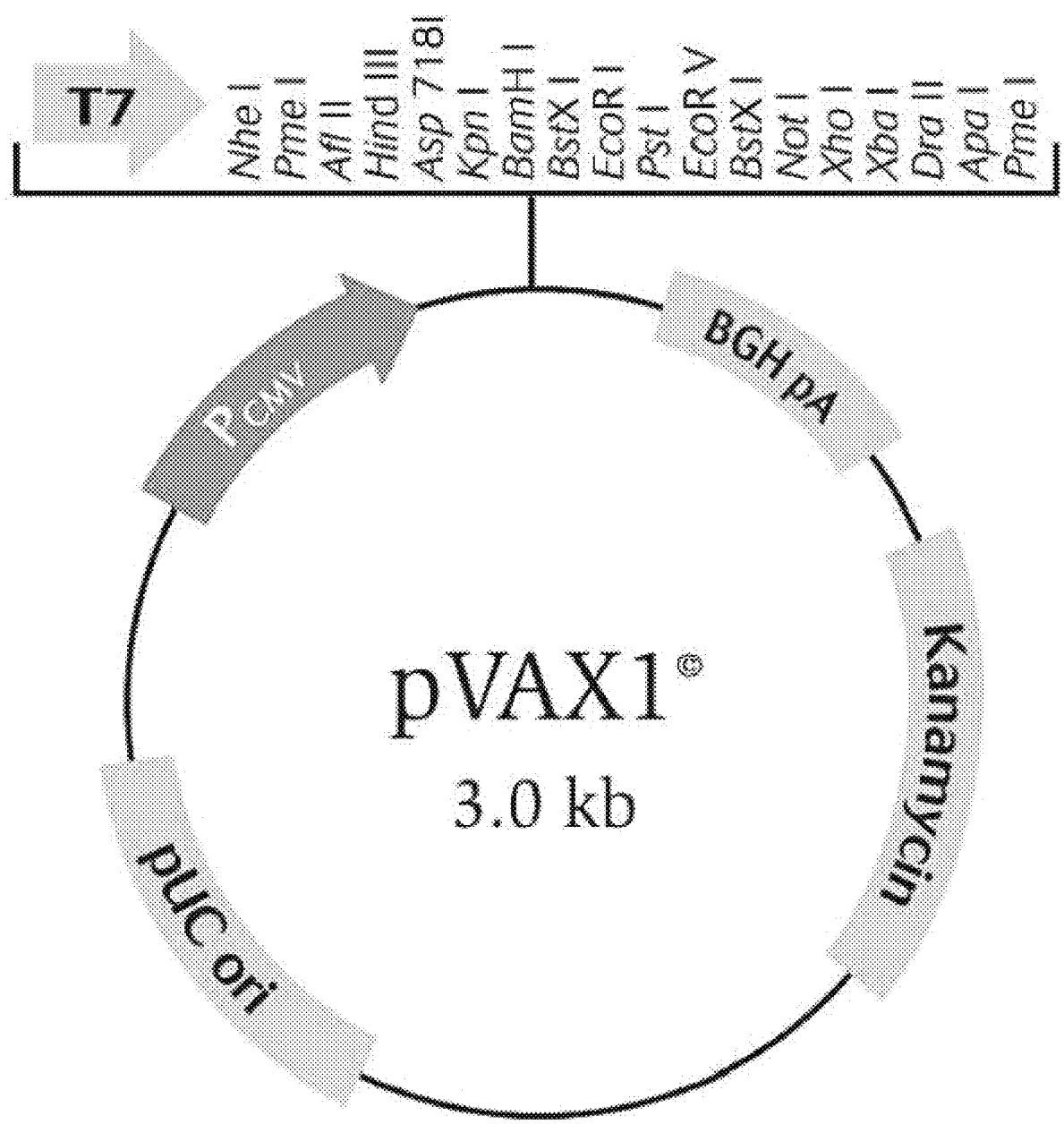

FIG. 14 is a restriction map of the plasmid vector pVAX1™ which is employed in certain aspects of the expression constructs, systems, formulations, and methods of the present disclosure for the target cell-specific production of a therapeutic protein, such as a pro-apoptotic protein, including a caspase protein, such as Caspase 9, as well as inducible and self-activating variants of a pro-apoptotic protein, including inducible and self-activating variants of caspase proteins, such as inducible Caspase 9 (iCasp9) and self-activating Caspase 9 (saCasp9). In certain embodiments, expression constructs and formulations may additionally include a safety element, such as a tamoxifen-inducible Cre construct (e.g., Life Technologies Gateway Cloning Vector System). A fusion protein of Cre and estrogen receptor is constitutively expressed and induced upon the addition of tamoxifen, which permits activated Cre to re-orient the p16-promoter, thereby expressing caspase 9 or inducible/self-activating variant thereof. pVAX1 is commercially available from ThermoFisher Scientific (Waltham, Mass.).

Figure 15:

FIG. 15 is a diagrammatic representation of an exemplary p16-targeting construct for the target cell-specific expression of an inducible Caspase 9 (iCasp9) or a self-activating Caspase 9 (saCasp9) protein in target cells expressing p16, such as target cells that are associated with aging and/or senescence, which p16-targeting construct comprises a p16s transcriptional promoter in operable connection to iCasp9 or saCasp9. An exemplary p16 transcriptional promoter is described in Baker et al., *Nature* 479(7372):232-67 (2011)).

Figure 16:
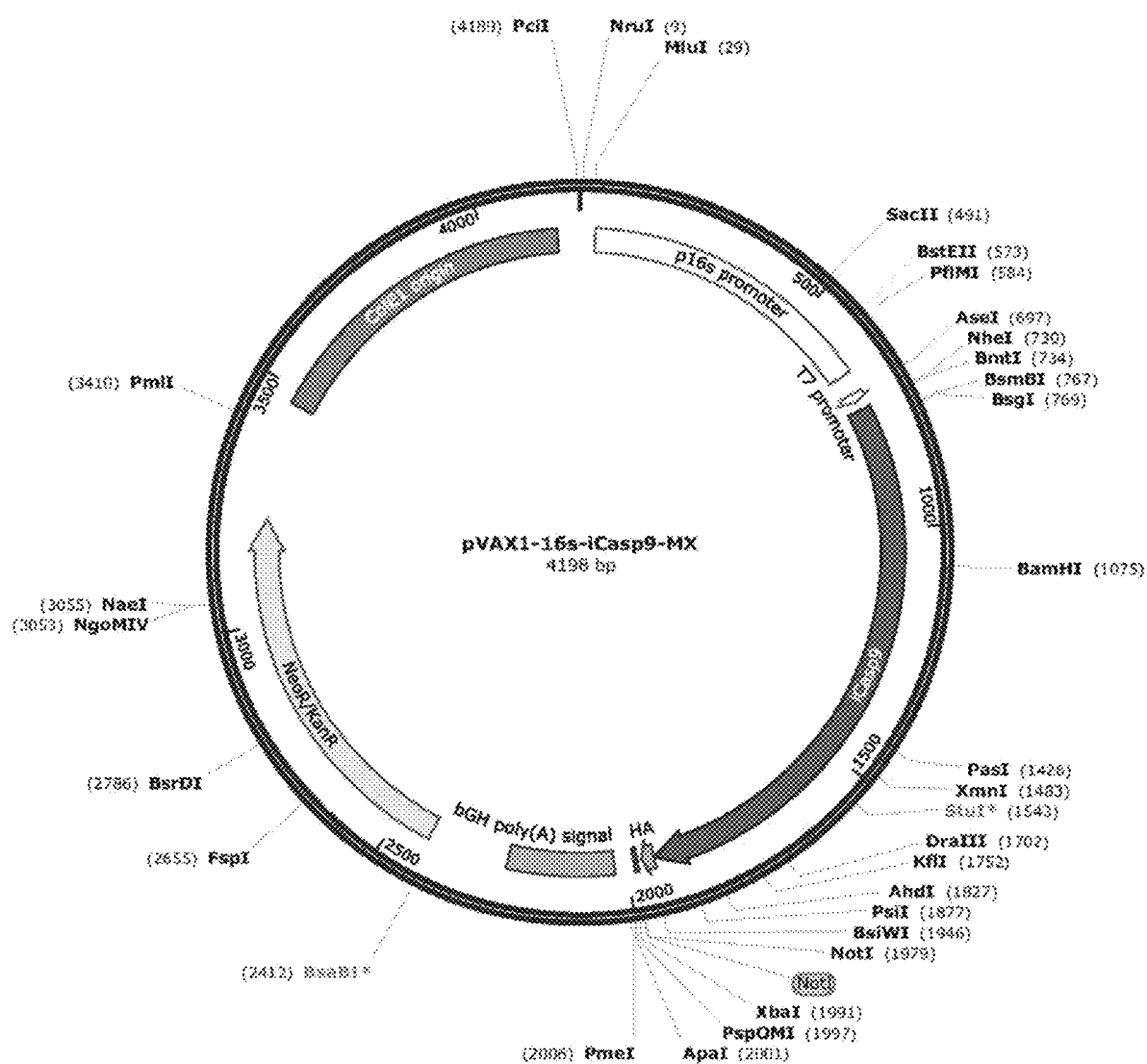

FIG. 16 is a restriction map of the plasmid vector pVAX1-16s-iCasp9-MX (SEQ ID NO: 6), which comprises an exemplary p16-targeting construct for the target cell-specific expression of an inducible Caspase 9 (iCasp9) protein in target cells expressing p16, such as target cells that are associated with aging and/or senescence, which p16-targeting construct comprises a p16s transcriptional promoter in operable connection to iCasp9.

Figure 17:
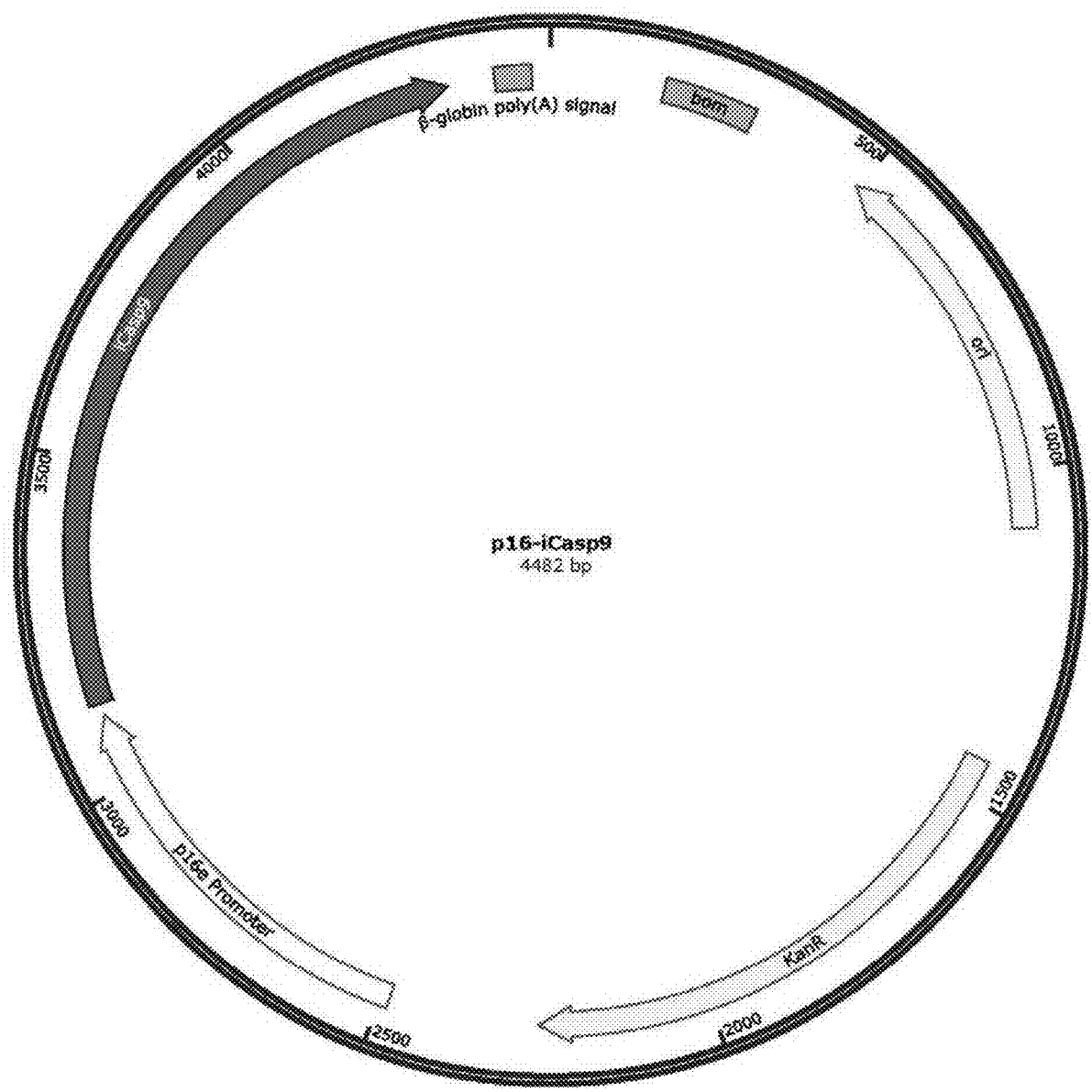

FIG. 17 is a plasmid map of the vector p10-p16-iCasp9 (SEQ ID NO: 12), which comprises an exemplary p16-targeting construct for the target cell-specific expression of an inducible Caspase 9 (iCasp9) protein in target cells expressing p16, such as target cells that are associated with aging and/or senescence, which p16-targeting construct comprises a p16e transcriptional promoter in operable connection to iCasp9.

Figure 18:
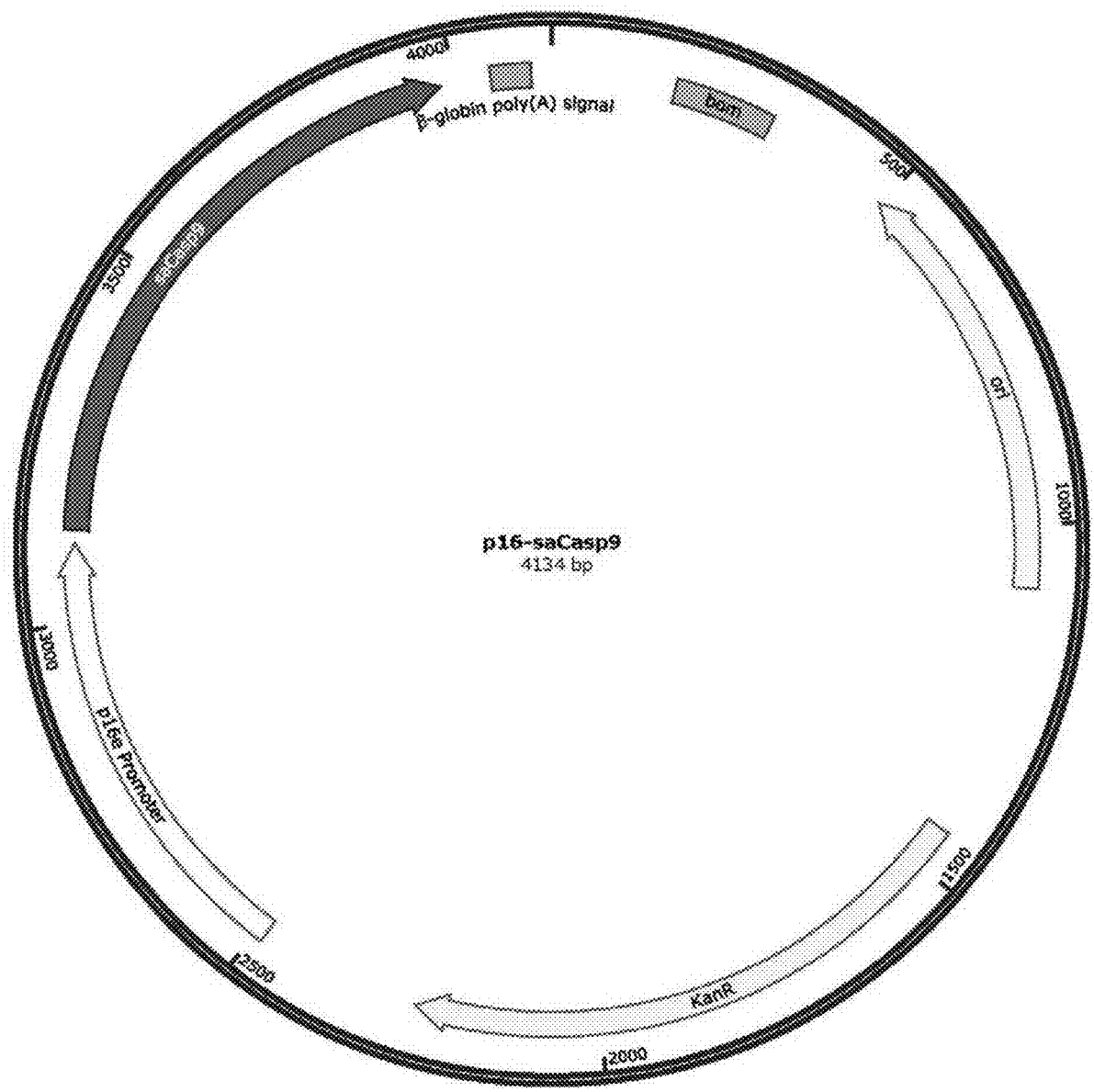

FIG. 18 is a plasmid map of the vector p10-p16-saCasp9 (SEQ ID NO: 13), which comprises an exemplary p16-targeting construct for the target cell-specific expression of an self-activating Caspase 9 (saCasp9) protein in target cells expressing p16, such as target cells that are associated with aging and/or senescence, which p16-targeting construct comprises a p16e transcriptional promoter in operable connection to saCasp9.

Figure 19:
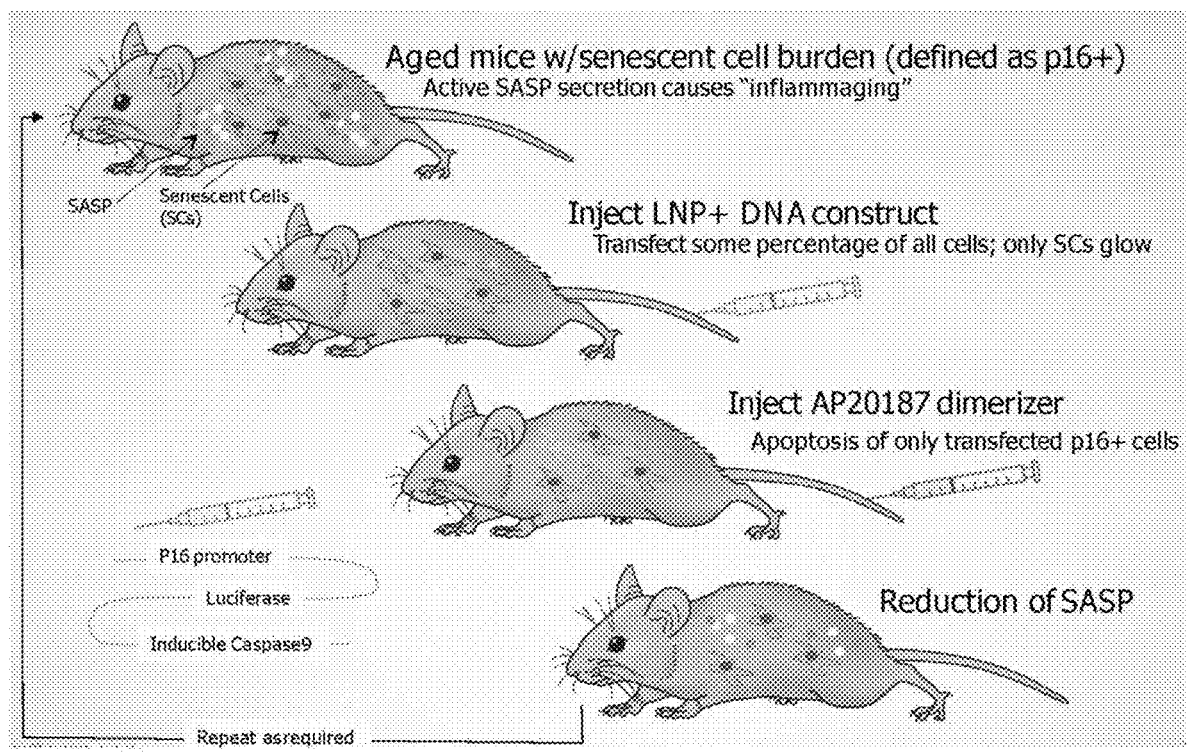

FIG. 19 is a diagrammatic representation of the in vivo administration of an exemplary p16-targeting construct in an mouse model system for aging, wherein the aging mouse model exhibits a senescent cell burden (as defined by the presence of p16$^+$ cells) and secretion of factors associated with a senescence-associated secretory phenotype (SASP; van Deursen, *Nature* 509(7501):439-446 (2014)). A formulation comprising a vector and an expression construct, such as a lipid nanoparticle (LNP) vector, e.g., a fusogenic LNP comprising a fusogenic protein such as p14 FAST, encompassing a p16-Casp9 expression construct, e.g., pVAX1-16s-iCasp9, p10-p16e-iCasp9, p10-p16e-saCasp9, or variant thereof expressing luciferase (for visualization), is administered in vivo to an aged mouse via injection into a tail vein and the LNP+expression construct transfects target and non-target cells without specificity. Upon subsequent in vivo administration of a chemical inducer of dimerization (CID), such as AP20187, p16+ target cells (e.g., senescent cells) expressing an iCasp9 protein undergo apoptosis, resulting in a reduction is SASP levels, while p16− cells remain viable.

FIGS. 20A-20C are photomicrographs of the histological staining of senescent-associated β-gal in kidney cells from an in vivo aged mouse model either untreated (FIG. 20A) or treated (low dose—FIG. 20B and high dose—FIG. 20C) following the in vivo administration (16 animals at 80 weeks of age) of a formulation comprising a vector and an expression construct, such as a lipid nanoparticle (LNP) vector, e.g., a fusogenic LNP comprising a fusogenic protein such as p14 FAST, encompassing a p16-Casp9 expression construct, e.g., pVAX1-16s-iCasp9, p10-p16e-iCasp9, p10-p16e-saCasp9, or variant thereof, is administered in vivo to an aged mouse and kidney cells stained for β-gal. These data demonstrated a dose-dependent reduction of p16+ senescent kidney cells (FIG. 20D).

FIGS. 20E-20G are photomicrographs of the histological staining of senescent-associated β-gal in seminal vesicle cells from an in vivo aged mouse model either untreated (FIG. 20E) or treated (low dose—FIG. 20F and high dose—FIG. 20G) following the in vivo administration (16 animals at 80 weeks of age) of a formulation comprising a vector and an expression construct, such as a lipid nanoparticle (LNP) vector, e.g., a fusogenic LNP comprising a fusogenic protein such as p14 FAST, encompassing a p16-iCasp9 expression construct, e.g., pVAX1-16s-iCasp9, p10-p16e-iCasp9, p10-p16e-saCasp9, or variant thereof, is administered in vivo to an aged mouse and seminal vesicle cells stained for β-gal. These data demonstrated a dose-dependent reduction of p16+ senescent seminal vesicle cells (FIG. 20H).

Figure 21:
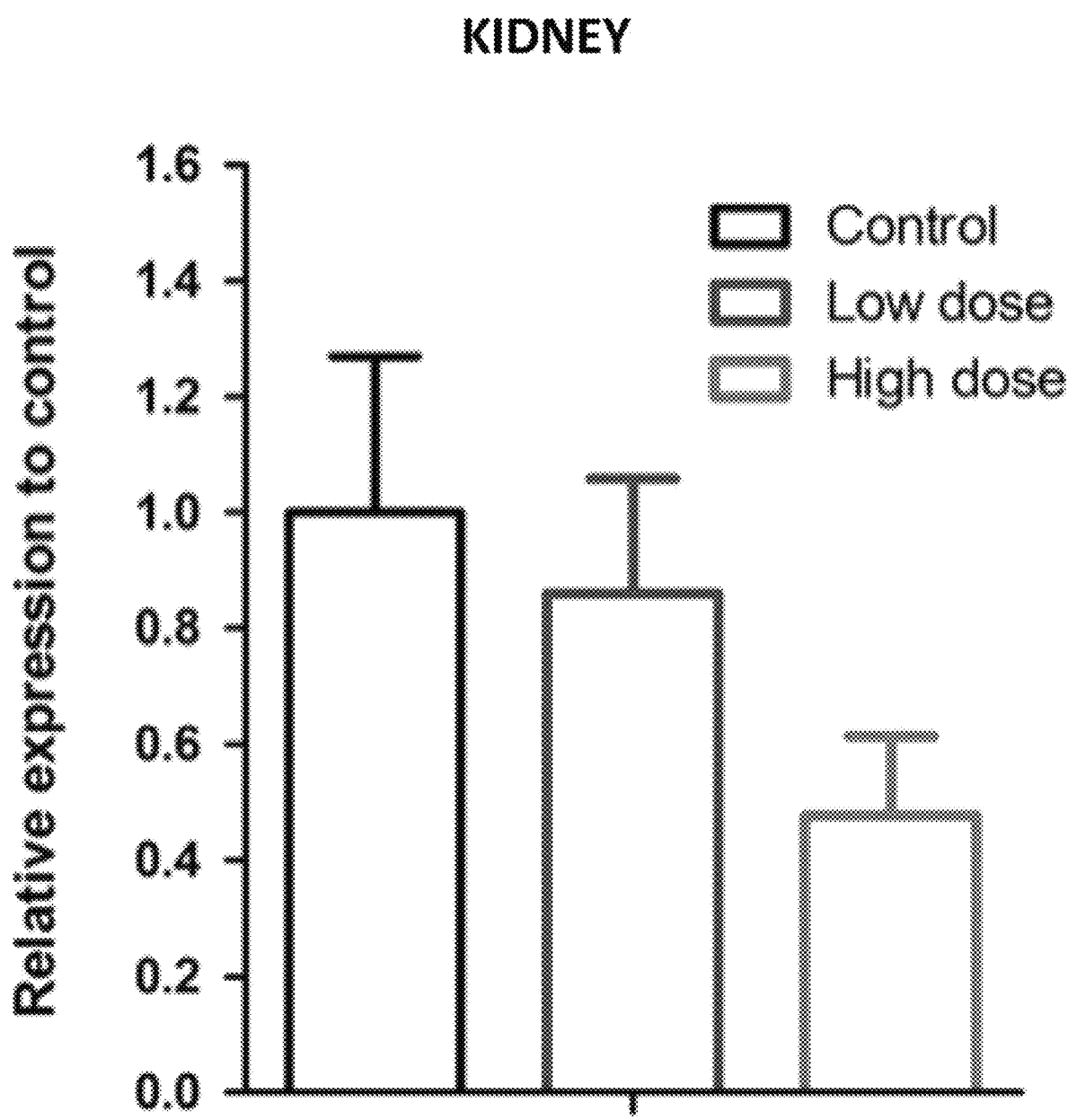

FIG. 21 is a bar graph demonstrating the dose-dependent targeting of p16+ kidney cells in naturally aged mice following the in vivo administration of a fusogenic lipid nanoparticle (LNP) formulation comprising a pVAX1-p16 expression construct. Kidney cells were subjected to a qRT-PCR reaction to detect p16$^{Ink4a}$ transcripts. Relative expression was calculated using 2ΔΔCt (Livak, *Methods* 25:402-408 (2001)).

Figure 22:
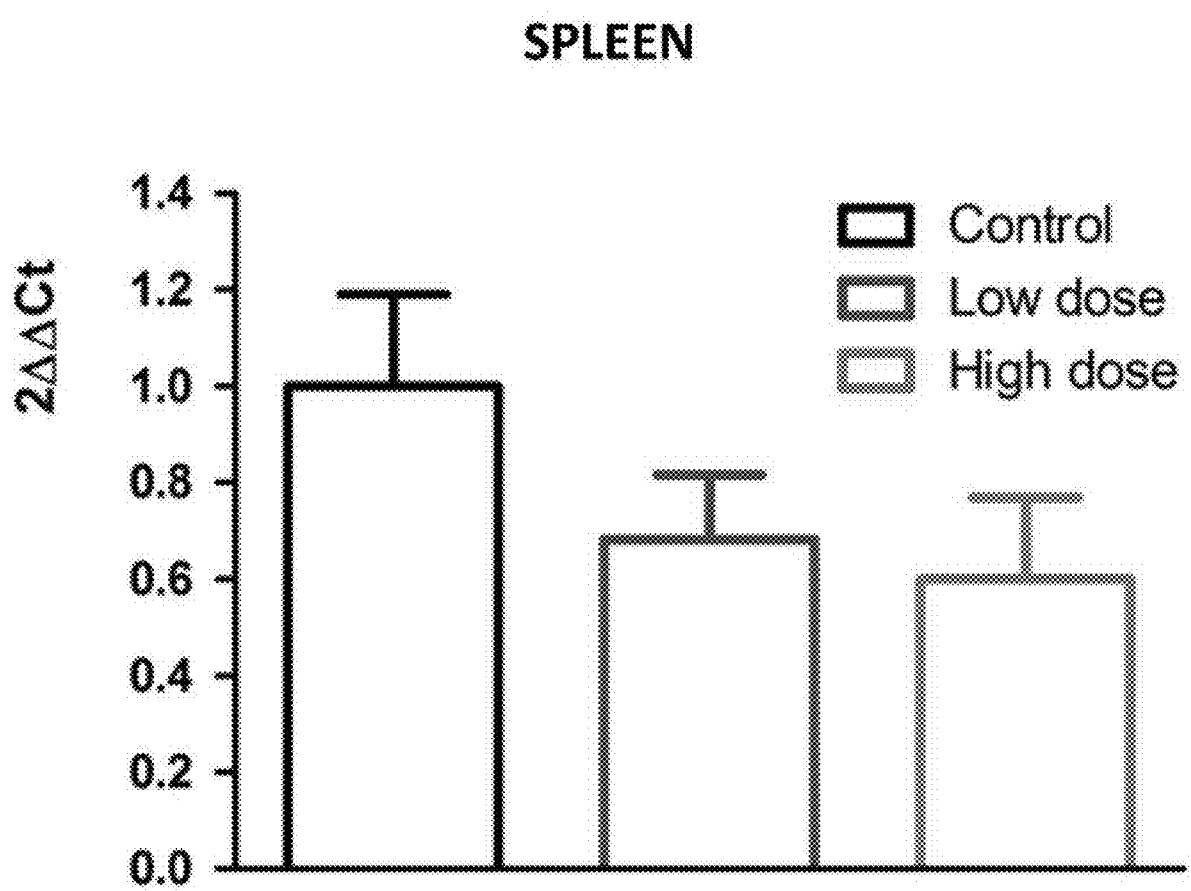

FIG. 22 is a bar graph demonstrating the dose-dependent targeting of p16+ spleen cells in naturally aged mice following the in vivo administration of a fusogenic lipid nanoparticle (LNP) formulation comprising a pVAX1-p16 expression construct. Spleen cells were subjected to a qRT-PCR reaction to detect p16$^{Ink4a}$ transcripts. Relative expression was calculated using 2ΔΔCt (Livak, *Methods* 25:402-408 (2001)).

Figure 23:
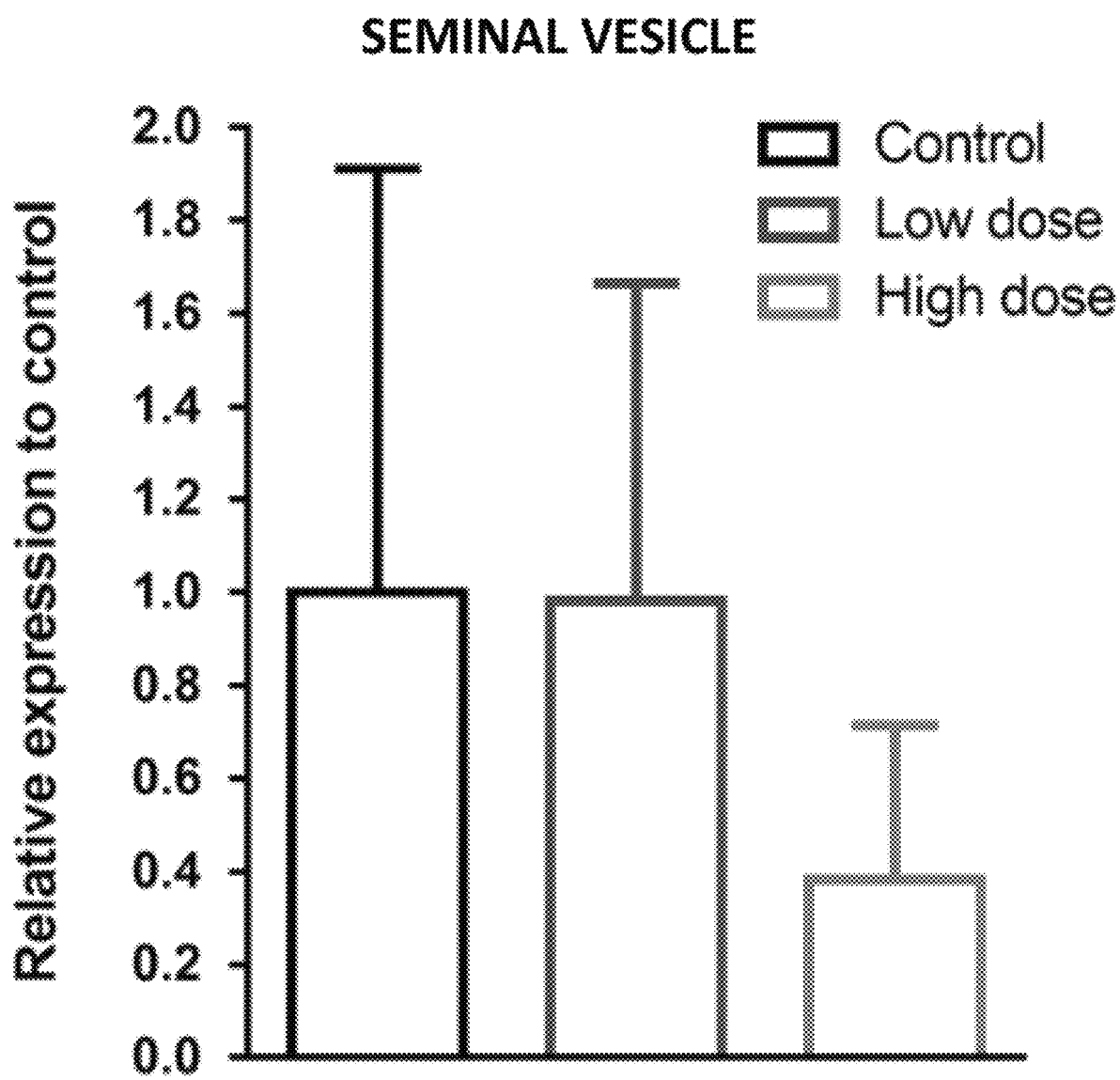

FIG. 23 is a bar graph demonstrating the dose-dependent targeting of p16+ seminal vesicle cells in naturally aged mice following the in vivo administration of a fusogenic lipid nanoparticle (LNP) formulation comprising a pVAX1-p16 expression construct. Seminal vesicle cells were subjected to a qRT-PCR reaction to detect p16$^{Ink4a}$ transcripts. Relative expression was calculated using 2ΔΔCt (Livak, *Methods* 25:402-408 (2001)).

Figure 24:
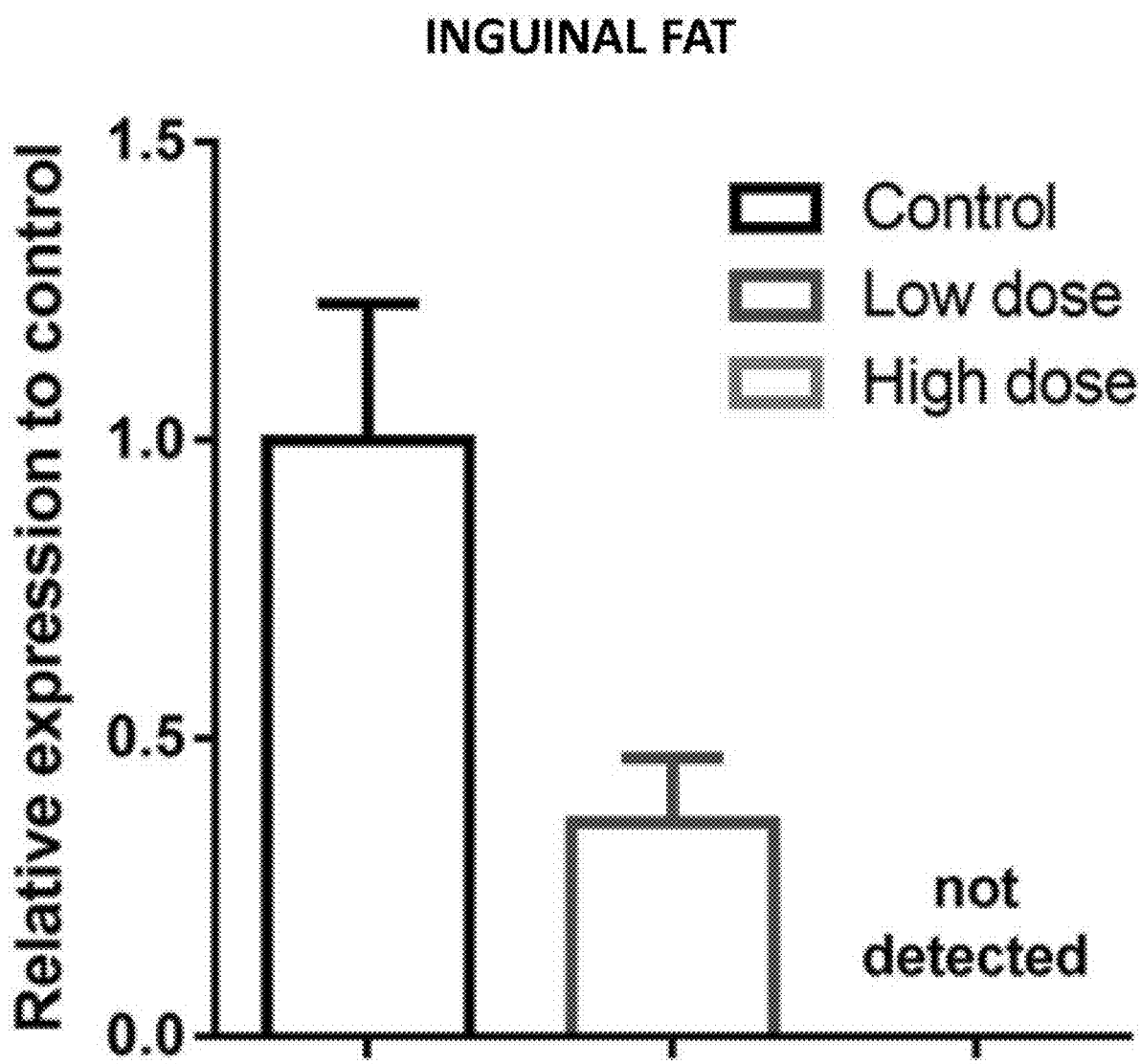

FIG. 24 is a bar graph demonstrating the dose-dependent targeting of p16+ inguinal fat cells in naturally aged mice following the in vivo administration of a fusogenic lipid nanoparticle (LNP) formulation comprising a pVAX1-p16 expression construct. Inguinal fat cells were subjected to a qRT-PCR reaction to detect p16$^{Ink4a}$ transcripts. Relative expression was calculated using 2ΔΔCt (Livak, *Methods* 25:402-408 (2001)).

Figure 25:
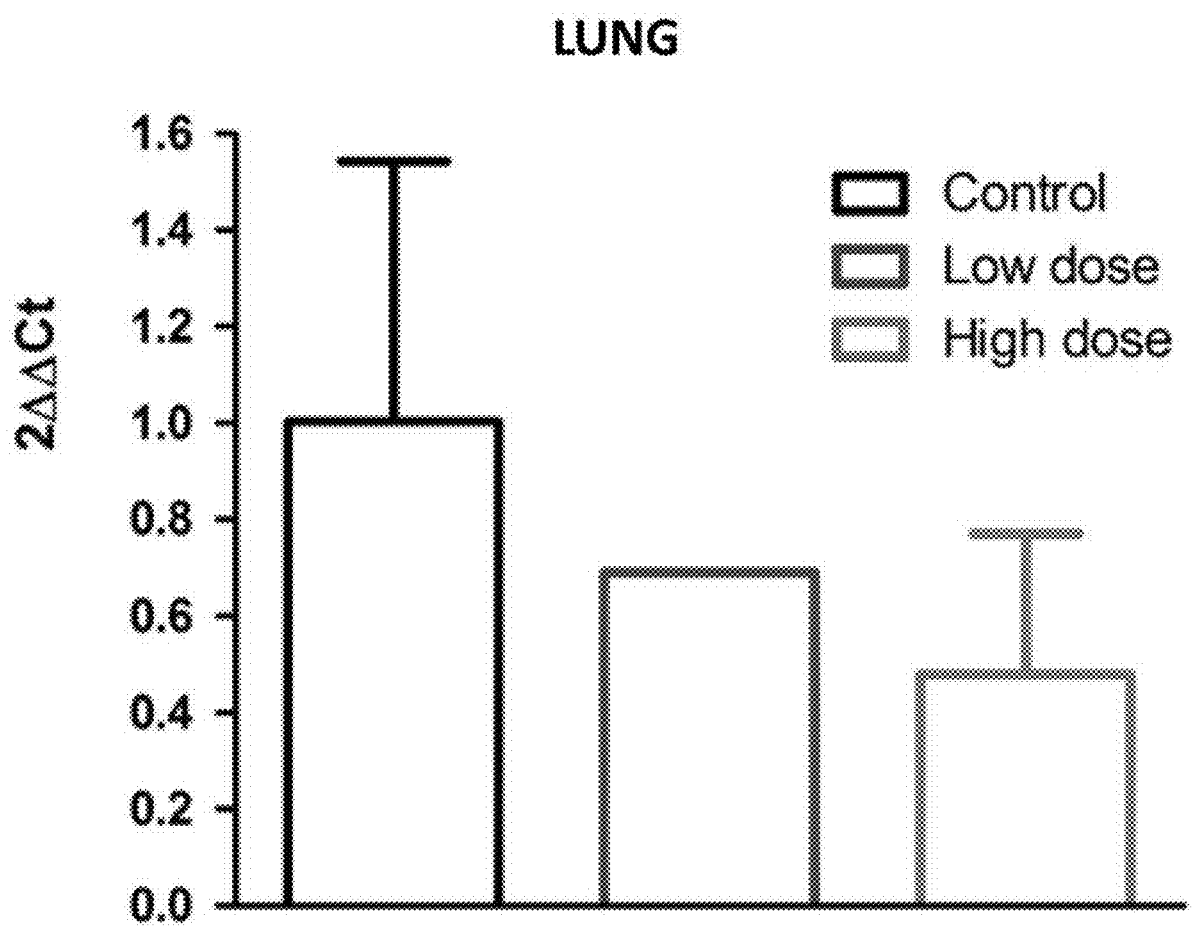

FIG. 25 is a bar graph demonstrating the dose-dependent targeting of p16+ lung cells in naturally aged mice following the in vivo administration of a fusogenic lipid nanoparticle (LNP) formulation comprising a pVAX1-p16 expression construct. Lung cells were subjected to a qRT-PCR reaction to detect p16$^{Ink4a}$ transcripts. Relative expression was calculated using 2ΔΔCt (Livak, *Methods* 25:402-408 (2001)).

Figure 26:
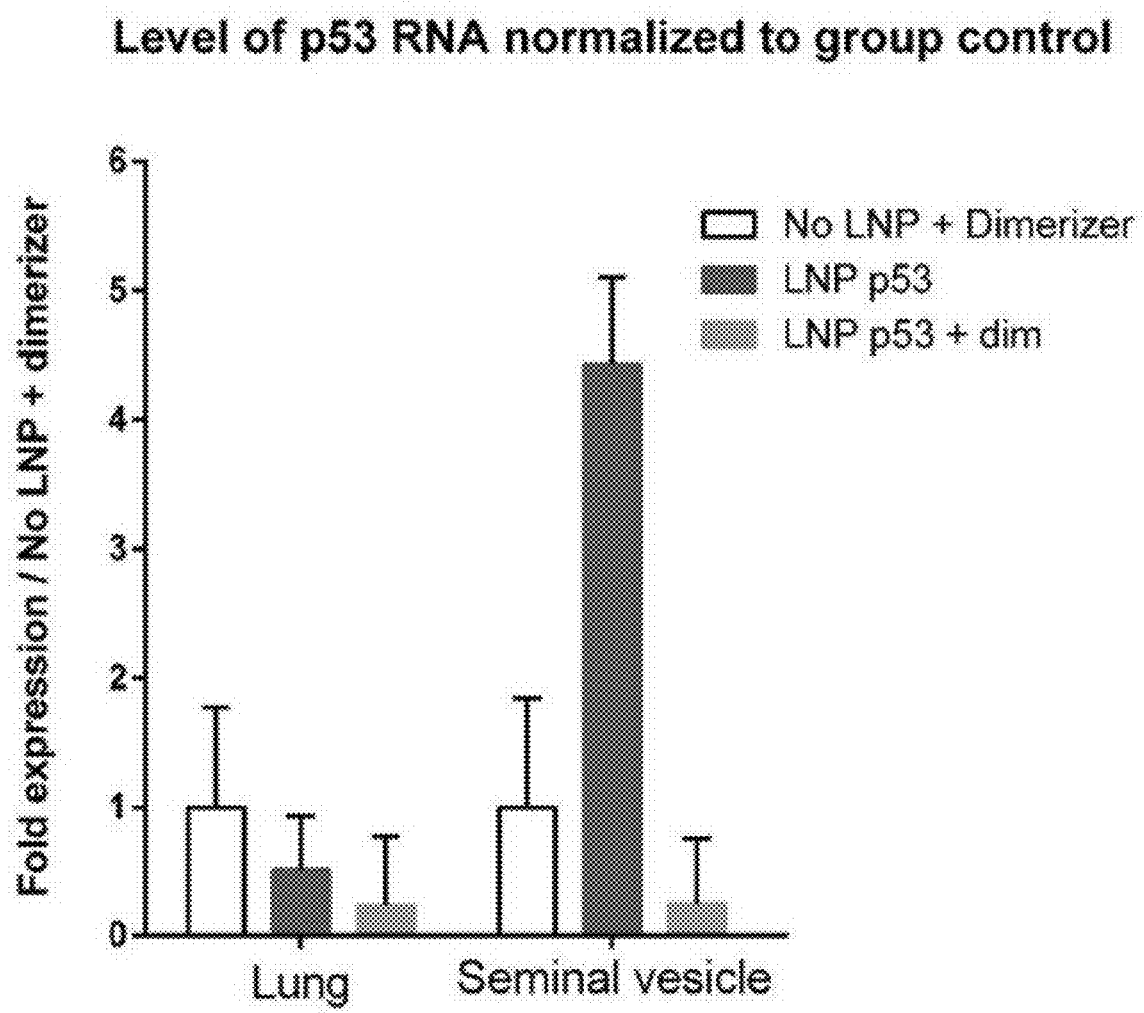

FIG. 26 is a bar graph of data demonstrating the remediation of chemotherapy-induced damage (as determined by the clearance of damaged cells (i.e., senescent cells) after treatment with doxorubicin). Senescence was induced in B6 mice with doxorubicin. Animals were treated with murine p53-iCasp9 and dimerizer or controls (dimerizer only and LNP only) and sacrificed. Tissues were assayed for p53 expression via rt-PCR.

Figure 27:

FIG. 27 is a diagrammatic representation of an exemplary p53-targeting cassette for use in treatment of cancers (oncology) by the selective killing of tumor cells according certain embodiments of the present disclosure. The p53-targeting cassette comprises a p53 transcriptional promoter, which drives the expression an inducible caspase 9 protein (iCasp9) or a self-activating caspase 9 protein (saCasp9).

Figure 28:
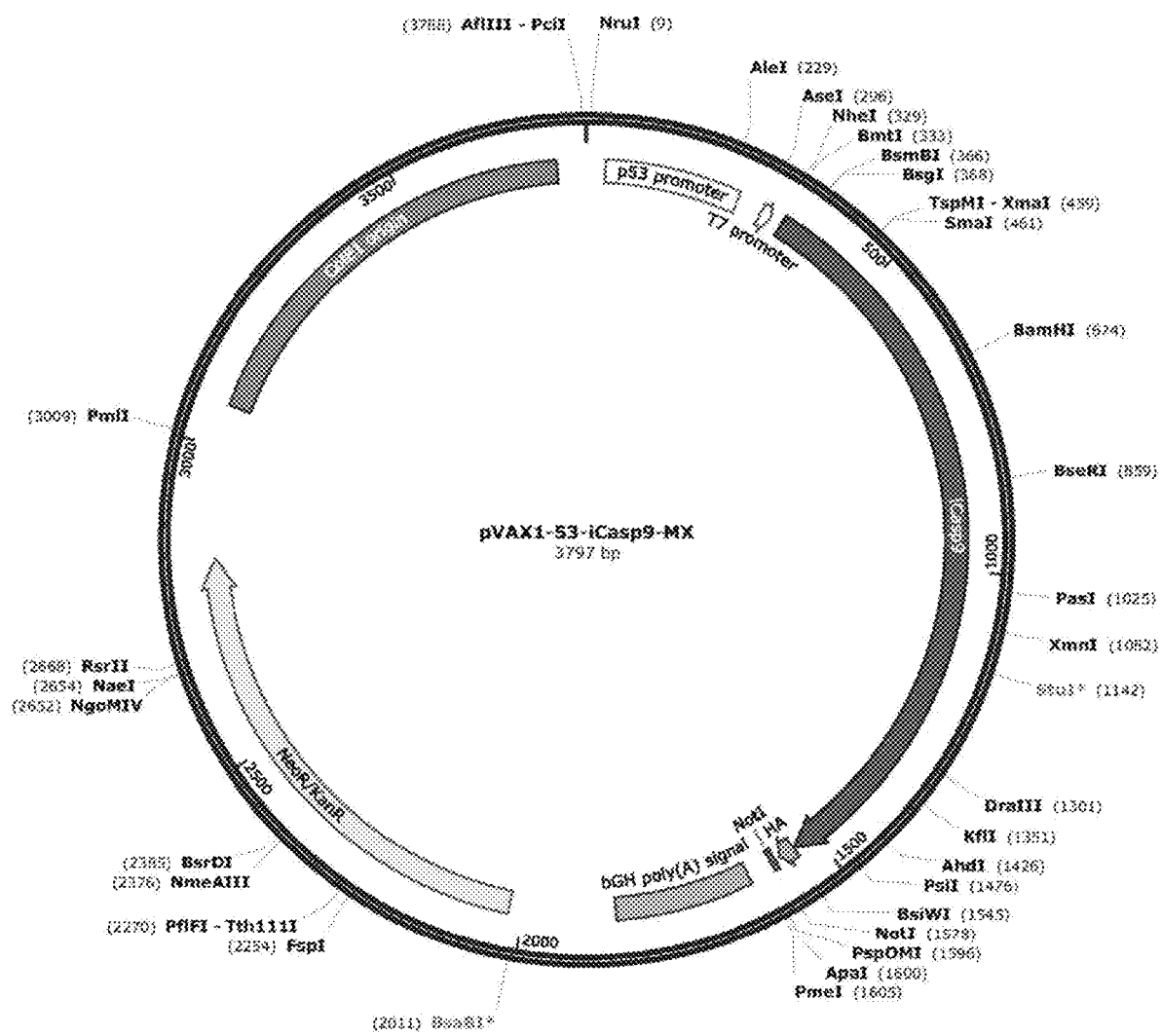

FIG. 28 is a restriction map of a plasmid (pVAX1-p53-iCasp9-MX; SEQ ID NO: 7) comprising a p53-targeting cassette as depicted in FIG. 27. Expression of an iCasp9 nucleic acid encoding an inducible Casp9 protein is regulated by the p53 transcriptional promoter.

Figure 29:
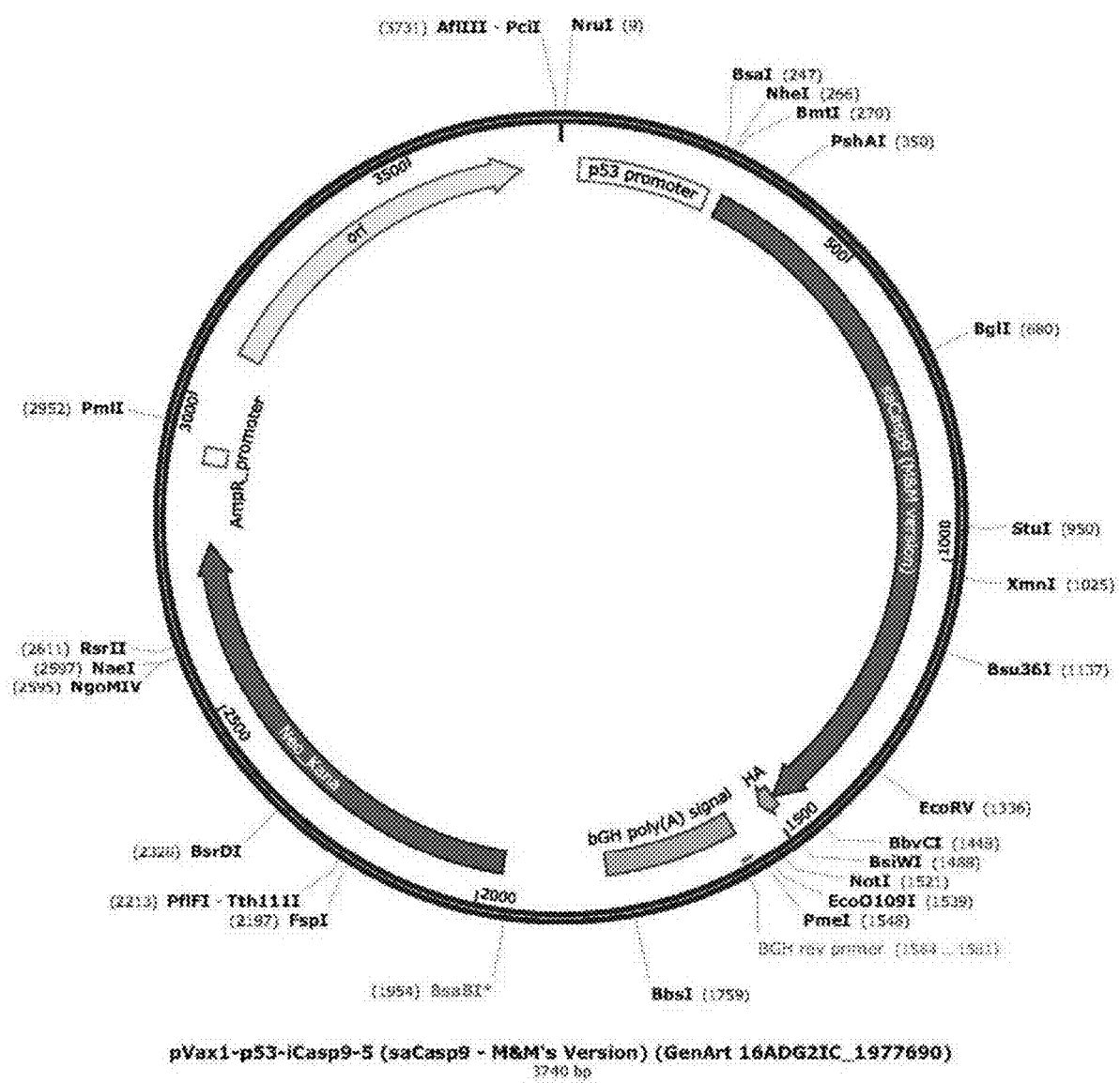

FIG. 29 is a restriction map of a plasmid (pVAX1-p53-saCasp9; SEQ ID NO: 8) comprising a p53-targeting cassette. Expression of a nucleic acid encoding a self-activating Caspase 9 (saCasp9) protein is regulated by the p53 transcriptional promoter.

Figure 30:
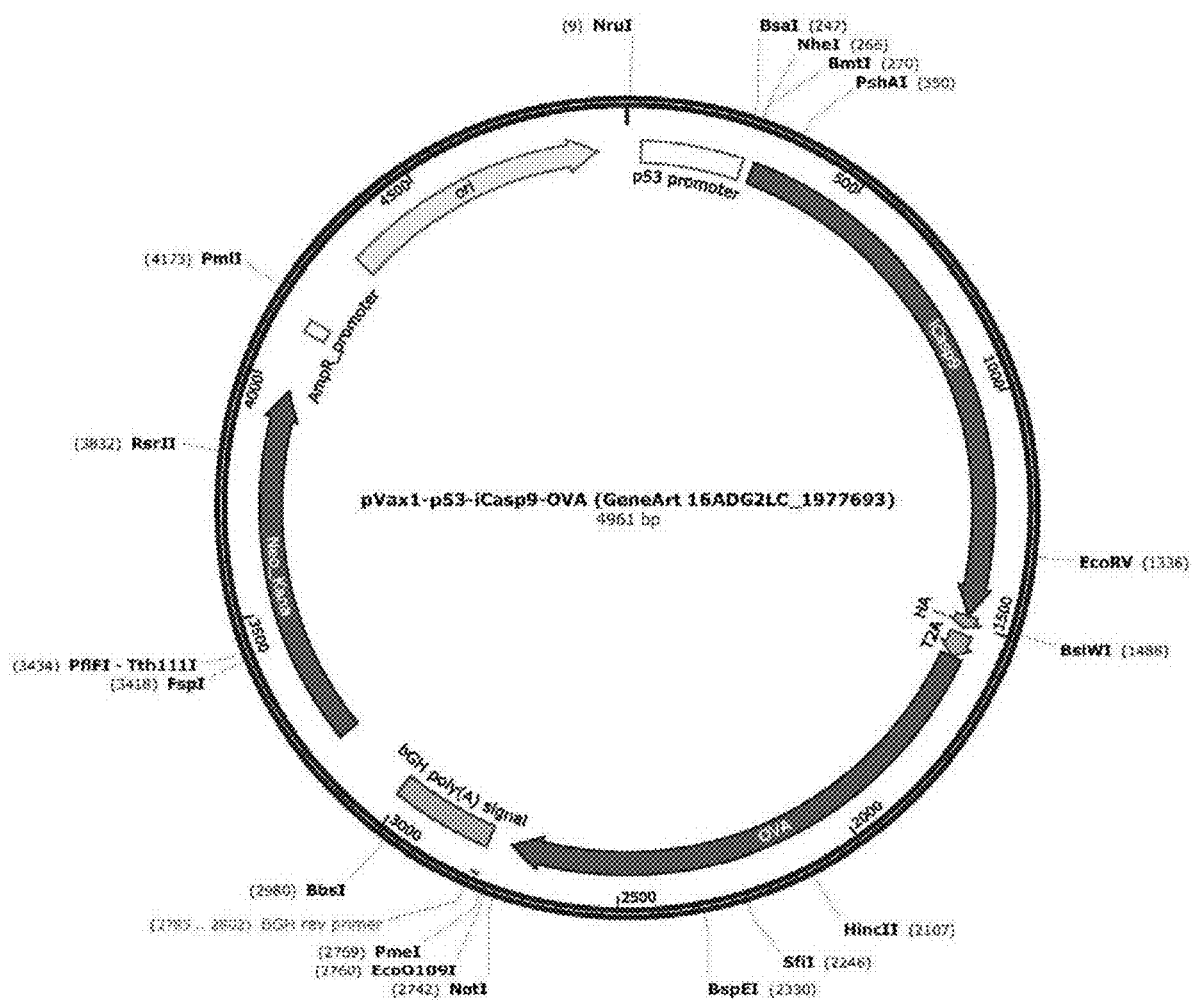

FIG. 30 is a restriction map of a plasmid (pVAX1-p53-iCasp9-OVA; SEQ ID NO: 11) comprising a p53-targeting cassette as depicted in FIG. 27. Expression of a nucleic acid encoding an inducible Casp9 protein is regulated by the p53 transcriptional promoter.

Figure 31:
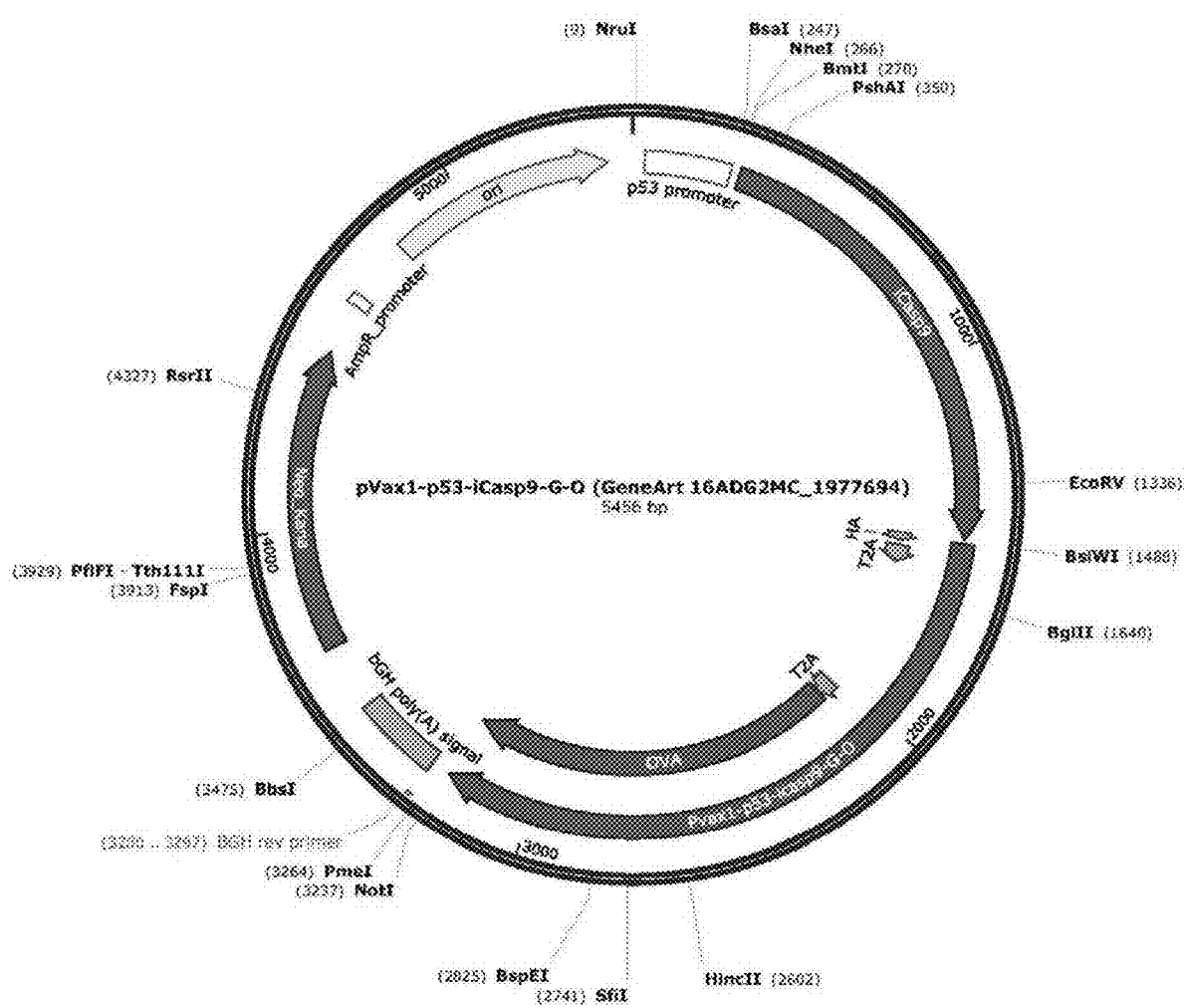

FIG. 31 is a restriction map of a plasmid (pVAX1-p53-iCasp9-G-O; SEQ ID NO: 9) comprising a p53-targeting cassette as depicted in FIG. 27. Expression of an iCasp9 nucleic acid encoding an inducible Casp9 protein is regulated by the p53 transcriptional promoter.

Figure 32:
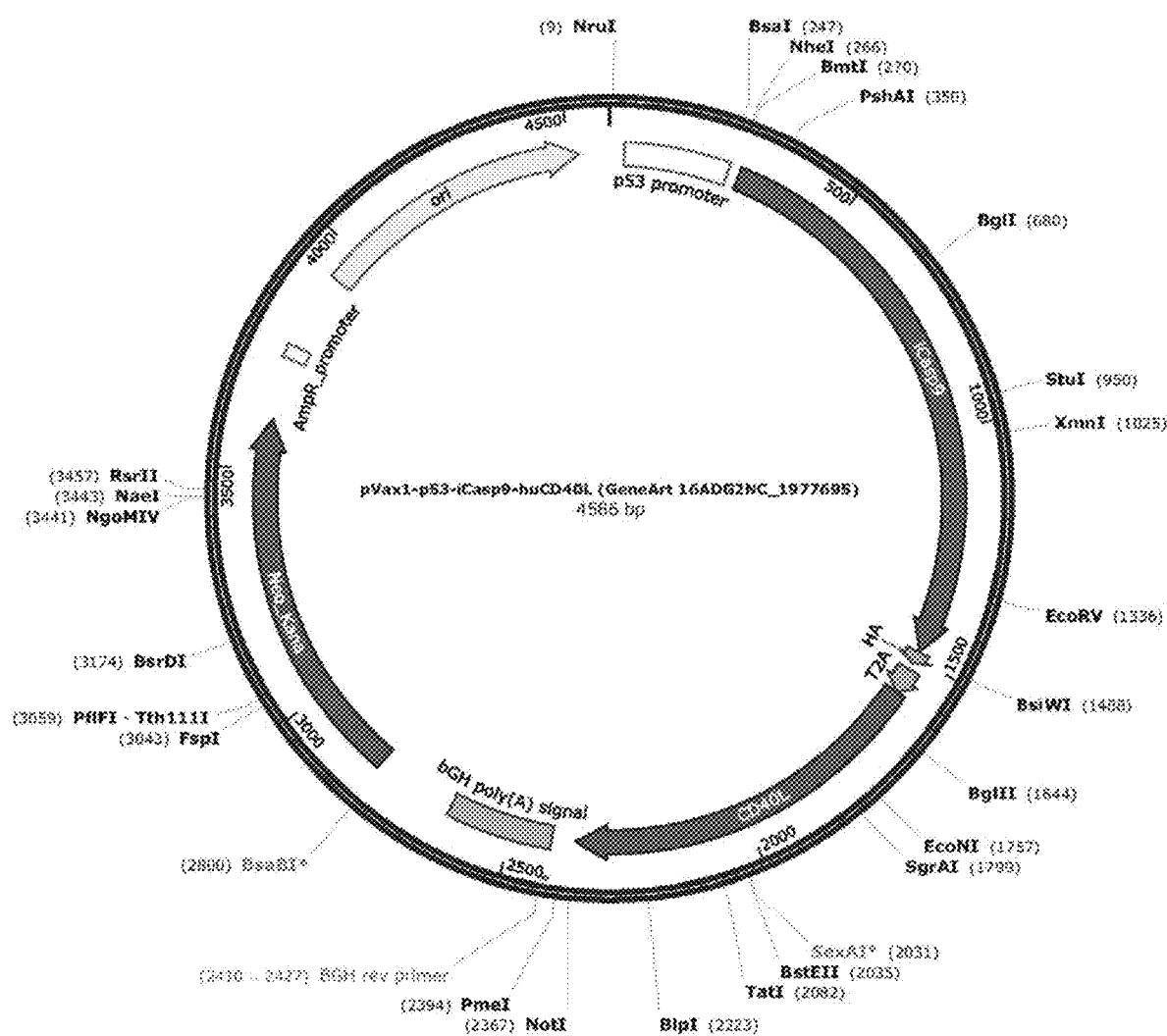

FIG. 32 is a restriction map of a plasmid (pVAX1-p53-iCasp9-huCD40L; SEQ ID NO: 10) comprising a p53-targeting cassette as depicted in FIG. 27. Expression of an iCasp9 nucleic acid encoding an inducible Casp9 protein is regulated by the p53 transcriptional promoter. Additional targeting cassettes and plasmid constructs have been developed for advanced oncology applications, as disclosed herein, which constructs employ nucleic acids encoding, for example, one or more immunostimulatory cytokines (such as huCD40L, as shown in FIG. 32, as well as GMCSF and IL12) and/or one or more antigens (such as chicken ovalbumin (OVA), as shown in FIG. 30, as well as Nt1, tetanus antigens, and influenza antigens).

Figure 33:
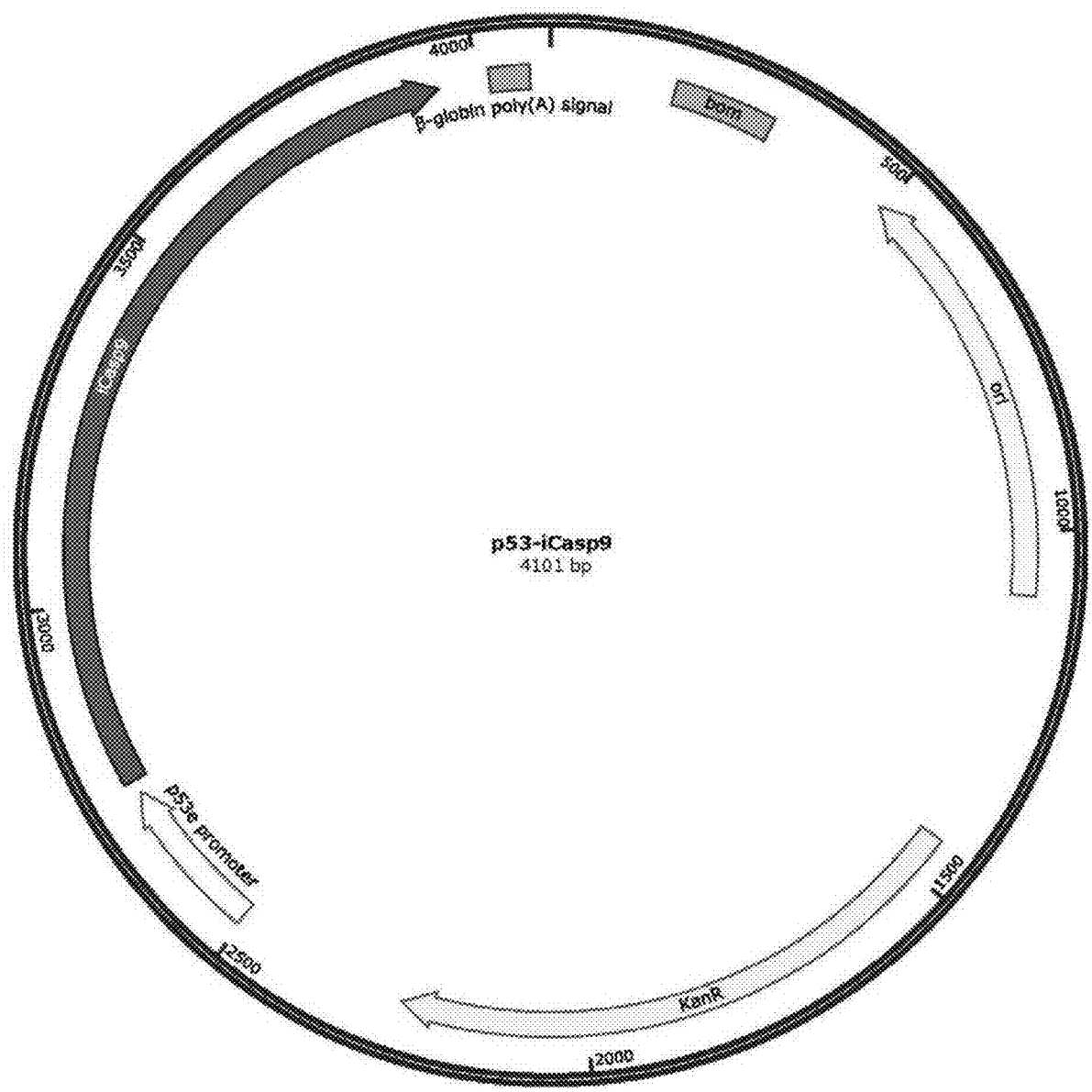

FIG. 33 is a map of a plasmid (p10-p53e-iCasp9; SEQ ID NO: 14) comprising a p53-targeting cassette as depicted in FIG. 27. Expression of an iCasp9 nucleic acid encoding an inducible Casp9 protein is regulated by the p53 transcriptional promoter. Additional targeting cassettes and plasmid constructs have been developed for advanced oncology applications, as disclosed herein, which constructs employ nucleic acids encoding, for example, one or more immunostimulatory cytokines (such as huCD40L, as shown in FIG. 32, as well as GMCSF and IL12) and/or one or more antigens (such as chicken ovalbumin (OVA), as shown in FIG. 30, as well as Nt1, tetanus antigens, and influenza antigens).

Figure 34:
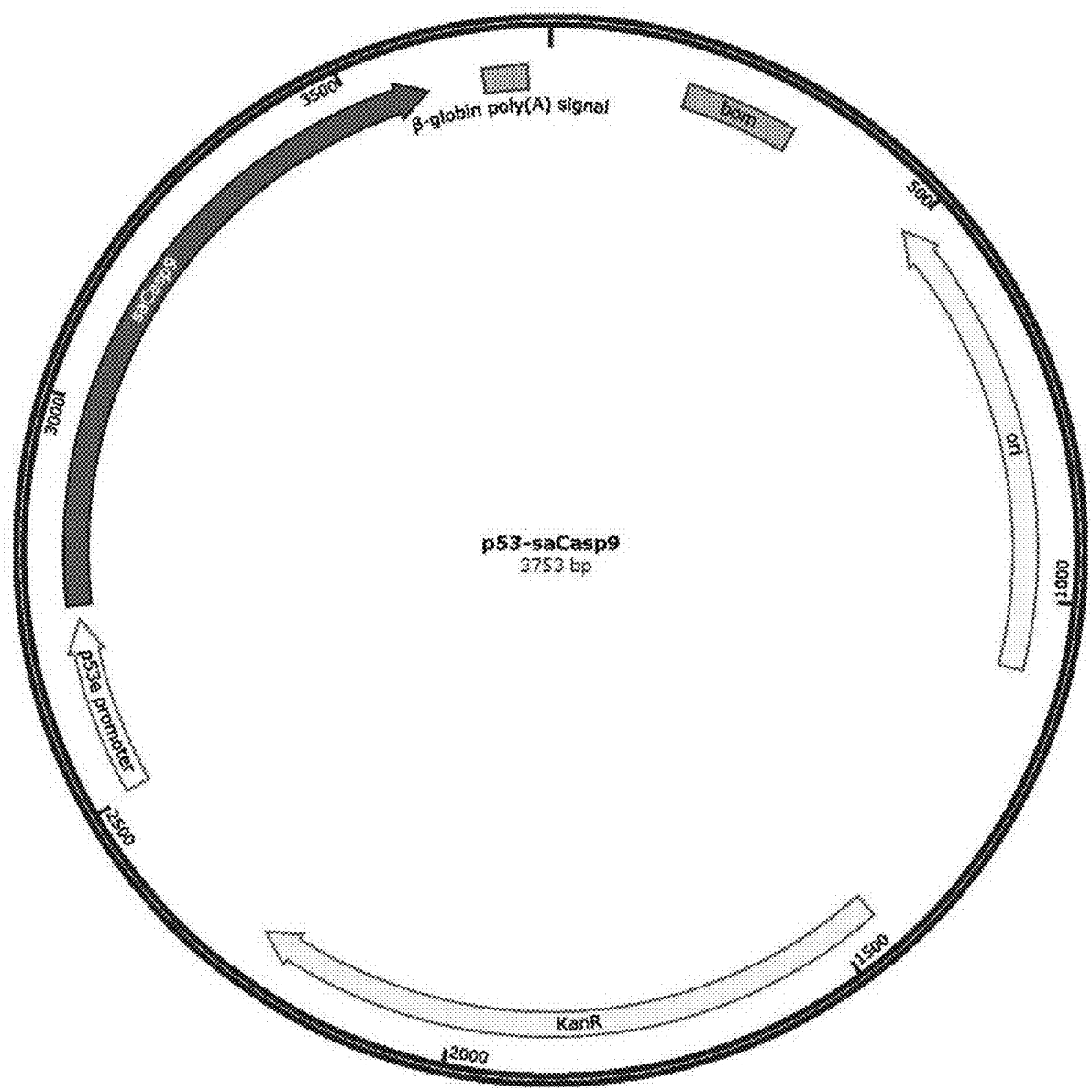

FIG. 34 is a map of a plasmid (p10-p53e-saCasp9; SEQ ID NO: 15) comprising a p53-targeting cassette as depicted in FIG. 27. Expression of an saCasp9 nucleic acid encoding a self-activating Casp9 protein is regulated by the p53 transcriptional promoter. Additional targeting cassettes and plasmid constructs have been developed for advanced oncology applications, as disclosed herein, which constructs employ nucleic acids encoding, for example, one or more immunostimulatory cytokines (such as huCD40L, as shown in FIG. 32, as well as GMCSF and IL12) and/or one or more antigens (such as chicken ovalbumin (OVA), as shown in FIG. 30, as well as Nt1, tetanus antigens, and influenza antigens).

Figure 35:
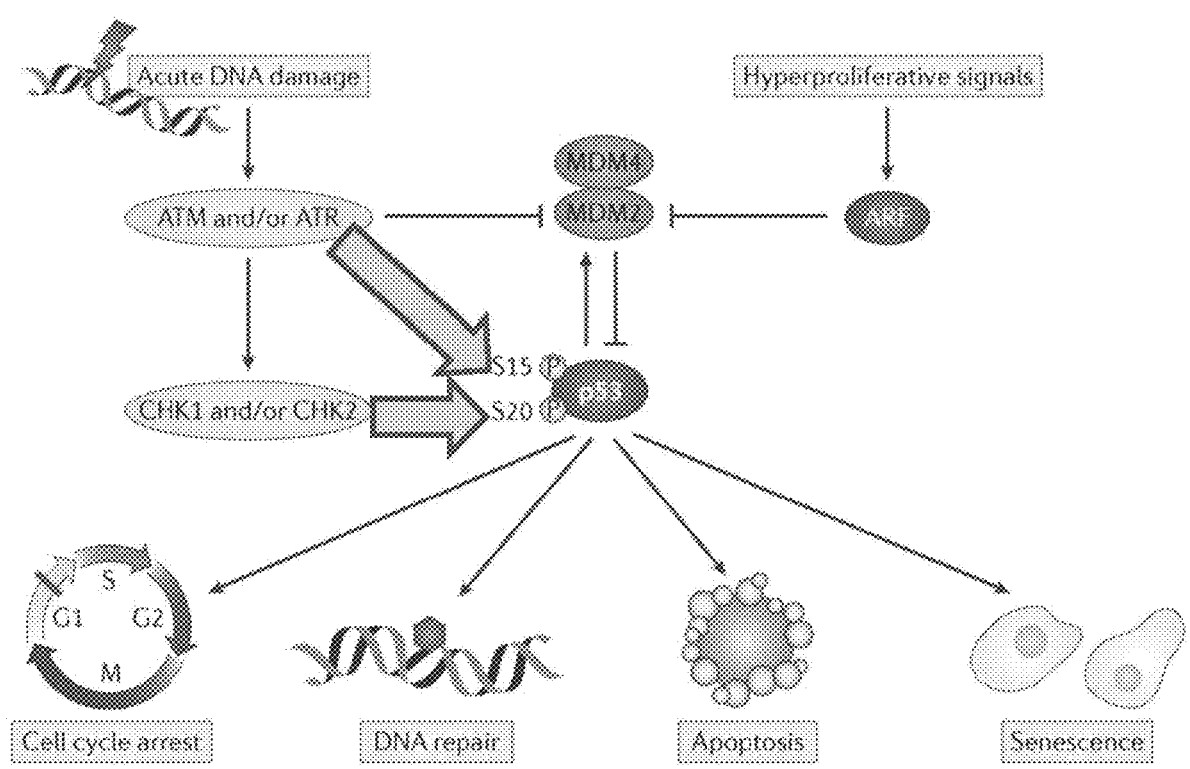

FIG. 35 is a diagram showing the rationale for targeting p53+ tumors with expression constructs comprising a p53 promoter in operable combination with a pro-apoptotic protein, such as a caspase protein, e.g., a Caspase 9 protein. Cancer cells often mutate or delete it so they can grow uncontrollably. However, even when the p53 gene is mutated, the transcription factors that bind to it are almost always still active.

Figure 36:
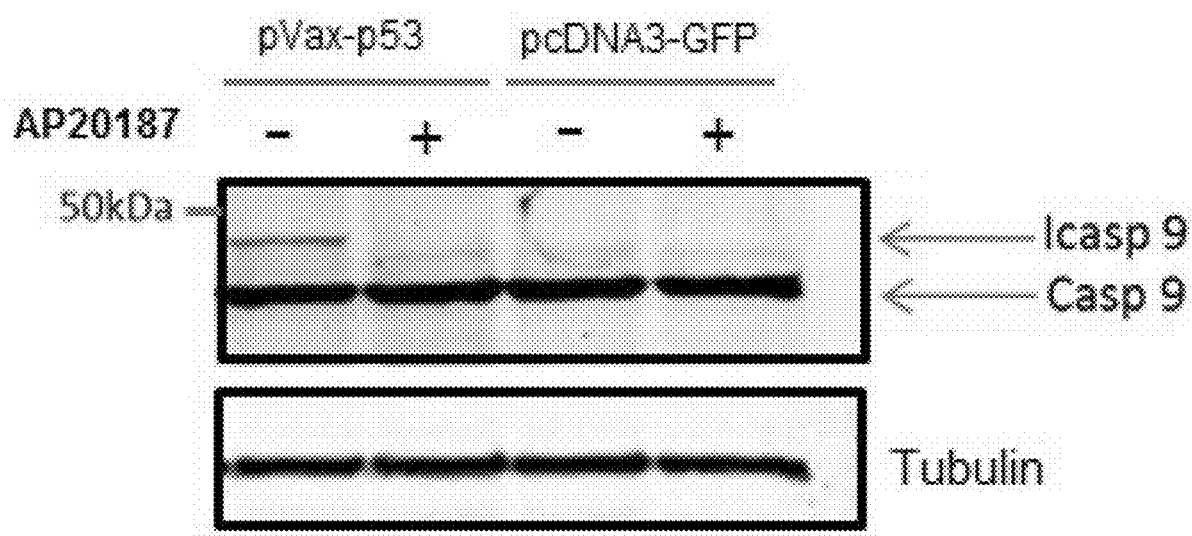

FIG. 36 is a Western blot of iCasp 9 and Casp 9 protein levels obtained with p53-expressing cells (pVax-p53) and control cells (pcDNA3-GFP). Human prostate cancer PC-3 cells were treated with Fusogenix lipid nanoparticles carrying the pVax-p53-iCasp9-luc (luciferin) plasmid (in the presence and absence of the homodimerizer AP201870) and assessed for iCasp9 expression. These data demonstrate that addition of the chemical inducer of dimerization (CID; e.g., AP20187 and AP1903) abolishes the expression of iCasp9 and luciferase in p53-expressing cells engineered to express iCasp9 or luciferase.

FIGS. 37A-37D are microscopic images of human prostate cancer (LNCaP, DU145, PC-3) or normal epithelial (RWPE) cells treated with Fusogenix lipid nanoparticles carrying the pVax-p53-iCasp9-luc plasmid and assessed for iCasp9 expression by Western blot (data not shown) and luminescence assays 24 hours after exposure to EtOH (negative control) or AP1903 (FIGS. 37A and 37C, respectively).

Figure 37:
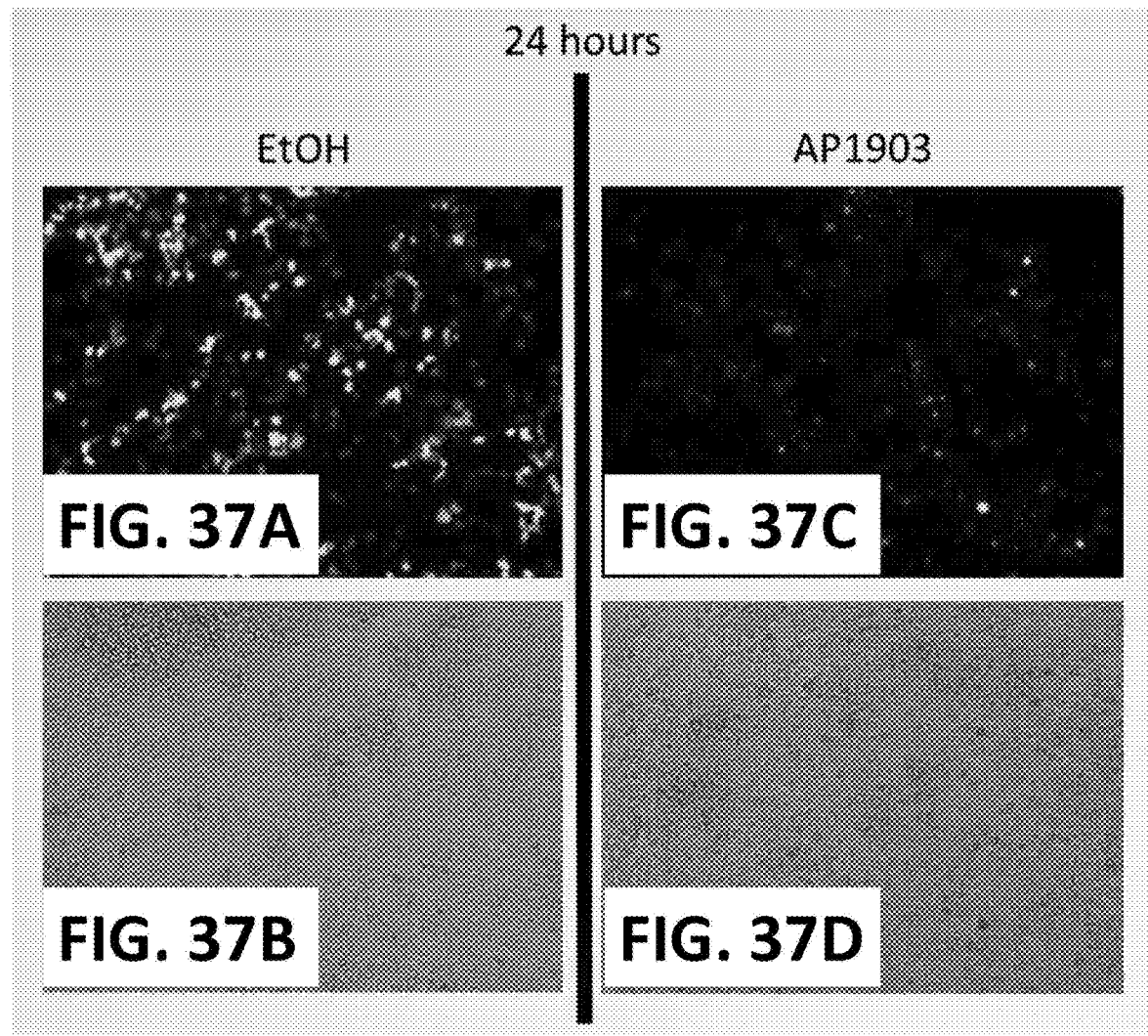
Figure 38:
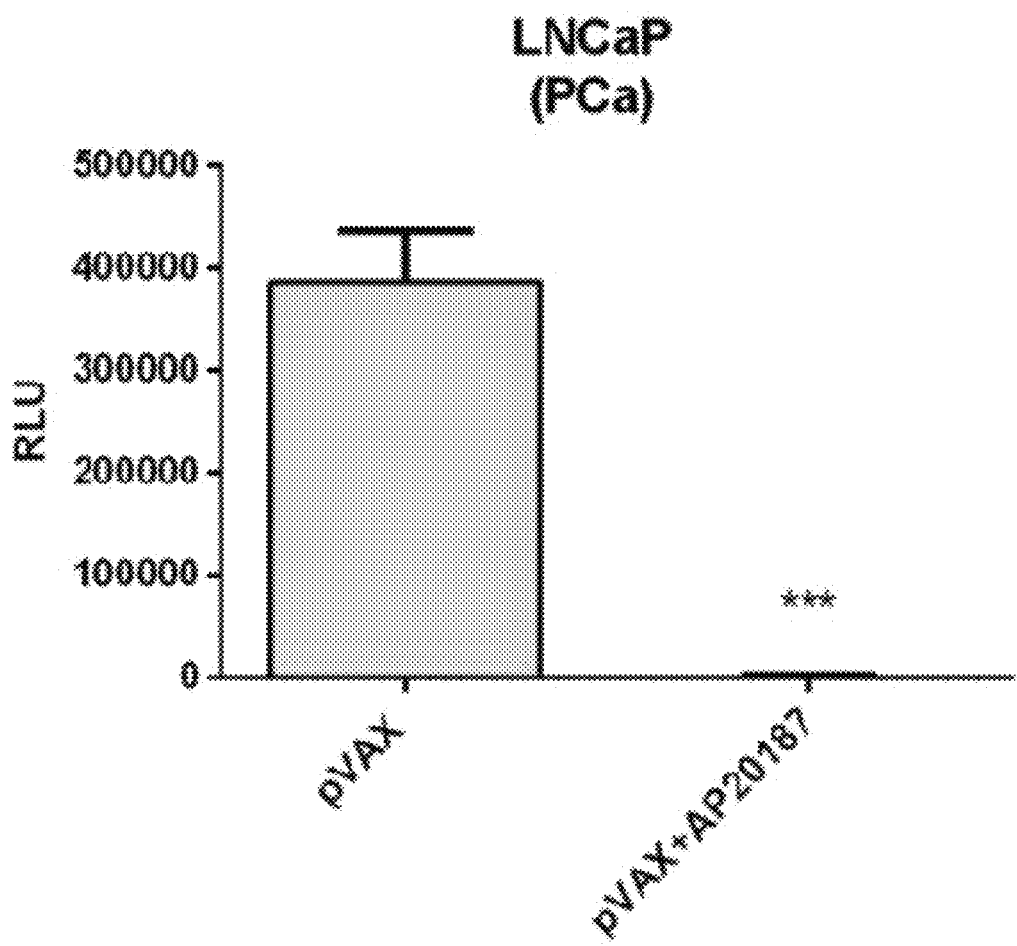
Figure 39:
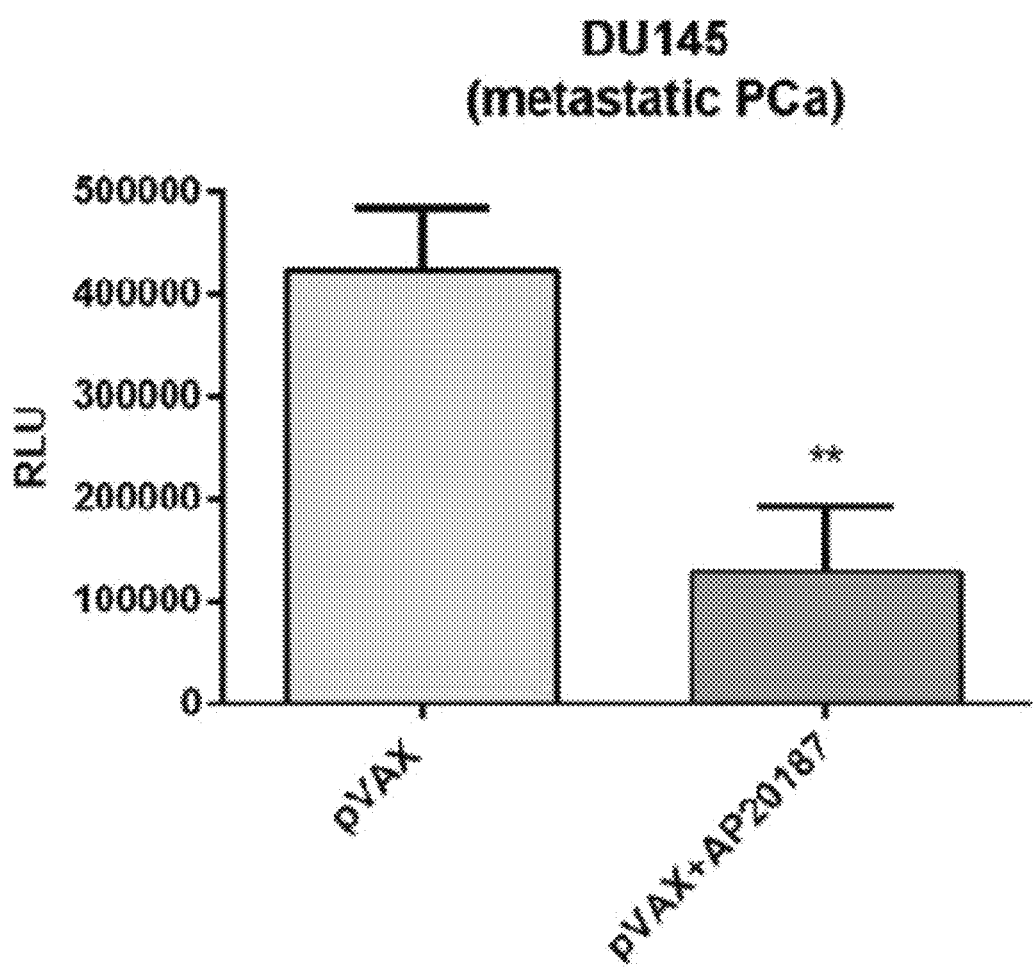
Figure 40:
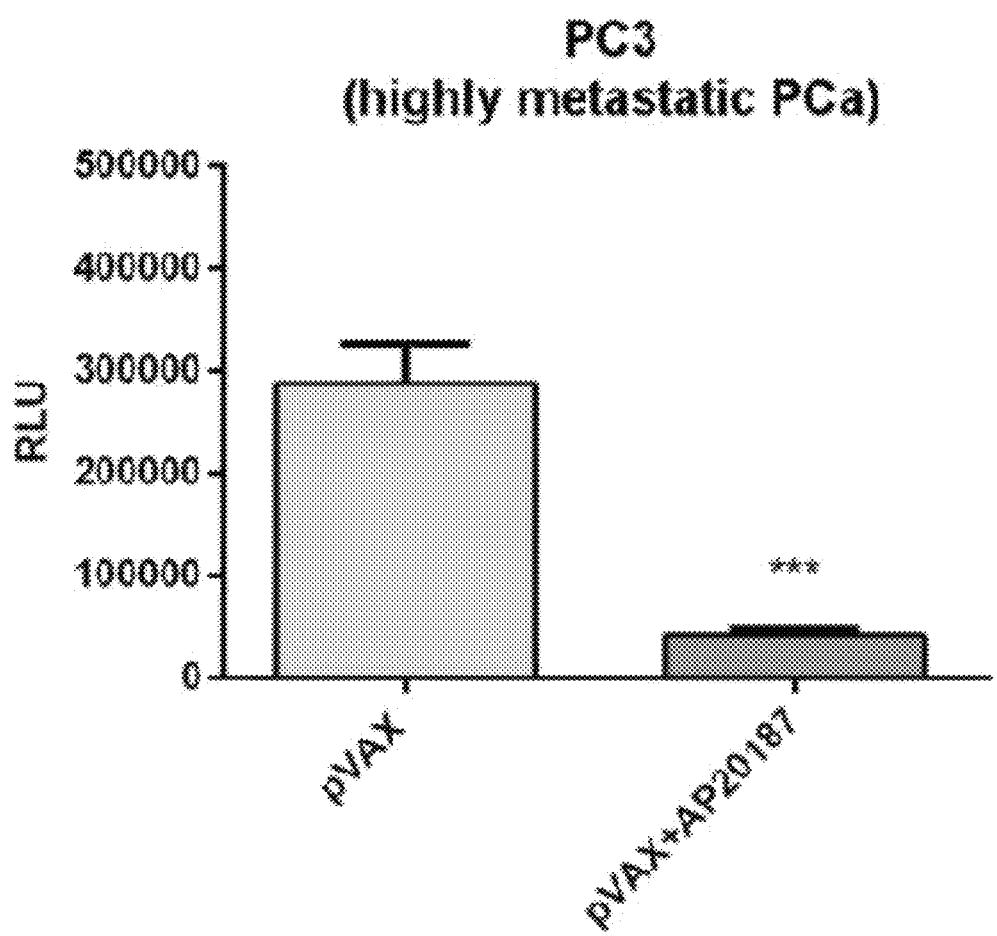
Figure 41:
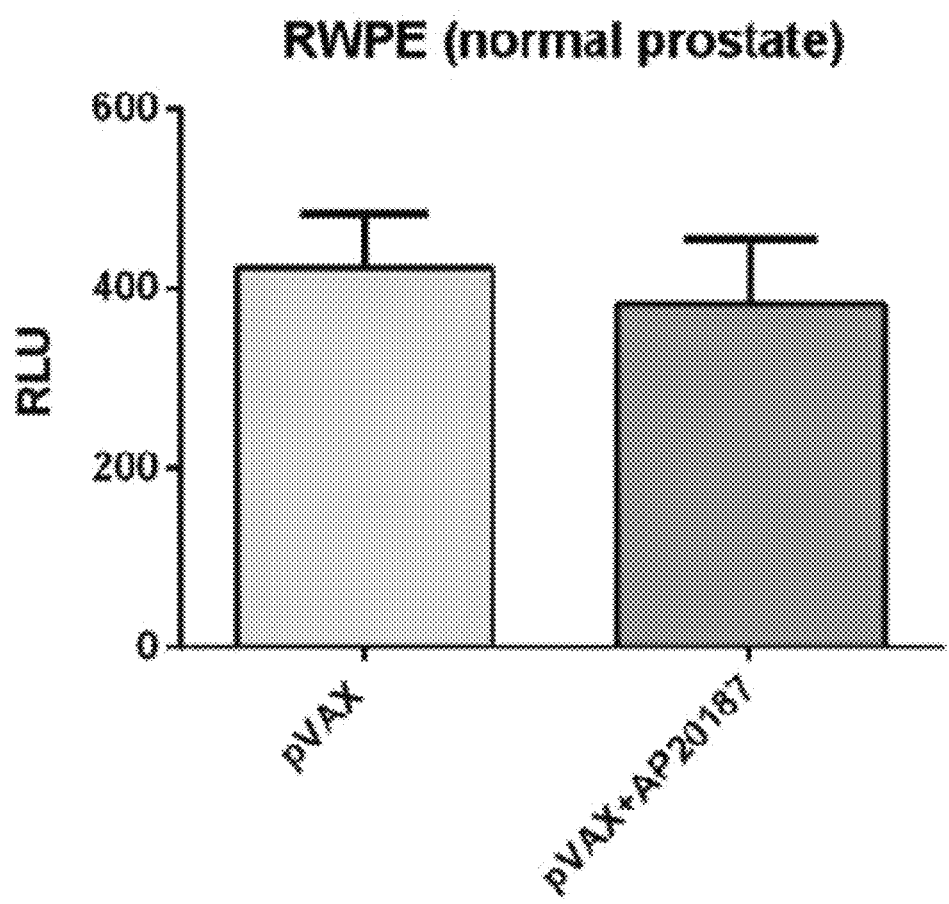

FIGS. 38-41 are bar graphs of data obtained with the p53-expressing cells presented in FIG. 37. Human prostate cancer (LNCaP (FIG. 38), DU145 (FIG. 39), PC-3 (FIG. 40) or normal epithelial (RWPE (FIG. 41)) cells were treated with Fusogenix lipid nanoparticles carrying the pVax-p53-iCasp9-luc plasmid and assessed for iCasp9 expression by Western blot and luminescence assays. These data demonstrate that addition of the chemical inducer of dimerization (CID; e.g., AP20187 and AP1903) abolishes the expression of iCasp9 and luciferase in p53-expressing cells engineered to express iCasp9 or luciferase.

Figure 42:
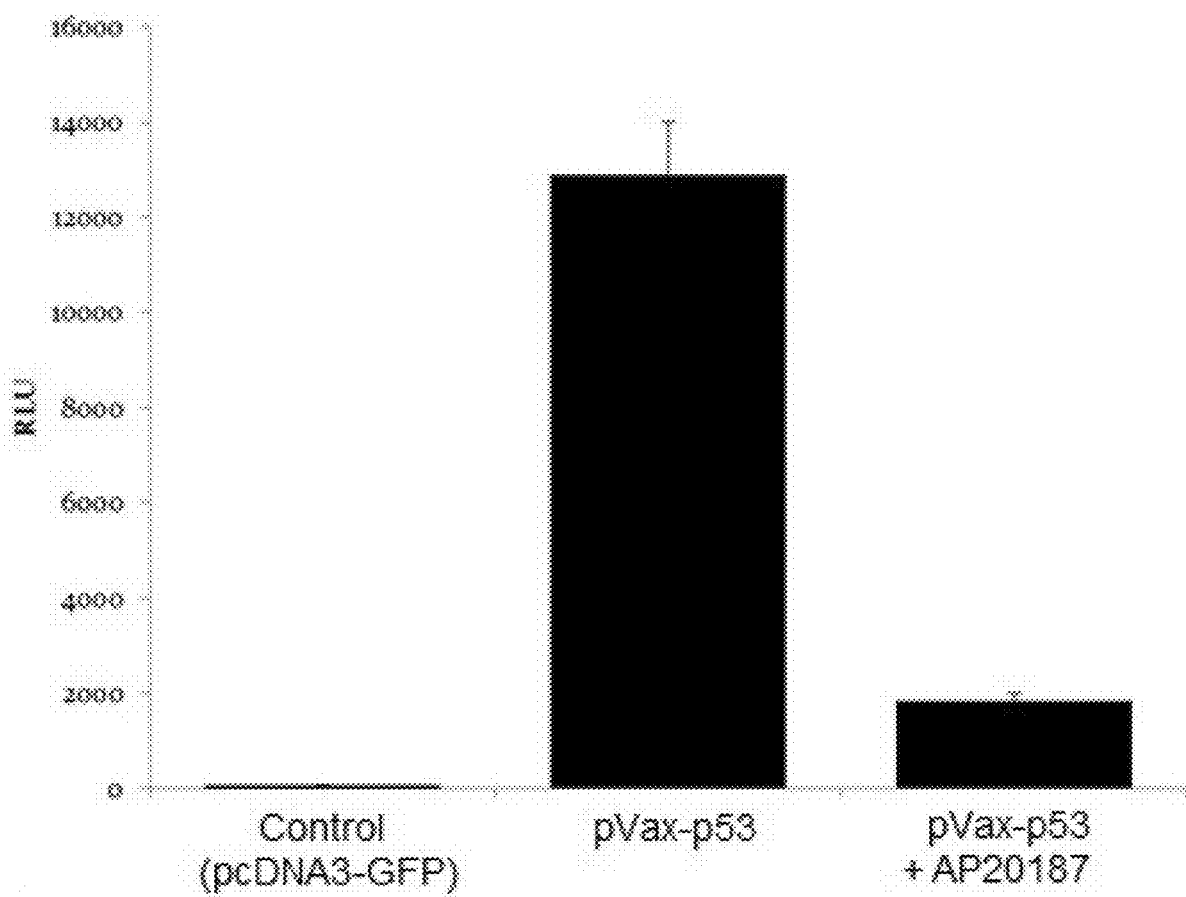

FIG. 42 is a bar graph of data from a luminescence assay of iCasp 9 and Casp 9 protein levels obtained with the p53-expressing cells presented in FIG. 36 (pVax-p53) and control cells (pcDNA3-GFP). Human prostate cancer PC-3 cells were treated with Fusogenix lipid nanoparticles carrying the pVax-p53-iCasp9-luc (luciferin) plasmid (in the presence and absence of the homodimerizer AP20187) and assessed for iCasp9 expression. These data demonstrate that addition of the chemical inducer of dimerization (CID; e.g., AP20187 and AP1903) abolishes the expression of iCasp9 and luciferase in p53-expressing cells engineered to express iCasp9 or luciferase.

FIGS. 43A, 43B, 44A, and 44B are flow cytometry apoptosis data (Annexin V) from human prostate cancer PC-3 cells treated with pVax-p53 Fusogenix lipid nanoparticles (in the absence and presence of AP20187, FIGS. 43A and 44A and 43B and 44B, respectively). The data presented in these figures demonstrates that suicide gene therapy selectively kills p53-expressing human prostate cancer cells in culture by inducing apoptosis (Luciferase-Annexin V flow cytometry).

Figure 45:
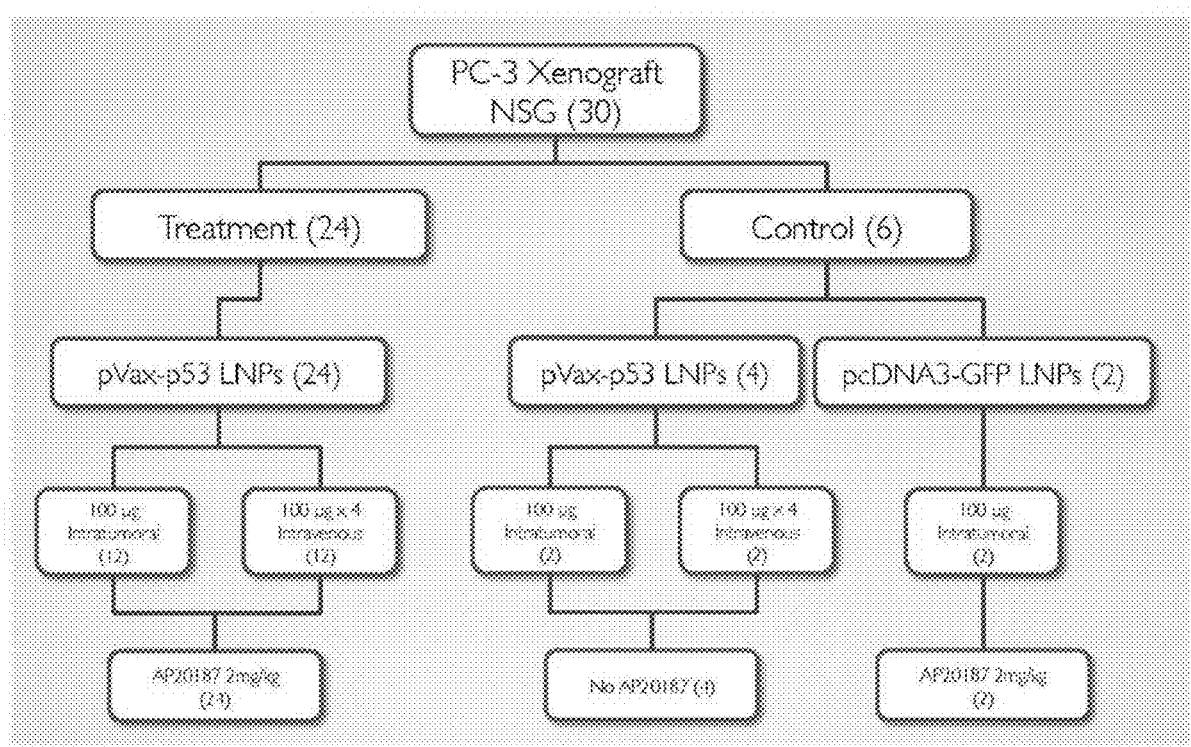

FIG. 45 is a flow diagram depicting a pre-clinical oncology study according to the present disclosure with 30×NSG mice implanted with human prostate tumor cells.

Figure 46:
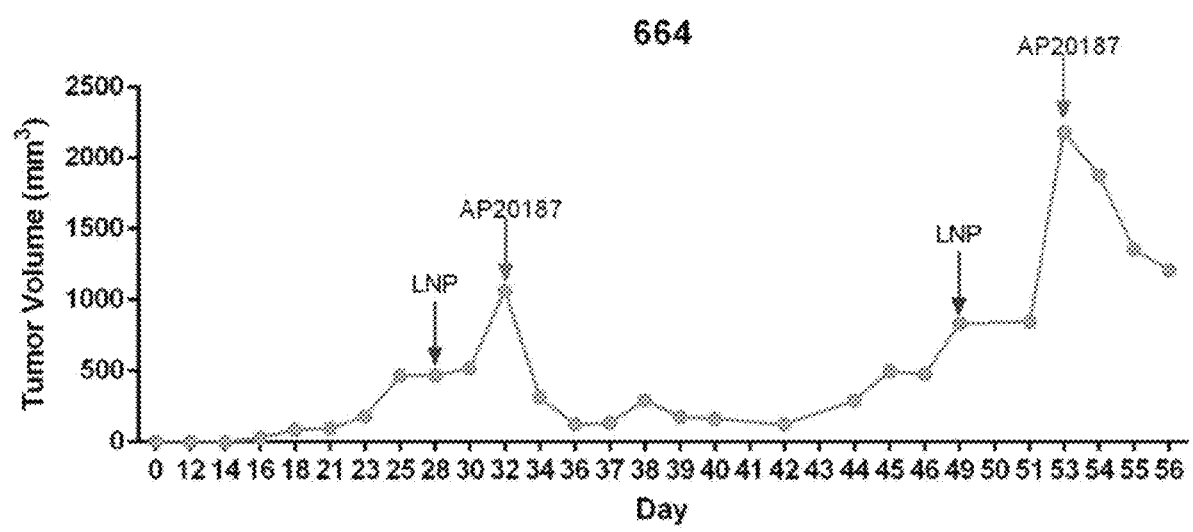

FIG. 46 is a graph of tumor volume (mm$^3$) from the pre-clinical oncology study depicted in FIG. 33 in which NSG mice bearing a subcutaneous human prostate PC-3 tumor was injected intratumorally (IT) with 100 µg Fusogenix pVax-p53 formulation, followed 96 hours later by intravenous (IV) administration of 2 mg/kg of the homodimerizer AP20187.

Figure 47A:
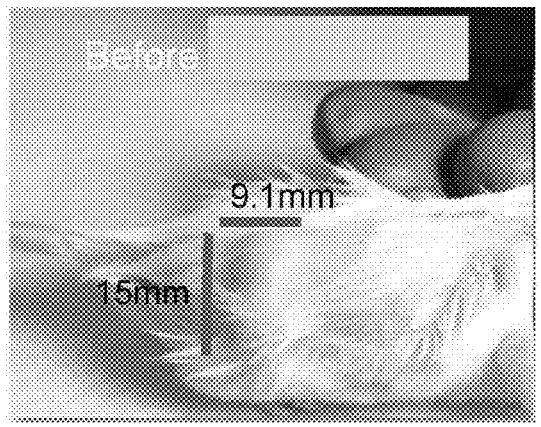
Figure 47B:
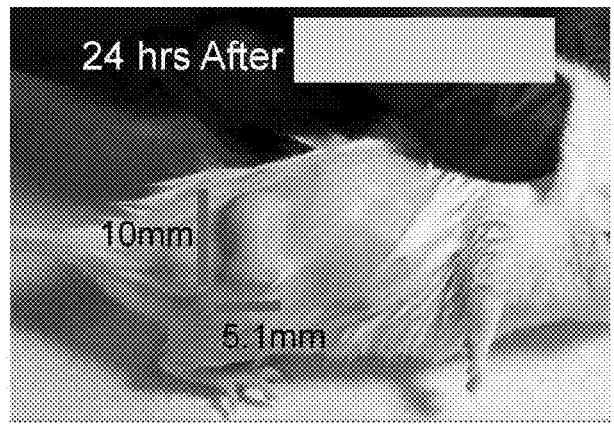
Figure 47C:
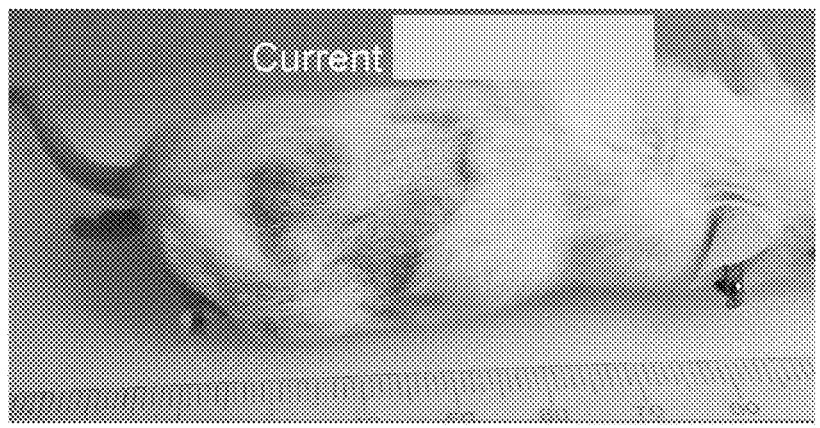

FIGS. 47A-47C are photographs of tumors from the IT injection oncology study of FIG. 46 in which NSG mouse bearing a subcutaneous human prostate PC-3 tumor was injected intratumorally with 100 µg Fusogenix pVax-p53 formulation, followed 96 hours by 2 mg/kg AP20187 IV. FIG. 47A shows tumor mass prior to administration of AP20187, FIG. 47B shows tumor mass at 24 hours following administration of AP20187, and FIG. 47C shows tumor mass at 96 hours following administration of AP20187.

Figure 48:
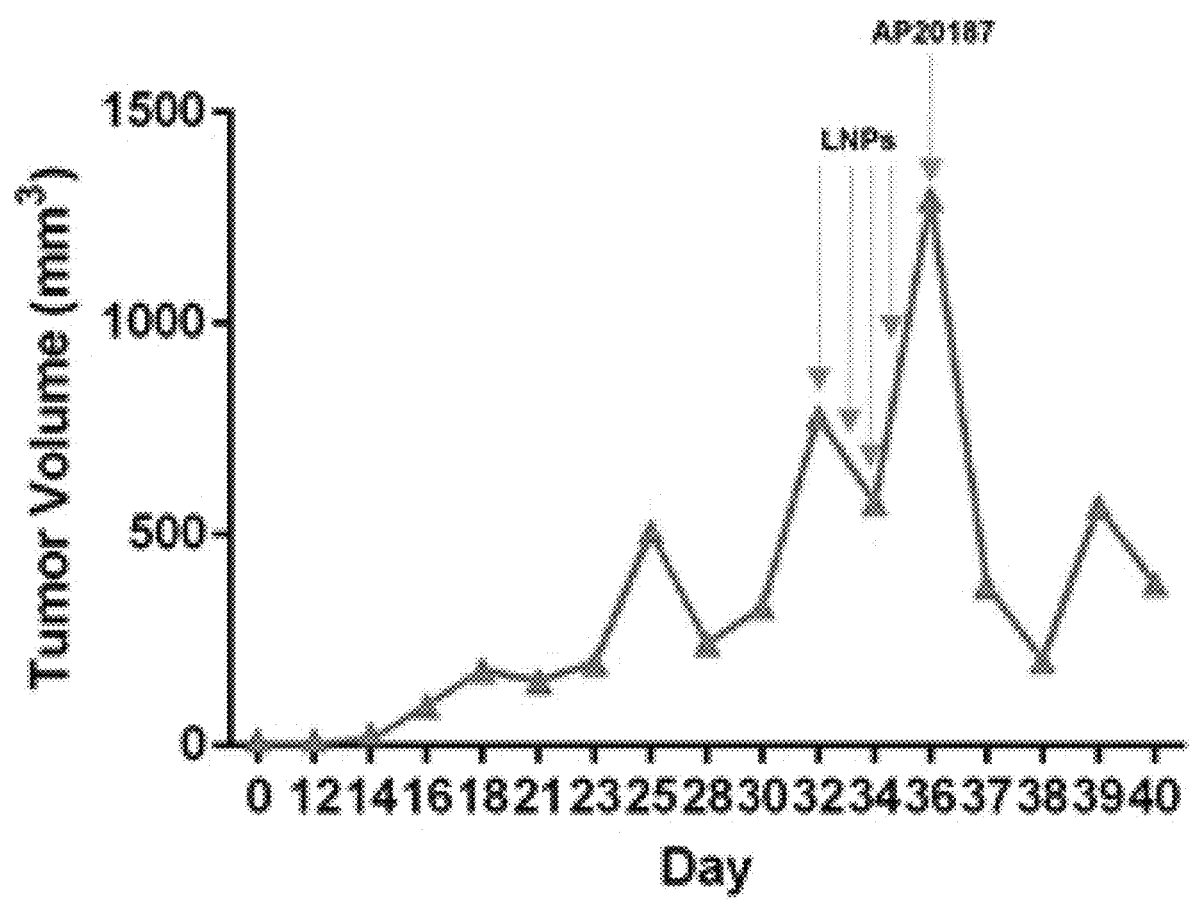

FIG. 48 is a graph from the first of four NSG mice bearing subcutaneous human prostate cancer PC-3 tumors that were injected intravenously (IV) with 4×100 µg doses of Fusogenix pVax-p53 formulation, followed 24 hours later by 2 mg/kg AP20187 IV.

Figure 49:
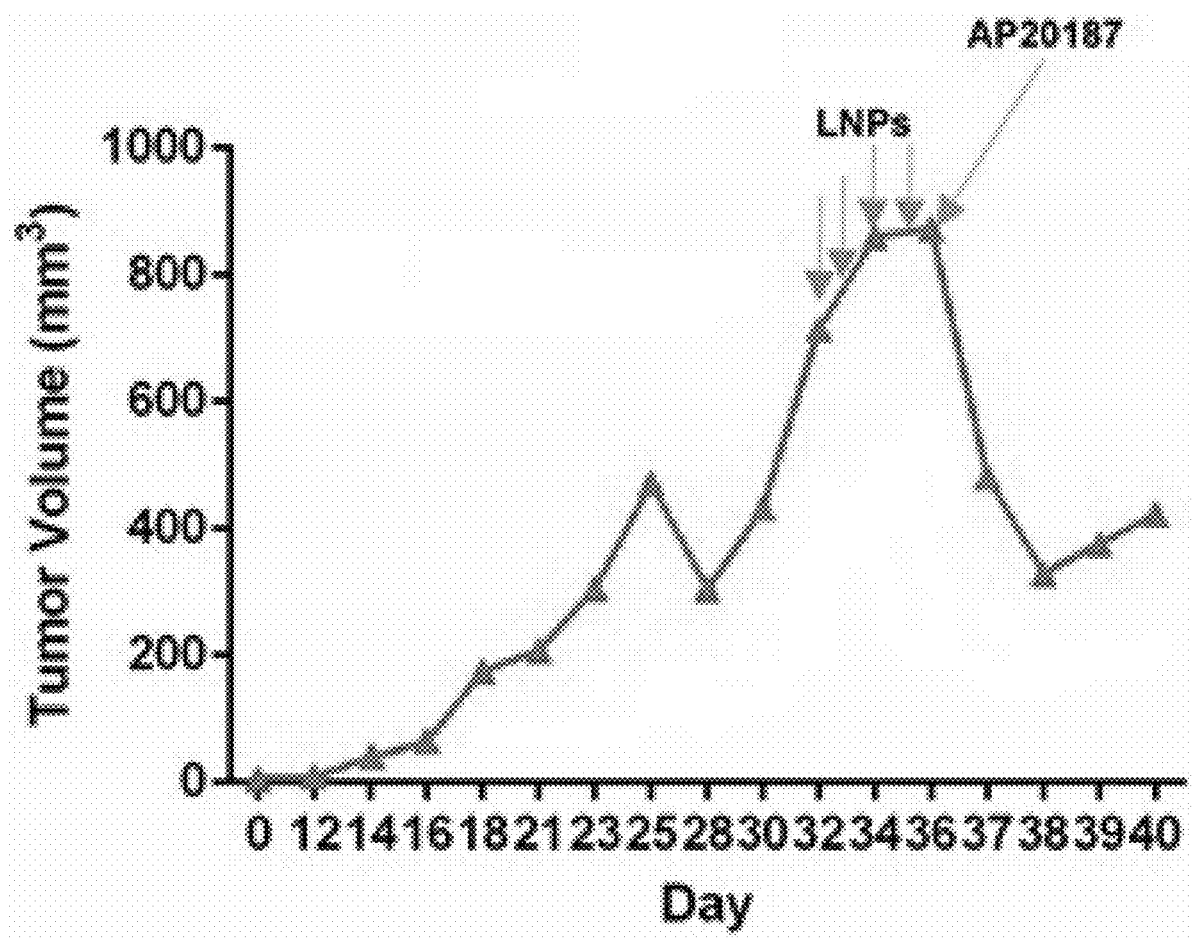

FIG. 49 is a graph from the second of four NSG mice bearing subcutaneous human prostate cancer PC-3 tumors that were injected intravenously (IV) with 4×100 µg doses of Fusogenix pVax-p53 formulation, followed 24 hours later by 2 mg/kg AP20187 IV.

Figure 50:
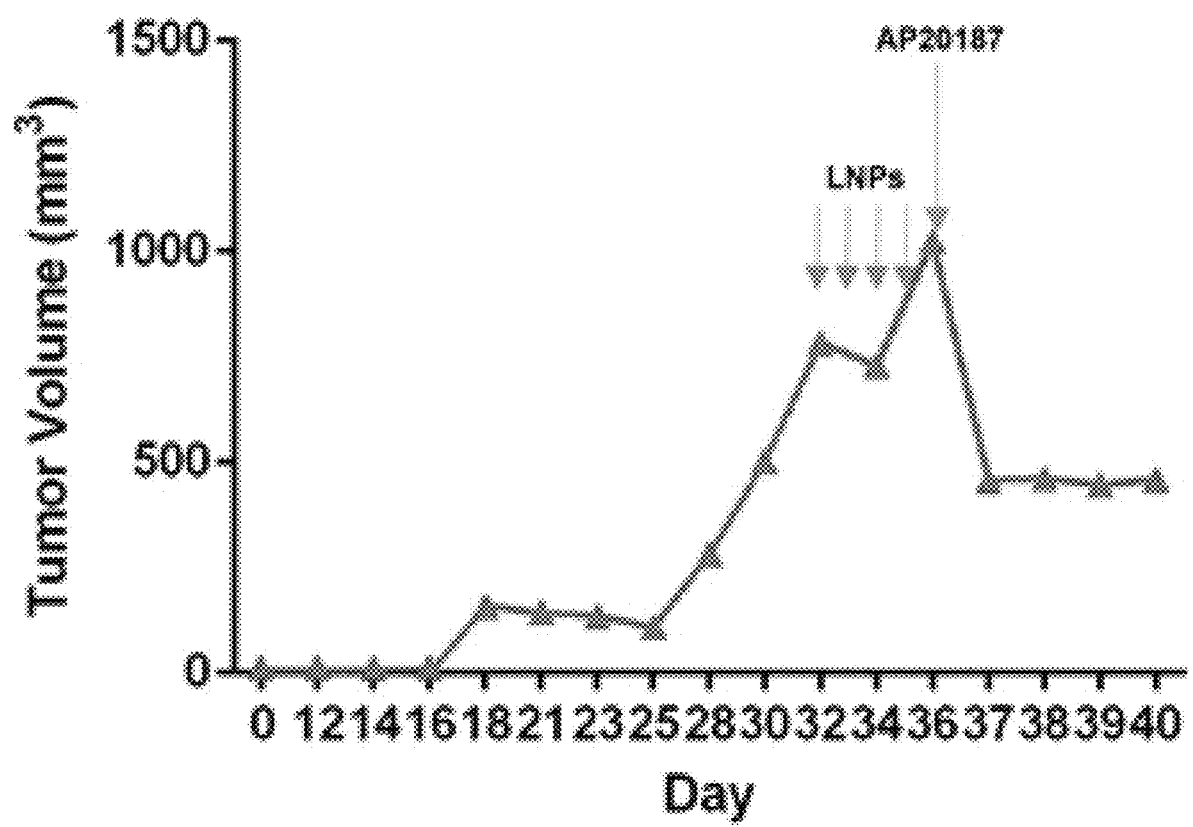

FIG. 50 is a graph from the third of four NSG mice bearing subcutaneous human prostate cancer PC-3 tumors that were injected intravenously (IV) with 4×100 µg doses of Fusogenix pVax-p53 formulation, followed 24 hours later by 2 mg/kg AP20187 IV.

Figure 51:
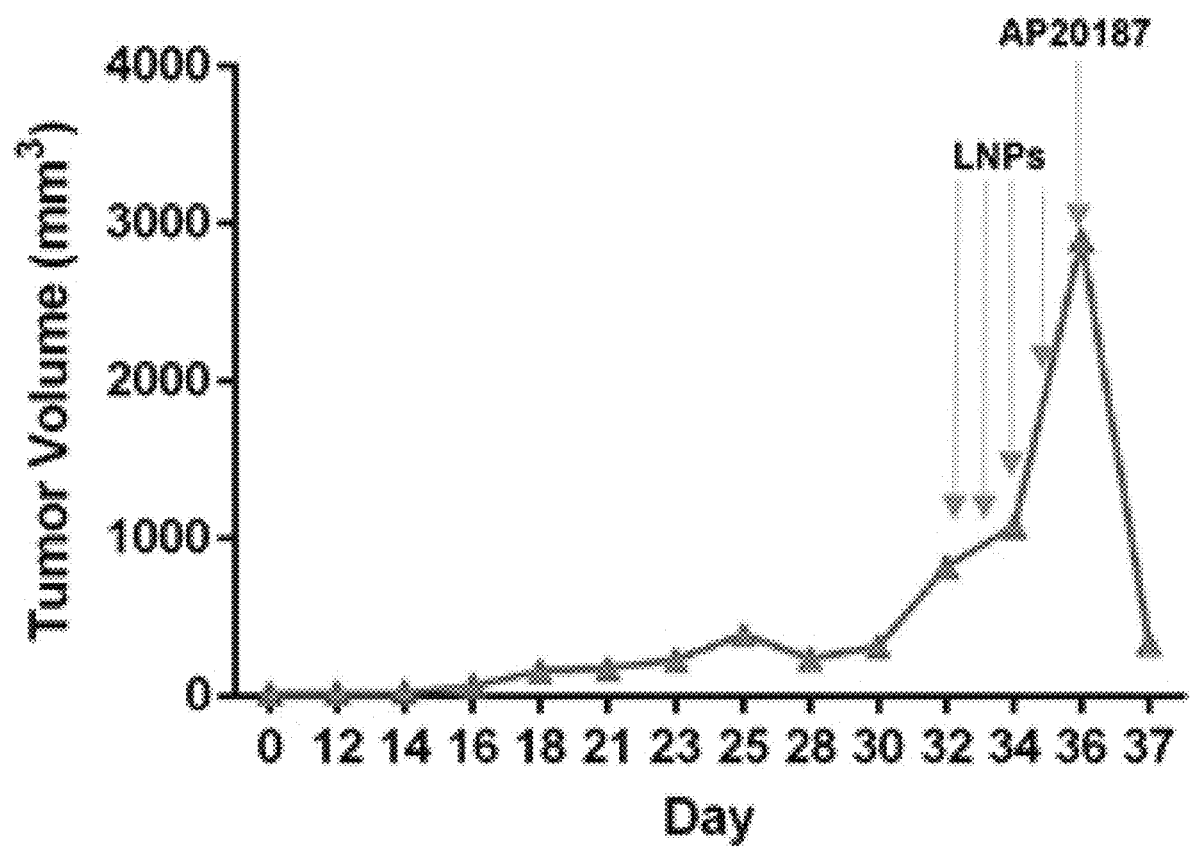

FIG. 51 is a graph from the fourth of four NSG mice bearing subcutaneous human prostate cancer PC-3 tumors that were injected intravenously (IV) with 4×100 µg doses of Fusogenix pVax-p53 formulation, followed 24 hours later by 2 mg/kg AP20187 IV.

Figure 52:
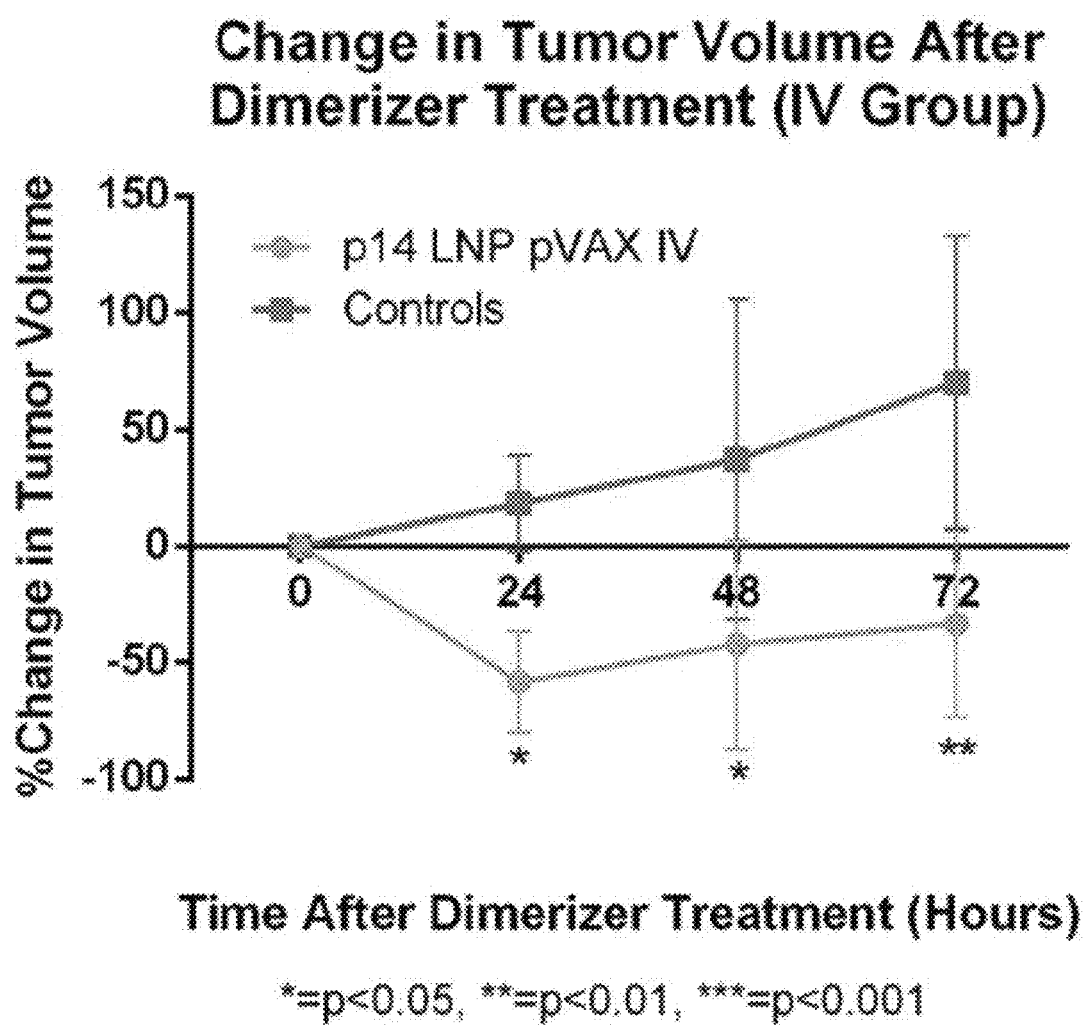

FIG. 52 is a graph showing the percentage change in tumor volume as a function of time after in vivo administration of a chemical inducer of dimerization (CID) in NSG mice (N=6 for all groups) bearing a prostate tumor that were treated with intravenous p14 LNP pVAX.

Figure 53:
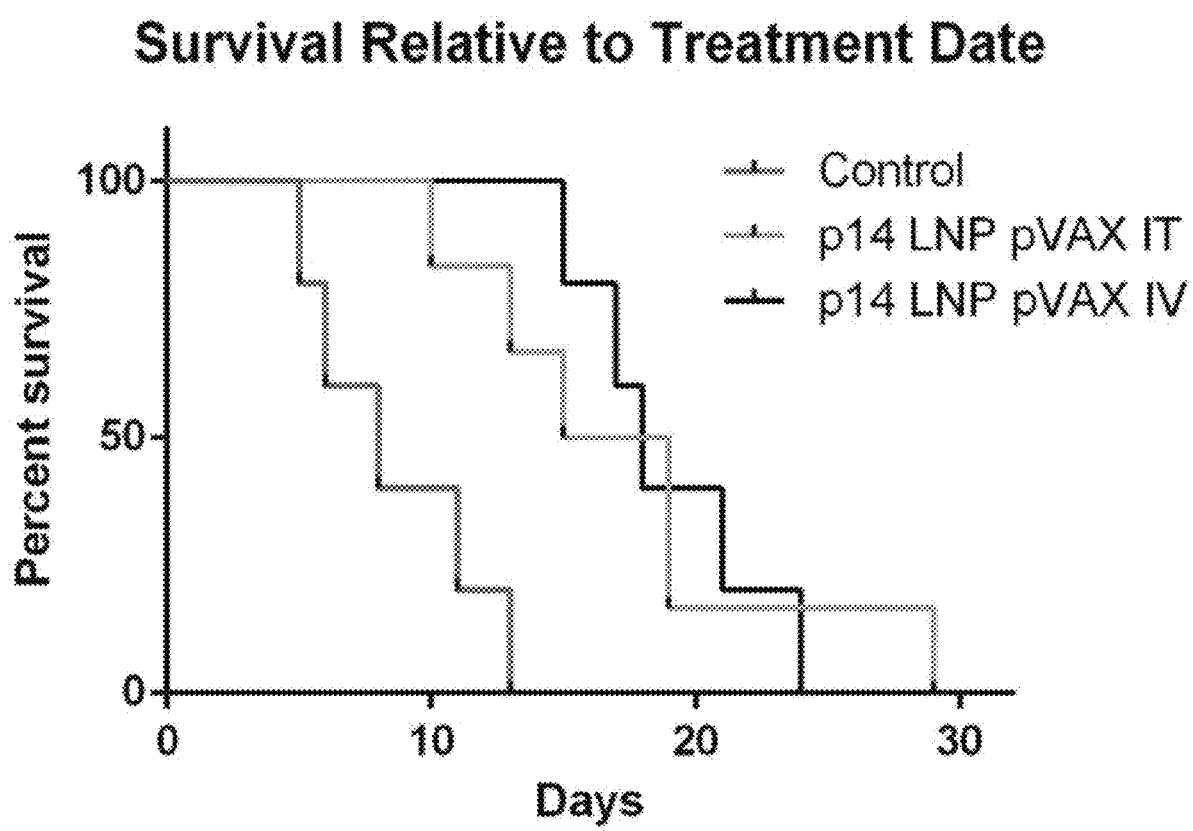

FIG. 53 is a survival curve showing the percent survival as a function of time after in vivo administration of a chemical inducer of dimerization (CID) in NSG mice (N=6 for all groups) bearing a prostate tumor that were treated with intravenous p14 LNP pVAX.

Figure 54:
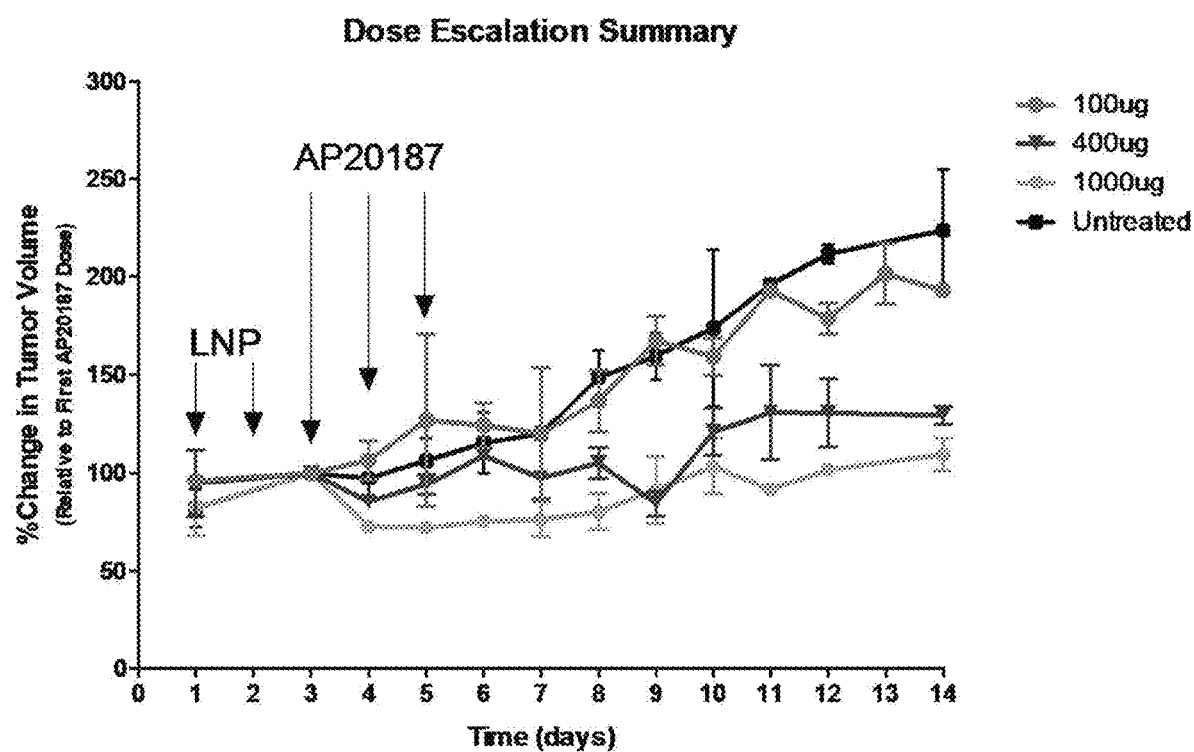

FIG. 54 is a graph of dose escalation data showing the percentage change in tumor volume as a function of time after in vivo administration of a chemical inducer of dimerization (CID) in NOD-SCID mice (N=6 for all groups) bearing a prostate tumor that were treated with 100 µg, 400 µg, and 1000 µg of intravenous p14 LNP pVAX. NOD-SCID mice were implanted subcutaneously with 500,000 PC-3 cells and randomized into treatment groups when their tumors reached 200 mm$^3$, (N=2 for all groups). Animals were injected with their assigned dose of p53-iCasp9 LNP IV twice followed by 2 mg/kg dimerizer. Tumors were measured directly every 24 hours.

Figure 55:
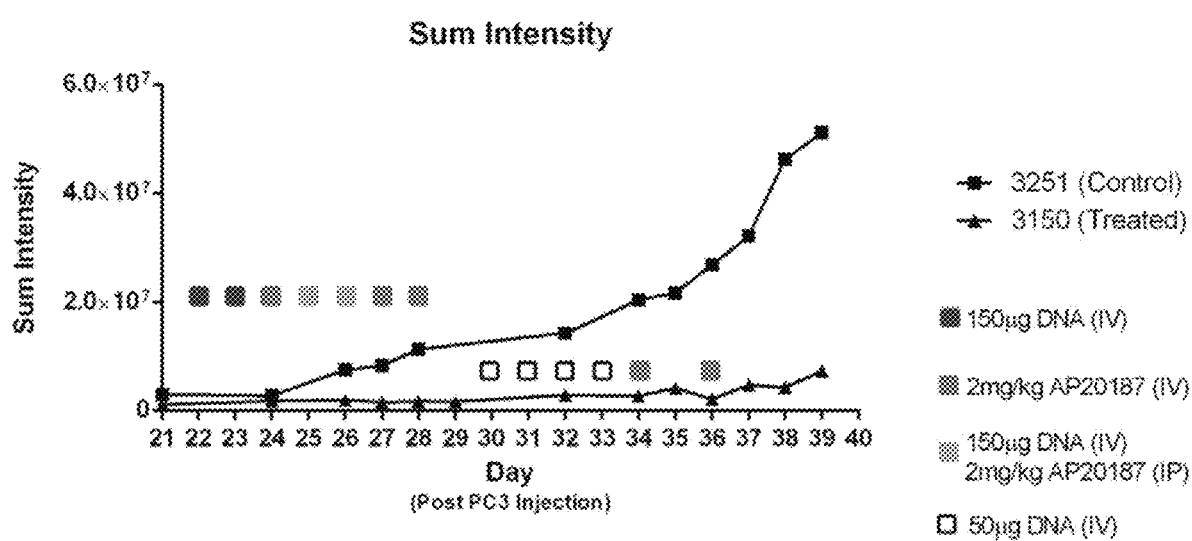

FIG. 55 is a graph showing the suppression of metastatic tumor growth with repeat treatment of a p53-iCasp9 LNP with or without a chemical inducer of dimerization (CID). NOD-SCID mice were injected with 500,000 PC-3M-luciferase cells on Day 0, LNP dosing was started on Day 22 with 150 µg p53-iCasp9 LNP. Dimerizer doses started Day 24 at 2 mg/kg. Mice were imaged every 24-48 hours to detect whole animal luminescence.

Figure 56:
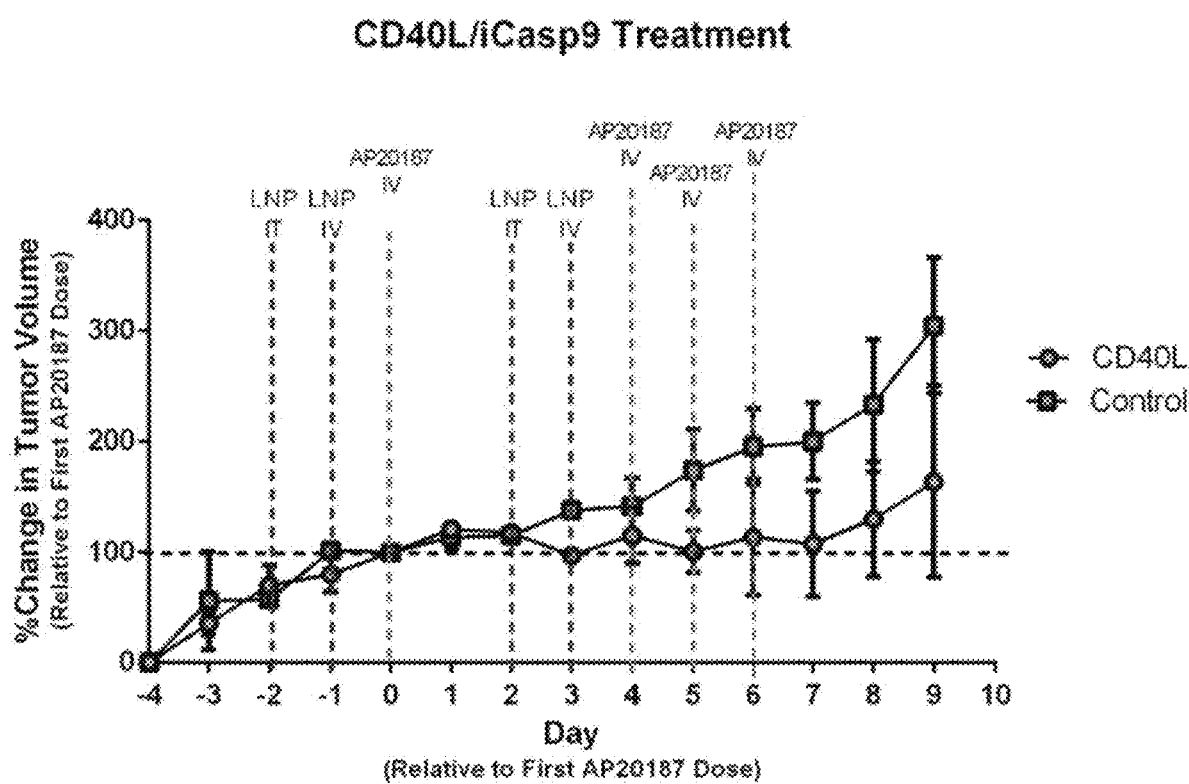
Figure 57:
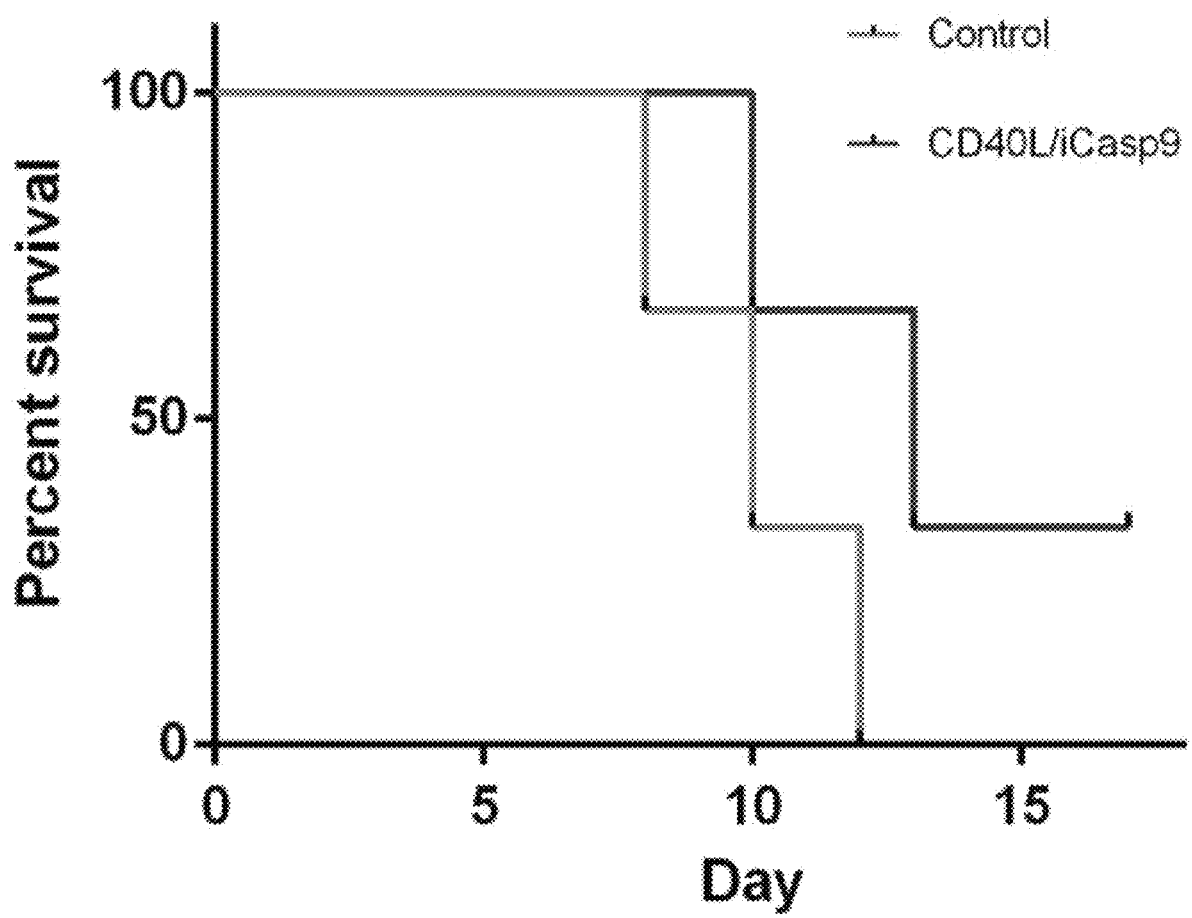
Figure 59:
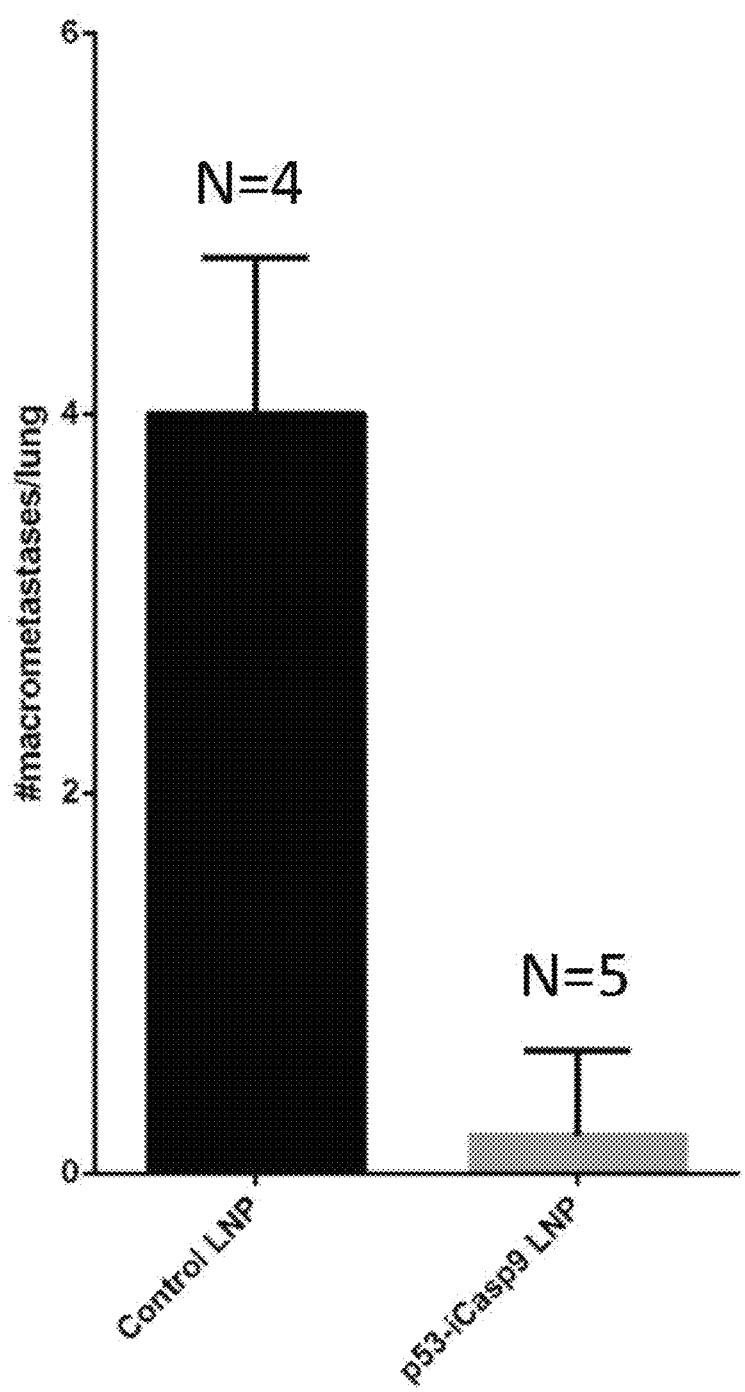

FIGS. 56 and 57 are graphs showing the percentage change in tumor volume (FIG. 56) and percent survival (FIG. 57) as a function of time after in vivo administration of a chemical inducer of dimerization (CID) in isogenic C57B6 mice implanted with B16 murine melanoma cells treated with LNPs containing a construct encoding iCasp9 and murine CD40L under control of the murine p53 promoter. Even though the rapid (10 hour) doubling time of the B16 cells made them largely refractory to the iCasp9-induced apoptosis, they still secreted enough CD40L to effectively halt the tumor's growth. A construct encoding GMCSF+OVA antigen was also tested and determined to be more effective than iCasp9 alone, but less effective than the CD40L version. N=3 for both groups.

FIGS. 58A-58D and 59 are photographs and a bar graph, respectively, of a B15F10 lung metastasis model data in which 100 µg of a control LNP (FIGS. 58A and 58B) or a p53-iCasp9 LNP (FIGS. 58C and 58D) was administered intravenously at days 3, 6, 9, and 12 following the intravenous injection of 75,000 B16F10 cells. At days 5, 8, 11, and 13, a chemical inducer of dimerization (CID) was administered intraperitoneally. Animals were sacrificed at day 14 and lung metastases were quantified.

Figure 60:
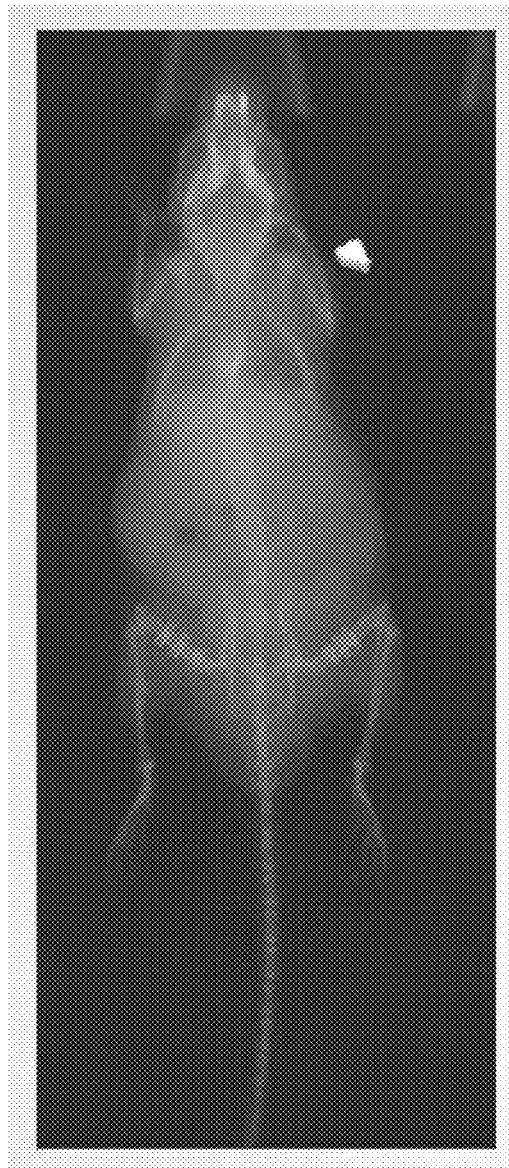
Figure 61:
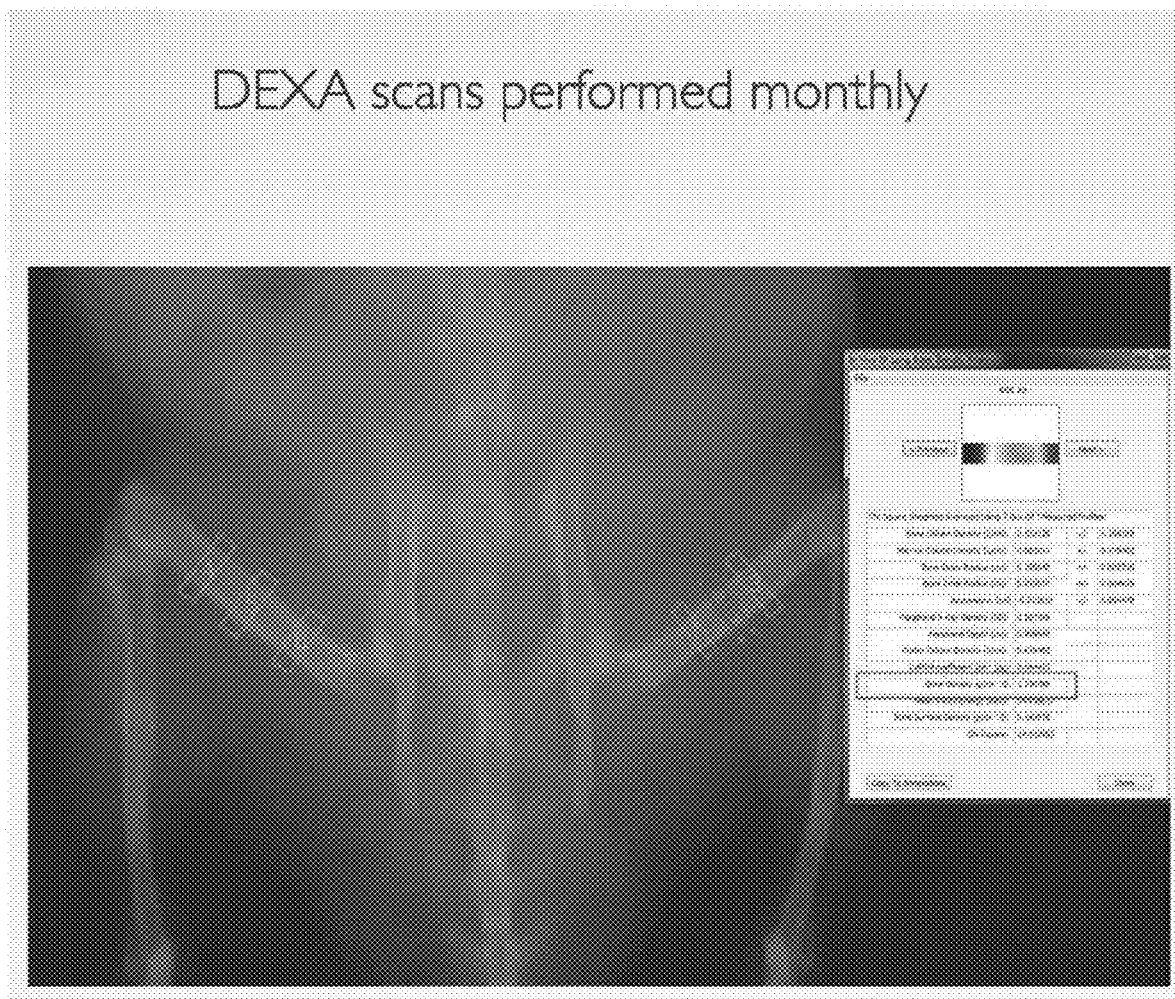

FIGS. 60 and 61 are DEXA scans, which were performed monthly, after in vivo administration of LNP formulations targeting p16, p53, or the combination (p16+p53) (N=10 for all groups). Mice were treated monthly starting at 728 days (104 weeks) of age.

Figure 62:
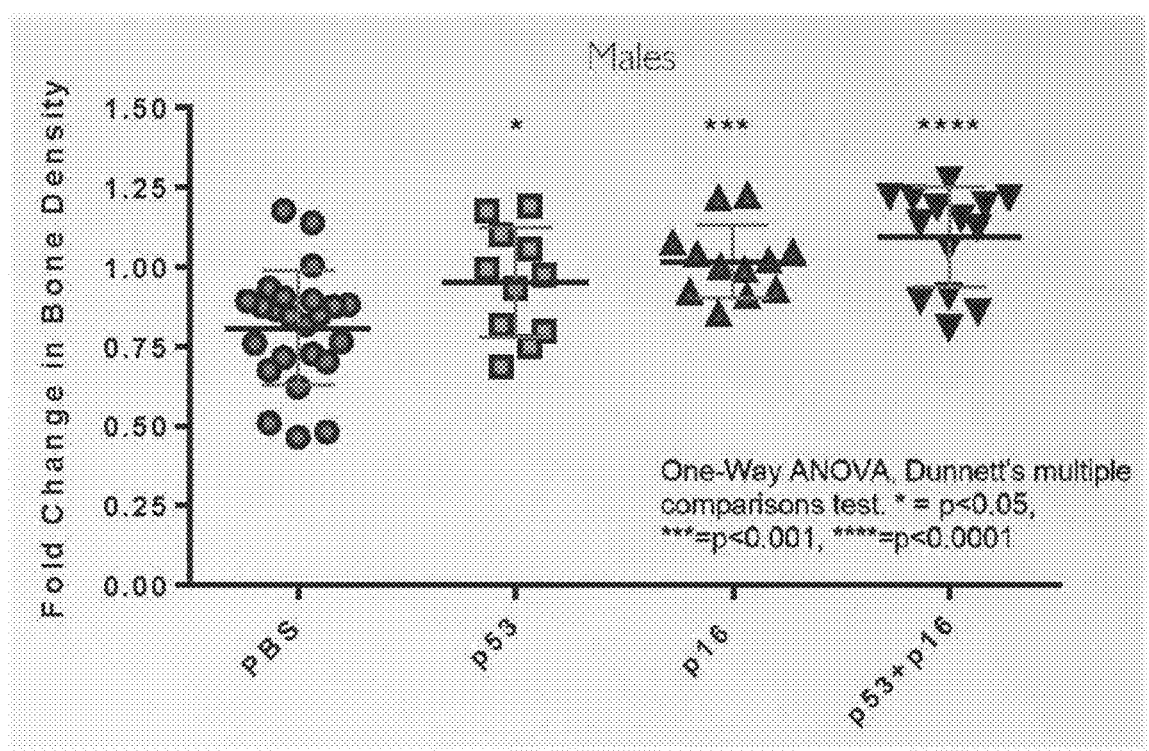
Figure 63:
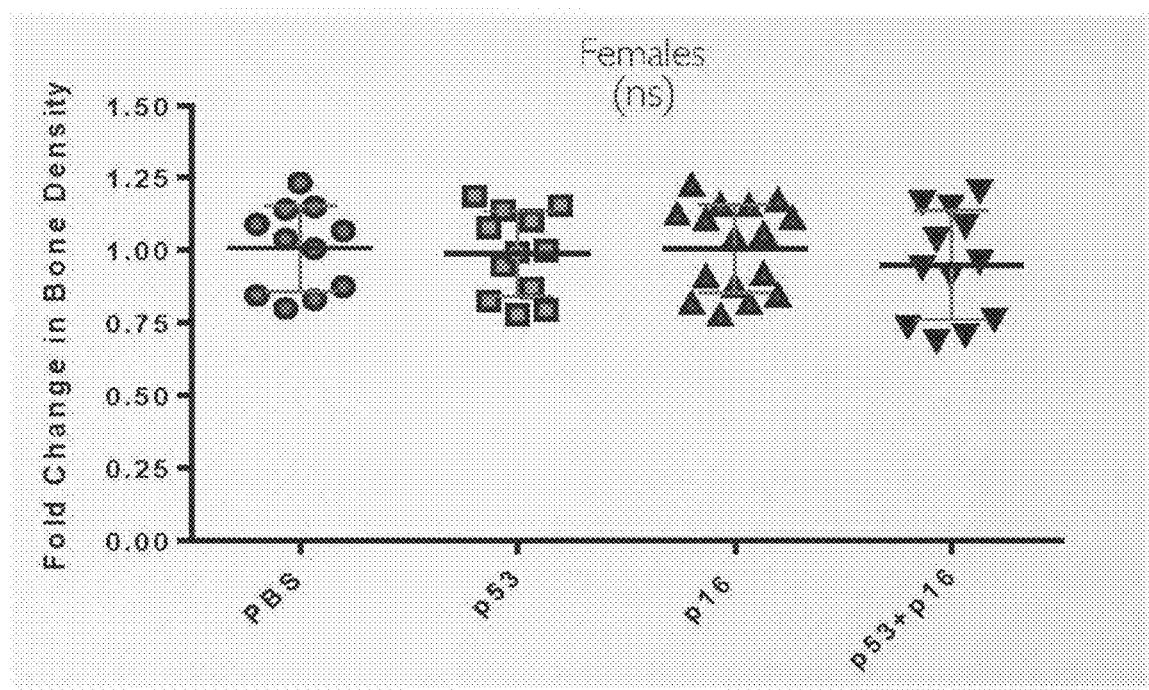

FIGS. 62 and 63 are graphs showing the change in bone density in male (FIG. 62) and female (FIG. 63) naturally aged mice after in vivo administration of LNP formulations targeting p16, p53, or the combination (p16+p53) (N=10 for all groups). Mice were treated monthly starting at 728 days (104 weeks) of age (arrows). At 896 days (128 weeks), the increase in bone density benefit for treated mice is apparent in the male mice.

Figure 64:
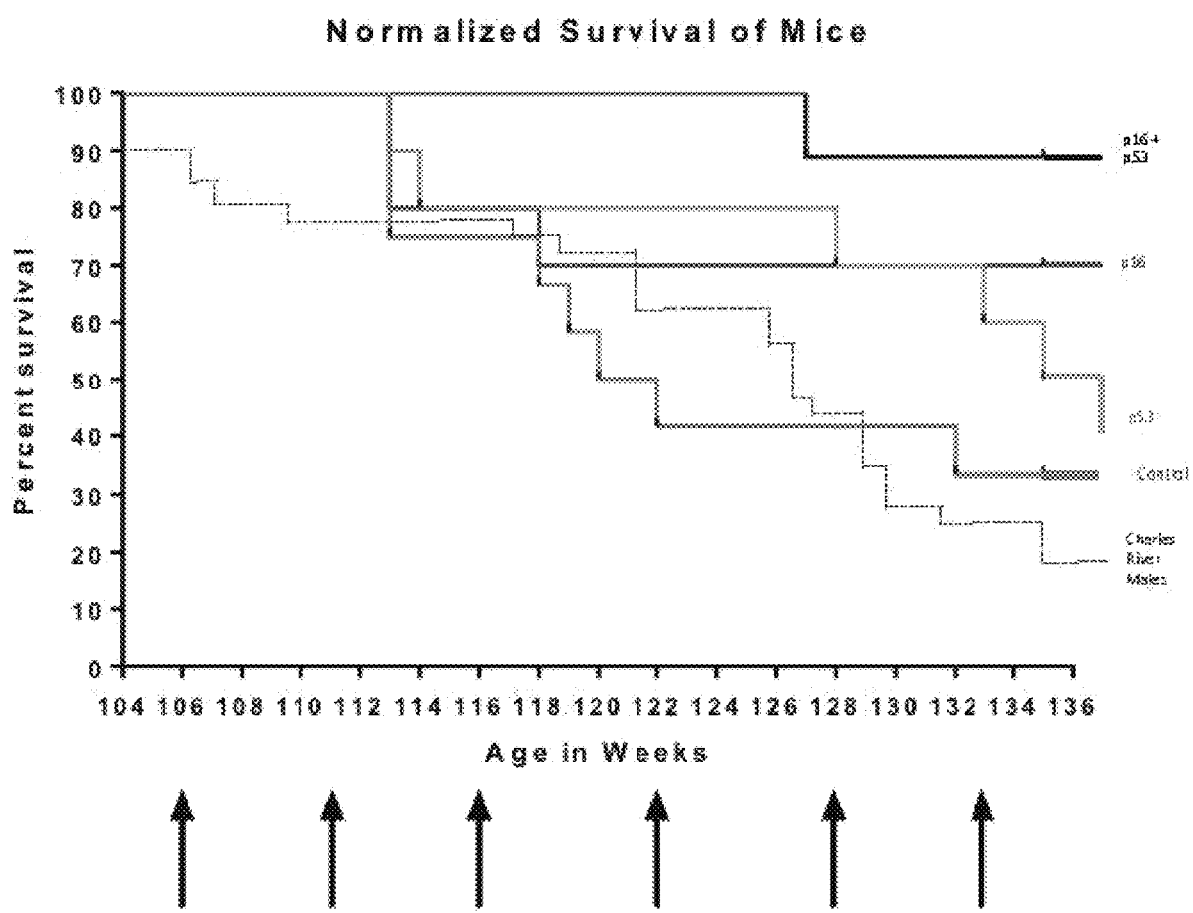

FIG. 64 is a survival curve showing the percent survival as a function of time after in vivo administration of LNP formulations targeting p16, p53, or the combination (p16+p53) (N=10 for all groups). Mice were treated monthly starting at 728 days (104 weeks) of age (arrows). At 931 days (133 weeks), the survival benefit for treated mice is apparent (>50% survival difference between combination treatment and control).

DETAILED DESCRIPTION

The present disclosure provides expression cassettes, systems, and methods for the selective reduction, prevention, and/or elimination in the growth and/or survival of a cell that is associated with aging, disease, or another condition (collectively "a target cell"), which expression cassettes, systems, and methods overcome the safety and efficacy concerns that are associated with existing technologies that rely on targeted delivery of a therapeutic compound and, as a result of, for example, inefficient target cell delivery and/or off-target effects, have limited therapeutic benefit.

More specifically, the expression cassettes, systems, and methods disclosed herein exploit the cell-specific transcription regulatory machinery that is intrinsic to a target cell and, thereby, achieve a target cell-specific therapeutic benefit without the need for targeted-delivery of a therapeutic compound. These expression cassettes, systems, and methods permit the target cell-specific induction of expression of a nucleic acid that encodes a therapeutic protein, which protein can reduce, prevent, and/or eliminate the growth and/or survival of a cell in which it is produced.

Thus, the various embodiments that are provided by the present disclosure include:

1. Expression constructs for the targeted production of therapeutic proteins within a target cell, such as a cell that is associated with aging, disease, and/or another condition, the expression construct comprising:
   a. transcriptional promoter that is activated in response to one or more factors each of which is produced within a target cell and
   b. a nucleic acid that is operably linked to and under regulatory control of the transcriptional promoter, wherein the nucleic acid encodes a therapeutic protein that can reduce, prevent, and/or eliminate the growth and/or survival of a cell, including the target cell.

2. Systems for the targeted production of a therapeutic protein within a target cell, the systems comprising a vector for delivering a nucleic acid to a cell, including a target cell as well as a non-target cell,
   wherein the vector comprises an expression construct for the targeted production of a therapeutic protein within a target cell (e.g., a cell that is associated with aging, cancer, and/or other disease and/or condition) but not within a non-target cell,
   wherein the expression construct comprises (i) a transcriptional promoter that is activated in response to one or more factors each of which is produced within a target cell and (ii) a nucleic acid that is operably linked to and under regulatory control of the transcriptional promoter,
   wherein the nucleic acid encodes a therapeutic protein that can reduce, prevent, and/or eliminate the growth and/or survival of a cell in which it is produced, including a target cell.

3. Methods for reducing, preventing, and/or eliminating the growth of a target cell, the methods comprising contacting a target cell with a system for the targeted production of a therapeutic protein within a target cell,
   wherein the system comprises a vector for delivery of a nucleic acid to a cell,
   wherein the vector comprises an expression construct for the targeted production of a therapeutic protein within a target cell (e.g., a cell that is associated with age, disease, or other condition) but not within a non-target cell,
   wherein the expression construct comprises (i) a transcriptional promoter that is activated in response to one or more factors each of which factors is produced within a target cell and (ii) a nucleic acid that is operably linked to and under regulatory control of the transcriptional promoter,
   wherein the nucleic acid encodes a therapeutic protein that is produced upon expression of the nucleic acid and
   wherein production of the therapeutic protein in the target cell (i.e., the cell that is associated with age, disease, or other condition) reduces, prevents, and/or eliminates growth and/or survival of the target cell.

4. Methods for the treatment of aging, disease, or other condition in a human, wherein aging, disease, or other condition is associated with a target cell, the methods comprising administering to the human a system for the targeted production of a therapeutic protein within a target cell,
   wherein the system comprises a vector that is capable of delivering a nucleic acid to a cell,
   wherein the vector comprises an expression construct for the targeted production of a therapeutic protein within a target cell (e.g., a cell that is associated with age, disease, or other condition) but not within a non-target cell,
   wherein the expression construct comprises (i) a transcriptional promoter that is activated in response to one or more factors each of which factors is produced within a target cell and (ii) a nucleic acid that is operably linked to and under regulatory control of the transcriptional promoter,
   wherein the nucleic acid encodes a therapeutic protein that is produced upon expression of the nucleic acid and
   wherein production of the therapeutic protein in the target cell (i.e., the cell that is associated with age, disease, or other condition) reduces, prevents, and/or eliminates growth and/or survival of the target cell thereby slowing aging in the human and/or slowing, reversing, and/or eliminating the disease or condition in the human.

Definitions

These and other aspects of the present disclosure can be better understood by reference to the following non-limiting definitions.

As used herein, the term "transcriptional promoter" refers to a region of DNA that initiates transcription of a particular gene. Promoters are located near transcription start sites of genes, on the same strand and upstream on the DNA (towards the 3' region of the anti-sense strand, also called template strand and non-coding strand). Promoters can be about 100-1000 base pairs long. For the transcription to take place, the enzyme that synthesizes RNA, known as RNA polymerase, must attach to the DNA near a gene. Promoters contain specific DNA sequences and response elements that provide a secure initial binding site for RNA polymerase and for proteins called transcription factors that recruit RNA polymerase. These transcription factors have specific activator or repressor sequences of corresponding nucleotides that attach to specific promoters and regulate gene expressions. The process is more complicated, and at least seven different factors are necessary for the binding of an RNA polymerase II to the promoter. Promoters represent critical elements that can work in concert with other regulatory regions (enhancers, silencers, boundary elements/insulators) to direct the level of transcription of a given gene.

Eucaryotic transcriptional promoters comprise a number of essential elements, which collectively constitute a core promoter (i.e., the minimal portion of a promoter that is required to initiate transcription). Those elements include (1) a transcription start site (TSS), (2) an RNA polymerase binding site (in particular an RNA polymerase II binding site in a promoter for a gene encoding a messenger RNA), (3) a general transcription factor binding site (e.g., a TATA box having a consensus sequence TATAAA, which is a binding site for a TATA-binding protein (TBP)), (4) a B recognition element (BRE), (5) a proximal promoter of approximately 250 bp that contains regulatory elements, (6) transcription factor binding sites (e.g., an E-box having the sequence CACGTF, which is a binding site for basic helix-loop-helix (bHLH) transcription factors including BMAL11-Clock nad cMyc), and (7) a distal promoter containing additional regulatory elements. As used herein, the term "transcriptional promoter" is distinct from the term "enhancer," which refers to a regulatory element that is distant from the transcriptional start site.

Eucaryotic promoters are often categorized according to the following classes: (1) AT-based class, (2) CG-based class, (3) ATCG-compact class, (4) ATCG-balanced class, (5) ATCG-middle class, (6) ATCG-less class, (7) AT-less class, (8) CG-spike class, (9) CG-less class, and (10) ATspike class. See, Gagniuc and Ionescu-Tirgoviste, *BMC Genomics* 13:512 (2012). Eucaryotic promoters can be "unidirectional" or "bidirectional." Unidirectional promoters regulate the transcription of a single gene and are characterized by the presence of a TATA box. Bidirectional promoters are short (<1 kbp), intergenic regions of DNA between the 5' ends of genes in a bidirectional gene pair (i.e., two adjacent genes coded on opposite strands having 5' ends oriented toward one another. Bidirectional genes are often functionally related and because they share a single promoter, can be co-regulated and co-expressed. Unlike unidirectional promoters, bidirectional promoters do not contain a TATA box but do contain GpC islands and exhibit symmetry around a midpoint of dominant Cs and As on one side and Gs and Ts on the other. CCAAT boxes are common in bidirectional promoters as are NRF-1, GABPA, YY1, and ACTACAnnTCCC motifs.

Transcriptional promoters often contain two or more transcription factor binding sites. Thus, the efficient expression of a nucleic acid that is downstream of a promoter having multiple transcription factor binding sites typically requires the cooperative action of multiple transcription factors. Accordingly, the specificity of transcriptional regulation, and hence expression of an associated nucleic acid, can be increased by employing transcriptional promoters having two or more transcription factor binding sites.

As used herein, the term "transcription factor" refers to sequence-specific DNA-binding factors that bind to specific sequences within a transcriptional promoter thereby regulating the transcription of a nucleic acid that is in operable proximity to and downstream of the promoter. Transcription factors include activators, which promote transcription, and repressors, which block transcription by preventing the recruitment or binding of an RNA polymerase. Transcription factors typically contain (1) one or more DNA-binding domains (DBDs), which facilitate sequence specific binding to a cognate transcription factor binding site (a/k/a response element) within a transcriptional promoter; (2) one or more signal-sensing domains (SSDs), which includes ligand binding domains that are responsive to external signals; and (3) one or more transactivation domains (TADs), which contain binding sites for other proteins, including transcription coregulators.

As used herein, the term "transcription factor" refers exclusively to those factors having one or more DBDs and is not intended to include other regulatory proteins such as coactivators, chromatin remodelers, histone acetylases, deacetylases, kinases, and methylases, which no not contain DBDs.

Of the approximately 2,600 human proteins that contain DNA-binding domains, the majority are believed to be transcription factors. Transcription factors are categorized according to structural features of the DNA-binding domain, which include basic helix-loop-helix domains, basic-leucine zipper (bZIP domains), C-terminal effector domains of bipartite response regulators, GCC box domains, helix-turn-helix domains, homeodomains, lambda repressor-like domains, serum response factor-like (srf-like) domains, paired box domains, winged helix domains, zinc finger domains, multi-$Cys_2His_2$ zinc finger domains, $Zn_2Cys_6$ domains, and $Zn_2Cys_8$ nuclear receptor zinc finger domains.

Many transcription factors are either tumor suppressors or oncogenes, and, thus, mutations within and the aberrant expression of such transcription factors is associated with some cancers and other diseases and conditions. For example, transcription factors within (1) the NF-kappaB family, (2) the AP-1 family, (3) the STAT family, and (4) the steroid receptor family have been implicated in the neurodevelopmental disorder Rett syndrome (the MECP2 transcription factor), diabetes (hepatocyte nuclear factors (HNFs) and insulin promoter factor-1 (IPF1/Pdx1)), developmental verbal dyspraxia (the FOXP2 transcription factor), autoimmune diseases (the FOXP3 transcription factor), Li-Raumeni syndrome (the p53 tumor suppressor), and multiple cancers (the STAT and HOX family of transcription factors). Clevenger, *Am. J. Pathol.* 165(5):1449-60 (2004); Carrithers et al., *Am J Pathol* 166(1):185-196 (2005); Herreros-Villanueve et al., *World J Gastroenterology* 20(9):2247-2254 (2014); and Campbell et al., *Am J Pathol* 158(1):25-32 (2001). Olsson et al., *Oncogene* 26(7):1028-37 (2007) describe the upregulation of the transcription factor E2F3, which is a key regulator of the cell cycle, in human bladder and prostate cancers. Cantile et al., *Curr Med Chem* 18(32):4872-84 (2011) describe the upregulation of HOX genes in urogenital cancers; Cillo et al., *Int J. Cancer* 129(11):2577-87 (2011) describe the upregulation of HOX genes in hepatocellular carcinoma; Cantile et al., *Int J. Cancer* 125(7):1532-41 (2009) describe HOX D13 expression across 79 tumor tissue types; Cantile et al., *J Cell Physiol* 205(2):202-10 (2005) describe upregulation of HOX D expression in prostate cancers; Cantile et al., *Oncogene* 22(41):6462-8 (2003) describe the hyperexpression of locus C genes in the HOX network in human bladder transitional cell carcinomas; Morgan et al., *BioMed Central* 14:15 (2014), describe HOX transcription factors as targets for prostate cancer; and Alharbi et al., *Leukemia* 27(5):1000-8 (2013) describe the role of HOXC genes in hematopoiesis and acute leukemia.

The AP-2 family includes five transcription factors that can act as both repressors and activators. AP-2γ regulates cancer cell survival by blocking p53 activation of the p21CIP gene. High levels of AP-2γ are associated with poor prognosis in breast cancer. Gee et al., *J Pathol* 217(1):32-41 (2009) and Williams et al., *EMBO J* 28(22):3591-601 (2009). A further transcription factor that promotes cell survival are the forkhead transcription factors (FOX), which can promote the expression of proteins involved in drug resistance and also block programmed cell death and may therefore protect cancer cells from chemotherapeutic drugs. Gomes et al., *Chin J. Cancer* 32(7):365-70 (2013) describe the role of FOXO3a and FOXM1 in carcinogenesis and drug resistance.

Transcription factors can bind to promoters as well as to enhancers. As used in the present disclosure, the term transcription factor refers to the subset of transcription factors that bind to transcription factor binding sites within a promoter and excludes those factors that bind to enhancer sequences. Transcription factors can also upregulate or downregulate the expression of an associated nucleic acid. The present disclosure employs transcriptional promoters having transcription factor binding sites for transcription factors that promote rather than inhibit expression and therefore cause the upregulation in the expression of an associated nucleic acid. Such transcription factors that upregulate nucleic acid expression include, for example and not limitation, transcription factors that (1) stabilize RNA polymerase binding to its cognate binding site, (2) recruit coactivator or corepressor proteins to a transcription factor DNA complex, and/or (3) catalyze the acetylation of histone proteins (or recruit one or more other proteins that catalyze the acetylation of histone proteins). Such histone acetyltransferase (HAT) activity reduces the affinity of histone binding to DNA thereby making the DNA more accessible for transcription.

As used herein, the term "necrosis" refers to a process leading to cell death that occurs when a cell is damaged by an external force, such as poison, a bodily injury, an infection, or loss of blood supply. Cell death from necrosis causes inflammation that can result in further distress or injury within the body. As used herein, the term "apoptosis" refers to a process leading to cell death in which a programmed sequence of events leads to the elimination of cells without releasing harmful substances. Apoptosis plays a crucial role in developing and maintaining the health of the body by eliminating old cells, unnecessary cells, and unhealthy cells. Apoptosis is mediated by proteins produced by suicide genes, including the caspase proteins, which break down cellular components needed for survival and induce the production of DNAses, which destroy nuclear DNA.

As used herein, the term "suicide gene" refers to a class of genes that produce proteins that induce p53-mediated apoptotic cell killing. Suicide genes that can be employed in the expression constructs and systems of the present disclosure include the caspases, Casp3, Casp8, Casp9, BAX, DFF40, Herpes Simplex Virus Thymidine Kinase (HSV-TK), and cytosine deaminase and inducible variants of Casp3, Casp8, Casp9, BAX, DFF40, Herpes HSV-TK, and cytosine deaminase.

The presently disclosed expression constructs and systems are used in methods for the treatment of aging, cancer infectious disease, bacterial infections, and/or other conditions as well as in methods for the killing of cells that are associated with aging, cancer, infectious disease, bacterial infections, and/or other conditions and employ a therapeutic protein that reduces the growth and/or proliferation of a target cell. In certain embodiments, the therapeutic protein can be expressed by a suicide gene, which encodes Casp3, Casp8, Casp9, BAX, DFF40, HSV-TK, or cytosine deaminase as well as a inducible variants of Casp3, Casp8, Casp9, BAX, DFF40, HSV-TK, or cytosine deaminase. The expression cassettes and systems can also be used in conjunction with conventional chemotherapeutics to enhance the effectiveness of therapeutic regimen for the treatment of aging, cancers, infectious diseases, bacterial infections, and other diseases and conditions.

Within certain aspects of the present disclosure, expression constructs are pVAX1 (FIG. 14) plasmid expression constructs comprising a polynucleotide encoding a pro-apoptotic protein under the regulatory control of a target cell-specific promoter, such as a senescent cell-specific promoter or a cancer cell-specific promoter.

Exemplary pVAX1™ plasmid expression constructs include pVAX-16s-iCasp9-MX (FIG. 16; SEQ ID NO: 6) for the target cell-specific expression of an inducible Caspase 9 protein (iCasp9) under the regulatory control of a p16s promoter, pVAX1-53-iCasp9-MX (FIG. 26; SEQ ID NO: 7) for the target cell-specific expression of an inducible Caspase 9 protein (iCasp9) under the regulatory control of a p53 promoter, pVax1-p53-saCasp9-5 (FIG. 27; SEQ ID NO: 8) for the target cell-specific expression of a self-activating Caspase 9 protein (saCASP9) under the regulatory control of a p53 promoter, pVax1-p53-iCasp9-OVA (FIG. 28; SEQ ID NO: 11) for the target cell-specific expression of an inducible Caspase 9 protein (iCasp9) and an ovalbumin protein under the regulatory control of a p53 promoter, pVax1-p53-iCasp9-G-O (FIG. 29; SEQ ID NO: 9) for the target cell-specific expression of an inducible Caspase 9 protein (iCasp9) and an ovalbumin protein under the regulatory control of a p53 promoter, pVax1-p53-iCasp9-huCD40L (FIG. 30; SEQ ID NO: 10) for the target cell-specific expression of an inducible Caspase 9 protein (iCasp9) and a CD40 ligand protein (CD40L) under the regulatory control of a p53 promoter.

Exemplary p10 plasmid expression constructs include p10-p16e-iCasp9 (FIG. 17; SEQ ID NO: 12) for the target cell-specific expression of an inducible Caspase 9 protein (iCasp9) under the regulatory control of a p16e promoter, p10-p16e-saCasp9 (FIG. 18; SEQ ID NO: 13) for the target cell-specific expression of a self-activating Caspase 9 protein (saCasp9) under the regulatory control of a p16e promoter, p10-p53-iCasp9 (FIG. 33; SEQ ID NO: 14) for the target cell-specific expression of an inducible Caspase 9 protein (iCasp9) under the regulatory control of a p53 promoter, and p10-p53-saCasp9 (FIG. 34; SEQ ID NO: 15) for the target cell-specific expression of a self-activating Caspase 9 protein (saCasp9) under the regulatory control of a p53 promoter.

Within other aspects of the present disclosure, expression constructs are NTC-based plasmid expression constructs, including NTC8385, NTC8685, and NTC9385 plasmid expression constructs, comprising a polynucleotide encoding a pro-apoptotic protein under the regulatory control of a target cell-specific promoter, such as a senescent cell-specific promoter or a cancer cell-specific promoter.

Within further aspects of the present disclosure, expression constructs are gWiz-based plasmid expression constructs comprising a polynucleotide encoding a pro-apoptotic protein under the regulatory control of a target cell-specific promoter, such as a senescent cell-specific promoter or a cancer cell-specific promoter.

The practice of the present disclosure will employ, unless indicated specifically to the contrary, conventional methodology and techniques that are in common use in the fields of virology, oncology, immunology, microbiology, molecular biology, and recombinant DNA, which methodology and techniques are well known by and readily available to those having skill of the art. Such methodology and techniques are explained fully in laboratory manuals as well as the scientific and patent literature. See, e.g., Sambrook, et al., "Molecular Cloning: A Laboratory Manual" (2nd Edition, Cold Spring Harbor Laboratory Press, Cold Spring Harbor, N.Y., 1989); Maniatis et al., "Molecular Cloning: A Laboratory Manual" (1982); "DNA Cloning: A Practical Approach, vol. I & II" (Glover, ed.); "Oligonucleotide Synthesis" (Gait, ed., 1984); Ausubel et al. (eds.), "Current Protocols in =Molecular Biology" (John Wiley & Sons, 1994); "Nucleic Acid Hybridization" (Hames & Higgins, eds., 1985); "Transcription and Translation" (Hames & Higgins, eds., 1984); "Animal Cell Culture" (Freshney, ed., 1986); and Perbal, "A Practical Guide to Molecular Cloning" (1984). All publications, patents and patent applications cited herein, whether supra or infra, are hereby incorporated by reference in their entirety.

Systems and Expression Constructs for Reducing, Preventing, and/or Eliminating the Growth and/or Survival of a Target Cell Within certain embodiments, the present disclosure provides expression constructs and systems comprising a delivery vector and an expression construct for achieving a target cell specific reduction, prevention, and/or elimination in the growth and/or survival of the target cell.

Systems

Systems of the present disclosure comprise (1) a vector that is capable of non-specific delivery of a nucleic acid to a cell, whether that cell is a target cell or a non-target cell, and (b) an expression construct comprising a target cell specific transcriptional promoter and a nucleic acid that encodes a therapeutic protein, which expression constructs achieve the target cell specific production of a therapeutic protein. The systems disclosed herein will find utility in a broad range of therapeutic applications in which it is desirable to effectuate the growth or survival characteristics of a target cell, such as a cell that is associated with aging, disease, or another condition, but, at the same time, to not effectuate the growth or survival characteristics of a normal, a non-target cell that is not associated with aging, disease, or another condition.

The present disclosure provides systems for effectuating the growth and/or survival of a broad range of cells that are associated with aging, disease, or other conditions that similarly comprises (1) a non-specific nucleic acid delivery vector and (2) an expression construct comprising (a) a target cell specific transcriptional promoter and (b) a nucleic acid that encodes a therapeutic protein. Each of these aspects of the presently disclosed systems are described in further detail herein.

Within certain embodiments, provided herein are systems for effectuating the growth and/or survival of target cells, which systems comprise: (1) a non-specific nucleic acid delivery vector and (2) an expression construct comprising: (a) a transcriptional promoter, which transcriptional promoter is activated in target cells but not in normal, non-target cells, and (b) a nucleic acid that is under the control of the transcriptional promoter, which nucleic acid encodes a therapeutic protein that can reduce, prevent, and/or eliminate the growth and/or survival of a target cell, for example by inducing a mechanism of programmed cell death in a cell in which it is produced. Thus, these systems achieve the selective killing of target cells by exploiting transcriptional machinery that is produced in, and intrinsic to, target cells; without the use of toxins and in the absence of target cell specific delivery of the expression construct.

In certain aspects of these embodiments wherein the human target cell is a senescent cell, the transcriptional promoter can include at least a transcription factor binding site (i.e., a response element) of p16INK4a/CDKN2A as described in Wang et al., *J. Biol. Chem.* 276(52):48655-61 (2001), which transcriptional promoter is responsive to activation by a factor such as SP1, ETS1, and ETS2. The transcriptional promoter can also include at least a transcription factor binding site (i.e., a response element) of p21/CDKN1A, which transcriptional promoter is responsive to activation by a factor such as p53/TP53. Transcriptional activation induces the expression of a nucleic acid that encodes a therapeutic protein such as Casp3, Casp8, Casp9, DFF40, BAX, HSV-TK, or carbonic anhydrase or an inducible variant of Casp3, Casp8, Casp9, BAX, DFF40, HSV-TK, or cytosine deaminase.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include at least a transcription factor binding site (i.e., a response element) of the $p21^{cip1/waf1}$ promoter, the $p27^{kip1}$ promoter, the $p57^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein such as, for example, Casp3, Casp8, Casp9, BAX, DFF40, HSV-TK, or cytosine deaminase or an inducible variant of Casp3, Casp8, Casp9, BAX, DFF40, HSV-TK, or cytosine deaminase which therapeutic protein reduces, prevents, and/or eliminates the growth and/or survival of the cancer cell, such as, for example, by inducing cell death in the senescent cell via a cellular process including apoptosis. Other therapeutic proteins may be employed that reduce, prevent, and/or eliminate the growth and/or survival of a cancer cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs. In still further aspects of these embodiments wherein the target cell is a human cell that is infected with an infectious agent, such as a virus, including, for example, a herpes virus, a polio virus, a hepatitis virus, a retrovirus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein such as, for example, Casp3, Casp8, Casp9, BAX, DFF40, HSV-TK, or cytosine deaminase or an inducible variant of Casp3, Casp8, Casp9, BAX, DFF40, HSV-TK, or cytosine deaminase which therapeutic protein reduces, prevents, and/or eliminates the growth and/or survival of the senescent cell, such as, for example, by inducing cell death in the senescent cell via a cellular process including apoptosis. Other therapeutic proteins may be employed that reduce, prevent, and/or eliminate the growth and/or survival of a senescent cell by, for example, inducing cell death via a cellular process including necrosis/necroptosis, autophagic cell death, endoplasmic reticulum-stress associated cytotoxicity, mitotic catastrophe, paraptosis, pyroptosis, pyronecrosis, and entosifs.

Each of these aspects of the presently disclosed systems are described in further detail herein.

1. Non-specific Nucleic Acid Delivery Vectors

The systems of the present disclosure achieve target cell specificity by exploiting transcriptional machinery that is unique to a target cell. Thus, the systems described herein employ nucleic acid delivery vectors that can be readily adapted for the non-specific delivery of expression constructs to a cell, including but not limited to a target cell.

A wide variety of both non-viral and viral nucleic acid delivery vectors are well known and readily available in the art and may be adapted for use for the non-specific cellular delivery of the expression constructs disclosed herein. See, for example, Elsabahy et al., *Current Drug Delivery* 8(3): 235-244 (2011) for a general description of viral and nonviral nucleic acid delivery methodologies. The successful delivery of a nucleic acid into mammalian cells relies on the use of efficient delivery vectors. Viral vectors exhibit desirable levels of delivery efficiency, but often also exhibit undesirable immunogenicity, inflammatory reactions, and problems associated with scale-up, all of which can limit their clinical use. The ideal vectors for the delivery of a nucleic acid are safe, yet ensure nucleic acid stability and the efficient transfer of the nucleic acid to the appropriate cellular compartments.

Non-limiting examples of non-viral and viral nucleic acid delivery vectors are described herein and disclosed in scientific and patent literature. More specifically, the presently disclosed systems may employ one or more liposomal vectors, viral vectors, nanoparticles, polyplexesm dendrimers, each of which has been developed for the non-specific delivery of nucleic acids, can be adapted for the non-specific delivery of the expression constructs described herein, and can be modified to incorporate one or more agents for promoting the targeted delivery of a system to a target cell of interest thereby enhancing the target cell specificity of the presently disclosed systems.

2. Liposomal Vectors and Nanoparticles

An expression cassette may be incorporated within and/or associated with a lipid membrane, a lipid bi-layer, and/or a lipid complex such as, for example, a liposome, a vesicle, a micelle and/or a microsphere. Suitable methodology for preparing lipid-based delivery systems that may be employed with the expression constructs of the present disclosure are described in Metselaar et al., *Mini Rev. Med. Chem.* 2(4):319-29 (2002); O'Hagen et al., *Expert Rev. Vaccines* 2(2):269-83 (2003); O'Hagan, *Curr. Drug Targets Infect. Disord.* 1(3):273-86 (2001); Zho et al., *Biosci Rep.* 22(2):355-69 (2002); Chikh et al., *Biosci Rep.* 22(2):339-53 (2002); Bungener et al., *Biosci. Rep.* 22(2):323-38 (2002); Park, *Biosci Rep.* 22(2):267-81 (2002); Ulrich, *Biosci. Rep.* 22(2):129-50; Lofthouse, *Adv. Drug Deliv. Rev.* 54(6):863-70 (2002); Zhou et al., *J. Immunother.* 25(4):289-303 (2002); Singh et al., *Pharm Res.* 19(6):715-28 (2002); Wong et al., *Curr. Med. Chem.* 8(9):1123-36 (2001); and Zhou et al., *Immunomethods* 4(3):229-35 (1994). Midoux et al., *British J. Pharmacol* 157:166-178 (2009) describe chemical vectors for the delivery of nucleic acids including polymers, peptides and lipids. Sioud and Sorensen, *Biochem Biophys Res Commun* 312(4):1220-5 (2003) describe cationic liposomes for the delivery of nucleic acids.

Due to their positive charge, cationic lipids have been employed for condensing negatively charged DNA molecules and to facilitate the encapsulation of DNA into liposomes. Cationic lipids also provide a high degree of stability to liposomes. Cationic liposomes interact with a cell membrane and are taken up by a cell through the process of endocytosis. Endosomes formed as the results of endocytosis, are broken down in the cytoplasm thereby releasing the cargo nucleic acid. Because of the inherent stability of cationic liposomes, however, transfection efficiencies can be low as a result of lysosomal degradation of the cargo nucleic acid.

Helper lipids (such as the electroneutral lipid DOPE and L-a-dioleoyl phosphatidyl choline (DOPC)) can be employed in combination with cationic lipids to form liposomes having decreased stability and, therefore, that exhibit improved transfection efficiencies. These electroneutral lipids are referred to as Fusogenix lipids. See, Gruner et al., *Biochemistry* 27(8):2853-66 (1988) and Farhood et al., *Biochim Biophys Acta* 1235(2):289-95 (1995). DOPE forms an HII phase structure that induces supramolecular arrangements leading to the fusion of a lipid bilayer at a temperature greater than 5° C. to 10° C. The incorporation of DOPE into liposomes also helps the formation of HII phases that destabilize endosomal membranes.

Cholesterol can be employed in combination with DOPE liposomes for applications in which a liposomal vector is administered intravenously. Sakurai et al., *Eur J Pharm Biopharm* 52(2):165-72 (2001). The presence of one unsaturation in the acyl chain of DOPE is a crucial factor for membrane fusion activity. Talbot et al., *Biochemistry* 36(19): 5827-36 (1997).

Fluorinated helper lipids having saturated chains, such as DF4C11PE (rac-2,3-Di[11-(F-butyl)undecanoyl) glycero-1-phosphoethanolamine) also enhance the transfection efficiency of lipopolyamine liposomes. Boussif et al., *J Gene Med* 3(2):109-14 (2001); Gaucheron et al., *Bioconj Chem* 12(6):949-63 (2001); and Gaucheron et al., *J Gene Med* 3(4):338-44 (2001).

The helper lipid 1,2-dioleoyl-3-trimethylammonium-propane (DOTAP) enhances efficient of in vitro cell transfection as compared to DOPE lipoplexes. Prata et al., *Chem Commun* 13:1566-8 (2008). Replacement of the double bond of the oleic chains of DOPE with a triple bond as in Distear-4-ynoyl L-a-phosphatidylethanolamine [DS(9-yne)PE] has also been shown to produce more stable lipoplexes. Fletcher et al., *Org Biomol Chem* 4(2):196-9 (2006).

Amphiphilic anionic peptides that are derived from the N-terminal segment of the HA-2 subunit of influenza virus haemagglutinin, such as the IFN7 (GLFEAIEGFIE NGWEGMIDGW YG) and E5CA (GLFEAIAEFI EGGWEGLIEG CA) peptides, can be used to increase the transfection efficiency of liposomes by several orders of magnitude. Wagner et al., *Proc Natl Acad Sci U.S.A.* 89(17): 7934-8 (1992); Midoux et al., *Nucl Acids Res.* 21(4):871-8 (1993); Kichler et al., *Bioconjug Chem* 8(2):213-21 (1997); Wagner, *Adv Drug Deliv Rev* 38(3):279-289 (1999); Zhang et al., *J Gene Med* 3(6):560-8 (2001). Some artificial peptides such as GALA have been also used as fusogenic peptides. See, for example, Li et al., *Adv Drug Deliv Rev* 56(7):967-85 (2004) and Sasaki et al., *Anal Bioanal Chem* 391(8):2717-27 (2008). The fusogenic peptide of the glycoprotein H from herpes simplex virus improves the endosomal release of DNA/Lipofectamine lipoplexes and transgene expression in human cell (Tu and Kim, *J Gene Med* 10(6):646-54 (2008).

PCT Patent Publication Nos. WO 1999024582A1 and WO 2002/044206 describe a class of proteins derived from the family Reoviridae that promote membrane fusion. These proteins are exemplified by the p14 protein from reptilian reovirus and the p16 protein from aquareovirus. PCT Patent Publication No. WO 2012/040825 describes recombinant polypeptides for facilitating membrane fusion, which polypeptides have at least 80% sequence identity with the ectodomain of p14 fusion-associated small transmembrane (FAST) protein and having a functional myristoylation motif, a transmembrane domain from a FAST protein and a sequence with at least 80% sequence identity with the endodomain of p15 FAST protein. The '825 PCT further describes the addition of a targeting ligand to the recombinant polypeptide for selective fusion. The recombinant polypeptides presented in the '825 PCT can be incorporated within the membrane of a liposome to facilitate the delivery of nucleic acids. Fusogenix liposomes for delivering therapeutic compounds, including nucleic acids, to the cytoplasm of a mammalian cell, which reduce liposome disruption and consequent systemic dispersion of the cargo nucleic acid and/or uptake into endosomes and resulting nucleic acid destruction are available commercially from Innovascreen Inc. (Halifax, Nova Scotia, CA).

A wide variety of inorganic nanoparticles, including gold, silica, iron oxide, titanium, hydrogels, and calcium phosphates have been described for the delivery of nucleic acids and can be adapted for the delivery of the expression constructs described herein. See, for example Wagner and Bhaduri, *Tissue Engineering* 18(1):1-14 (2012) (describing inorganic nanoparticles for delivery of nucleic acid sequences); Ding et al., *Mol Ther* e-pub (2014) (describing gold nanoparticles for nucleic acid delivery); Zhang et al., *Langmuir* 30(3):839-45 (2014) (describing titanium dioxide nanoparticles for delivery of DNA oligonucleotides); Xie et al., *Curr Pharm Biotechnol* 14(10):918-25 (2014) (describing biodegradable calcium phosphate nanoparticles fro gene delivery); Sizovs et al., *J Am Chem Soc* 136(1):234-40 (2014) (describing sub-30 monodisperse oligonucleotide nanoparticles).

Among the advantages of inorganic vectors are their storage stability, low immunogenicity, and resistance to microbial attack. Nanoparticles of less than 100 nm can efficiently trap nucleic acids and allows its escape from endosomes without degradation. Inorganic nanoparticles exhibit improved in vitro transfection for attached cell lines due to their high density and preferential location on the base of the culture dish. Quantum dots have been described that permit the coupling of nucleic acid delivery with stable fluorescence markers.

Hydrogel nanoparticles of defined dimensions and compositions, can be prepared via a particle molding process referred to as PRINT (Particle Replication in Non-wetting Templates), and can be used as delivery vectors for the expression constructs disclosed herein. Nucleic acids can be encapsulated in particles through electrostatic association and physical entrapment. To prevent the disassociation of cargo nucleic acids from nanoparticles following systemic administration, a polymerizable conjugate with a degradable, disulfide linkage can be employed.

The PRINT technique permits the generation of engineered nanoparticles having precisely controlled properties including size, shape, modulus, chemical composition and surface functionality for enhancing the targeting of the expression cassette to a target cell. See, e.g., Wang et al., *J Am Chem Soc* 132:11306-11313 (2010); Enlow et al., *Nano Lett* 11:808-813 (2011); Gratton et al., *Proc Natl Acad Sci USA* 105:11613-11618 (2008); Kelly, *J Am Chem Soc* 130:5438-5439 (2008); Merkel et al. *Proc Natl Acad Sci USA* 108:586-591 (2011). PRINT is also amenable to continuous roll-to-roll fabrication techniques that permit the scale-up of particle fabrication under good manufacturing practice (GMP) conditions.

Nanoparticles can be encapsulated with a lipid coating to improve oral bioavailability, minimize enzymatic degradation and cross blood brain barrier. The nanoparticle surface can also be PEGylated to improve water solubility, circulation in vivo, and stealth properties.

3. Viral Vectors

A wide variety of viral vectors are well known by and readily available to those of skill in the art, including, for example, herpes simplex viral vectors lentiviral vectors, adenoviral vectors, and adeno-associated viral vectors, which viral vectors can be adapted for use in the systems disclosed herein for the delivery of nucleic acids, in particular nucleic acids comprising an expression cassette for the target cell specific expression of a therapeutic protein.

The tropisms of natural or engineered viruses towards specific receptors are the foundations for constructing viral vectors for delivery of nucleic acids. The attachment of these vectors to a target cell is contingent upon the recognition of specific receptors on a cell surface by a ligand on the viral vector. Viruses presenting very specific ligands on their surfaces anchor onto the specific receptors on a cell. Viruses can be engineered to display ligands for receptors presented on the surface of a target cell of interest. The interactions between cell receptors and viral ligands are modulated in vivo by toll like receptors.

The entry of a viral vector into a cell, whether via receptor mediated endocytosis or membrane fusion, requires a specific set of domains that permit the escape of the viral vector from endosomal and/or lysosomal pathways. Other domains facilitate entry into nuclei. Replication, assembly, and latency determine the dynamics of interactions between the vector and the cell and are important considerations in the choice of a viral vector, as well as in engineering therapeutic cargo carrying cells, in designing cancer suicide gene therapies.

Herpes simplex virus (HSV) belongs to a family of herpesviridae, which are enveloped DNA viruses. HSV binds to cell receptors through orthologs of their three main ligand glycoproteins: gB, gH, and gL, and sometimes employ accessory proteins. These ligands play decisive roles in the primary routes of virus entry into oral, ocular, and genital forms of the disease. HSV possesses high tropism towards cell receptors of the nervous system, which can be utilized for engineering recombinant viruses for the delivery of expression cassettes to target cells, including senescent cells, cancer cells, and cells infected with an infectious agent. Therapeutic bystander effects are enhanced by inclusion of connexin coding sequences into the constructs. Herpes Simplex Virus vectors for the delivery of nucleic acids to target cells have been reviewed in Anesti and Coffin, *Expert Opin Biol Ther* 10(1):89-103 (2010); Marconi et al., *Adv Exp Med Biol* 655:118-44 (2009); and Kasai and Saeki, *Curr Gene Ther* 6(3):303-14 (2006).

Lentivirus belongs to a family of retroviridae, which are enveloped, single stranded RNA retroviruses and include the Human immunodeficiency virus (HIV). HIV envelope protein binds CD4, which is present on the cells of the human immune system such as CD4+ T cells, macrophages, and dendritic cells. Upon entry into a cell, the viral RNA genome is reverse transcribed into double-stranded DNA, which is imported into the cell nucleus and integrated into the cellular DNA. HIV vectors have been used to deliver the therapeutic genes to leukemia cells. Recombinant lentiviruses have been described for mucin-mediated delivery of nucleic acids into pancreatic cancer cells, to epithelial ovarian carcinoma cells, and to glioma cells, without substantial non-specific delivery to normal cells. Lentiviral vectors for the delivery of nucleic acids to target cells have been reviewed in Primo et al., *Exp Dermatol* 21(3):162-70 (2012); Staunstrup and Mikkelsen, *Curr Gene Ther* 11(5):350-62 (2011); and Dreyer, *Mol Biotechnol* 47(2):169-87 (2011).

Adenovirus is a non-enveloped virus consisting of a double-stranded, linear DNA genome and a capsid. Naturally, adenovirus resides in adenoids and may be a cause of upper respiratory tract infections. Adenovirus utilizes a cell's coxsackie virus and adenovirus receptor (CAR) for the adenoviral fiber protein for entry into nasal, tracheal, and pulmonary epithelia. CARs are expressed at low levels on senescent and cancer cells. Recombinant adenovirus can be generated that are capable of nucleic acid deliver to target cells. Replication-competent adenovirus-mediated suicide gene therapy (ReCAP) is in the clinical trials for newly-diagnosed prostate cancer. Adenoviral vectors for the delivery of nucleic acids to target cells have been reviewed in Huang and Kamihira, *Biotechnol Adv.* 31(2):208-23 (2013); Alemany, *Adv Cancer Res* 115:93-114 (2012); Kaufmann and Nettelbeck, *Trends Mol Med* 18(7):365-76 (2012); and Mowa et al., *Expert Opin Drug Deliv* 7(12):1373-85 (2010).

Adeno-associated virus (AAV) is a small virus that infects humans and some other primate species. AAV is not currently known to cause disease and consequently the virus causes a very mild immune response. Vectors using AAV can infect both dividing and quiescent cells and persist in an extrachromosomal state without integrating into the genome of the host cell. These features make AAV a very attractive candidate for creating viral vectors for use in the systems of the present disclosure. Adeno-associated virus (AAV) vectors for the delivery of nucleic acids to target cells have been reviewed in Li et al., *J. Control Release* 172(2):589-600 (2013); Hajitou, *Adv Genet* 69:65-82 (2010); McCarty, *Mol Ther* 16(10):1648-56 (2008); and Grimm et al., *Methods Enzymol* 392:381-405 (2005).

4. Polyplexes

Polyplexes are complexes of polymers with DNA. Polyplexes consist of cationic polymers and their fabrication is based on self-assembly by ionic interactions. One important difference between the methods of action of polyplexes and liposomes and lipoplexes is that polyplexes cannot directly release their nucleic acid cargo into the cytoplasm of a target cell. As a result co-transfection with endosome-lytic agents such as inactivated adenovirus is required to facilitate escape from the endocytic vesicle made during particle uptake. better understanding of the mechanisms by which DNA can escape from endolysosomal pathway (i.e., the proton sponge effect) has triggered new polymer synthesis strategies such as the incorporation of protonable residues in polymer backbone and has revitalized research on polycation-based systems. See, e.g., Parhamifar et al., *Methods* e-pub (2014); Rychgak and Kilbanov, *Adv Drug Deliv Rev* e-pub (2014); Jafari et al., *Curr Med Chem* 19(2):197-208 (2012).

Due to their low toxicity, high loading capacity, and ease of fabrication, polycationic nanocarriers exhibit substantial advantages over viral vectors, which show high immunogenicity and potential carcinogenicity and lipid-based vectors which cause dose dependent toxicity. Polyethyleneimine, chitosan, poly(beta-amino esters), and polyphosphoramidate have been described for the delivery of nucleic acids. See, e.g., Buschmann et al., *Adv Drug Deliv Rev* 65(9):1234-70 (2013). The size, shape, and surface chemistry of these polymeric nano-carriers can be easily manipulated.

5. Dendrimers

Dendrimers are highly branched macromolecules having a spherical shape. The surface of dendrimer particles may be functionalized such as, for example, with positive surface charges (cationic dendrimers), which may be employed for the delivery of nucleic acids. Dendrimer-nucleic acid complexes are taken into a cell via endocytosis. Dendrimers offer robust covalent construction and extreme control over molecule structure and size. Dendrimers are available commercially from Dendritic Nanotechnologies Inc. (Priostar; Mt Pleasant, Mich.), who produce dendrimers using kinetically driven chemistry, which can be adapted fro the delivery of nucleic acids and can transfect cells at a high efficiency with low toxicity.

It will be understood that, while targeted delivery of an expression construct is not required by the systems of the present disclosure and that the targeted reduction, prevention, and/or elimination in the growth and/or survival of a target cell may be achieved by exploiting the intracellular transcriptional machinery of a target cell that is unique to the target cell, it may be desirable, depending upon the precise application contemplated, the incorporate into an otherwise non-specific delivery vector one or more components that facilitate the targeted delivery to a subset of cells at least some of which include a target cell that is susceptible to the growth and/or survival inhibition by the expression constructs of the present disclosure.

The targeted delivery of nucleic acids by liposome, nanoparticle, viral and other vectors described herein has been described in the scientific and patent literature and is well known by and readily available to those of skill in the art. Such targeted delivery technologies may, therefore, be suitably adapted for targeting the delivery of expression constructs of the present disclosure to enhance the specificity of the growth and/or survival reduction, prevention, and/or elimination that is achieved within a target cell. The following examples of targeted delivery technologies are provided herein to exemplify, not to limit, the targeted delivery vectors that may be adapted to achieve the systems of the present disclosure.

Expression Constructs

Expression constructs of the present disclosure comprise: (a) a transcriptional promoter that is responsive to a factor or factors that are produced in a target cell, one or more of which factors is not produced, is produced at a substantially reduced level, is inactive, and/or exhibits a substantially reduced activity in a non-target cell; and (b) a nucleic acid that is operably linked to and under the regulatory control of the transcriptional promoter, wherein the nucleic acid encodes a protein that is capable of reducing, preventing, and/or eliminating the growth and/or survival of a cell in which it is produced, including a target cell.

1. Target Cell Specific Transcriptional Promoters

The present disclosure provides systems comprising a vector for delivering a nucleic acid to a cell wherein the nucleic acid is under the transcriptional control of a promoter that is derepressed or activated in a target cell, but is repressed or inactivated in a normal cell, non-target cell.

It will be understood the specificity of the presently disclosed systems toward a target cell is achieved, therefore, through the target cell-specific transcriptional activation of a nucleic acid that encodes a protein that reduces, prevents, and/or eliminates the growth and/or survival of a cell without regard to whether that cell is a target cell. Thus, the target cell specificity of the presently-disclosed systems derives from the transcriptional promoter that regulates the expression of the nucleic acid within the expression cassette in conjunction with transcription-regulatory machinery that is provided by, and unique to, the target cell.

Thus, transcriptional promoters that may be suitably employed in the expression constructs, systems, and methods of the present disclosure include those transcriptional promoters that are capable of promoting the expression of a nucleic acid in a target cell (i.e., a cell that is associated with aging, disease, or other condition), but incapable of, or exhibit a substantially reduced capability of, promoting expression of that nucleic acid in a non-target cell.

Exemplified herein are expression constructs and systems comprising expression constructs wherein the transcriptional promoter is activated in a target cell that is associated with aging, disease, or another condition.

In some embodiments, the present disclosure provides expression constructs and systems that may be employed in methods for the treatment of aging reducing, preventing, and/or eliminating the growth and/or survival of a cell, such as a senescent cell, which is associated with aging. In certain aspects of those embodiments, expression constructs employ a transcriptional promoter that is responsive to one or more factors that are produced within a target cell, such as a senescent cell, but are not produced in a non-target cell wherein those one or more factors derepress and/or activate the transcriptional promoter and, as a consequence, promote the expression of a nucleic acid encoding a therapeutic protein that reduces, prevents, and/or eliminates the growth and/or survival of a cell that is associated with aging, including a senescent cell.

The transcriptional promoter itself is the primary mechanism by which senescent cells are preferentially targeted by the systems described in this disclosure. A prototypic example of a target specific transcriptional promoter for use with the systems in this disclosure is a promoter that is only active or mostly active in senescent cells. A number of promoters known by artisans to be active in senescent cells may be used with this system.

In certain aspects of these embodiments wherein the human target cell is a senescent cell, the transcriptional promoter can include the promoter region of p 16INK4a/CDKN2A as described in Wang et al., *J. Biol. Chem.* 276(52):48655-61 (2001), which transcriptional promoter is responsive to activation by a factor such as SP1, ETS1, and ETS2. The transcriptional promoter can also include the promoter region of p21/CDKN1A, which transcriptional promoter is responsive to activation by a factor such as p53/TP53.

In other aspects of these embodiments wherein the human target cell is a cancer cell, such as a brain cancer cell, a prostate cancer cell, a lung cancer cell, a colorectal cancer cell, a breast cancer cell, a liver cancer cell, a hematologic cancer cell, and a bone cancer cell, the transcriptional promoter can include the p21$^{cip1/waf1}$ promoter, the p27$^{kip1}$ promoter, the p57$^{kip2}$ promoter, the TdT promoter, the Rag-1 promoter, the B29 promoter, the Blk promoter, the CD19 promoter, the BLNK promoter, and/or the λ5 promoter, which transcriptional promoter is responsive to activation by one or more transcription factors such as an EBF3, O/E-1, Pax-5, E2A, p53, VP16, MLL, HSF1, NF-IL6, NFAT1, AP-1, AP-2, HOX, E2F3, and/or NF-κB transcription factor, and which transcriptional activation induces the expression of a nucleic acid that encodes a therapeutic protein.

In still further aspects of these embodiments wherein the target cell is a human cell that is infected with an infectious agent, such as a virus, including, for example, a herpes virus, a polio virus, a hepatitis virus, a retrovirus virus, an influenza virus, and a rhino virus, or the target cell is a bacterial cell, the transcriptional promoter can be activated by a factor that is expressed by the infectious agent or bacterial cell, which transcriptional activation induces the expression of a nucleic acid that encodes a therapeutic protein.

2. The p16 Transcriptional Promoter

In one embodiment, the suicide gene could be placed under control of a p16 promoter, such as a p16Ink4a gene promoter, which is transcriptionally active in senescent, but not in non-senescent cells.

In humans, p16 is encoded by the CDKN2A gene, which gene is frequently mutated or deleted in a wide variety of tumors. p16 is an inhibitor of cyclin dependent kinases such as CDK4 and CDK6, which phosphorylate retinoblastoma protein (pRB) thereby causing the progression from G1 phase to S phase. p16 plays an important role in cell cycle regulation by decelerating cell progression from G1 phase to S phase, and therefore acts as a tumor suppressor that is implicated in the prevention of cancers, including, for example, melanomas, oropharyngeal squamous cell carcinomas, and esophageal cancers. The designation p16Ink4A refers to the molecular weight (15,845) of the protein encoded by one of the splice variants of the CDKN2A gene and to its role in inhibiting CDK4.

In humans, p16 is encoded by CDKN2A gene, located on chromosome 9 (9p21.3). This gene generates several transcript variants that differ in their first exons. At least three alternatively spliced variants encoding distinct proteins have been reported, two of which encode structurally related isoforms known to function as inhibitors of CDK4. The remaining transcript includes an alternate exon 1 located 20 kb upstream of the remainder of the gene; this transcript contains an alternate open reading frame (ARF) that specifies a protein that is structurally unrelated to the products of the other variants. The ARF product functions as a stabilizer of the tumor suppressor protein p53, as it can interact with and sequester MDM2, a protein responsible for the degradation of p53. In spite of their structural and functional differences, the CDK inhibitor isoforms and the ARF product encoded by this gene, through the regulatory roles of CDK4 and p53 in cell cycle G1 progression, share a common functionality in control of the G1 phase of the cell cycle. This gene is frequently mutated or deleted in a wide variety of tumors and is known to be an important tumor suppressor gene.

Concentrations of p16INK4a increase dramatically as tissue ages. Liu et al., *Aging Cell* 8(4):439-48 (2009) and Krishnamurthy et al., *Nature* 443(7110):453-7 (2006). The increased expression of the p16 gene with age reduces the proliferation of stem cells thereby increasing the cellular senescence-associated health risks in a human.

p16 is a cyclin-dependent kinase (CDK) inhibitor that slows down the cell cycle by prohibiting progression from G1 phase to S phase. Normally, CDK4/6 binds cyclin D and forms an active protein complex that phosphorylates retinoblastoma protein (pRB). Once phosphorylated, pRB disassociates from the transcription factor E2F1, liberating E2F1 from its cytoplasm bound state allowing it to enter the nucleus. Once in the nucleus, E2F1 promotes the transcription of target genes that are essential for transition from G1 to S phase.

p16 acts as a tumor suppressor by binding to CDK4/6 and preventing its interaction with cyclin D. This interaction ultimately inhibits the downstream activities of transcription factors, such as E2F1, and arrests cell proliferation. This pathway connects the processes of tumor oncogenesis and senescence, fixing them on opposite ends of a spectrum.

On one end, the hypermethylation, mutation, or deletion of p16 leads to downregulation of the gene and can lead to cancer through the dysregulation of cell cycle progression. Conversely, activation of p16 through the ROS pathway, DNA damage, or senescence leads to the build up of p16 in tissues and is implicated in aging of cells.

Regulation of p16 is complex and involves the interaction of several transcription factors, as well as several proteins involved in epigenetic modification through methylation and repression of the promoter region. PRC1 and PRC2 are two protein complexes that modify the expression of p16 through the interaction of various transcription factors that execute methylation patterns that can repress transcription of p16. These pathways are activated in cellular response to reduce senescence.

3. The p21 Transcriptional Promoter

A nucleic acid encoding a therapeutic protein could be placed under the control of the p21/CDKN1A transcriptional promoter that is often transcriptionally active in senescent, and cancerous or pre-cancerous cells. p53/TP53 plays a central role in the regulation of p21 and, therefore, in the growth arrest of cells when damaged. p21 protein binds directly to cyclin-CDK complexes that drive the cell cycle and inhibits their kinase activity thereby causing cell cycle arrest to allow repair to take place. p21 also mediates growth arrest associated with differentiation and a more permanent growth arrest associated with cellular senescence. The p21 gene contains several p53 response elements that mediate direct binding of the p53 protein, resulting in transcriptional activation of the gene encoding the p21 protein. The role of p53 gene regulation in cellular senescence is described in Kelley et al., *Cancer Research* 70(9):3566-75. (2010).

Nucleic Acids and Therapeutic Proteins Encoded Thereby

Nucleic acids that may be suitably employed in the expression constructs, systems, and methods of the present disclosure encode a protein that is capable of reducing, preventing, and/or eliminating the growth and/or survival of a cell in which it is produced, including a target cell. Thus, the target cell specificity of the presently disclosed expression constructs and systems is achieved by the expression within a target cell, but not within a non-target cell, of a nucleic acid that encodes a therapeutic protein.

Nucleic acids encoding therapeutic proteins that may be employed in the expression constructs and systems of the present disclosure include nucleic acids encoding one or more protein that induces apoptosis in a cell in which it is produced. Exemplified herein are expression constructs and systems comprising one or more "suicide genes," such as a nucleic acid encoding Herpes Simplex Virus Thymidine Kinase (HSV-TK), cytosine deaminase, Casp3, Casp8, Casp9, BAX, DFF40, cytosine deaminase, or other nucleic acid that encodes a protein that is capable of inducing apoptosis is a cell.

Apoptosis, or programmed cell death (PCD), is a common and evolutionarily conserved property of all metazoans. In many biological processes, apoptosis is required to eliminate supernumerary or dangerous (such as pre-cancerous) cells and to promote normal development. Dysregulation of apoptosis can, therefore, contribute to the development of many major diseases including cancer, autoimmunity and neuro-degenerative disorders. In most cases, proteins of the caspase family execute the genetic programme that leads to cell death.

Apoptosis is triggered in a mammalian cell, in particular in a human cell, through the activation of caspase proteins, in particular the caspase proteins CASP3, CASP8, and CASP9. See, for example, Xie et al., *Cancer Res* 61(18): 186-91 (2001); Carlotti et al., *Cancer Gene Ther* 12(7):627-39 (2005); Lowe et al., *Gene Ther* 8(18):1363-71 (2001); and Shariat et al., *Cancer Res* 61(6):2562-71 (2001).

DNA fragmentation factor (DFF) is a complex of the DNase DFF40 (CAD) and its chaperone/inhibitor DFF45 (ICAD-L). In its inactive form, DFF is a heterodimer composed of a 45 kDa chaperone inhibitor subunit (DFF45 or ICAD), and a 40 kDa latent endonuclease subunit (DFF40 or CAD). Upon caspase-3 cleavage of DFF45, DFF40 forms active endonuclease homo-oligomers. It is activated during apoptosis to induce DNA fragmentation. DNA binding by DFF is mediated by the nuclease subunit, which can also form stable DNA complexes after release from DFF. The nuclease subunit is inhibited in DNA cleavage but not in DNA binding. DFF45 can also be cleaved and inactivated by caspase-7 but not by caspase-6 and caspase-8. The cleaved DFF45 fragments dissociate from DFF40, allowing DFF40 to oligomerise, forming a large complex that cleaves DNA by introducing double strand breaks. Histone H1 confers DNA binding ability to DFF and stimulates the nuclease activity of DFF40. Activation of the apoptotic endonuclease DFF-40 is described in Liu et al., *J Biol Chem* 274(20): 13836-40 (1999).

Thymidine kinase (TK) is an ATP-thymidine 5'-phosphotransferase that is present in all living cells as well as in certain viruses including herpes simplex virus (HSV), varicella zoster virus (VZV), and Epstein-Barr virus (EBV). Thymidine kinase converts deoxythymidine into deoxythymidine 5'-monophosphate (TMP), which is phosphorylated to deoxythymidine diphosphate and to deoxythymidine triphosphate by thymidylate kinase and nucleoside diphosphate kinase, respectively. Deoxythymidine triphosphase is incorporated into cellular DNA by DNA polymerases and viral reverse transcriptases.

When incorporated into DNA, certain dNTP analogs, such as synthetic analogues of 2'-deoxy-guanosine (e.g., Ganciclovir), cause the premature termination of DNA synthesis, which triggers cellular apoptosis.

Within certain embodiments, the expression cassettes and systems of the present disclosure employ a nucleic acid that encodes HSV-TK. Following the administration to a human of a system employing a nucleic acid encoding HSV-TK, an analogue of a 2'-deoxy-nucleotide, such as 2'-deoxy-guanosine, is administered to the human. The HSV-TK efficiently converts the 2'-deoxy-nucleotide analogue into a dNTP analogue, which when incorporated into the DNA induces apoptosis in the target cell.

Cytosine deaminase (CD) catalyzes the hydrolytic conversion in DNA of cytosine to uracil and ammonia. If a CD-modified site is recognized by an endonuclease, the phosphodiester bond is cleaved and, in a normal cell, is repaired by incorporating a new cytosine. In the presence of 5-fluorocytosine (5-FC), cytosine deaminase converts 5-FC into 5-fluorouracil (5-FU), which can inhibit target cell growth. Transgenic expression of CD in a target cell, therefore, reduces the growth and/or survival of the target cell.

The present disclosure provides expression constructs and systems that further comprise one or more safety features to ensure that the expression of a nucleic acid encoding a therapeutic protein is upregulated in appropriate cells, over a desired time period, and/or to a specified level.

Within one such embodiments, expression constructs and systems of the present disclosure employ nucleic acids that encode inducible variants of therapeutic proteins, including, for example, inducible variants of Casp3, Casp8, Casp9, which require the further contacting of a cell with or administration to a human of a chemical or biological compound that activates the therapeutic protein.

Inducible suicide gene systems are well known and readily available in the art and have been described, for example, in Miller et al., PCT Patent Publication No. WO 2008/154644 and Brenner, US Patent Publication No. 2011/0286980. In addition, Shah et al., *Genesis* 45(4):104-199 (2007) describe a double-inducible system for Caspase 3 and 9 that employs RU486 and chemical inducers of dimerization (CID). Straathof et al., *Blood* 105(11):4247-4254 (2005) describe an inducible caspase 9 system in which caspase 9 is fused to a human FK506 binding protein (FKBP) to allow the conditional dimerization using the small molecule AP20187 (ARIAD Pharmaceuticals, Cambridge, Mass.), which is a non-toxic synthetic analog of FK506. Carlotti et al., *Cancer Gene Ther* 12(7):627-39 (2005) describe an inducible caspase 8 system by employing the ARIAD™ homodimerization system (FKC8; ARIAD Pharmaceuticals).

Full-length inducible caspase 9 (F'F-C-Casp9.I.GFP) comprises a full-length caspase 9, including its caspase recruitment domain (CARD; GenBank NM001 229) linked to two 12 kDa human FK506 binding proteins (FKBP12; GenBank AH002 818) that contain an F36V mutation as described in Clackson et al., Proc. Natl. Acad. Sci. U.S.A. 95:10437-10442 (1998) and are connected by a Ser-Gly-Gly-Gly-Ser linker that connects the FKBPs and caspase 9 to enhance flexibility.

In a further embodiment, the inducible suicide gene could be linked to the nucleic acid sequence for a detectable biomarker such as luciferase or green fluorescent protein to permit the detection of the targeted cells prior to administering a compound to activate an inducible therapeutic protein.

Compositions and Formulations of Systems Comprising Vectors and Expression Cassettes The present disclosure provides systems comprising a vector and an expression cassette wherein the expression cassette comprises a transcriptional promoter that is responsive to one or more transcription factors that are expressed in a target cell and a nucleic acid encoding a therapeutic protein. Systems can be administered to a human patient by themselves or in pharmaceutical compositions where they are mixed with suitable carriers or excipient(s) at doses to treat or ameliorate a disease or condition as described herein. Mixtures of these systems can also be administered to the patient as a simple mixture or in pharmaceutical compositions.

Compositions within the scope of this disclosure include compositions wherein the therapeutic agent is a system comprising a vector and an expression cassette in an amount effective to reduce or eliminate the growth and/or survival of a target cell such as a senescent cell, a cancer cell, a cell infected with an infectious agent, a bacterial cell, or a cell that is associated with another disease or condition. Determination of optimal ranges of effective amounts of each component is within the skill of the art. The effective dose is a function of a number of factors, including the specific system, the presence of one or more additional therapeutic agent within the composition or given concurrently with the system, the frequency of treatment, and the patient's clinical status, age, health, and weight.

Compositions comprising a system may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be orally.

Compositions comprising a system may, for example, be administered intravenously via an intravenous push or bolus. Alternatively, compositions comprising a system may be administered via an intravenous infusion.

Compositions include a therapeutically effective amount of a system, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The systems disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Methods for Treatment of a Disease or Condition Associated with, and for Reducing, Inhibiting, and/or Preventing the Growth and/or Survival of, a Cell that is Associated with Aging, Cancer, Infectious Disease, Bacterial Infection, and/or Other Disease or Condition The present disclosure provides methods for reducing, inhibiting, and/or preventing the growth and or survival of a cell that is associated with aging, cancer, infectious disease, bacterial infection, and/or other disease or condition, which methods comprise contacting a target cell or a population of cell comprising a target cell with a system as described herein, which system comprises a vector and an expression construct, which expression construct comprises a transcriptional promoter and a nucleic acid.

The present disclosure also provides methods for the treatment of aging, cancer, infectious disease, bacterial infection, and/or other disease or condition in a patient, which methods comprise the administration of a system as described herein, which system comprises a vector and an expression construct, which expression construct comprises a transcriptional promoter and a nucleic acid.

The present therapeutic methods involve contacting a target cell with, or administering to a human patient, a composition comprising one or more system comprising a vector and an expression cassette to a human patient for reducing and/or eliminating the growth and/or survival of a cell that is associated with senescence, cancer, an infectious disease, a bacterial infection or another disease or condition.

The amount of the system that will be effective in the treatment, inhibition, and/or prevention of aging, cancer, infectious disease, bacterial infection, or other disease or condition that is associated with the elevated expression of one or more transcription factors can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The systems or pharmaceutical compositions of the present disclosure can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a system on a cell line or a patient tissue sample. The effect of the system or pharmaceutical composition thereof on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods for the treatment and growth and/or survival inhibition by administration to a subject of an effective amount of a system or pharmaceutical composition thereof as described herein. In one aspect, the system is substantially purified such that it is substantially free from substances that limit its effect or produce undesired side-effects.

Methods of administration include, but are not limited to, intradermal, intramuscular, intraperitoneal, intravenous, subcutaneous, intranasal, epidural, and oral routes. The systems or compositions thereof may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

It may be desirable to administer the systems or compositions thereof locally to the area in need of treatment; this may be achieved by, for example, local infusion during surgery, topical application, by injection, by means of a catheter, by means of a suppository, or by means of an implant, said implant being of a porous, non-porous, or gelatinous material, including membranes, such as sialastic membranes, or fibers.

The system can be delivered in a controlled release system placed in proximity of the therapeutic target, thus requiring only a fraction of the systemic dose (see, e.g., Goodson, in Medical Applications of Controlled Release 2:115-138 (1984)).

Intravenous infusion of a compositions comprising a system may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a system may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise infusion protocol adopted, it will be understood that continuous infusion of a composition comprising a system will continue until either desired efficacy is achieved or an unacceptable level of toxicity becomes evident.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

EXAMPLES

While various embodiments have been disclosed herein, other embodiments will be apparent to those skilled in the art. The various embodiments disclosed herein are for purposes of illustration and are not intended to be limiting, with the true scope and spirit being indicated by the claims. The present disclosure is further described with reference to the following examples, which are provided to illustrate certain embodiments and are not intended to limit the scope of the present disclosure or the subject matter claimed.

Example 1 p14 FAST Fusogenic Lipid Nanoparticles (LNP) Enhance Gene Delivery to Tumors

This Example demonstrates that Fusogenix™ (Innovascreen, Halifax, Nova Scotia, Canada) lipid nanoparticles utilizing a p14 FAST fusion from reptilian reovirus are effective at delivering a plasmid DNA construct to a target tumor.

Fusogenix lipid nanoparticles labeled with $^{64}$Cu ($^{64}$Cu NOTA-liposomes) either with or without a p14 FAST fusion protein (described in PCT Patent Publication Nos. WO2002044206A2 and WO2012040825A1) were administered intravenously to a M16 mouse model system for prostate cancer (PC3 cells). Seo, *Bioconjug Chem* 19(12): 2577-2585 (2009) and Reeves, *Cancer Therapy* 136(7): 1731-1740 (2014). 24 hours post-immunization, PC3 tumors were visualize using positron emission tomography (PET). FIGS. 7A and 7B.

Figure 1:
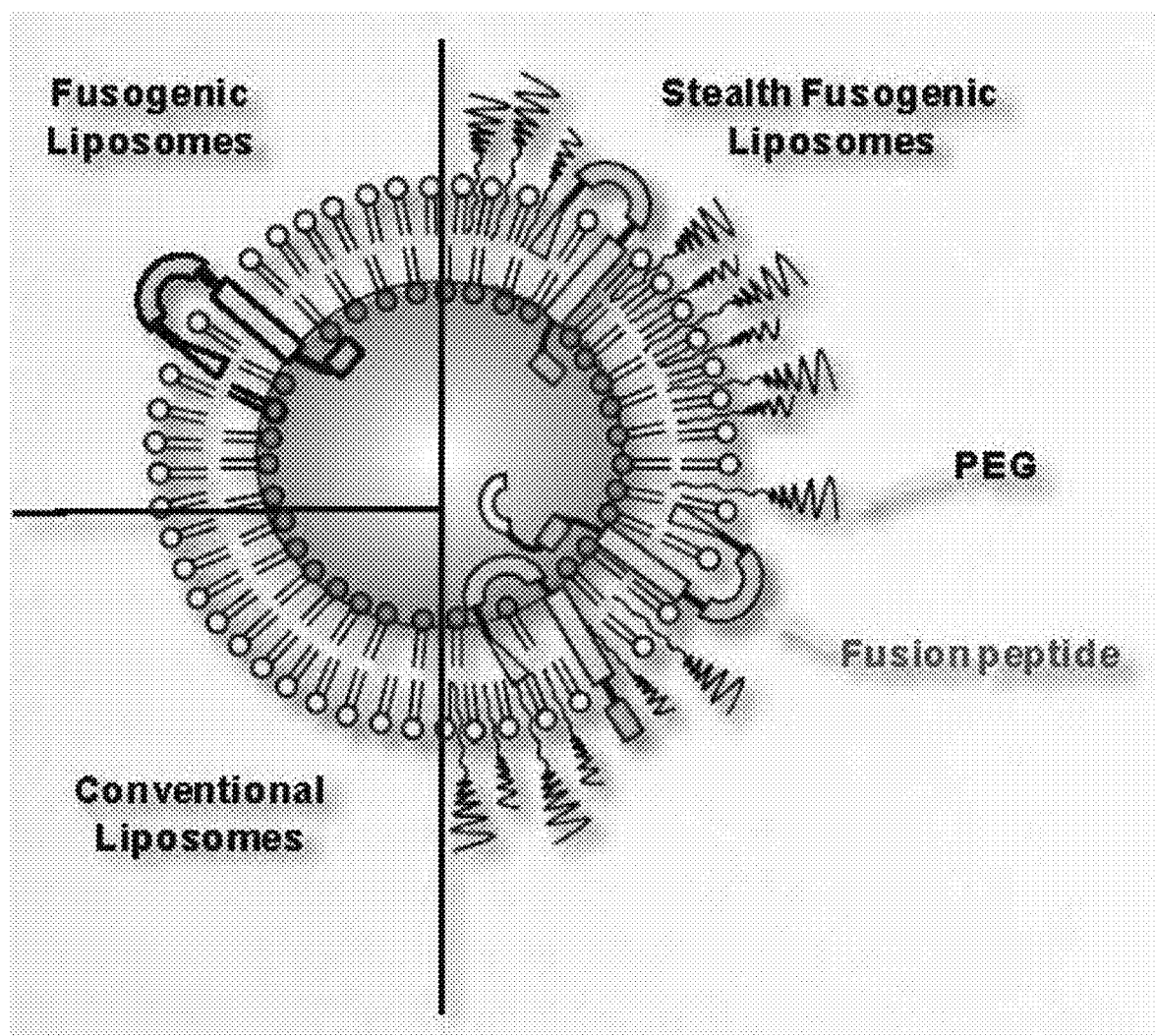
FIG. 1 is a diagrammatic representation of conventional and fusogenic liposomes, including stealth fusogenic liposomes, including lipid nanoparticles employing Innovascreen's Fusogenix™ Platform according to certain aspects of the present disclosure. Shown are Fusogenix™ lipid nanoparticles utilizing a p14 FAST fusion protein from reptilian reovirus and including a plasmid vector encoding an inducible Caspase 9 (iCasp9) under a promoter that is active in a target cell population, such as a senescent target cell population or a cancer target cell population. Exemplified in this diagram are Casp9 fusion peptides that are activated via a small molecule dimerizer such as AP1903.
Figure 2:
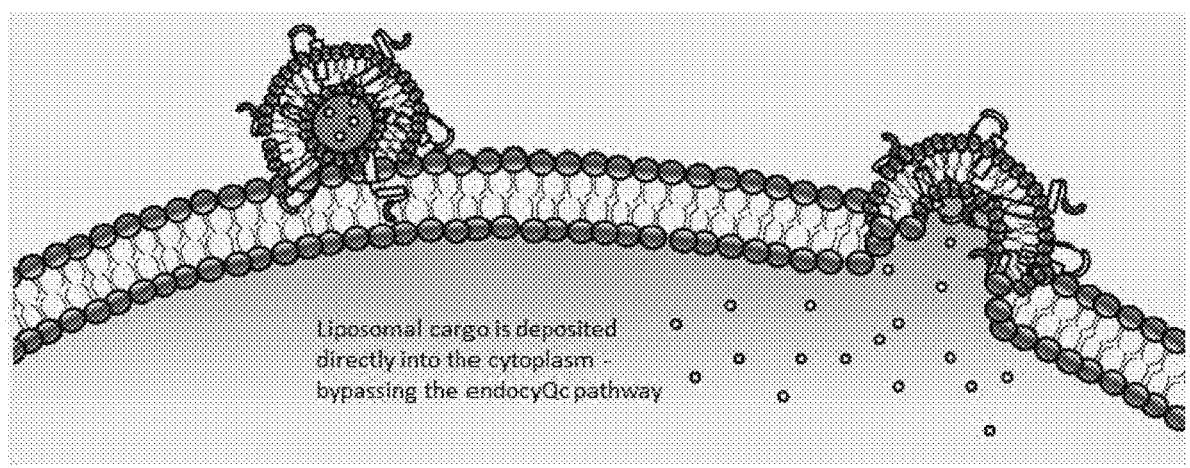
FIG. 2 is a diagrammatic representation of the liposomal delivery to the cytoplasm of a target cell, according to certain aspects of the present disclosure. Shown are Fusogenix™ lipid nanoparticles (LNPs) that are configured for the delivery of nucleic acids, such as those encoding a pro-apoptotic protein, such as Caspase 9, under the regulatory control of a target cell-specific transcriptional promoter, such as a target senescent cell encoding p16 or a target cancer cell encoding p53. Exemplified are Fusogenix™ lipid nanoparticles comprising a p14 FAST protein to catalyze the rapid lipid mixing between the lipid nanoparticle (LNP) and the target cell plasma membrane. Such Fusogenix™ lipid nanoparticles (i) deliver the cargo nucleic acids directly into the cytoplasm thereby bypassing the endocytic pathway, (ii) are non-toxic (i.e., non-immunogenic) in animals at doses of ≥15 mg/kg, (iii) are 80× more efficient than neutral lipid formulations, (iv) are 2-5× more efficient than cationic lipid formulations, and (iv) are manufacturable at scale.
Figure 4A:
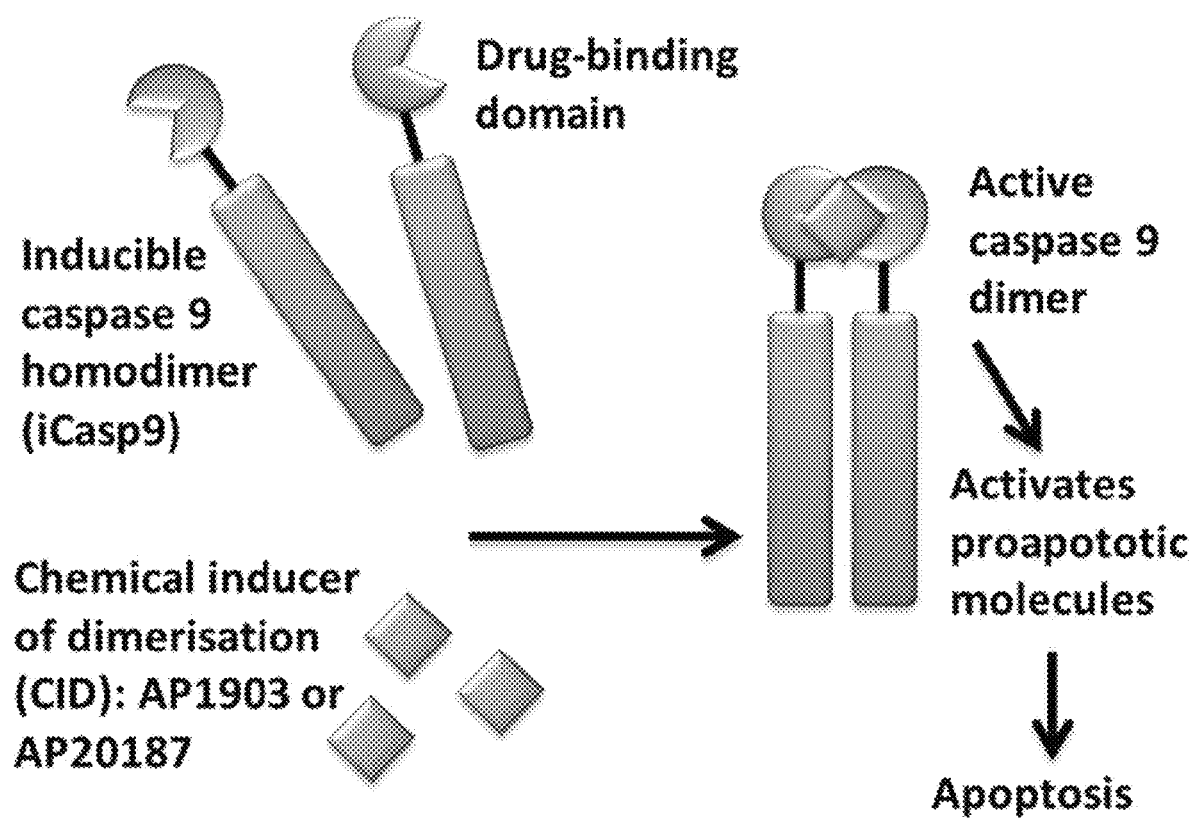
FIG. 4A is a diagrammatic representation of the induction of an inducible Caspase 9 homodimer (iCasp9), which iCasp9 is a fusion protein comprising a drug-binding domain for binding to a chemical inducer of dimerization (CID) and an active portion of Caspase 9. A CID, as exemplified by CDs designated AP1903 and AP20187, binds to the drug-binding domain of the iCasp9 fusion protein to dimerize and, thereby, activate iCasp9, which results in the intracellular activation of pro-apoptotic molecules and the induction of apoptosis within a target cell.
Figure 4B:
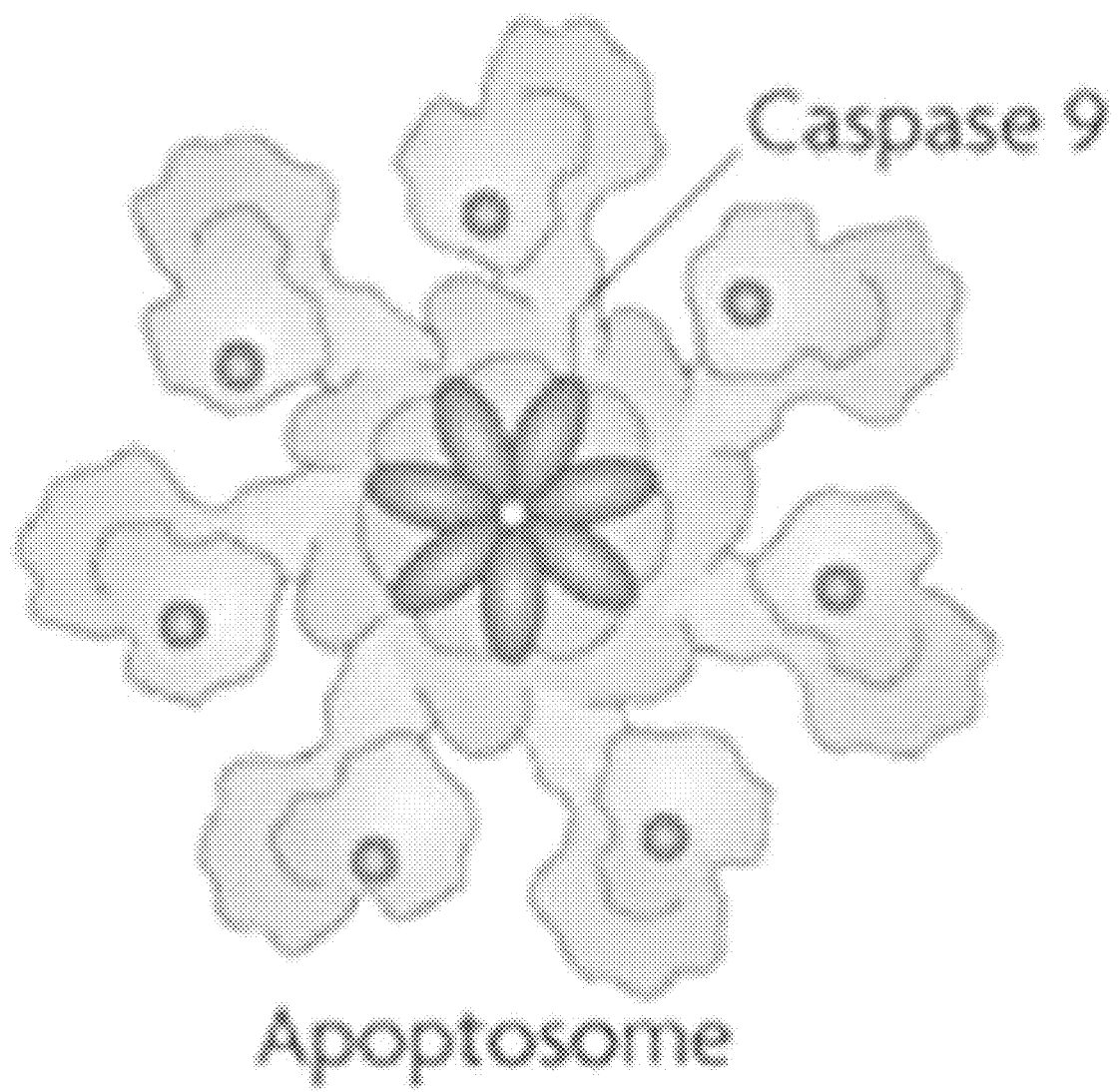
FIG. 4B is a diagrammatic representation of an exemplary apoptosome according to certain aspects of the present disclosure.
Figure 5:
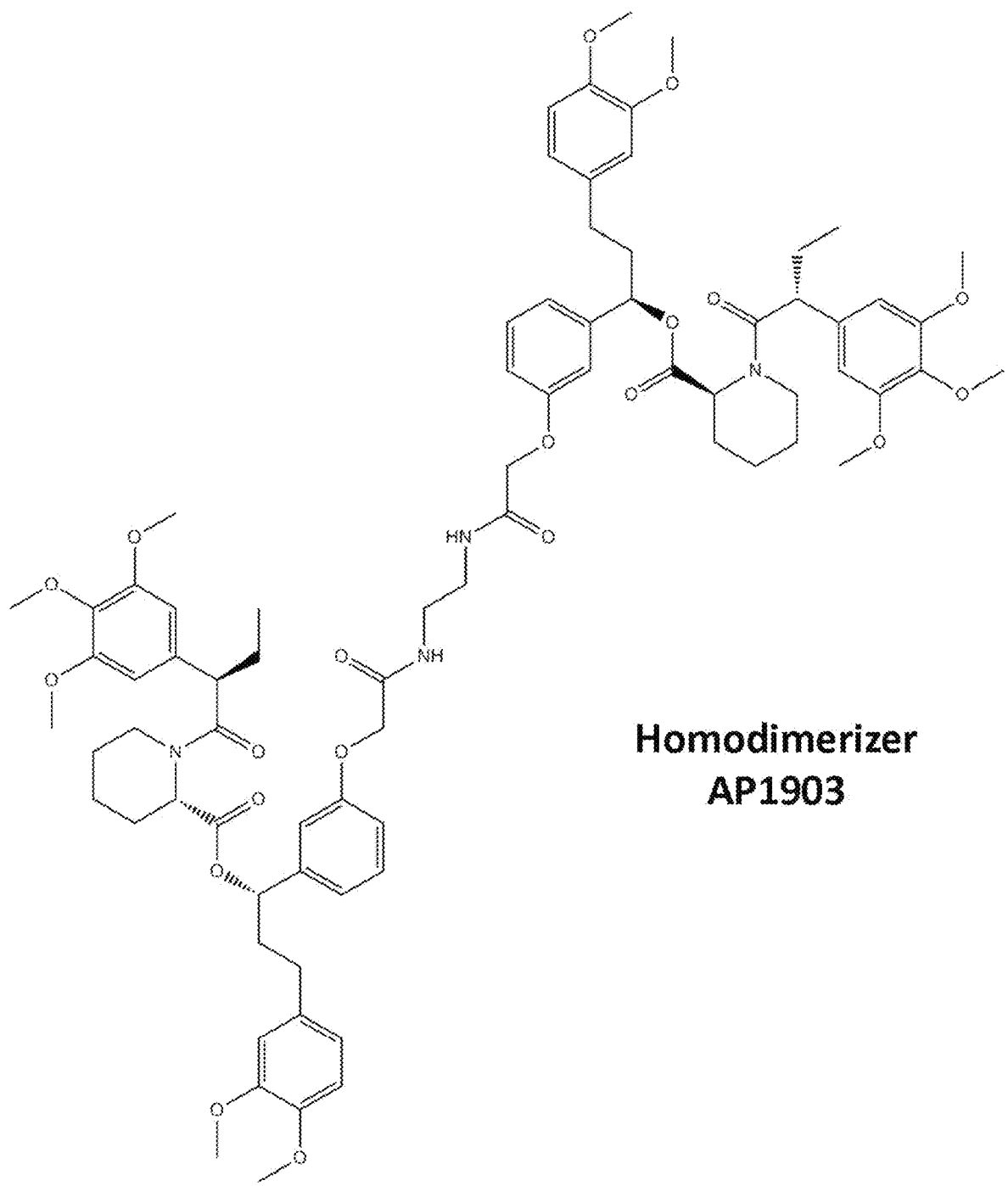
FIG. 5 depicts the chemical structure of an exemplary chemical inducer of dimerization (CID), which is a homodimerizer designated herein as AP1903 (APExBIO, Houston, Tex.) that may be employed in various embodiments of the present disclosure for inducing the activity of an inducible pro-apoptotic protein, such as an inducible caspase protein (e.g., iCasp9).
Figure 6:
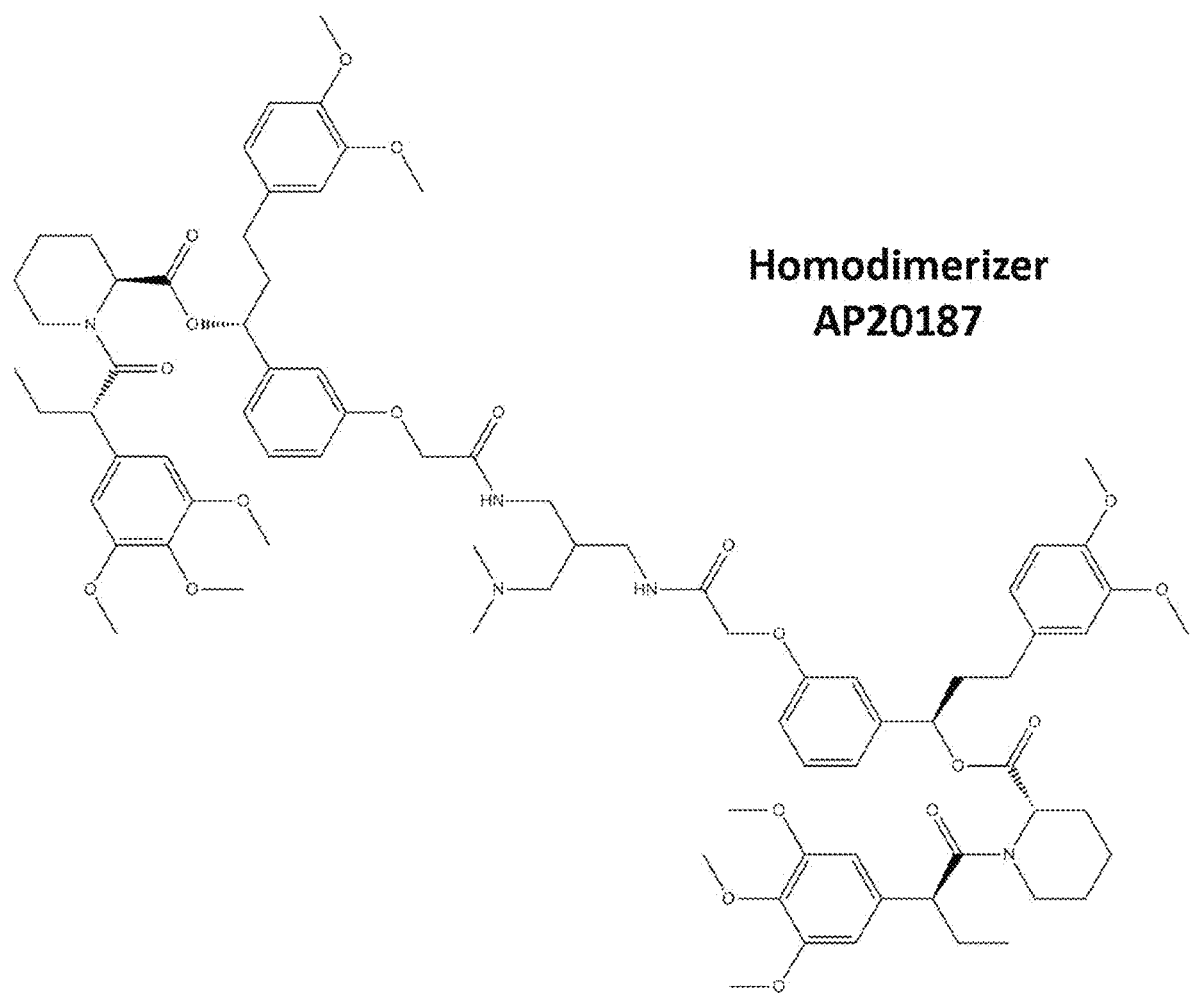
FIG. 6 depicts the chemical structure of an exemplary chemical inducer of dimerization (CID), which is a homodimerizer designated herein as AP20187 (APExBIO, Houston, Tex.) that may be employed in various embodiments of the present disclosure for inducing the activity of an inducible pro-apoptotic protein, such as an inducible caspase protein (e.g., iCasp9).
Figure 8:
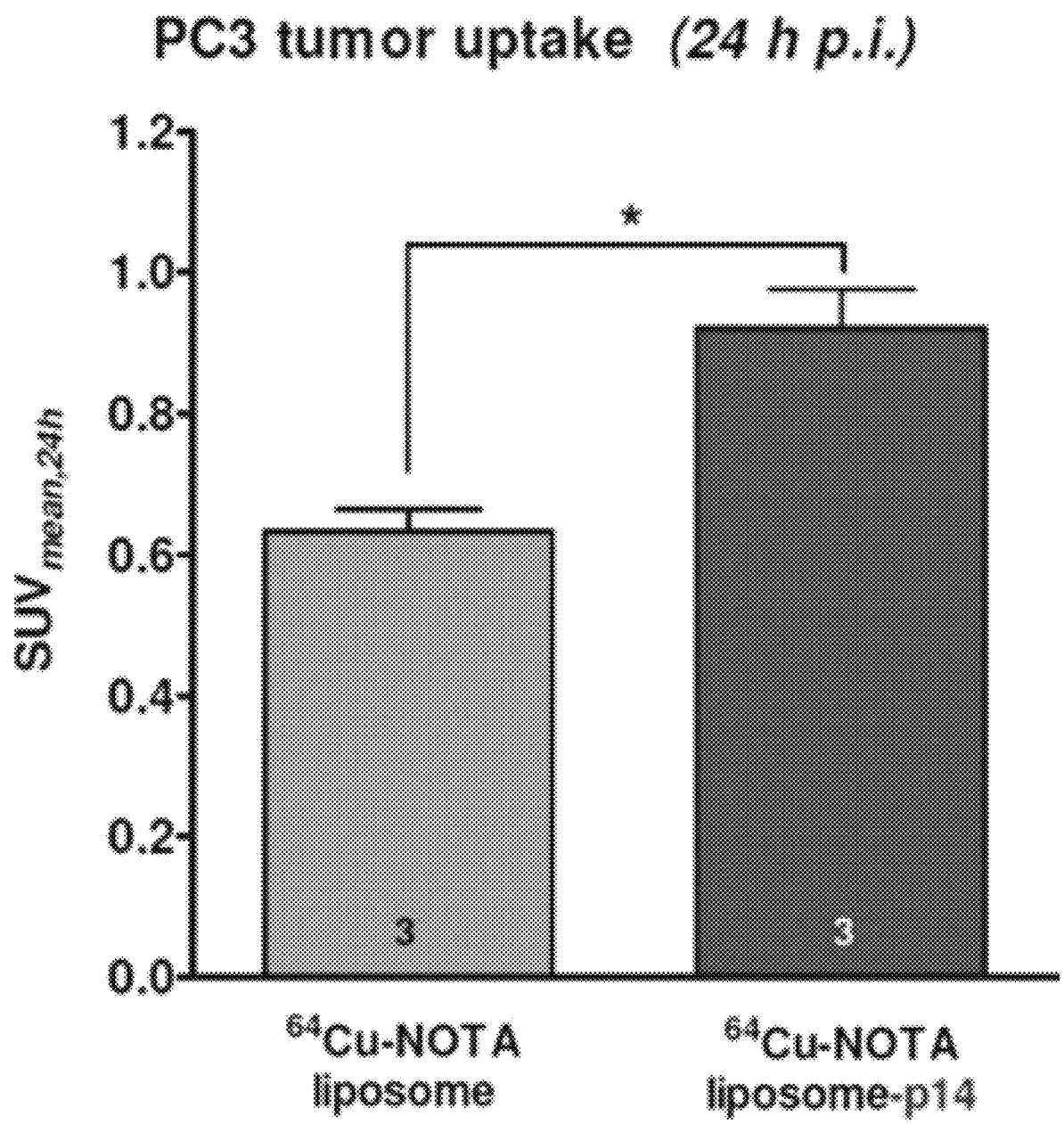
FIG. 8 is a bar graph of data obtained with Fusogenix lipid nanoparticles comparing $SUV_{mean,\ 24th}$ for $^{64}$Cu-NOTA-liposomes without protein and $^{64}$Cu-NOTA-liposome-p14. The data presented in FIGS. 7 and 8 demonstrate a 50% increase in gene/siRNA delivery to prostate tumors as compared to a competing formulation.
Figure 9:
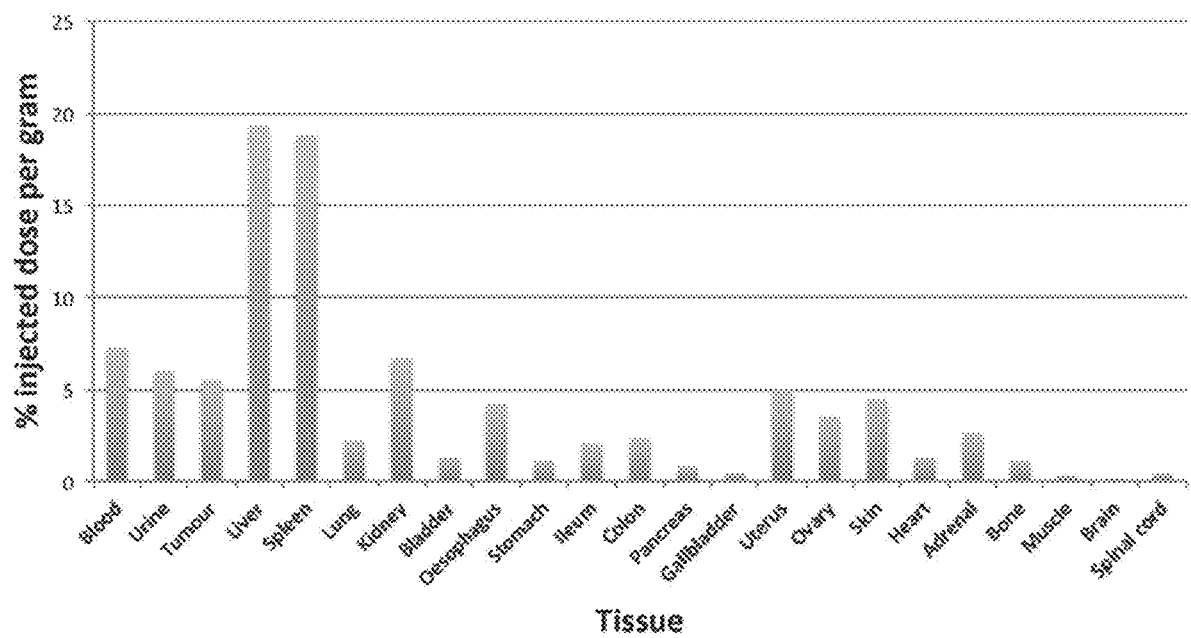
FIG. 9 is a bar graph of the biodistribution of labelled pegylated liposomes in nude mice expressed after 24 hours as discussed in Example 1.

The data presented in FIG. 8 demonstrate a 50% increase in PC3 prostate tumor uptake of $^{64}$Cu NOTA-liposomes with p14 FAST fusion protein as compared to $^{64}$Cu NOTA-liposomes without p14 FAST fusion protein. The biodistribution of labelled pegylated liposomes in nude mice expressed after 24 hours is presented in FIG. 9.

Example 2

In Vivo Administered p14 FAST Fusogenix Lipid Nanoparticles are Non-toxic and Well Tolerated This Example demonstrates that Fusogenix™ (Innovascreen, Halifax, Nova Scotia, Canada) lipid nanoparticles utilizing a p14 FAST fusion from reptilian reovirus do not exhibit adverse side-effects in any of the major mammalian organ systems examined when administered in vivo to Sprague-Dawley rats. are effective at delivering a plasmid DNA construct to a target tumor.

Presented herein are comparative studies that were performed with N=20 male rats treated with either (i) no LNPs (PBS), (ii) LNPs without p14, or (iii) p14 containing Fusogenix lipid nanoparticles (LNPs). Each animal received a total of three injections of 15 mg/kg in their tail, over a 4 day period. Treatment of the animals with p14 containing LNPs did not result in any acute changes in animal behavior and animal growth was not affected by treatment with p14 containing LNPs. Animals treated with p14 containing LNPs had similar organ weights as compared to all other animal groups studied.

Treatment with p14 containing LNPs did not affect the microscopic appearance of tissues from major organ systems. Tissues from the lungs, brain, heart, kidney, liver, reproductive organs, gut, endocrine system, lymph nodes, spleen, pancreas, bladder and tail were all independently examined and p14 did not elicit any visible signs of toxicity. Importantly, the liver appeared to be unaffected by exposure to p14. Moreover, no differences were identified between the tissues of p14 treated animals versus control groups.

A number of blood chemistry values were measured to determine the impact of p14 on physiological function and inflammation. Parameters such as ALT and AST that denote acute liver function were all within normal ranges. Fusogenix LNPs containing p14 do not show any adverse side-effects in any of the major mammalian organ systems examined. Histological appearance of tissues was also normal.

Figure 10:
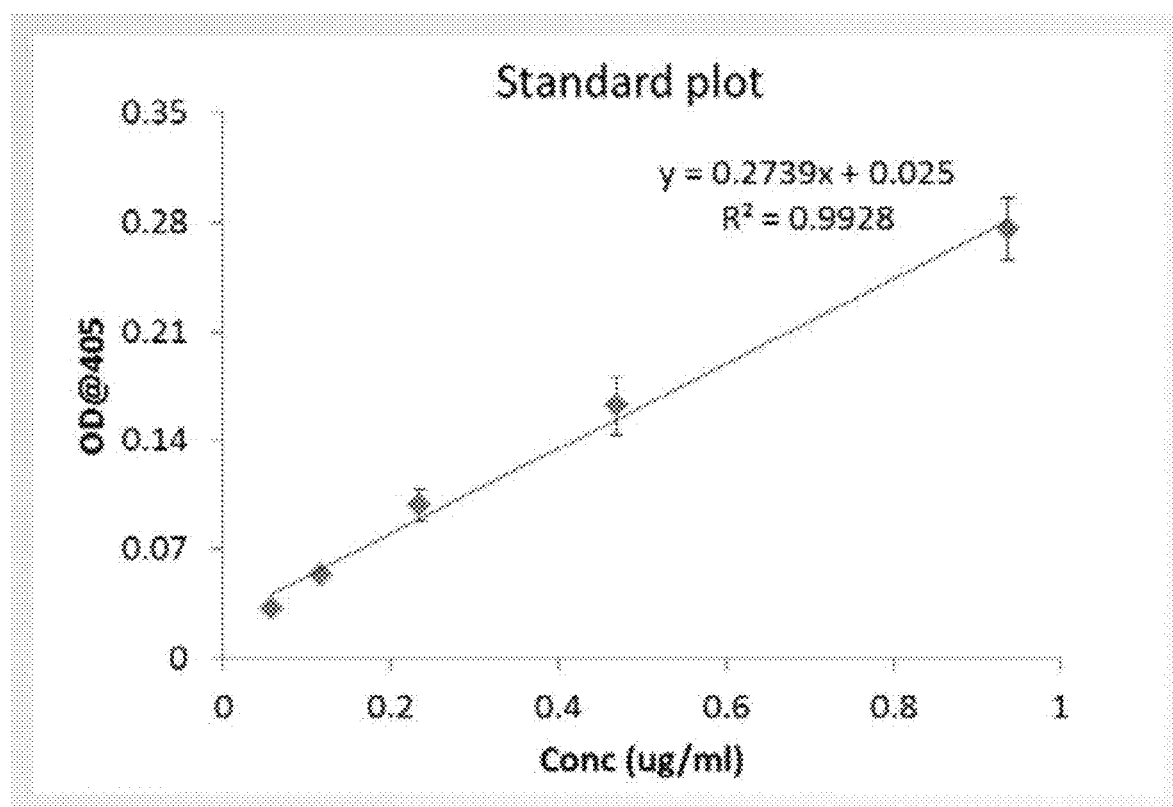
FIGS. 10 and 11 are graphs of optical density at 405 nm as a function of concentration (μg/ml.
Figure 11:
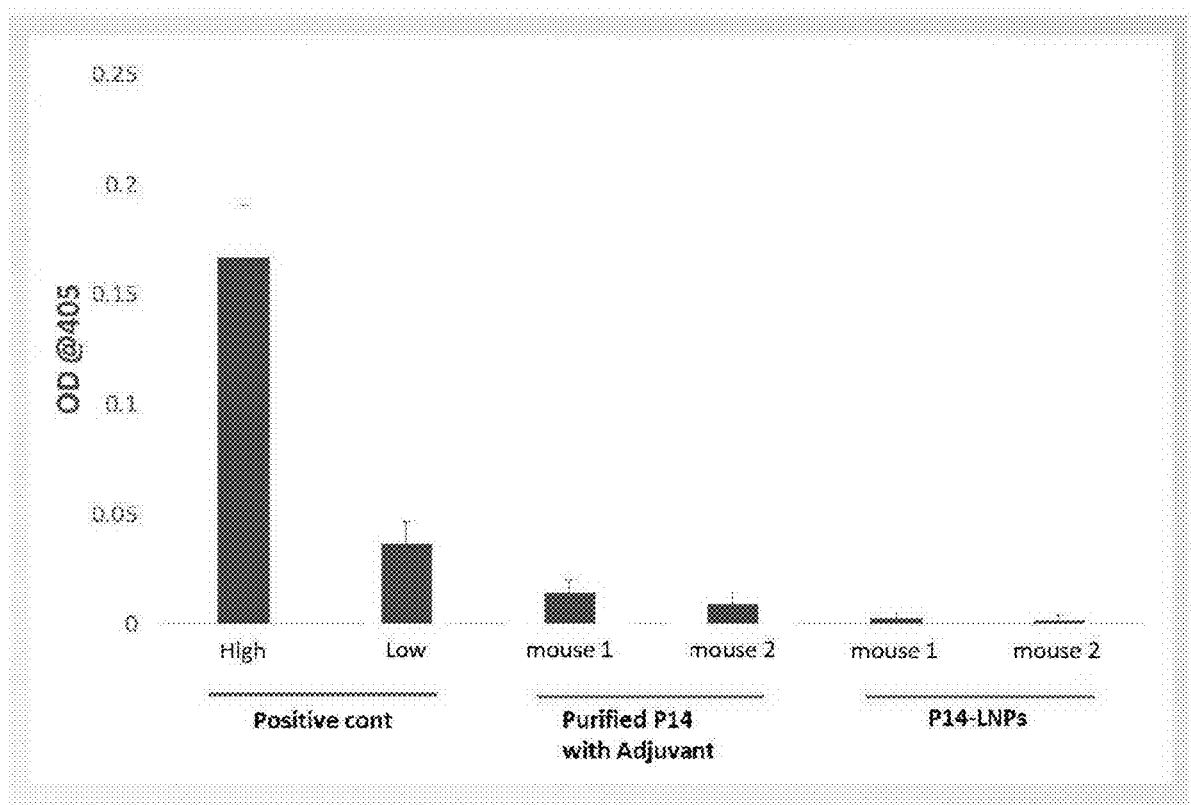

Mice were injected three (3) times at 10 day intervals with purified p14 mixed with Freund's adjuvant. A first dose contained CFA (complete Freund's adjuvant) while second and third doses contained IFA (incomplete Freund's adjuvant). Each injection was with 50 µg of p14. Mice were sacrificed after 30 days and sera was analyzed for anti-p14 antibodies. p14 lipid nanoparticles were also tested in two (2) mice via intravenous injection of 400 µg of p53-iCasp9 Fusogenix lipid nanoparticles containing 240 µg of p14. Mice were sacrificed after 30 days of injection and serum was analyzed for anti-p14 antibodies. A positive control included purified antibodies spiked in serum at a high dose of 250 ng/ml and a low dose of 50 ng/ml. The data presented in FIGS. 10 and 11 demonstrate the safety and tolerability of Fusogenix lipid nanoparticles utilizing a reptilian reovirus p14 FAST fusion protein. Anti-p14 and anti-LNP antibody assays demonstrated that virtually no antibody response was observed in immune competent mice (with and without adjuvant).

Ten (10) human serum samples were tested for Complement activation-related psuedoallergy (CARPA) using C4d and iC3b complement ELISA assays as described in Szebeni, *Mol Immunol* 61(2):163-73 (2014). The data presented in FIGS. 12 and 13 demonstrate that LNP formulations according to the present disclosure were non-reactive with C4d (FIG. 12) and less reactive with iC3b (FIG. 13) as compared to Doxil in 8 out of 10 human samples (approximately 5-10% of humans exhibit a CARPA reaction to nanomedicines such as Doxil).

In vitro anti-p14 and anti-LNP antibody neutralization assays revealed that vector neutralization required very high antibody concentrations. Moreover, vaccination or pretreatment with p14-LNPs did not result in a decrease in therapeutic efficacy and repeated in vivo dosing was effective and well tolerated. CARPA assays with Fusogenix™ p14 FAST lipid nanoparticles elicit less complement activity as compared to a control pegylated liposomal doxorubicin (Doxil).

Example 3

In Vivo Suppression of p16-Positive Senescent Cell Burden in Aged Mice

This Example demonstrates the target-cell specific suppression in p16-positive senescent cell burden following the in vivo administration of an exemplary p16-targeting construct in an mouse model system for aging.

The aging mouse model exhibits a senescent cell burden (as defined by the presence of p16$^+$ cells) and secretion of factors associated with a senescence-associated secretory phenotype (SASP; van Deursen, *Nature* 509(7501):439-446 (2014)).

A formulation comprising a vector and an expression construct, such as a lipid nanoparticle (LNP) vector, e.g., a fusogenic LNP comprising a fusogenic protein such as p14 FAST, encompassing a p16-iCasp9 expression construct (pVAX1-16s-iCasp9; SEQ ID NO: 06; FIG. 16) which comprises an exemplary p16-targeting construct for the target cell-specific expression of an inducible Caspase 9 (iCasp9) protein in target cells expressing p16, such as target cells that are associated with aging and/or senescence, which p16-targeting construct comprises a p16s transcriptional promoter in operable connection to iCasp9.or variant thereof expressing luciferase (for visualization), was administered in vivo to an aged mouse via injection into a tail vein and the LNP+expression construct transfects target and non-target cells without specificity. FIG. 19. Upon subsequent in vivo administration of the chemical inducer of dimerization (CID), AP20187, p16+ target cells (e.g., senescent cells) underwent apoptosis, resulting in a reduction is SASP levels, while p16– cells remained viable.

Histological staining of senescent-associated β-gal in kidney cells from an in vivo aged mouse model either untreated (upper left panel) or treated (upper right panel) following the in vivo administration (16 animals at 80 weeks of age) of a formulation comprising a vector and an expression construct, such as a lipid nanoparticle (LNP) vector, e.g., a fusogenic LNP comprising a fusogenic protein such as p14 FAST, encompassing a p16-iCasp9 expression construct, e.g., pVAX1-16s-iCasp9 or variant thereof, was administered in vivo to an aged mouse and kidney cells stained for β-gal. FIGS. 20A-D. The lower panel is a photomicrograph of the histological staining of senescent-associated β-gal in 4-month old kidney cells from a normal mouse. These data demonstrated a dose-dependent reduction of p16+ senescent kidney cells.

The dose-dependent targeting of p16+ kidney cells (FIG. 21), spleen cells (FIG. 22), seminal vesicle cells (FIG. 23), inguinal fat cells (FIG. 24), and lung cells (FIG. 25) was demonstrated in naturally aged mice following the in vivo administration of a fusogenic lipid nanoparticle (LNP) formulation comprising a pVAX1-p16 expression construct. Kidney cells were subjected to a qRT-PCR reaction to detect p16$^{Ink4a}$ transcripts. Relative expression was calculated using 2ΔΔCt (Livak, *Methods* 25:402-408 (2001)).

Example 4

In Vivo Oncology Study with NSG Mice Implanted with a Human Prostate Tumor

This Example demonstrates the target-cell specific suppression of p53-expressing prostate cancer cells in NSG mice implanted with a human prostate tumor (i.e., a PC-3 xenograft).

Human prostate cancer PC-3 cells were treated with Fusogenix lipid nanoparticles carrying the pVax-p53-iCasp9-luc (luciferin) plasmid (in the presence and absence of the homodimerizer AP201870) and assessed for iCasp9 expression and subjected to Western blot analysis of iCasp 9 and Casp 9 protein levels obtained with p53-expressing cells (pVax-p53) and control cells (pcDNA3-GFP). FIG. 36. These data demonstrated that the addition of the chemical inducer of dimerization (CID; e.g., AP20187 and AP1903) abolishes the expression of iCasp9 and luciferase in p53-expressing cells engineered to express iCasp9 or luciferase.

Human prostate cancer cells (LNCaP (FIG. 38), DU145 (FIG. 39), and PC-3 (FIG. 40)) and normal epithelial cells (RWPE (FIG. 41)) were treated with Fusogenix lipid nanoparticles carrying the pVax-p53-iCasp9-luc plasmid and assessed for iCasp9 expression by Western blot and luminescence assays. These data demonstrated that addition of the chemical inducer of dimerization (CID; e.g., AP20187 and AP1903) abolished the expression of iCasp9 and luciferase in p53-expressing cells engineered to express iCasp9 or luciferase.

Human prostate cancer PC-3 cells were treated with Fusogenix lipid nanoparticles carrying the pVax-p53-iCasp9-luc (luciferin) plasmid (in the presence and absence of the homodimerizer AP20187) and assessed for iCasp9 expression. The data presented in FIG. 42 demonstrated that the addition of the chemical inducer of dimerization (CID; e.g., AP20187 and AP1903) abolished the expression of iCasp9 and luciferase in p53-expressing cells engineered to express iCasp9 or luciferase.

Flow cytometry apoptosis data (Annexin V) from human prostate cancer PC-3 cells treated with pVax-p53 Fusogenix lipid nanoparticles (in the absence and presence of AP20187, FIGS. 43A and 44A and 43B and 44B, respectively) demonstrated that suicide gene therapy selectively killed p53-expressing human prostate cancer cells in culture by inducing apoptosis (Luciferase-Annexin V flow cytometry).

A pre-clinical oncology study according to the present disclosure was conducted with 30×NSG mice implanted with human prostate tumor cells. FIG. 45. NSG mice bearing a subcutaneous human prostate PC-3 tumor were injected intratumorally (IT) with 100 µg Fusogenix pVax-p53 formulation, followed 96 hours later by intravenous (IV) administration of 2 mg/kg of the homodimerizer AP20187. FIG. 46. Tumors from the NSG mice bearing subcutaneous human prostate PC-3 tumors injected intratumorally with 100 µg Fusogenix pVax-p53 formulation, followed 96 hours by 2 mg/kg AP20187 IV, were photographed (FIGS. 47A-47C).

Four NSG mice bearing subcutaneous human prostate cancer PC-3 tumors that were injected intravenously (IV) with 4×100 µg doses of Fusogenix pVax-p53 formulation, followed 24 hours later by 2 mg/kg AP20187 IV. Tumor volume was measured and plotted as a function of time following IV injection. FIGS. 48-51.

The percentage change in tumor volume was determined and plotted as a function of time after in vivo administration of a chemical inducer of dimerization (CID) in NSG mice (N=6 for all groups) bearing a prostate tumor that were treated with intravenous p14 LNP pVAX. FIG. 52. The percent survival was determined and plotted as a function of time after in vivo administration of a chemical inducer of dimerization (CID) in NSG mice (N=6 for all groups) bearing a prostate tumor that were treated with intravenous p14 LNP pVAX. FIG. 53.

A dose escalation study was carried out in which the percentage change in tumor volume as a function of time after in vivo administration of a chemical inducer of dimerization (CID) in NOD-SCID mice (N=6 for all groups) bearing a prostate tumor that were treated with 100 µg, 400 µg, and 1000 µg of intravenous p14 LNP pVAX. NOD-SCID mice were implanted subcutaneously with 500,000 PC-3 cells and randomized into treatment groups when their tumors reached 200 mm³, (N=2 for all groups). Animals were injected with their assigned dose of p53-iCasp9 LNP IV twice followed by 2 mg/kg dimerizer. Tumors were measured directly every 24 hours. FIG. 54.

In total, the data presented herein demonstrate that apoptosis can be reliably induced in a p53+ prostate cancer cell-specific manner by the intravenous administration of fusogenic lipid nanoparticle formulations comprising a p53-iCasp9 expression construct.

Example 5

In Vivo Suppression of Metastases in NOD-SCID Mice Implanted with a Metastatic Tumor The suppression of metastatic tumor growth with repeat treatment of a p53-iCasp9 LNP with or without a chemical inducer of dimerization (CID) was demonstrated in a NOD-SCID mouse model system.

NOD-SCID mice were injected with 500,000 PC-3M-luciferase cells on Day 0, LNP dosing was started on Day 22 with 150 µg p53-iCasp9 LNP. Dimerizer doses started Day 24 at 2 mg/kg. Mice were imaged every 24-48 hours to detect whole animal luminescence. FIG. 55.

Example 6

In Vivo Suppression of Melanoma in Isogenic C57B6 Mice Implanted with B16 Murine Melanoma Cells Isogenic C57B6 mice implanted with B16 murine melanoma cells were treated with LNPs containing a construct encoding iCasp9 and murine CD40L under control of the murine p53 promoter followed by the AP20187 dimerizer.

The percentage change in tumor volume (FIG. 56) and percent survival (FIG. 57) mas measured as a function of time after in vivo administration of a chemical inducer of dimerization (CID) in isogenic C57B6 mice implanted by subcutaneous injection with 250,000 B16 murine melanoma cells treated (grown to 400 mm$^3$) with LNPs containing a construct encoding iCasp9 and murine CD40L under control of the murine p53 promoter.

These data demonstrated that, even though the rapid (10 hour) doubling time of the B16 cells made them largely refractory to the iCasp9-induced apoptosis, they still secreted enough CD40L to effectively halt the tumor's growth. A construct encoding GMCSF+OVA antigen was also tested and determined to be more effective than iCasp9 alone, but less effective than the CD40L version. N=3 for both groups.

Example 7

In Vivo Suppression of Lung Cancer Metastasis in Mice Implanted with B16F10 Murine Melanoma Cells This Example demonstrates the in vivo p53+ target cell suppression murine p53+ B26F10 melanoma target cells implanted in a lung metastasis mouse model system.

A B16F10 lung metastasis model system was employed in which 100 µg of a control LNP or a p53-iCasp9 LNP was administered intravenously at days 3, 6, 9, and 12 following the intravenous injection of 75,000 B16F10 cells. At days 5, 8, 11, and 13, a chemical inducer of dimerization (CID) was administered intraperitoneally. Animals were sacrificed at day 14 and lung metastases were quantified. FIGS. 58A-58D and 59.

What is claimed is:

1. A lipid-based nanoparticle (LNP) formulation for targeted production of a therapeutic protein within Hall target cells, the LNP formulation comprising:
   a. a lipid nanoparticle vector for non-specific delivery of an expression construct to mammalian cells that comprise both the target cells and non-target cells, wherein the lipid nanoparticle vector comprises:
      (i) a fusogenic protein;
      (ii) 1,2-dioleoyl-sn-glycero-3-phosphoethanolamine (DOPE) at a molar ratio of 22.5-37.5 mole %; and
      (iii) 1,2-dimyristoyl-rac-glycero-3-methoxypolyethylene glycol (DMG-PEG) at a molar ratio of 3-5 mole %; and
   b. the expression construct, wherein the expression construct is configured for preferential production of the therapeutic protein within the target cells, wherein the expression construct comprises:
      i. a transcriptional promoter that is activated in response to one or more factors that are preferentially produced within the target cells as compared to the non-target cells; and
      ii. a nucleic acid that is operably linked to and under regulatory control of the transcriptional promoter, wherein the nucleic acid encodes the therapeutic protein, wherein the therapeutic protein is capable of reducing, preventing, or eliminating growth or survival of the mammalian cells, wherein the therapeutic protein is produced within the target cells but is not produced in the non-target cells.

2. The LNP formulation of claim 1, wherein the DOPE or the DMG-PEG is present in the LNP formulation at a concentration ranging from 1 mM to 100 mM.

3. The LNP formulation of claim 1, wherein the lipid nanoparticle vector further comprises 1,2-dioleoyl-3-dimethylammonium-propane (DODAP).

4. The LNP formulation of claim 3, wherein the lipid nanoparticle vector comprises the DODAP at a molar ratio of at least 35 mole %.

5. The LNP formulation of claim 1, wherein the lipid nanoparticle vector comprises the DOPE at a molar ratio of about 30 mole %.

6. The LNP formulation of claim 5, wherein the lipid nanoparticle vector comprises the DMG-PEG at a molar ratio of about 4 mole %.

7. The LNP formulation of claim 1, wherein the fusogenic protein is present in the LNP formulation at a concentration ranging from 0.5 µM to 20 µM.

8. The LNP formulation of claim 1, wherein the fusogenic protein a p14 fusogenic protein that comprises the amino acid sequence of SEQ ID NO: 16.

9. The LNP formulation of claim 1, wherein the expression construct is present in the LNP formulation at a concentration ranging from 20 µg/mL to 1.5 mg/mL.

10. The LNP formulation of claim 1, wherein the transcriptional promoter is a p16 transcriptional promoter or a p53 transcriptional promoter.

11. The LNP formulation of claim 1, wherein the transcriptional promoter is responsive to a factor selected from the group consisting of SP1, ETS1, ETS2, and p53/TP53.

12. The LNP formulation of claim 10, wherein the transcriptional promoter is a p16INK4a/CDKN2A transcriptional promoter.

13. The LNP formulation of claim 1, wherein the transcriptional promoter is responsive to an EBF3, O/E-1, Pax-5, E2A, p53, VP16, MLL, HSF1, NF-IL6, NFAT1, AP-1, AP-2, HOX, E2F3, or NF-κB transcription factor.

14. The LNP formulation of claim 13, wherein the transcriptional promoter is selected from the group consisting of a $p21^{cip1/waf1}$ promoter, a $p27^{kip1}$ promoter, a $p57^{kip2}$ promoter, a TdT promoter, a Rag-1 promoter, a B29 promoter, a Blk promoter, a CD19 promoter, a BLNK promoter, and a λ5 promoter.

15. The LNP formulation of claim 1, wherein the therapeutic protein is selected from the group consisting of a caspase (Casp), an inducible caspase (iCasp), a self-activating caspase (saCasp), BAX, DFF40, HSV-TK, and cytosine deaminase.

16. The LNP formulation of claim 1, wherein the therapeutic protein is a caspase selected from the group consisting of a Casp3, a Casp8, and a Casp9.

17. The LNP formulation of claim 1, wherein the therapeutic protein is Casp9.

18. The LNP formulation of claim 1, wherein the therapeutic protein is an inducible Casp9 (iCasp9).

19. The LNP formulation of claim 1, wherein the therapeutic protein is a self-activating Casp9 (saCasp9).

20. The LNP formulation of claim 1, wherein the fusogenic protein is a p14e15 fusogenic protein that comprises the amino acid sequence of SEQ ID NO: 17.

21. A method of treating a condition in a subject in need thereof, the method comprising administering to the subject one or more lipid-based nanoparticle (LNP) formulations, the one or more LNP formulations comprising:
   (a) a first nucleic acid sequence comprising a p16 transcriptional promoter operably linked to a first polynucleotide that encodes a first therapeutic protein; and
   (b) a second nucleic acid sequence comprising a p53 transcriptional promoter operably linked to a second polynucleotide that encodes a second therapeutic protein.

22. The method of claim 21, wherein the first therapeutic protein or the second therapeutic protein is capable of reducing or eliminating growth or survival of target cells in the subject.

23. The method of claim 21, wherein the first therapeutic protein or the second therapeutic protein is a caspase (Casp), an inducible caspase (iCasp), a self-activating caspase (saCasp), BAX, DFF40, HSV-TK, or cytosine deaminase.

24. The method of claim 21, wherein the first therapeutic protein or the second therapeutic protein is a Casp3, Casp8, or Casp9.

25. The method of claim 21, wherein the first therapeutic protein or the second therapeutic protein is Casp9.

26. The method of claim 21, wherein the first therapeutic protein or the second therapeutic protein is inducible Casp9 (iCasp9).

27. The method of claim 21, wherein the first therapeutic protein or the second therapeutic protein is self-activating Casp9 (saCasp9).

28. The method of claim 21, wherein each of the first therapeutic protein and the second therapeutic protein is a caspase (Casp), an inducible caspase (iCasp), or a self-activating caspase (saCasp).

* * * * *

```
                        SEQUENCE LISTING

<160> NUMBER OF SEQ ID NOS: 17

<210> SEQ ID NO 1
<211> LENGTH: 3017
<212> TYPE: DNA
<213> ORGANISM: Homo sapiens

<400> SEQUENCE: 1
ttcagagaaa tccctgaatt cactgaaagt tttatctaga aatacatgtg caagtgaaca      60 catcttttttt aaaaaaaatc attacctact ttcttttttg agaagaaggt atttatttca    120
acagactctt gaaggagcct actcttccca ctctcccacc cccattaaga accactgtag    180
gccgggcacg atggctcatg cctgtaatcc cagcactttg ggaggctaag gtgggtggat    240
cacctgaggt caggagttcg agacaagcct agccaacata gtgaaacccc gtctctacta    300
ataatacaaa aattagctgg gtatggcagc atgtgcctgt aatcccagct actcgggagg    360
ctgaggcagg agaattgctc gaacccggga ggcggaggtt gcagtgaacc gagagagatc    420
gtgcggtgcc atttcactcc agcctgggca acagagcgaa actccatctc aaaaaaacac    480
acaaaacaaa caaacaaaaa gaaagaacca ttgtattagt gatggaaatg tgttccctcc    540
ctcccatcct ggcaaccact ttcttcctcc tccatcataa aatatcttaa actaaactaa    600
aataatttta tttatcgata gtttgaattt tccctatcat tgctacacag ctaattgaga    660
ggtaccccga ggaaaatata aatggtacag taatgcattg tagattttaa taacatactt    720
gacatcccaa attgttttca ttggcttcat tttaaaaact acatgtttta aaatcaagca    780
gacactaaaa gtacaagata tactgggtct acaaggttta agtcaaccag ggattgaaat    840
```

-continued

| | |
|---|---|
| ataactttta aacagagctg gattatccag taggcagatt aagcatgtgc ttaaggcatc | 900 |
| agcaaagtct gagcaatcca ttttttaaaa cgtagtacat gttttgata agcttaaaaa | 960 |
| gtagtagtca caggaaaaat tagaactttt acctccttgc gcttgttata ctctttagtg | 1020 |
| ctgtttaact tttctttgta agtgagggtg gtggagggtg cccataatct tttcagggag | 1080 |
| taagttcttc ttggtctttc tttctttctt tctttctttt tttcttgaga ccaagtttcg | 1140 |
| ctcttgtctc ccaggctgga gtgcaatggc gcgatctcgg ctcactgcaa cctccgcctt | 1200 |
| ctcctgggtt caagcgattc tcctacatca gcctccgagt agctgggatt acaggcatgc | 1260 |
| gccaccaagc cccgctaatt ttgtattttt tagtagagac agggtttcgc catgttggtc | 1320 |
| aggcttgtct cgaactcctg gcctcaggtg atccgcctgt ctcggcctcc cagaatgctg | 1380 |
| ggattataga cgtgagccac cgcatccgga cttttccttt atgtaatagt gataattcta | 1440 |
| tccaaagcat tttttttttt tttttgagt cggagtctca ttctgtcacc caggctggag | 1500 |
| ggtggtggcg cgatctcggc ttactgcaac ctctgcctcc cgggttcaag cgattctcct | 1560 |
| gcctcagcct cctgagtagc tggaattaca cacgtgcgcc accatggcca gctaattttt | 1620 |
| gtattttag tagagacggg gtgtcaccat tttggccaag ctggcctcga actcctgacc | 1680 |
| tcaggtgatc tgcccgcctc ggcttcccaa agtgctggga ttacaggtgt gagccaccgc | 1740 |
| gtcctgctcc aaagcatttt cttttctatgc ctcaaaacaa gattgcaagc cagtcctcaa | 1800 |
| agcggataat tcaagagcta acaggtatta gcttaggatg tgtggcactg ttcttaaggc | 1860 |
| ttatatgtat taatacatca tttaaactca caacaacccc tataaagcag ggggcactca | 1920 |
| tattcccttc cccctttata attacgaaaa atgcaaggta ttttcagtag aaagagaaa | 1980 |
| tgtgagaagt gtgaaggaga caggacagta tttgaagctg gtctttggat cactgtgcaa | 2040 |
| ctctgcttct agaacactga gcactttttc tggtctagga attatgactt tgagaatgga | 2100 |
| gtccgtcctt ccaatgactc cctccccatt ttcctatctg cctacaggca gaattctccc | 2160 |
| ccgtccgtat taaataaacc tcatcttttc agagtctgct cttataccag gcaatgtaca | 2220 |
| cgtctgagaa acccttgccc cagacagccg ttttacacgc aggaggggaa ggggagggga | 2280 |
| aggagagagc agtccgactc tccaaaagga atcctttgaa ctagggtttc tgacttagtg | 2340 |
| aaccccgcgc tcctgaaaat caagggttga gggggtaggg ggacactttc tagtcgtaca | 2400 |
| ggtgatttcg attctcggtg gggctctcac aactaggaaa gaatagtttt gcttttttctt | 2460 |
| atgattaaaa gaagaagcca tactttccct atgacaccaa acaccccgat tcaatttggc | 2520 |
| agttaggaag gttgtatcgc ggaggaagga aacggggcgg gggcggattt cttttttaaca | 2580 |
| gagtgaacgc actcaaacac gcctttgctg gcaggcgggg gagcgcggct gggagcaggg | 2640 |
| aggccggagg gcggtgtggg gggcaggtgg ggaggagccc agtcctcctt ccttgccaac | 2700 |
| gctggctctg gcgagggctg cttccggctg gtgccccgg gggagaccca acctggggcg | 2760 |
| acttcagggg tgccacattc gctaagtgct cggagttaat agcacctcct ccgagcactc | 2820 |
| gctcacggcg tccccttgcc tggaaagata ccgcggtccc tccagaggat ttgagggaca | 2880 |
| gggtcggagg gggctcttcc gccagcaccg gaggaagaaa gaggagggc tggctggtca | 2940 |
| ccagagggtg gggcggaccg cgtgcgctcg gcggctgcgg agagggggag agcaggcagc | 3000 |
| gggcggcggg gagcagc | 3017 |

<210> SEQ ID NO 2
<211> LENGTH: 20
<212> TYPE: DNA
<213> ORGANISM: Homo sapiens

-continued

<400> SEQUENCE: 2
gggcatgtcc gggcatgtcc                                          20

<210> SEQ ID NO 3
<211> LENGTH: 1251
<212> TYPE: DNA
<213> ORGANISM: Homo sapiens

<400> SEQUENCE: 3
atggacgaag cggatcggcg gctcctgcgg cggtgccggc tgcggctggt ggaagagctg      60
caggtggacc agctctggga cgccctgctg agccgcgagc tgttcaggcc ccatatgatc     120
gaggacatcc agcgggcagg ctctggatct cggcgggatc aggccaggca gctgatcata     180
gatctggaga ctcgagggag tcaggctctt cctttgttca tctcctgctt agaggacaca     240
ggccaggaca tgctggcttc gtttctgcga actaacaggc aagcagcaaa gttgtcgaag     300
ccaaccctag aaaaccttac cccagtggtg ctcagaccag agattcgcaa accagaggtt     360
ctcagaccgg aaacacccag accagtggac attggttctg gaggatttgg tgatgtcggt     420
gctcttgaga gtttgagggg aaatgcagat ttggcttaca tcctgagcat ggagccctgt     480
ggccactgcc tcattatcaa caatgtgaac ttctgccgtg agtccgggct ccgcacccgc     540
actggctcca acatcgactg tgagaagttg cggcgtcgct ctcctcgct gcatttcatg     600 gtggaggtga agggcgacct gactgccaag aaaatggtgc tggctttgct ggagctggcg     660
cagcaggacc acgtgctct ggactgctgc gtggtggtca ttctctctca cggctgtcag     720
gccagccacc tgcagttccc aggggctgtc tacggcacag atggatgccc tgtgtcggtc     780
gagaagattg tgaacatctt caatgggacc agctgcccca gcctgggagg aagcccaag     840 ctctttttca tccaggcctg tggtggggag cagaaagacc atgggtttga ggtggcctcc     900
acttcccctg aagacgagtc ccctggcagt aaccccgagc cagatgccac cccgttccag     960
gaaggtttga ggaccttcga ccagctggac gccatatcta gtttgccac acccagtgac    1020 atctttgtgt cctactctac tttcccaggt tttgtttcct ggagggaccc caagagtggc    1080
tcctggtacg ttgagaccct ggacgacatc tttgagcagt gggctcactc tgaagacctg    1140
cagtccctcc tgcttagggt cgctaatgct gtttcggtga agggatttta taaacagatg    1200
cctggttgct ttaatttcct ccggaaaaaa cttttcttta aacatcata a              1251

<210> SEQ ID NO 4
<211> LENGTH: 834
<212> TYPE: DNA
<213> ORGANISM: Homo sapiens

<400> SEQUENCE: 4
atggagaaca ctgaaaactc agtggattca aaatccatta aaatttgga accaaagatc      60 atacatggaa gcgaatcaat ggactctgga atatccctgg acaacagtta taaaatggat     120
tatcctgaga tgggtttatg tataataatt aataataaga ttttcataa aagcactgga     180 atgcatctc ggtctggtac agatgtcgat gcagcaaacc tcagggaaac attcagaaac     240
ttgaaatatg aagtcaggaa taaaaatgat cttacacgtg aagaaattgt ggaattgatg     300
cgtgatgttt ctaaagaaga tcacagcaaa aggagcagtt tgtttgtgt gcttctgagc     360 catggtgaag aaggaataat ttttggaaca aatggacctg ttgacctgaa aaaaataaca     420
aacttttttc gagggggatcg ttgtagaagt ctaactggaa aacccaaact tttcattatt     480

-continued

| | |
|---|---|
| caggcctgcc gtggtacaga actggactgt ggcattgaga cagacagtgg tgttgatgat | 540 |
| gacatggcgt gtcataaaat accagtggag gccgacttct tgtatgcata ctccacagca | 600 |
| cctggttatt attcttggcg aaattcaaag gatggctcct ggttcatcca gtcgctttgt | 660 |
| gccatgctga acagtatgc cgacaagctt gaatttatgc acattcttac ccgggttaac | 720 |
| cgaaaggtgg caacagaatt tgagtccttt tcctttgacg ctactttca tgcaaagaaa | 780 |
| cagattccat gtattgtttc catgctcaca aagaactct atttttatca ctaa | 834 |

<210> SEQ ID NO 5
<211> LENGTH: 1089
<212> TYPE: DNA
<213> ORGANISM: Homo sapiens

<400> SEQUENCE: 5

| | |
|---|---|
| atgctccaga agcccaagag cgtgaagctg cgggccctgc gcagcccgag gaagttcggc | 60 |
| gtggctggcc ggagctgcca ggaggtgctg cgcaagggct gtctccgctt ccagctccct | 120 |
| gagcgcggtt cccggctgtg cctgtacgag gatggcacgg agctgacgga agattacttc | 180 |
| cccagtgttc ccgacaacgc cgagctggtg ctgctcacct tgggccaggc ctggcagggc | 240 |
| tgtgagtggc aaggactttg gaggatgtgt cttctgctgg accggcacct tttgtttgtc | 300 |
| ccattggtgg cagatgtgag cgacatcagg cgcttcctca gtgcatttca cgagccacag | 360 |
| gtggggctca tccaggccgc ccagcagctg ctgtgtgatg agcaggcccc acagaggcag | 420 |
| aggctgctgg ctgacctcct gcacaacgtc agccagaaca tcgcggccga cccgggct | 480 |
| gaggaccccgc cgtggtttga aggcttggag tcccgatttc agagcaagtc tggctatctg | 540 |
| agatacagct gtgagagccg gatccggagt tacctgaggg aggtgagctc ctaccctcc | 600 |
| acggtgggtg cggaggctca ggaggaattc ctgcgggtcc tcggctccat gtgccagagg | 660 |
| ctccggtcca tgcagtacaa tggcagctac ttcgacagag gagccaaggg cggcagccgc | 720 |
| ctctgcacac cggaaggctg gttctcctgc agggtcctt tgacatgga cagctgctta | 780 |
| tcaagacact ccatcaaccc ctacagtaac agggagagca ggatcctctt cagcacctgg | 840 |
| aacctggatc acataataga aagaaacgc accatcattc ctacactggt ggaagcaatt | 900 |
| aaggaacaag atggaagaga agtggactgg gagtattttt atggcctgct tttacctca | 960 |
| gagaacctaa aactagtgca cattgtctgc cataagaaaa ccacccacaa gctcaactgt | 1020 |
| gacccaagca gaatctacaa accccagaca aggttgaagc ggaagcagcc tgtgcggaaa | 1080 |
| cgccagtga | 1089 |

<210> SEQ ID NO 6
<211> LENGTH: 4198
<212> TYPE: DNA
<213> ORGANISM: Homo sapiens

<400> SEQUENCE: 6

| | |
|---|---|
| gactcttcgc gatgtacggg ccagatatac gcgtacaggt gatttcgatt ctcggtgggg | 60 |
| ctctcacaac taggaaagaa tagttttgct ttttcttatg attaaaagaa gaagccatac | 120 |
| tttccctatg acaccaaaca ccccgattca atttggcagt taggaaggtt gtatcgcgga | 180 |
| ggaaggaaac ggggcggggg cggatttctt tttaacagag tgaacgcact caaacacgcc | 240 |
| tttgctggca ggcggggag cgcggctggg agcaggagg ccggagggcg gtgtgggggg | 300 |
| caggtgggga ggagcccagt cctccttcct tgccaacgct ggctctgcg agggctgctt | 360 |
| ccggctggtg cccccggggg agacccaacc tggggcgact tcagggtgc cacattcgct | 420 |

```
aagtgctcgg agttaatagc acctcctccg agcactcgct cacggcgtcc ccttgcctgg    480
aaagataccg cggtccctcc agaggatttg agggacaggg tcggaggggg ctcttccgcc    540
agcaccggag gaagaaagag gaggggctgg ctggtcacca gagggtgggg cggaccgcgt    600
gcgctcggcg gctgcggaga gggggagagc aggcagcggg cggcggggag cagctctggc    660
taactagaga acccactgct tactggctta tcgaaattaa tacgactcac tatagggaga    720
cccaagctgg ctagcatgct cgagggagtg caggtggaaa ccatctcccc aggagacggg    780
cgcaccttcc ccaagcgcgg ccagacctgc gtggtgcact acaccgggat gcttgaagat    840
ggaaagaaag ttgattcctc ccgggacaga aacaagccct ttaagtttat gctaggcaag    900
caggaggtga tccgaggctg gaagaaggg gttgcccaga tgagtgtggg tcagagagcc    960
aaactgacta tatctccaga ttatgcctat ggtgccactg gcacccagg catcatccca   1020
ccacatgcca ctctcgtctt cgatgtggag cttctaaaac tggaatctgg cggtggatcc   1080
ggagtcgacg gatttggtga tgtcggtgct cttgagagtt tgaggggaaa tgcagatttg   1140
gcttacatcc tgagcatgga gccctgtggc cactgcctca ttatcaacaa tgtgaacttc   1200
tgccgtgagt ccgggctccg cacccgcact ggctccaaca tcgactgtga aagttgcgg   1260
cgtcgcttct cctcgctgca tttcatggtg gaggtgaagg gcgacctgac tgccaagaaa   1320
atggtgctgg ctttgctgga gctggcgcag caggaccacg tgctctgga ctgctgcgtg   1380
gtggtcattc tctctcacgg ctgtcaggcc agccacctgc agttcccagg ggctgtctac   1440
ggcacagatg gatgccctgt gtcggtcgag aagattgtga acatcttcaa tgggaccagc   1500
tgccccagcc tgggagggaa gcccaagctc tttttcatcc aggcctgtgg tggggagcag   1560
aaagaccatg ggtttgaggt ggcctccact tcccctgaag acgagtcccc tggcagtaac   1620
cccgagccag atgccacccc gttccaggaa ggtttgagga ccttcgacca gctggacgcc   1680
atatctagtt tgcccacacc cagtgacatc tttgtgtcct actctacttt cccaggtttt   1740
gtttcctgga gggaccccaa gagtggctcc tggtacgttg agaccctgga cgacatcttt   1800
gagcagtggg ctcactctga agacctgcag tccctcctgc ttagggtcgc taatgctgtt   1860
tcggtgaaag ggatttataa acagatgcct ggttgcttta atttcctccg gaaaaaactt   1920
ttctttaaaa catcagtcga ctatccgtac gacgtaccag actacgcact cgactaagcg   1980
gccgctcgag tctagagggc ccgtttaaac ccgctgatca gcctcgactg tgccttctag   2040
ttgccagcca tctgttgttt gcccctcccc cgtgccttcc ttgaccctgg aaggtgccac   2100
tcccactgtc ctttcctaat aaaatgagga aattgcatcg cattgtctga gtaggtgtca   2160
ttctattctg gggggtgggg tggggcagga cagcaagggg gaggattggg aagacaatag   2220
caggcatgct ggggatgcgg tgggctctat ggcttctact gggcggtttt atggacagca   2280
agcgaaccgg aattgccagc tggggcgccc tctggtaagg ttgggaagcc ctgcaaagta   2340
aactggatgg ctttctcgcc gccaaggatc tgatggcgca ggggatcaag ctctgatcaa   2400
gagacaggat gaggatcgtt tcgcatgatt gaacaagatg gattgcacgc aggttctccg   2460
gccgcttggg tggagaggct attcggctat gactgggcac aacagacaat cggctgctct   2520
gatgccgccg tgttccggct gtcagcgcag ggcgcccgg ttcttttgt caagaccgac   2580
ctgtccggtg ccctgaatga actgcaagac gaggcagcgc ggctatcgtg gctggccacg   2640
acgggcgttc cttgcgcagc tgtgctcgac gttgtcactg aagcgggaag ggactggctg   2700
ctattgggcg aagtgccggg gcaggatctc ctgtcatctc accttgctcc tgccgagaaa   2760
```

| | |
|---|---|
| gtatccatca tggctgatgc aatgcggcgg ctgcatacgc ttgatccggc tacctgccca | 2820 |
| ttcgaccacc aagcgaaaca tcgcatcgag cgagcacgta ctcggatgga agccggtctt | 2880 |
| gtcgatcagg atgatctgga cgaagagcat caggggctcg cgccagccga actgttcgcc | 2940 |
| aggctcaagg cgagcatgcc cgacggcgag gatctcgtcg tgacccatgg cgatgcctgc | 3000 |
| ttgccgaata tcatggtgga aaatggccgc ttttctggat tcatcgactg tggccggctg | 3060 |
| ggtgtggcgg accgctatca ggacatagcg ttggctaccc gtgatattgc tgaagagctt | 3120 |
| ggcggcgaat gggctgaccg cttcctcgtg ctttacggta tcgccgctcc cgattcgcag | 3180 |
| cgcatcgcct tctatcgcct tcttgacgag ttcttctgaa ttattaacgc ttacaatttc | 3240 |
| ctgatgcggt attttctcct tacgcatctg tgcggtattt cacaccgcat acaggtggca | 3300 |
| cttttcgggg aaatgtgcgc ggaaccccta tttgtttatt tttctaaata cattcaaata | 3360 |
| tgtatccgct catgagacaa taaccctgat aaatgcttca ataatagcac gtgctaaaac | 3420 |
| ttcatttta atttaaaagg atctaggtga agatcctttt tgataatctc atgaccaaaa | 3480 |
| tcccttaacg tgagttttcg ttccactgag cgtcagaccc cgtagaaaag atcaaaggat | 3540 |
| cttcttgaga tccttttttt ctgcgcgtaa tctgctgctt gcaaacaaaa aaaccaccgc | 3600 |
| taccagcggt ggtttgtttg ccggatcaag agctaccaac tctttttccg aaggtaactg | 3660 |
| gcttcagcag agcgcagata ccaaatactg tccttctagt gtagccgtag ttaggccacc | 3720 |
| acttcaagaa ctctgtagca ccgcctacat acctcgctct gctaatcctg ttaccagtgg | 3780 |
| ctgctgccag tggcgataag tcgtgtctta ccgggttgga ctcaagacga tagttaccgg | 3840 |
| ataaggcgca gcggtcgggc tgaacggggg gttcgtgcac acagcccagc ttggagcgaa | 3900 |
| cgacctacac cgaactgaga tacctacagc gtgagctatg agaaagcgcc acgcttcccg | 3960 |
| aagggagaaa ggcggacagg tatccggtaa gcggcagggt cggaacagga gagcgcacga | 4020 |
| gggagcttcc agggggaaac gcctggtatc tttatagtcc tgtcgggttt cgccacctct | 4080 |
| gacttgagcg tcgatttttg tgatgctcgt caggggggcg gagcctatgg aaaaacgcca | 4140 |
| gcaacgcggc cttttacgg ttcctgggct tttgctggcc ttttgctcac atgttctt | 4198 |

<210> SEQ ID NO 7
<211> LENGTH: 3797
<212> TYPE: DNA
<213> ORGANISM: Homo sapiens

<400> SEQUENCE: 7

| | |
|---|---|
| gactcttcgc gatgtacggg ccagatatac gcttgtcatg gcgactgtcc agctttgtgc | 60 |
| caggagcctc gcaggggttg atgggattgg ggttttcccc tcccatgtgc tcaagactgg | 120 |
| cgctaaaagt tttgagcttc tcaaaagtct agagccaccg tccagggagc aggtagctgc | 180 |
| tgggctccgg ggacactttg cgttcgggct gggagcgtgc tttccacgac ggtgacacgc | 240 |
| ttccctggat tggtctggct aactagagaa cccactgctt actggcttat cgaaattaat | 300 |
| acgactcact atagggagac ccaagctggc tagcatgctc gagggagtgc aggtggaaac | 360 |
| catctcccca ggagacgggc gcaccttccc caagcgcggc cagacctgcg tggtgcacta | 420 |
| caccgggatg cttgaagatg gaagaaaagt tgattcctcc cggacagaa acaagccctt | 480 |
| taagtttatg ctaggcaagc aggaggtgat ccgaggctgg gaagaagggg ttgcccagat | 540 |
| gagtgtgggt cagagagcca aactgactat atctccagat tatgcctatg gtgccactgg | 600 |
| gcacccaggc atcatcccac acatgccac tctcgtcttc gatgtggagc ttctaaaact | 660 |
| ggaatctggc ggtggatccg gagtcgacgg atttggtgat gtcggtgctc ttgagagttt | 720 |

```
gaggggaaat gcagatttgg cttacatcct gagcatggag ccctgtgcc  actgcctcat    780 tatcaacaat gtgaacttct gccgtgagtc cgggctccgc acccgcactg ctccaacat    840 cgactgtgag aagttgcggc gtcgcttctc ctcgctgcat ttcatggtgg aggtgaaggg    900
cgacctgact gccaagaaaa tggtgctggc tttgctggag ctggcgcagc aggaccacgg    960
tgctctggac tgctgcgtgg tggtcattct ctctcacggc tgtcaggcca gccacctgca   1020
gttcccaggg gctgtctacg gcacagatgg atgccctgtg tcggtcgaga agattgtgaa   1080
catcttcaat gggaccagct gccccagcct gggagggaag cccaagctct ttttcatcca   1140
ggcctgtggt ggggagcaga agaccatggt gtttgaggtg gcctccactt cccctgaaga   1200
cgagtcccct ggcagtaacc ccgagccaga tgccaccccg ttccaggaag gtttgaggac   1260
cttcgaccag ctggacgcca tatctagttt gcccacaccc agtgacatct tgtgtcccta   1320
ctctactttc ccaggttttg tttcctggag ggaccccaag agtggctcct ggtacgttga   1380
gaccctggac gacatctttg agcagtgggc tcactctgaa gacctgcagt ccctcctgct   1440
tagggtcgct aatgctgttt cggtgaaagg gatttataaa cagatgcctg gttgctttaa   1500
tttcctccgg aaaaaacttt tctttaaaac atcagtcgac tatccgtacg acgtaccaga   1560
ctacgcactc gactaagcgg ccgctcgagt ctagagggcc cgtttaaacc cgctgatcag   1620
cctcgactgt gccttctagt tgccagccat ctgttgtttg cccctccccc gtgccttcct   1680
tgaccctgga aggtgccact cccactgtcc tttcctaata aaatgaggaa attgcatcgc   1740
attgtctgag taggtgtcat tctattctgg ggggtggggt ggggcaggac agcaaggggg   1800
aggattggga agacaatagc aggcatgctg gggatgcggt gggctctatg gcttctactg   1860
ggcggtttta tggacagcaa gcgaaccgga attgccagct ggggcgccct ctggtaaggt   1920
tgggaagccc tgcaaagtaa actggatggc tttctcgccg ccaaggatct gatggcgcag   1980
gggatcaagc tctgatcaag agacaggatg aggatcgttt cgcatgattg aacaagatgg   2040
attgcacgca ggttctccgg ccgcttgggt ggagaggcta ttcggctatg actgggcaca   2100
acagacaatc ggctgctctg atgccgccgt gttccggctg tcagcgcagg gcgcccggt    2160 tcttttttgtc aagaccgacc tgtccggtgc cctgaatgaa ctgcaagacg aggcagcgcg   2220
gctatcgtgg ctggccacga cgggcgttcc ttgcgcagct gtgctcgacg ttgtcactga   2280
agcgggaagg gactggctgc tattgggcga agtgccgggg caggatctcc tgtcatctca   2340
ccttgctcct gccgagaaag tatccatcat ggctgatgca atgcggcggc tgcatacgct   2400
tgatccggct acctgcccat tcgaccacca agcgaaacat cgcatcgagc gagcacgtac   2460
tcggatggaa gccggtcttg tcgatcagga tgatctggac gaagagcatc aggggctcgc   2520
gccagccgaa ctgttcgcca ggctcaaggc gagcatgccc gacggcgagg atctcgtcgt   2580
gacccatggc gatgcctgct tgccgaatat catggtggaa aatggccgct ttctggatt    2640 catcgactgt ggccggctgg gtgtggcgga ccgctatcag acatagcgt tggctacccg    2700 tgatattgct gaagagcttg gcggcgaatg ggctgaccgc ttcctcgtgc tttacggtat   2760
cgccgctccc gattcgcagc gcatcgcctt ctatcgcctt cttgacgagt tcttctgaat   2820
tattaacgct tacaatttcc tgatgcggta ttttctcctt acgcatctgt gcggtatttc   2880
acaccgcata caggtggcac ttttcgggga atgtgcgcg  gaacccctat tgtttatttt   2940
ttctaaatac attcaaatat gtatccgctc atgagacaat aaccctgata aatgcttcaa   3000
taatagcacg tgctaaaact tcatttttaa tttaaaagga tctaggtgaa gatcctttt    3060
```

-continued

| | |
|---|---|
| gataatctca tgaccaaaat cccttaacgt gagttttcgt tccactgagc gtcagacccc | 3120 |
| gtagaaaaga tcaaaggatc ttcttgagat cctttttttc tgcgcgtaat ctgctgcttg | 3180 |
| caaacaaaaa aaccaccgct accagcggtg gtttgtttgc cggatcaaga gctaccaact | 3240 |
| cttttttccga aggtaactgg cttcagcaga gcgcagatac caaatactgt ccttctagtg | 3300 |
| tagccgtagt taggccacca cttcaagaac tctgtagcac cgcctacata cctcgctctg | 3360 |
| ctaatcctgt taccagtggc tgctgccagt ggcgataagt cgtgtcttac cgggttggac | 3420 |
| tcaagacgat agttaccgga taaggcgcag cggtcgggct gaacggggggg ttcgtgcaca | 3480 |
| cagcccagct tggagcgaac gacctacacc gaactgagat acctacagcg tgagctatga | 3540 |
| gaaagcgcca cgcttcccga agggagaaag gcggacaggt atccggtaag cggcagggtc | 3600 |
| ggaacaggag agcgcacgag ggagcttcca gggggaaacg cctggtatct ttatagtcct | 3660 |
| gtcgggtttc gccacctctg acttgagcgt cgatttttgt gatgctcgtc agggggggcgg | 3720 |
| agcctatgga aaaacgccag caacgcggcc ttttttacggt tcctgggctt tgctggcct | 3780 |
| tttgctcaca tgttctt | 3797 |

<210> SEQ ID NO 8
<211> LENGTH: 3740
<212> TYPE: DNA
<213> ORGANISM: Homo sapiens

<400> SEQUENCE: 8

| | |
|---|---|
| gactcttcgc gatgtacggg ccagatatac gcttgtcatg gcgactgtcc agctttgtgc | 60 |
| caggagcctc gcaggggttg atgggattgg ggttttcccc tcccatgtgc tcaagactgg | 120 |
| cgctaaaagt tttgagcttc tcaaaagtct agagccaccg tccagggagc aggtagctgc | 180 |
| tgggctccgg ggacactttg cgttcgggct gggagcgtgc tttccacgac ggtgacacgc | 240 |
| ttccctggat tggagaccca agctggctag cgccaccatg ctggaaggcg tgcaggtcga | 300 |
| gacaatttct cctggcgacg gcagaacatt ccccaagaga ggacagacct gcgtcgtgca | 360 |
| ctataccggc atgctcgagg atggcaagaa ggtggacagc agcagagaca gaaacaagcc | 420 |
| cttcaagttc atgctgggca gcaagaagt gatcagaggc tgggaagagg gcgtcgcaca | 480 |
| gatgtctgtg ggacagagag ccaagctgac aatcagccct gattacgcct acggcgccac | 540 |
| aggacatcct ggaatcatcc ctccacacgc cacactggtg ttcgacgtgg aactgctgaa | 600 |
| gctggaatct ggcggtggaa gcggagtgga tggctttgga gatgtgggag ccctggaatc | 660 |
| tctgagagga aacgccgatc tggcctacat cctgtccatg gaaccttgcg gccactgcct | 720 |
| gattatcaac aacgtgaact ctgcagagag agcggcctg agaaccagaa ccggcagcaa | 780 |
| catcgactgc gagaagctga aagaagatt cagcagcctg cacttcatgg tggaagtgaa | 840 |
| gggcgaccctg accgccaaga aaatggtgct ggctctgctg aactggccc agcaagatca | 900 |
| tggcgctctg gactgttgtg tggtggtcat cctgagtcac ggctgtcagg cctctcatct | 960 |
| gcaattccct ggcgccgtgt acggcacaga tggatgtcca gtgtccgtgg aaaagatcgt | 1020 |
| gaacatcttc aacggcacaa gctgccctag cctcggcgga agcccaagc tgttctttat | 1080 |
| ccaagcctgt ggcggcgagc agaaggatca cggatttgag gtggccagca caagccctga | 1140 |
| ggatgagtct cctggaagca accctgagcc tgacgccaca cctttccaag agggactgag | 1200 |
| aaccttcgac cagctggacg ctatcagctc cctgcctaca cctagcgaca tcttcgtgtc | 1260 |
| ctacagcaca ttccccggct tcgtgtcttg gagagatccc aagtctggct cttggtacgt | 1320 |
| ggaaaccctg gacgatatct tcgagcagtg ggcccatagc gaggatctgc agtctctgct | 1380 |

```
cctgagagtg gccaacgctg tgtccgtgaa gggcatctac aagcagatgc cctgcatcgt    1440
gtccatgctg aggaagaagc tgttttttcaa gaccagcgtg gactacccgt acgacgtgcc    1500
agattacgcc ctggactaag cggccgctcg agtctagagg gcccgtttaa acccgctgat    1560
cagcctcgac tgtgccttct agttgccagc catctgttgt ttgcccctcc cccgtgcctt    1620
ccttgaccct ggaaggtgcc actcccactg tcctttccta ataaaatgag gaaattgcat    1680
cgcattgtct gagtaggtgt cattctattc tggggggtgg ggtggggcag gacagcaagg    1740
gggaggattg ggaagacaat agcaggcatg ctggggatgc ggtgggctct atggcttcta    1800
ctgggcggtt ttatggacag caagcgaacc ggaattgcca gctggggcgc cctctggtaa    1860
ggttgggaag ccctgcaaag taaactggat ggctttctcg ccgccaagga tctgatggcg    1920
caggggatca agctctgatc aagagacagg atgaggatcg tttcgcatga ttgaacaaga    1980
tggattgcac gcaggttctc cggccgcttg ggtggagagg ctattcggct atgactgggc    2040
acaacagaca atcggctgct ctgatgccgc cgtgttccgg ctgtcagcgc aggggcgccc    2100
ggttcttttt gtcaagaccg acctgtccgg tgccctgaat gaactgcaag acgaggcagc    2160
gcggctatcg tggctggcca cgacgggcgt tccttgcgca gctgtgctcg acgttgtcac    2220
tgaagcggga agggactggc tgctattggg cgaagtgccg gggcaggatc tcctgtcatc    2280
tcaccttgct cctgccgaga aagtatccat catggctgat gcaatgcggc ggctgcatac    2340
gcttgatccg gctacctgcc cattcgacca ccaagcgaaa catcgcatcg agcgagcacg    2400
tactcggatg aagccggtc ttgtcgatca ggatgatctg gacgaagagc atcaggggct    2460
cgcgccagcc gaactgttcg ccaggctcaa ggcgagcatg cccgacggcg aggatctcgt    2520
cgtgacccat ggcgatgcct gcttgccgaa tatcatggtg gaaaatggcc gcttttctgg    2580
attcatcgac tgtggccggc tgggtgtggc ggaccgctat caggacatag cgttggctac    2640
ccgtgatatt gctgaagagc ttggcggcga atgggctgac cgcttcctcg tgctttacgg    2700
tatcgccgct cccgattcgc agcgcatcgc cttctatcgc cttcttgacg agttcttctg    2760
aattattaac gcttacaatt tcctgatgcg gtattttctc cttacgcatc tgtgcggtat    2820
ttcacaccgc atacaggtgg cacttttcgg ggaaatgtgc gcggaacccc tatttgttta    2880
tttttctaaa tacattcaaa tatgtatccg ctcatgagac aataaccctg ataaatgctt    2940
caataatagc acgtgctaaa acttcatttt taatttaaaa ggatctaggt gaagatcctt    3000
tttgataatc tcatgaccaa aatcccttaa cgtgagtttt cgttccactg agcgtcagac    3060
cccgtagaaa agatcaaagg atcttcttga tccttttttt ttctgcgcgt aatctgctgc    3120
ttgcaaacaa aaaaaccacc gctaccagcg gtggtttgtt tgccggatca agagctacca    3180
actctttttc cgaaggtaac tggcttcagc agagcgcaga taccaaatac tgtccttcta    3240
gtgtagccgt agttaggcca ccacttcaag aactctgtag caccgcctac atacctcgct    3300
ctgctaatcc tgttaccagt ggctgctgcc agtggcgata gtcgtgtct taccgggttg    3360
gactcaagac gatagttacc ggataaggcg cagcggtcgg gctgaacggg gggttcgtgc    3420
acacagccca gcttggagcg aacgacctac accgaactga gatacctaca gcgtgagcta    3480
tgagaaagcg ccacgcttcc cgaagggaga aaggcggaca ggtatccggt aagcggcagg    3540
gtcggaacag gagagcgcac gagggagctt ccagggggaa acgcctggta tctttatagt    3600
cctgtcgggt ttcgccacct ctgacttgag cgtcgatttt tgtgatgctc gtcaggggg    3660
cggagcctat ggaaaaacgc cagcaacgcg gcctttttac ggttcctggg cttttgctgg    3720
```

| | |
|---|---:|
| ccttttgctc acatgttctt | 3740 |

<210> SEQ ID NO 9
<211> LENGTH: 5456
<212> TYPE: DNA
<213> ORGANISM: Homo sapiens

<400> SEQUENCE: 9

| | |
|---|---:|
| gactcttcgc gatgtacggg ccagatatac gcttgtcatg gcgactgtcc agctttgtgc | 60 |
| caggagcctc gcaggggttg atgggattgg ggttttcccc tcccatgtgc tcaagactgg | 120 |
| cgctaaaagt tttgagcttc tcaaaagtct agagccaccg tccagggagc aggtagctgc | 180 |
| tgggctccgg ggacactttg cgttcgggct gggagcgtgc tttccacgac ggtgacacgc | 240 |
| ttccctggat tggagaccca agctggctag cgccaccatg ctggaaggcg tgcaggtcga | 300 |
| gacaatttct cctggcgacg gcagaacatt ccccaagaga ggacagacct gcgtcgtgca | 360 |
| ctataccggc atgctcgagg atggcaagaa ggtggacagc agcagagaca gaaacaagcc | 420 |
| cttcaagttc atgctgggca gcaagaagt gatcagaggc tgggaagagg gcgtcgcaca | 480 |
| gatgtctgtg ggacagagag ccaagctgac aatcagccct gattacgcct acggcgccac | 540 |
| aggacatcct ggaatcatcc ctccacacgc cacactggtt ttcgacgtgg aactgctgaa | 600 |
| gctggaatct ggcggtggat ctggcgtgga cggctttgga gatgtgggag ccctggaatc | 660 |
| tctgagagga aacgccgatc tggcctacat cctgtccatg gaaccttgcg ccactgcct | 720 |
| gattatcaac aacgtgaact ctgcagagag agcggcctg agaaccagaa ccggcagcaa | 780 |
| catcgactgc gagaagctga aagaagatt cagcagcctg cacttcatgg tggaagtgaa | 840 |
| gggcgacctg accgccaaga aaatggtgct ggctctgctg gaactggccc agcaagatca | 900 |
| tggcgctctg gactgttgtg tggtggtcat cctgagtcac ggctgtcagg cctctcatct | 960 |
| gcaattccct ggcgccgtgt acggcacaga tggatgtcca gtgtccgtgg aaaagatcgt | 1020 |
| gaacatcttc aacggcacaa gctgccctag cctcggcgga aagcccaagc tgttctttat | 1080 |
| ccaagcctgt ggcggcgagc agaaggatca cggatttgag gtggccagca agccctga | 1140 |
| ggatgagtct cctggaagca acctgagcc tgacgccaca cctttccaag agggactgag | 1200 |
| aaccttcgac cagctggacg ctatcagctc cctgcctaca cctagcgaca tcttcgtgtc | 1260 |
| ctacagcaca ttccccggct tcgtgtcttg gagagatccc aagtctggct cttggtacgt | 1320 |
| ggaaaccctg gacgatatct tcgagcagtg ggcccatagc gaggatctgc agtctctgct | 1380 |
| cctgagagtg gccaacgctg tgtccgtgaa gggcatctac aagcagatgc ccggctgctt | 1440 |
| caacttcctg aggaagaagc tgttttttcaa gaccagcgtg gactaccgt acgacgtgcc | 1500 |
| agattacgcc ctggatggct ctggcgaagg cagaggatct ctgctgacat gtggcgacgt | 1560 |
| ggaagagaac cctggaccta tgtggctgca gtctctgctg ctgctgggaa cagtggcctg | 1620 |
| ttctatctct gcccctgcca gatctccatc tcctagcaca cagccttggg agcacgtgaa | 1680 |
| cgctatccaa gaagccagaa ggctgctgaa cctgagcaga gatacagccg ccgagatgaa | 1740 |
| cgagacagtg gaagtgatca gcgagatgtt cgacctgcaa gagcctacct gcctgcagac | 1800 |
| cagactggaa ctgtacaagc agggcctgag aggcagcctg acaaagctga agggccctct | 1860 |
| gacaatgatg gccagccact acaagcagca ctgccctcca cacctgaga caagctgcgc | 1920 |
| cacacagatc atcaccttcg agagcttcaa agagaacctg aaggacttcc tgctggtcat | 1980 |
| ccccttcgac tgctgggagc ctgttcaaga aggcagcgga aaggacgag cagtctgct | 2040 |
| gacttgcgga gatgtcgaag aaaatcccgg accaatggga tctatcggag ccgccagcat | 2100 |

```
ggaattctgc ttcgacgtgt tcaaagagct gaaggtccac cacgccaacg agaacatctt    2160
ctactgccct atcgccatca tgagcgccct ggccatggtg tatctgggcg ccaaggatag    2220
caccagaaca cagatcaaca aggtcgtcag attcgacaag ctgcccggct tcggagatag    2280
catcgaagcc cagtgtggca ccagcgtgaa cgtgcacagc agcctgagag acatcctgaa    2340
ccagatcacc aagcctaacg acgtgtacag cttcagcctg ccagcagac tgtacgccga     2400 ggaaagatac cccatcctgc ctgagtacct gcagtgcgtg aaagagctgt acagaggcgg    2460
cctggaacct atcaacttcc agacagccgc cgatcaggcc agagagctga tcaactcttg    2520
ggtcgagagc cagaccaacg gcatcatcag aaacgtgctg cagcctagca gcgtggactc    2580
tcagacagcc atggtgctgg tcaacgccat cgtgtttaaa ggcctgtggg aaaagacctt    2640
caaggacgag atacccagg ccatgccttt cagagtgacc gagcaagagt ccaagcctgt      2700
gcagatgatg taccagatcg gcctgtttag agtggcctcc atggcctccg agaagatgaa    2760
gatcctggaa ctgcctttcg cctccggcac catgtctatg ctggtgctgc tgcctgatga    2820
ggtgtccgga ctgaacagc tggaatccat catcaacttc gagaagctga ccgagtggac     2880
cagcagcaac gtgatggaag aacggaagat caaggtgtac ctgcctcgga tgaagatgga    2940
agagaagtac aacctgacca gcgtgctgat ggccatggga atcaccgatg tgttcagcag    3000
ctctgccaac ctgagcggca tctcttctgc cgagagcctg aagatttctc aggccgtgca    3060
tgctgcccac gccgagatta cgaagccgg cagagaagtt gtgggatctg ctgaagcagg     3120
cgtggacgcc gcttctgtgt ctgaggaatt cagagccgac catcctttc tgttctgcat     3180 caagcacatt gccaccaacg ccgtgctgtt cttcggcaga tgtgtgtccc cttgagcggc    3240
cgctcgagtc tagagggccc gtttaaaccc gctgatcagc ctcgactgtg ccttctagtt    3300
gccagccatc tgttgtttgc ccctcccccg tgccttcctt gaccctggaa ggtgccactc    3360
ccactgtcct ttcctaataa aatgaggaaa ttgcatcgca ttgtctgagt aggtgtcatt    3420
ctattctggg gggtggggtg gggcaggaca gcaaggggga ggattgggaa gacaatagca    3480
ggcatgctgg ggatgcggtg ggctctatgg cttctactgg gcggttttat ggacagcaag    3540
cgaaccggaa ttgccagctg gggcgccctc tggtaaggtt gggaagccct gcaaagtaaa    3600
ctggatggct ttctcgccgc caaggatctg atggcgcagg ggatcaagct ctgatcaaga    3660
gacaggatga ggatcgtttc gcatgattga acaagatgga ttgcacgcag gttctccggc    3720
cgcttgggtg gagaggctat tcggctatga ctgggcacaa cagacaatcg gctgctctga    3780
tgccgccgtg ttccggctgt cagcgcaggg gcgcccggtt ctttttgtca agaccgacct    3840
gtccggtgcc ctgaatgaac tgcaagacga ggcagcgcgg ctatcgtggc tggccacgac    3900
gggcgttcct tgcgcagctg tgctcgacgt tgtcactgaa gcgggaaggg actggctgct    3960
attgggcgaa gtgccggggc aggatctcct gtcatctcac cttgctcctg ccgagaaagt    4020
atccatcatg gctgatgcaa tgcggcggct gcatacgctt gatccggcta cctgcccatt    4080
cgaccaccaa gcgaaacatc gcatcgagcg agcacgtact cggatggaag ccggtcttgt    4140
cgatcaggat gatctggacg aagagcatca ggggctcgcg ccagccgaac tgttcgccag    4200
gctcaaggcg agcatgcccg acggcgagga tctcgtcgtg acccatggcg atgcctgctt    4260
gccgaatatc atggtggaaa atggccgctt ttctggattc atcgactgtg gccggctggg    4320
tgtggcggac cgctatcagg acatagcgtt ggctacccgt gatattgctg aagagcttgg    4380
cggcgaatgg gctgaccgct tcctcgtgct ttacggtatc gccgctcccg attcgcagcg    4440
```

```
catcgccttc tatcgccttc ttgacgagtt cttctgaatt attaacgctt acaatttcct    4500
gatgcggtat tttctcctta cgcatctgtg cggtatttca caccgcatac aggtggcact    4560
tttcggggaa atgtgcgcgg aacccctatt tgtttatttt tctaaataca ttcaaatatg    4620
tatccgctca tgagacaata accctgataa atgcttcaat aatagcacgt gctaaaactt    4680
cattttttaat ttaaaaggat ctaggtgaag atcctttttg ataatctcat gaccaaaatc    4740
ccttaacgtg agttttcgtt ccactgagcg tcagacccCg tagaaaagat caaaggatct    4800
tcttgagatc ctttttttct gcgcgtaatc tgctgcttgc aaacaaaaaa accaccgcta    4860
ccagcggtgg tttgtttgcc ggatcaagag ctaccaactc ttttttccgaa ggtaactggc    4920
ttcagcagag cgcagatacc aaatactgtc cttctagtgt agccgtagtt aggccaccac    4980
ttcaagaact ctgtagcacc gcctacatac ctcgctctgc taatcctgtt accagtggct    5040
gctgccagtg gcgataagtc gtgtcttacc gggttggact caagacgata gttaccggat    5100
aaggcgcagc ggtcgggctg aacggggggt tcgtgcacac agcccagctt ggagcgaacg    5160
acctacaccg aactgagata cctacagcgt gagctatgag aaagcgccac gcttcccgaa    5220
gggagaaagg cggacaggta tccggtaagc ggcagggtcg aacaggaga gcgcacgagg    5280
gagcttccag ggggaaacgc ctggtatctt tatagtcctg tcgggtttcg ccacctctga    5340
cttgagcgtc gatttttgtg atgctcgtca gggggcgga gcctatggaa aaacgccagc    5400
aacgcggcct tttacggtt cctgggcttt tgctggcctt tgctcacat gttctt          5456
```

<210> SEQ ID NO 10
<211> LENGTH: 4586
<212> TYPE: DNA
<213> ORGANISM: Homo sapiens

<400> SEQUENCE: 10

```
gactcttcgc gatgtacggg ccagatatac gcttgtcatg gcgactgtcc agctttgtgc      60
caggagcctc gcaggggttg atgggattgg ggttttcccc tcccatgtgc tcaagactgg     120
cgctaaaagt tttgagcttc tcaaaagtct agagccaccg tccagggagc aggtagctgc     180
tgggctccgg ggacactttg cgttcgggct gggagcgtgc tttccacgac ggtgacacgc     240
ttccctggat tggagaccca agctggctag cgccaccatg ctggaaggcg tgcaggtcga     300
gacaatttct cctggcgacg gcagaacatt ccccaagaga ggacagacct gcgtcgtgca     360
ctataccggc atgctcgagg atggcaagaa ggtggacagc agcagagaca gaaacaagcc     420
cttcaagttc atgctgggca gcaagaagt gatcagaggc tgggaagagg cgtcgcaca     480
gatgtctgtg ggacagagag ccaagctgac aatcagccct gattacgcct acggcgccac     540
aggacatcct ggaatcatcc ctccacacgc cacactggtg ttcgacgtgg aactgctgaa     600
gctggaatct ggcggtggat ctggcgtgga cggctttgga gatgtgggag ccctggaatc     660
tctgagagga aacgccgatc tggcctacat cctgtccatg gaaccttgcg gccactgcct     720
gattatcaac aacgtgaact ctgcagagag agcggccctg agaaccagaa ccggcagcaa     780
catcgactgc gagaagctga agaagatt cagcagcctg cacttcatgg tggaagtgaa     840
gggcgacctg accgccaaga aaatggtgct ggctctgctg aactggccc agcaagatca     900
tggcgctctg gactgttgtg tggtggtcat cctgagtcac ggctgtcagg cctctcatct     960
gcaattccct ggcgccgtgt acggcacaga tggatgtcca gtgtccgtgg aaaagatcgt    1020
gaacatcttc aacggcacaa gctgcccag cctcggcgga aagcccaagc tgttctttat    1080
ccaagcctgt ggcggcgagc agaaggatca cggatttgag gtggccagca caagccctga    1140
```

```
ggatgagtct cctggaagca accctgagcc tgacgccaca cctttccaag agggactgag    1200
aaccttcgac cagctggacg ctatcagctc cctgcctaca cctagcgaca tcttcgtgtc    1260
ctacagcaca ttcccccggct tcgtgtcttg gagagatccc aagtctggct cttggtacgt    1320
ggaaaccctg gacgatatct tcgagcagtg ggcccatagc gaggatctgc agtctctgct    1380
cctgagagtg gccaacgctg tgtccgtgaa gggcatctac aagcagatgc ccggctgctt    1440
caacttcctg aggaagaagc tgttttttcaa gaccagcgtg gactacccgt acgacgtgcc    1500
agattacgcc ctggatggct ctggcgaagg cagaggatct ctgctgacat gtggcgacgt    1560
ggaagagaac cctggaccta tgatcgagac atacaaccag acaagcccca gaagcgccgc    1620
cacaggactg cctatcagca tgaagatctt tatgtacctg ctgaccgtgt cctgatcac     1680 ccagatgatc ggctctgccc tgtttgccgt gtacctgcac agaaggctgg acaagatcga    1740
ggacgagaga aacctgcacg aggacttcgt gttcatgaag accatccaga gatgcaacac    1800
cggcgagaga agcctgagcc tgctgaactg cgaggaaatc aagagccagt cgagggctt     1860 cgtgaaggac atcatgctga caaagagga aacgaagaaa gaaaactcct tcgagatgca     1920
gaagggcgat cagaaccctc agatcgccgc tcacgtgatc agcgaggcca gcagcaaaac    1980
aacatctgtg ctgcagtggg ccgagaaggg ctactacacc atgagcaaca acctggtcac    2040
cctggaaaac ggcaagcagc tgacagtgaa gagacagggc ctgtactaca tctacgccca    2100
agtgaccttc tgcagcaaca gagaggcttc ctctcaggcc cctttttatcg ccagcctgtg    2160 tctgaagtcc cctggcagat tgagagaat cctgctgaga gccgccaaca cacacagctc    2220
tgctaagcct tgtggccagc agtctatcca cctcggcgga gtgtttgaac tgcagcctgg    2280
cgcctctgtg ttcgtgaacg tgacagatcc ttctcaggtg tcccacgca ccggcttcac     2340 atcttttgga ctgctgaagc tctgagcggc cgctcgagtc tagagggccc gtttaaaccc    2400
gctgatcagc ctcgactgtg ccttctagtt gccagccatc tgttgtttgc cctcccccg    2460 tgccttcctt gaccctggaa ggtgccactc ccactgtcct ttcctaataa atgaggaaa     2520 ttgcatcgca ttgtctgagt aggtgtcatt ctattctggg gggtggggtg gggcaggaca    2580
gcaaggggga ggattgggaa gacaatagca ggcatgctgg ggatgcggtg ggctctatgg    2640
cttctactgg gcggttttat ggacagcaag cgaaccggaa ttgccagctg ggcgccctc     2700 tggtaaggtt gggaagccct gcaaagtaaa ctggatggct ttctcgccgc caaggatctg    2760
atggcgcagg ggatcaagct ctgatcaaga gacaggatga ggatcgtttc gcatgattga    2820
acaagatgga ttgcacgcag gttctccggc cgcttgggtg gagaggctat tcggctatga    2880
ctgggcacaa cagacaatcg gctgctctga tgccgccgtg ttccggctgt cagcgcaggg    2940
gcgcccggtt ctttttgtca agaccgacct gtccggtgcc ctgaatgaac tgcaagacga    3000
ggcagcgcgg ctatcgtggc tggccacgac gggcgttcct tgcgcagctg tgctcgacgt    3060
tgtcactgaa gcgggaaggg actggctgct attgggcgaa gtgccggggc aggatctcct    3120
gtcatctcac cttgctcctg ccgagaaagt atccatcatg gctgatgcaa tgcggcggct    3180
gcatacgctt gatccggcta cctgcccatt cgaccaccaa gcgaaacatc gcatcgagcg    3240
agcacgtact cggatggaag ccggtcttgt cgatcaggat gatctggacg aagagcatca    3300
ggggctcgcg ccagccgaac tgttcgccag gctcaaggcg agcatgcccg acggcgagga    3360
tctcgtcgtg acccatggcg atgcctgctt gccgaatatc atggtggaaa atggccgctt    3420
ttctggattc atcgactgtg gccggctggg tgtggcggac cgctatcagg acatagcgtt    3480
```

```
ggctacccgt gatattgctg aagagcttgg cggcgaatgg gctgaccgct tcctcgtgct    3540
ttacggtatc gccgctcccg attcgcagcg catcgccttc tatcgccttc ttgacgagtt    3600
cttctgaatt attaacgctt acaatttcct gatgcggtat tttctcctta cgcatctgtg    3660
cggtatttca caccgcatac aggtggcact tttcggggaa atgtgcgcgg aacccctatt    3720
tgtttatttt tctaaataca ttcaaatatg tatccgctca tgagacaata accctgataa    3780
atgcttcaat aatagcacgt gctaaaactt cattttaat ttaaaaggat ctaggtgaag    3840 atccttttg ataatctcat gaccaaaatc ccttaacgtg agttttcgtt ccactgagcg    3900
tcagaccccg tagaaaagat caaaggatct tcttgagatc ctttttttct gcgcgtaatc    3960
tgctgcttgc aaacaaaaaa accaccgcta ccagcggtgg tttgtttgcc ggatcaagag    4020
ctaccaactc tttttccgaa ggtaactggc ttcagcagag cgcagatacc aaatactgtc    4080
cttctagtgt agccgtagtt aggccaccac ttcaagaact ctgtagcacc gcctacatac    4140
ctcgctctgc taatcctgtt accagtggct gctgccagtg cgataagtc gtgtcttacc    4200 gggttggact caagacgata gttaccggat aaggcgcagc ggtcgggctg aacggggggt    4260
tcgtgcacac agcccagctt ggagcgaacg acctacaccg aactgagata cctacagcgt    4320
gagctatgag aaagcgccac gcttcccgaa gggagaaagg cggacaggta tccggtaagc    4380
ggcagggtcg gaacaggaga gcgcacgagg gagcttccag ggggaaacgc ctggtatctt    4440
tatagtcctg tcgggtttcg ccacctctga cttgagcgtc gatttttgtg atgctcgtca    4500
ggggggcgga gcctatggaa aaacgccagc aacgcggcct ttttacggtt cctgggcttt    4560
tgctggcctt ttgctcacat gttctt                                        4586

<210> SEQ ID NO 11
<211> LENGTH: 4961
<212> TYPE: DNA
<213> ORGANISM: Homo sapiens

<400> SEQUENCE: 11
gactcttcgc gatgtacggg ccagatatac gcttgtcatg gcgactgtcc agctttgtgc      60
caggagcctc gcaggggttg atgggattgg ggttttcccc tcccatgtgc tcaagactgg     120
cgctaaaagt tttgagcttc tcaaaagtct agagccaccg tccagggagc aggtagctgc     180
tgggctccgg ggacactttg cgttcgggct gggagcgtgc tttccacgac ggtgacacgc     240
ttccctggat tggagaccca agctggctag cgccaccatg ctggaaggcg tgcaggtcga     300
gacaatttct cctggcgacg gcagaacatt ccccaagaga ggacagacct gcgtcgtgca     360
ctataccggc atgctcgagg atggcaagaa ggtggacagc agcagagaca gaaacaagcc     420
cttcaagttc atgctgggca gcaagaagt gatcagaggc tgggaagagg gcgtcgcaca     480
gatgtctgtg ggacagagag ccaagctgac aatcagccct gattacgcct acggcgccac     540
aggacatcct ggaatcatcc ctccacacgc cacactggtg ttcgacgtgg aactgctgaa     600
gctggaatct ggcggtggat ctggcgtgga cggctttgga gatgtgggag ccctggaatc     660
tctgagagga aacgccgatc tggcctacat cctgtccatg gaaccttgcg ccactgcct     720 gattatcaac aacgtgaact tctgcagaga gagcggcctg agaaccagaa ccggcagcaa     780
catcgactgc gagaagctga agaagatt cagcagcctg cacttcatgg tggaagtgaa     840
gggcgacctg accgccaaga aaatggtgct ggctctgctg gaactggccc agcaagatca     900
tggcgctctg gactgttgtg tggtggtcat cctgagtcac ggctgtcagg cctctcatct     960
gcaattccct ggcgccgtgt acggcacaga tggatgtcca gtgtccgtgg aaaagatcgt    1020
```

```
gaacatcttc aacggcacaa gctgccctag cctcggcgga aagcccaagc tgttctttat    1080
ccaagcctgt ggcggcgagc agaaggatca cggatttgag gtggccagca caagccctga    1140
ggatgagtct cctggaagca accctgagcc tgacgccaca cctttccaag agggactgag    1200
aaccttcgac cagctggacg ctatcagctc cctgcctaca cctagcgaca tcttcgtgtc    1260
ctacagcaca ttccccggct tcgtgtcttg agagatcccc aagtctggct cttggtacgt    1320 ggaaccctg  gacgatatct tcgagcagtg ggcccatagc gaggatctgc agtctctgct    1380
cctgagagtg gccaacgctg tgtccgtgaa gggcatctac aagcagatgc ccggctgctt    1440
caacttcctg aggaagaagc tgttttttcaa gaccagcgtg gactacccgt acgacgtgcc    1500
agattacgcc ctggatggct ctggcgaagg cagaggatct ctgctgacat gtggcgacgt    1560
ggaagagaac cctggaccta tgggatctat cggagccgcc agcatggaat ctgcttcga    1620 cgtgttcaaa gagctgaagg tccaccacgc caacgagaac atcttctact gccctatcgc    1680
catcatgagc ccctggcca  tggtgtatct gggcgccaag gatagcacca gaacacagat    1740
caacaaggtc gtcagattcg acaagctgcc cggcttcgga gatagcatcg aagcccagtg    1800
tggcaccagc gtgaacgtgc acagcagcct gagagacatc ctgaaccaga tcaccaagcc    1860
taacgacgtg tacagcttca gcctggccag cagactgtac gccgaggaaa gatacccat    1920 cctgcctgag tacctgcagt gcgtgaaaga gctgtacaga ggcggcctgg aacctatcaa    1980
cttccagaca gccgccgatc aggccagaga gctgatcaac tcttgggtcg agagccagac    2040
caacggcatc atcagaaacg tgctgcagcc tagcagcgtg gactctcaga cagccatggt    2100
gctggtcaac gccatcgtgt ttaaaggcct gtgggaaaag accttcaagg acgaggatac    2160
ccaggccatg cctttcagag tgaccgagca agagtccaag cctgtgcaga tgatgtacca    2220
gatcggcctg tttagagtgg cctccatggc ctccgagaag atgaagatcc tggaactgcc    2280
tttcgcctcc ggcaccatgt ctatgctggt gctgctgcct gatgaggtgt ccggactgga    2340
acagctggaa tccatcatca acttcgagaa gctgaccgag tggaccagca gcaacgtgat    2400
ggaagaacgg aagatcaagg tgtacctgcc tcggatgaag atggaagaga agtacaacct    2460
gaccagcgtg ctgatggcca tgggaatcac cgatgtgttc agcagctctg ccaacctgag    2520
cggcatctct tctgccgaga gcctgaagat ttctcaggcc gtgcatgctg cccacgccga    2580
gattaacgaa gccggcagag aagttgtggg atctgctgaa gcaggcgtgg acgccgcttc    2640
tgtgtctgag gaattcagag ccgaccatcc tttttctgttc tgcatcaagc acattgccac    2700
caacgccgtg ctgttcttcg gcagatgtgt gtccccttga gcggccgctc gagtctagag    2760
ggcccgttta acccgctga  tcagcctcga ctgtgccttc tagttgccag ccatctgttg    2820
tttgcccctc ccccgtgcct tccttgaccc tggaaggtgc cactcccact gtcctttcct    2880
aataaaatga ggaaattgca tcgcattgtc tgagtaggtg tcattctatt ctgggggtg    2940 gggtggggca ggacagcaag ggggaggatt gggaagacaa tagcaggcat gctgggatg    3000 cggtgggctc tatggcttct actgggcggt tttatggaca gcaagcgaac cggaattgcc    3060
agctggggcg ccctctggta aggttgggaa gccctgcaaa gtaaactgga tggctttctc    3120
gccgccaagg atctgatggc gcaggggatc aagctctgat caagagacag gatgaggatc    3180
gtttcgcatg attgaacaag atggattgca cgcaggttct ccggccgctt gggtggagag    3240
gctattcggc tatgactggg cacaacagac aatcggctgc tctgatgccg ccgtgttccg    3300
gctgtcagcg caggggcgcc cggttctttt tgtcaagacc gacctgtccg gtgccctgaa    3360
```

```
tgaactgcaa gacgaggcag cgcggctatc gtggctggcc acgacgggcg ttccttgcgc    3420
agctgtgctc gacgttgtca ctgaagcggg aagggactgg ctgctattgg gcgaagtgcc    3480
ggggcaggat ctcctgtcat ctcaccttgc tcctgccgag aaagtatcca tcatggctga    3540
tgcaatgcgg cggctgcata cgcttgatcc ggctacctgc ccattcgacc accaagcgaa    3600
acatcgcatc gagcgagcac gtactcggat ggaagccggt cttgtcgatc aggatgatct    3660
ggacgaagag catcagggc tcgcgccagc cgaactgttc gccaggctca aggcgagcat    3720
gcccgacggc gaggatctcg tcgtgaccca tggcgatgcc tgcttgccga atatcatggt    3780
ggaaaatggc cgcttttctg gattcatcga ctgtggccgg ctgggtgtgg cggaccgcta    3840
tcaggacata gcgttggcta cccgtgatat tgctgaagag cttggcggcg aatgggctga    3900
ccgcttcctc gtgctttacg gtatcgccgc tcccgattcg cagcgcatcg ccttctatcg    3960
ccttcttgac gagttcttct gaattattaa cgcttacaat ttcctgatgc ggtatttcct    4020
ccttacgcat ctgtgcggta tttcacaccg catacaggtg gcacttttcg ggaaatgtg    4080 cgcggaaccc ctatttgttt attttctaa atacattcaa atatgtatcc gctcatgaga    4140
caataaccct gataaatgct tcaataatag cacgtgctaa aacttcattt ttaatttaaa    4200
aggatctagg tgaagatcct ttttgataat ctcatgacca aaatcccta acgtgagttt    4260 tcgttccact gagcgtcaga ccccgtagaa aagatcaaag gatcttcttg agatccttt    4320 tttctgcgcg taatctgctg cttgcaaaca aaaaaaccac cgctaccagc ggtggtttgt    4380
ttgccggatc aagagctacc aactcttttt ccgaaggtaa ctggcttcag cagagcgcag    4440
ataccaaata ctgtccttct agtgtagccg tagttaggcc accacttcaa gaactctgta    4500
gcaccgccta catacctcgc tctgctaatc ctgttaccag tggctgctgc cagtggcgat    4560
aagtcgtgtc ttaccgggtt ggactcaaga cgatagttac cggataaggc gcagcggtcg    4620
ggctgaacgg ggggttcgtg cacacagccc agcttggagc gaacgaccta caccgaactg    4680
agatacctac agcgtgagct atgagaaagc gccacgcttc ccgaagggag aaaggcggac    4740
aggtatccgg taagcggcag ggtcggaaca ggagagcgca cgagggagct tccaggggga    4800
aacgcctggt atctttatag tcctgtcggg tttcgccacc tctgacttga gcgtcgattt    4860
ttgtgatgct cgtcaggggg gcggagccta tggaaaaacg ccagcaacgc ggccttttta    4920
cggttcctgg cttttgctg gccttttgct cacatgttct t                         4961
```

<210> SEQ ID NO 12
<211> LENGTH: 4482
<212> TYPE: DNA
<213> ORGANISM: Homo sapiens

<400> SEQUENCE: 12

```
ccgcctaatg agcgggcttt ttttcttag gctgcctcgc gcgtttcggt gatgacggtg      60
aaaacctctg acacatgcag ctcccggaga cggtcacagc ttgtctgtaa gcggatgccg     120
ggagcagaca gcccgtcag ggcgcgtcag cgggtgttgg cgggtgtcgg ggcgcagcca     180
tgacccagtc acgtagcgat agcggagtgt atactggctt aactatgcgg catcagagca     240
gattgtactg agagtgcacc atatgcggtg tgaaataccg cacagatgcg taaggagaaa     300
ataccgcatc aggcgctctt ccgcttcctc gctcactgac tcgctgcgct cggtcgttcg     360
gctgcggcga gcggtatcag ctcactcaaa ggcggtaata cggttatcca cagaatcagg     420
ggataacgca ggaaagaaca tgtgagcaaa aggccagcaa aaggccagga accgtaaaaa     480
ggccgcgttg ctggcgtttt tccataggct ccgcccccct gacgagcatc acaaaaatcg     540
```

```
acgctcaagt cagaggtggc gaaacccgac aggactataa agataccagg cgtttccccc    600
tggaagctcc ctcgtgcgct ctcctgttcc gaccctgccg cttaccggat acctgtccgc    660
ctttctccct tcgggaagcg tggcgctttc tcatagctca cgctgtaggt atctcagttc    720
ggtgtaggtc gttcgctcca agctgggctg tgtgcacgaa ccccccgttc agcccgaccg    780
ctgcgcctta tccggtaact atcgtcttga gtccaacccg gtaagacacg acttatcgcc    840
actggcagca gccactggta acaggattag cagagcgagg tatgtaggcg gtgctacaga    900
gttcttgaag tggtggccta actacggcta cactagaaga acagtatttg gtatctgcgc    960
tctgctgaag ccagttacct tcggaaaaag agttggtagc tcttgatccg gcaaacaaac   1020
caccgctggt agcggtggtt ttttgtttg caagcagcag attacgcgca gaaaaaagg    1080
atctcaagaa gatcctttga tcttttctac ggggtctgac gctcagtgga acgaaaactc   1140
acgttaaggg attttggtca tgagattatc aaaaaggatc ttcacctaga tccttttaaa   1200
ttaaaaatga agttttaaat caatctaaag tatatatgag taaacttggt ctgacagtta   1260
ccaatgctta atcagtgagg cacctatctc agcgatctgt ctatttcgtt catccatagt   1320
tgcctgactc ctgcaaacca cgttgtgtct caaaatctct gatgttacat tgcacaagat   1380
aaaaatatat catcatgaac aataaaactg tctgcttaca taaacagtaa tacaaggggt   1440
gttatgagcc atattcaacg ggaaacgtct tgctcgaggc cgcgattaaa ttccaacatg   1500
gatgctgatt tatatgggta taaatgggct cgcgataatg tcgggcaatc aggtgcgaca   1560
atctatcgat tgtatgggaa gcccgatgcg ccagagttgt ttctgaaaca tggcaaaggt   1620
agcgttgcca atgatgttac agatgagatg gtcagactaa actggctgac ggaatttatg   1680
cctcttccga ccatcaagca ttttatccgt actcctgatg atgcatggtt actcaccact   1740
gcgatccccg ggaaaacagc attccaggta ttagaagaat atcctgattc aggtgaaaat   1800
attgttgatg cgctggcagt gttcctgcgc cggttgcatt cgattcctgt ttgtaattgt   1860
ccttttaaca gcgatcgcgt atttcgtctc gctcaggcgc aatcacgaat gaataacggt   1920
ttggttgatg cgagtgattt tgatgacgag cgtaatggct ggcctgttga acaagtctgg   1980
aaagaaatgc ataagctttt gccattctca ccggattcag tcgtcactca tggtgatttc   2040
tcacttgata accttatttt tgacgagggg aaattaatag gttgtattga tgttggacga   2100
gtcggaatcg cagaccgata ccaggatctt gccatcctat ggaactgcct cggtgagttt   2160
tctccttcat tacagaaacg gcttttcaa aaatatggta ttgataatcc tgatatgaat   2220
aaattgcagt ttcatttgat gctcgatgag ttttctaac cctgatcact gtggaatgtg   2280
tgtcagttag ggtgtggaaa gtccccaggc tccccagcag gcagaagtat gcaaagcatg   2340
catctcaatt agtcagcaac caggtgtgga agtccccag gctccccagc aggcagaagt   2400
atgcaaagca tgcatctcaa ttagtcagca accatagtcc gcccctaac tccgcccatc   2460
ccgcccctaa ctccgcccag gatcgcgta caggtgattt cgattctcgg tggggctctc   2520
acaactagga agaatagtt tgcttttc ttatgattaa agaagaagc catactttcc    2580
ctatgacacc aaacacccg attcaatttg gcagttagga aggttgtatc gcggaggaag   2640
gaaacggggc ggggcggat ttcttttaa cagagtgaac gcactcaaac acgcctttgc   2700
tggcaggcgg gggagcgcgg ctgggagcag ggaggccgga gggcggtgtg gggggcaggt   2760
ggggaggagc ccagtcctcc ttccttgcca acgctggctc tggcgagggc tgcttccggc   2820
tggtgccccc gggggagacc caacctgggg cgacttcagg ggtgccacat tcgctaagtg   2880
```

```
ctcggagtta atagcacctc ctccgagcac tcgctcacgg cgtcccttg cctggaaaga    2940
taccgcggtc cctccagagg atttgaggga cagggtcgga gggggctctt ccgccagcac    3000
cggaggaaga aagaggaggg gctggctggt caccagaggg tggggcggac cgcgtgcgct    3060
cggcggctgc ggagaggggg agagcaggca gcggcggcg gggagcagca gacccaagct    3120
ggtcgacatg gtggaaggcg tgcaggtcga gacaatttct cctggcgacg gcagaacatt    3180
ccccaagaga ggacagacct gcgtcgtgca ctataccggc atgctcgagg atggcaagaa    3240
ggtggacagc agcagagaca gaaacaagcc cttcaagttc atgctgggca gcaagaagt    3300
gatcagaggc tgggaagagg gcgtcgcaca gatgtctgtg ggacagagag ccaagctgac    3360
aatcagccct gattacgcct acggcgccac aggacatcct ggaatcatcc ctccacacgc    3420
cacactggtg ttcgacgtgg aactgctgaa gctggaatct ggcggtggaa gcggagtgga    3480
tggcttttgga gatgtgggag ccctggaatc tctgagagga aacgccgatc tggcctacat    3540
cctgtccatg gaaccttgcg ccactgcct gattatcaac aacgtgaact tctgcagaga    3600
gagcggcctg agaaccagaa ccggcagcaa catcgactgc gagaagctga agaagatt     3660
cagcagcctg cacttcatgg tggaagtgaa gggcgacctg accgccaaga aaatggtgct    3720
ggctctgctg gaactggccc agcaagatca tggcgctctg gactgttgtg tggtggtcat    3780
cctgagtcac ggctgtcagg cctctcatct gcaattccct ggcgccgtgt acggcacaga    3840
tggatgtcca gtgtccgtgg aaaagatcgt gaacatcttc aacggcacaa gctgccctag    3900
cctcggcgga aagcccaagc tgttcttat ccaagcctgt ggcggcgagc agaaggatca    3960
cggatttgag gtgccagca caagcccga ggatgagtct cctggaagca accctgagcc    4020
tgacgccaca cctttccaag agggactgag aaccttcgac cagctggacg ctatcagctc    4080
cctgcctaca cctagcgaca tcttcgtgtc ctacagcaca ttccccggct tcgtgtcttg    4140
gagagatccc aagtctggct cttggtacgt ggaaaccctg gacgatatct tcgagcagtg    4200
ggcccatagc gaggatctgc agtctctgct cctgagagtg gccaacgctg tgtccgtgaa    4260
gggcatctac aagcagatgc ccggctgttt taacttcctg aggaagaagc tgttttttcaa    4320
gaccagctaa agatctttt ccctctgcca aaaattatgg ggacatcatg aagcccttg     4380
agcatctgac ttctggctaa taaggaaat ttatttttcat tgcaatagtg tgttggaatt    4440
ttttgtgtct ctcactcgga aggacataag gcggccgcta gc                       4482
```

<210> SEQ ID NO 13
<211> LENGTH: 4135
<212> TYPE: DNA
<213> ORGANISM: Homo sapiens

<400> SEQUENCE: 13

```
ccgcctaatg agcgggcttt ttttcttag gctgcctcgc gcgtttcggt gatgacggtg      60
aaaacctctg acacatgcag ctcccggaga cggtcacagc ttgtctgtaa gcggatgccg    120
ggagcagaca agcccgtcag ggcgcgtcag cgggtgttgg cgggtgtcgg ggcgcagcca    180
tgacccagtc acgtagcgat agcggagtgt atactggctt aactatgcgg catcagagca    240
gattgtactg agagtgcacc atatgcggtg tgaaataccg cacagatgcg taaggagaaa    300
ataccgcatc aggcgctctt ccgcttcctc gctcactgac tcgctgcgct cggtcgttcg    360
gctgcggcga gcggtatcag ctcactcaaa ggcggtaata cggttatcca cagaatcagg    420
ggataacgca ggaaagaaca tgtgagcaaa aggccagcaa aaggccagga accgtaaaaa    480
ggccgcgttg ctggcgtttt tccataggct ccgcccccct gacgagcatc acaaaaatcg    540
```

```
acgctcaagt cagaggtggc gaaacccgac aggactataa agataccagg cgtttccccc      600
tggaagctcc ctcgtgcgct ctcctgttcc gaccctgccg cttaccggat acctgtccgc      660
cttttctccct tcgggaagcg tggcgctttc tcatagctca cgctgtaggt atctcagttc     720
ggtgtaggtc gttcgctcca agctgggctg tgtgcacgaa ccccccgttc agcccgaccg      780
ctgcgcctta tccggtaact atcgtcttga gtccaacccg gtaagacacg acttatcgcc      840
actggcagca gccactggta acaggattag cagagcgagg tatgtaggcg gtgctacaga      900
gttcttgaag tggtggccta actacggcta cactagaaga acagtatttg gtatctgcgc      960
tctgctgaag ccagttacct tcggaaaaag agttggtagc tcttgatccg gcaaacaaac     1020
caccgctggt agcggtggtt ttttgtttg caagcagcag attacgcgca gaaaaaaagg      1080
atctcaagaa gatcctttga tcttttctac ggggtctgac gctcagtgga acgaaaactc     1140
acgttaaggg attttggtca tgagattatc aaaaaggatc ttcacctaga tccttttaaa     1200
ttaaaaatga agttttaaat caatctaaag tatatatgag taaacttggt ctgacagtta     1260
ccaatgctta atcagtgagg cacctatctc agcgatctgt ctatttcgtt catccatagt     1320
tgcctgactc ctgcaaacca cgttgtgtct caaaatctct gatgttacat tgcacaagat     1380
aaaaatatat catcatgaac aataaaactg tctgcttaca taaacagtaa tacaaggggt     1440
gttatgagcc atattcaacg ggaaacgtct tgctcgaggc cgcgattaaa ttccaacatg     1500
gatgctgatt tatatgggta taaatgggct cgcgataatg tcgggcaatc aggtgcgaca     1560
atctatcgat tgtatgggaa gcccgatgcg ccagagttgt ttctgaaaca tggcaaaggt     1620
agcgttgcca atgatgttac agatgagatg gtcagactaa actggctgac ggaatttatg     1680
cctcttccga ccatcaagca ttttatccgt actcctgatg atgcatggtt actcaccact     1740
gcgatccccg ggaaaacagc attccaggta ttagaagaat atcctgattc aggtgaaaat     1800
attgttgatg cgctggcagt gttcctgcgc cggttgcatt cgattcctgt ttgtaattgt     1860
ccttttaaca gcgatcgcgt atttcgtctc gctcaggcgc aatcacgaat gaataacggt     1920
ttggttgatg cgagtgattt tgatgacgag cgtaatggct ggcctgttga acaagtctgg     1980
aaagaaatgc ataagctttt gccattctca ccggattcag tcgtcactca tggtgatttc     2040
tcacttgata accttatttt tgacgagggg aaattaatag gttgtattga tgttggacga     2100
gtcggaatcg cagaccgata ccaggatctt gccatcctat ggaactgcct cggtgagttt     2160
tctccttcat tacagaaacg gcttttcaa aaatatggta ttgataatcc tgatatgaat      2220
aaattgcagt ttcatttgat gctcgatgag ttttttctaac cctgatcact gtggaatgtg     2280
tgtcagttag ggtgtggaaa gtccccaggc tccccagcag gcagaagtat gcaaagcatg     2340
catctcaatt agtcagcaac caggtgtgga agtccccag gctccccagc aggcagaagt      2400
atgcaaagca tgcatctcaa ttagtcagca accatagtcc gcccctaac tccgcccatc      2460
ccgcccctaa ctccgcccag gatccgcgta caggtgattt cgattctcgg tggggctctc     2520
acaactagga agaatagtt ttgctttttc ttatgattaa aagaagaagc catactttcc       2580
ctatgacacc aaaacacccg attcaatttg gcagttagga aggttgtatc gcggaggaag     2640
gaaacggggc gggggcggat ttctttttaa cagagtgaac gcactcaaac acgcctttgc     2700
tggcaggcgg gggagcgcgg ctgggagcag ggaggccgga gggcggtgtg gggggcaggt     2760
ggggaggagc ccagtcctcc ttccttgcca acgctggctc tggcgagggc tgcttccggc     2820
tggtgccccc gggggagacc caacctgggg cgacttcagg ggtgccacat tcgctaagtg     2880
```

-continued

| | |
|---|---|
| ctcggagtta atagcacctc ctccgagcac tcgctcacgg cgtccccttg cctggaaaga | 2940 |
| taccgcggtc cctccagagg atttgaggga cagggtcgga gggggctctt ccgccagcac | 3000 |
| cggaggaaga aagaggaggg gctggctggt caccagaggg tggggcggac cgcgtgcgct | 3060 |
| cggcggctgc ggagagggg agagcaggca gcggcggcg gggagcagca gacccaagct | 3120 |
| ggtcgacatg ggctttggag atgtgggagc cctggaatct ctgagaggaa acgccgatct | 3180 |
| ggcctacatc ctgtccatgg aaccttgcgg ccactgcctg attatcaaca acgtgaactt | 3240 |
| ctgcagagag agcggcctga aaccagaac cggcagcaac atcgactgcg agaagctgag | 3300 |
| aagaagattc agcagcctgc acttcatggt ggaagtgaag ggcgacctga ccgccaagaa | 3360 |
| aatggtgctg gctctgctgg aactggccca gcaagatcat ggcgctctgg actgttgtgt | 3420 |
| ggtggtcatc ctgagtcacg gctgtcaggc ctctcatctg caattccctg cgccgtgta | 3480 |
| cggcacagat ggatgtccag tgtccgtgga aaagatcgtg aacatcttca acggcacaag | 3540 |
| ctgccctagc ctcggcggaa agcccaagct gttctttatc caagcctgtg gcggcgagca | 3600 |
| gaaggatcac ggatttgagg tggccagcac aagccctgag gatgagtctc ctggaagcaa | 3660 |
| ccctgagcct gacgccacac ctttccaaga gggactgaga accttcgacc agctggacgc | 3720 |
| tatcagctcc ctgcctacac ctagcgacat cttcgtgtcc tacagcacat tccccggctt | 3780 |
| cgtgtcttgg agagatccca agtctggctc ttggtacgtg gaaaccctgg acgatatctt | 3840 |
| cgagcagtgg gcccatagcg aggatctgca gtctctgctc ctgagagtgg ccaacgctgt | 3900 |
| gtccgtgaag ggcatctaca agcagatgcc ctgcatcgtg tccatgctga ggaagaagct | 3960 |
| gttttttcaag accagctaac cgcagatctt tttccctctg ccaaaaatta tggggacatc | 4020 |
| atgaagcccc ttgagcatct gacttctggc taataaagga aatttatttt cattgcaata | 4080 |
| gtgtgttgga attttttgtg tctctcactc ggaaggacat aaggcggccg ctagc | 4135 |

<210> SEQ ID NO 14
<211> LENGTH: 4105
<212> TYPE: DNA
<213> ORGANISM: Homo sapiens

<400> SEQUENCE: 14

| | |
|---|---|
| ccgcctaatg agcgggcttt ttttttcttag gctgcctcgc gcgtttcggt gatgacggtg | 60 |
| aaaacctctg acacatgcag ctcccggaga cggtcacagc ttgtctgtaa gcggatgccg | 120 |
| ggagcagaca agcccgtcag ggcgcgtcag cgggtgttgg cgggtgtcgg ggcgcagcca | 180 |
| tgacccagtc acgtagcgat agcggagtgt atactggctt aactatgcgg catcagagca | 240 |
| gattgtactg agagtgcacc atatgcggtg tgaaataccg cacagatgcg taaggagaaa | 300 |
| ataccgcatc aggcgctctt ccgcttcctc gctcactgac tcgctgcgct cggtcgttcg | 360 |
| gctgcggcga gcggtatcag ctcactcaaa ggcggtaata cggttatcca cagaatcagg | 420 |
| ggataacgca ggaaagaaca tgtgagcaaa aggccagcaa aaggccagga accgtaaaaa | 480 |
| ggccgcgttg ctggcgtttt tccataggct ccgcccccct gacgagcatc acaaaaatcg | 540 |
| acgctcaagt cagaggtggc gaaacccgac aggactataa agataccagg cgtttccccc | 600 |
| tggaagctcc ctcgtgcgct ctcctgttcc gaccctgccg cttaccggat acctgtccgc | 660 |
| ctttctccct tcgggaagcg tggcgctttc tcatagctca cgctgtaggt atctcagttc | 720 |
| ggtgtaggtc gttcgctcca agctgggctg tgtgcacgaa ccccccgttc agcccgaccg | 780 |
| ctgcgcctta tccggtaact atcgtcttga gtccaacccg gtaagacacg acttatcgcc | 840 |
| actggcagca gccactggta acaggattag cagagcgagg tatgtaggcg gtgctacaga | 900 |

```
gttcttgaag tggtggccta actacggcta cactagaaga acagtatttg gtatctgcgc    960
tctgctgaag ccagttacct tcggaaaaag agttggtagc tcttgatccg gcaaacaaac   1020
caccgctggt agcggtggtt tttttgtttg caagcagcag attacgcgca gaaaaaaagg   1080
atctcaagaa gatcctttga tcttttctac ggggtctgac gctcagtgga acgaaaactc   1140
acgttaaggg attttggtca tgagattatc aaaaaggatc ttcacctaga tccttttaaa   1200
ttaaaaatga agttttaaat caatctaaag tatatatgag taaacttggt ctgacagtta   1260
ccaatgctta atcagtgagg cacctatctc agcgatctgt ctatttcgtt catccatagt   1320
tgcctgactc ctgcaaacca cgttgtgtct caaaatctct gatgttacat tgcacaagat   1380
aaaaatatat catcatgaac aataaaactg tctgcttaca taaacagtaa tacaaggggt   1440
gttatgagcc atattcaacg ggaaacgtct tgctcgaggc cgcgattaaa ttccaacatg   1500
gatgctgatt tatatgggta taaatgggct cgcgataatg tcgggcaatc aggtgcgaca   1560
atctatcgat tgtatgggaa gcccgatgcg ccagagttgt ttctgaaaca tggcaaaggt   1620
agcgttgcca atgatgttac agatgagatg gtcagactaa actggctgac ggaatttatg   1680
cctcttccga ccatcaagca ttttatccgt actcctgatg atgcatggtt actcaccact   1740
gcgatccccg ggaaaacagc attccaggta ttagaagaat atcctgattc aggtgaaaat   1800
attgttgatg cgctggcagt gttcctgcgc cggttgcatt cgattcctgt ttgtaattgt   1860
ccttttaaca gcgatcgcgt atttcgtctc gctcaggcgc aatcacgaat gaataacggt   1920
ttggttgatg cgagtgattt tgatgacgag cgtaatggct ggcctgttga acaagtctgg   1980
aaagaaatgc ataagctttt gccattctca ccggattcag tcgtcactca tggtgatttc   2040
tcacttgata accttatttt tgacgagggg aaattaatag gttgtattga tgttggacga   2100
gtcggaatcg cagaccgata ccaggatctt gccatcctat ggaactgcct cggtgagttt   2160
tctccttcat tacagaaacg gctttttcaa aaatatggta ttgataatcc tgatatgaat   2220
aaattgcagt ttcatttgat gctcgatgag ttttttctaac cctgatcact gtggaatgtg   2280
tgtcagttag ggtgtggaaa gtccccaggc tccccagcag gcagaagtat gcaaagcatg   2340
catctcaatt agtcagcaac caggtgtgga aagtccccag gctccccagc aggcagaagt   2400
atgcaaagca tgcatctcaa ttagtcagca accatagtcc cgcccctaac tccgcccatc   2460
ccgcccctaa ctccgcccag atccgctgtg acgggccaga tatacgcttg tcatggcgac   2520
tgtccagctt tgtgccagga gcctcgcagg ggttgatggg attggggttt tcccctccca   2580
tgtgctcaag actggcgcta aaagttttga gcttctcaaa agtctagagc caccgtccag   2640
ggagcaggta gctgctgggc tccggggaca ctttgcgttc gggctgggag cgtgctttcc   2700
acgacggtga cacgcttccc tggattggag acccaagctg gtcgacatgg tggaaggcgt   2760
gcaggtcgag acaatttctc ctggcgacgg cagaacattc cccaagagag acagacctg   2820 cgtcgtgcac tataccggca tgctcgagga tggcaagaag gtggacagca gcagagacag   2880
aaacaagccc ttcaagttca tgctgggcaa gcaagaagtg atcagaggct gggaagaggg   2940
cgtcgcacag atgtctgtgg acagagagc caagctgaca atcagccctg attacgccta   3000
cggcgccaca ggacatcctg gaatcatccc tccacacgcc acactggtgt cgacgtggaa   3060
actgctgaag ctggaatctg gcggtggaag cggagtggat ggctttggag atgtgggagc   3120
cctggaatct ctgagaggaa acgccgatct ggcctacatc ctgtccatgg aaccttgcgg   3180
ccactgcctg attatcaaca acgtgaactt ctgcagagag agcggcctga gaccagaac   3240
```

| | |
|---|---|
| cggcagcaac atcgactgcg agaagctgag aagaagattc agcagcctgc acttcatggt | 3300 |
| ggaagtgaag ggcgacctga ccgccaagaa aatggtgctg gctctgctgg aactggccca | 3360 |
| gcaagatcat ggcgctctgg actgttgtgt ggtggtcatc ctgagtcacg gctgtcaggc | 3420 |
| ctctcatctg caattccctg cgccgtgta cggcacagat ggatgtccag tgtccgtgga | 3480 |
| aaagatcgtg aacatcttca cggcacaag ctgccctagc ctcggcggaa agcccaagct | 3540 |
| gttctttatc caagcctgtg gcggcgagca gaaggatcac ggatttgagg tggccagcac | 3600 |
| aagccctgag gatgagtctc ctggaagcaa ccctgagcct gacgccacac ctttccaaga | 3660 |
| gggactgaga accttcgacc agctggacgc tatcagctcc ctgcctacac ctagcgacat | 3720 |
| cttcgtgtcc tacagcacat tccccggctt cgtgtcttgg agagatccca gtctggctc | 3780 |
| ttggtacgtg gaaaccctgg acgatatctt cgagcagtgg gcccatagcg aggatctgca | 3840 |
| gtctctgctc ctgagagtgg ccaacgctgt gtccgtgaag ggcatctaca agcagatgcc | 3900 |
| cggctgtttt aacttcctga ggaagaagct gttttcaag accagctaac cgcagatctt | 3960 |
| tttccctctg ccaaaaatta tggggacatc atgaagcccc ttgagcatct gacttctggc | 4020 |
| taataaagga aatttatttt cattgcaata gtgtgttgga attttttgtg tctctcactc | 4080 |
| ggaaggacat aaggcggccg ctagc | 4105 |

<210> SEQ ID NO 15
<211> LENGTH: 3754
<212> TYPE: DNA
<213> ORGANISM: Homo sapiens

<400> SEQUENCE: 15

| | |
|---|---|
| ccgcctaatg agcgggcttt tttttcttag gctgcctcgc gcgtttcggt gatgacggtg | 60 |
| aaaacctctg acacatgcag ctcccggaga cggtcacagc ttgtctgtaa gcggatgccg | 120 |
| ggagcagaca agcccgtcag ggcgcgtcag cgggtgttgg cgggtgtcgg ggcgcagcca | 180 |
| tgacccagtc acgtagcgat agcggagtgt atactggctt aactatgcgg catcagagca | 240 |
| gattgtactg agagtgcacc atatgcggtg tgaaataccg cacagatgcg taaggagaaa | 300 |
| ataccgcatc aggcgctctt ccgcttcctc gctcactgac tcgctgcgct cggtcgttcg | 360 |
| gctgcggcga gcggtatcag ctcactcaaa ggcggtaata cggttatcca cagaatcagg | 420 |
| ggataacgca ggaaagaaca tgtgagcaaa aggccagcaa aaggccagga accgtaaaaa | 480 |
| ggccgcgttg ctggcgtttt tccataggct ccgcccccct gacgagcatc acaaaaatcg | 540 |
| acgctcaagt cagaggtggc gaaacccgac aggactataa agataccagg cgtttccccc | 600 |
| tggaagctcc ctcgtgcgct ctcctgttcc gaccctgccg cttaccggat acctgtccgc | 660 |
| ctttctccct tcgggaagcg tggcgctttc tcatagctca cgctgtaggt atctcagttc | 720 |
| ggtgtaggtc gttcgctcca agctgggctg tgtgcacgaa ccccccgttc agcccgaccg | 780 |
| ctgcgcctta tccggtaact atcgtcttga gtccaacccg gtaagacacg acttatcgcc | 840 |
| actggcagca gccactggta acaggattag cagagcgagg tatgtaggcg gtgctacaga | 900 |
| gttcttgaag tggtggccta actacggcta cactagaaga acagtatttg gtatctgcgc | 960 |
| tctgctgaag ccagttacct tcggaaaaag agttggtagc tcttgatccg gcaaacaaac | 1020 |
| caccgctggt agcggtggtt tttttgtttg caagcagcag attacgcgca gaaaaaaagg | 1080 |
| atctcaagaa gatcctttga tcttttctac ggggtctgac gctcagtgga acgaaaactc | 1140 |
| acgttaaggg attttggtca tgagattatc aaaaaggatc ttcacctaga tccttttaaa | 1200 |
| ttaaaaatga agttttaaat caatctaaag tatatatgag taaacttggt ctgacagtta | 1260 |

```
ccaatgctta atcagtgagg cacctatctc agcgatctgt ctatttcgtt catccatagt    1320
tgcctgactc ctgcaaacca cgttgtgtct caaaatctct gatgttacat tgcacaagat    1380
aaaaatatat catcatgaac aataaaactg tctgcttaca taaacagtaa tacaaggggt    1440
gttatgagcc atattcaacg ggaaacgtct tgctcgaggc cgcgattaaa ttccaacatg    1500
gatgctgatt tatatgggta taaatgggct cgcgataatg tcgggcaatc aggtgcgaca    1560
atctatcgat tgtatgggaa gcccgatgcg ccagagttgt ttctgaaaca tggcaaaggt    1620
agcgttgcca atgatgttac agatgagatg gtcagactaa actggctgac ggaatttatg    1680
cctcttccga ccatcaagca tttttatccgt actcctgatg atgcatggtt actcaccact    1740
gcgatcccg ggaaaacagc attccaggta ttagaagaat atcctgattc aggtgaaaat    1800
attgttgatg cgctggcagt gttcctgcgc cggttgcatt cgattcctgt ttgtaattgt    1860
ccttttaaca gcgatcgcgt atttcgtctc gctcaggcgc aatcacgaat gaataacggt    1920
ttggttgatg cgagtgattt tgatgacgag cgtaatggct ggcctgttga acaagtctgg    1980
aaagaaatgc ataagctttt gccattctca ccggattcag tcgtcactca tggtgatttc    2040
tcacttgata accttatttt tgacgagggg aaattaatag gttgtattga tgttggacga    2100
gtcggaatcg cagaccgata ccaggatctt gccatcctat ggaactgcct cggtgagttt    2160
tctccttcat tacagaaacg cttttttcaa aaatatggta ttgataatcc tgatatgaat    2220
aaattgcagt ttcatttgat gctcgatgag tttttctaac cctgatcact gtggaatgtg    2280
tgtcagttag ggtgtggaaa gtccccaggc tccccagcag gcagaagtat gcaaagcatg    2340
catctcaatt agtcagcaac caggtgtgga aagtccccag gctccccagc aggcagaagt    2400
atgcaaagca tgcatctcaa ttagtcagca accatagtcc cgcccctaac tccgcccatc    2460
ccgcccctaa ctccgcccag gatccgctgt acgggccaga tatacgcttg tcatggcgac    2520
tgtccagctt tgtgccagga gcctcgcagg ggttgatggg attggggttt tcccctccca    2580
tgtgctcaag actggcgcta aaagttttga gcttctcaaa agtctagagc caccgtccag    2640
ggagcaggta gctgctgggc tccgggggaca ctttgcgttc gggctgggag cgtgctttcc    2700
acgacggtga cacgcttccc tggattggag acccaagctg gtcgacatgg gctttggaga    2760
tgtgggagcc ctggaatctc tgagaggaaa cgccgatctg gcctacatcc tgtccatgga    2820
accttgcggc cactgcctga ttatcaacaa cgtgaacttc tgcagagaga gcggcctgag    2880
aaccagaacc ggcagcaaca tcgactgcga gaagctgaga agaagattca gcagcctgca    2940
cttcatggtg gaagtgaagg gcgacctgac cgccaagaaa atggtgctgg ctctgctgga    3000
actggcccag caagatcatg gcgctctgga ctgttgtgtg gtggtcatcc tgagtcacgg    3060
ctgtcaggcc tctcatctgc aattccctgg cgccgtgtac ggcacagatg gatgtccagt    3120
gtccgtggaa aagatcgtga acatcttcaa cggcacaagc tgccctagcc tcggcggaaa    3180
gcccaagctg ttcttatcc aagcctgtgg cggcagcag aaggatcacg gatttgaggt    3240
ggccagcaca agccctgagg atgagtctcc tggaagcaac cctgagcctg acgccacacc    3300
tttccaagag ggactgagaa ccttcgacca gctggacgct atcagctccc tgcctacacc    3360
tagcgacatc ttcgtgtcct acagcacatt ccccggcttc gtgtcttgga gagatcccaa    3420
gtctggctct tggtacgtgg aaaccctgga cgatatcttc gagcagtggg cccatagcga    3480
ggatctgcag tctctgctcc tgagagtggc caacgctgtg tccgtgaagg gcatctacaa    3540
gcagatgccc tgcatcgtgt ccatgctgag gaagaagctg ttttcaaga ccagctaacc    3600
```

```
gcagatcttt tccctctgc caaaaattat ggggacatca tgaagcccct tgagcatctg    3660
acttctggct aataaaggaa atttattttc attgcaatag tgtgttggaa ttttttgtgt    3720
ctctcactcg gaaggacata aggcggccgc tagc                                3754
```

<210> SEQ ID NO 16
<211> LENGTH: 125
<212> TYPE: PRT
<213> ORGANISM: Homo sapiens

<400> SEQUENCE: 16

```
Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile Ala Gly Leu Val Ala Leu Leu Thr
        35                  40                  45

Phe Leu Ala Phe Gly Phe Trp Leu Phe Lys Tyr Leu Gln Lys Arg Arg
    50                  55                  60

Glu Arg Arg Arg Gln Leu Thr Glu Phe Gln Lys Arg Tyr Leu Arg Asn
65                  70                  75                  80

Ser Tyr Arg Leu Ser Glu Ile Gln Arg Pro Ile Ser Gln His Glu Tyr
                85                  90                  95

Glu Asp Pro Tyr Glu Pro Pro Ser Arg Arg Lys Pro Pro Pro Pro
            100                 105                 110

Tyr Ser Thr Tyr Val Asn Ile Asp Asn Val Ser Ala Ile
        115                 120                 125
```

<210> SEQ ID NO 17
<211> LENGTH: 154
<212> TYPE: PRT
<213> ORGANISM: Homo sapiens

<400> SEQUENCE: 17

```
Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile Ala Gly Leu Val Ala Leu Leu Thr
        35                  40                  45

Phe Leu Ala Phe Gly Phe Trp Leu Phe Lys Tyr Leu Gln Trp Tyr Asn
    50                  55                  60

Arg Lys Ser Lys Asn Lys Lys Arg Lys Glu Gln Ile Arg Glu Gln Ile
65                  70                  75                  80

Glu Leu Gly Leu Leu Ser Tyr Gly Ala Gly Val Ala Ser Leu Pro Leu
                85                  90                  95

Leu Asn Val Ile Ala His Asn Pro Gly Ser Val Ile Ser Ala Thr Pro
            100                 105                 110

Ile Tyr Lys Gly Pro Cys Thr Gly Val Pro Asn Ser Arg Leu Leu Gln
        115                 120                 125

Ile Thr Ser Gly Thr Ala Glu Glu Asn Thr Arg Ile Leu Asn His Asp
    130                 135                 140

Gly Arg Asn Pro Asp Gly Ser Ile Asn Val
145                 150
```